(12) United States Patent
Draper et al.

(10) Patent No.: US 12,377,138 B2
(45) Date of Patent: Aug. 5, 2025

(54) TREATMENT AND PREVENTION OF MALARIA

(71) Applicant: Oxford University Innovation Limited, Oxford (GB)

(72) Inventors: Simon Draper, Oxford (GB); Matthew Higgins, Oxford (GB); Daniel G. W. Alanine, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1076 days.

(21) Appl. No.: 17/284,617

(22) PCT Filed: Oct. 10, 2019

(86) PCT No.: PCT/GB2019/052885
§ 371 (c)(1),
(2) Date: Apr. 12, 2021

(87) PCT Pub. No.: WO2020/074908
PCT Pub. Date: Apr. 16, 2020

(65) Prior Publication Data
US 2022/0233667 A1     Jul. 28, 2022

(30) Foreign Application Priority Data

Oct. 10, 2018 (GB) .................................. 1816542
May 29, 2019 (GB) .................................. 1907609

(51) Int. Cl.
| | | |
|---|---|---|
| *C07K 16/00* | (2006.01) | |
| *A61K 39/015* | (2006.01) | |
| *A61K 39/395* | (2006.01) | |
| *A61P 33/06* | (2006.01) | |
| *C07K 16/20* | (2006.01) | |
| *C12N 15/115* | (2010.01) | |
| *A61K 39/00* | (2006.01) | |

(52) U.S. Cl.
CPC ...... *A61K 39/015* (2013.01); *A61K 39/39575* (2013.01); *A61P 33/06* (2018.01); *C07K 16/205* (2013.01); *C12N 15/115* (2013.01); *A61K 39/00* (2013.01); *A61K 2039/5256* (2013.01); *A61K 2039/5258* (2013.01); *A61K 2039/53* (2013.01); *C07K 2317/31* (2013.01); *C07K 2317/56* (2013.01); *C07K 2317/565* (2013.01); *C07K 2317/76* (2013.01)

(58) Field of Classification Search
CPC ............ A61K 39/015; A61K 39/39575; A61K 39/00; A61K 2039/5256; A61K 2039/5258; A61K 2039/53; A61P 33/06; C07K 16/205; C12N 15/115
See application file for complete search history.

(56) References Cited

FOREIGN PATENT DOCUMENTS

| WO | 2012/046081 A1 | 4/2012 |
| WO | 2012/114125 A2 | 8/2012 |
| WO | WO2012114125 | * 8/2012 |
| WO | 2016/016651 A2 | 2/2016 |

OTHER PUBLICATIONS

Williams et al., PLOS pathogens, 8:1-15, e1002991, 2012 (Year: 2012).*
International Search Report and Written Opinion for WO WO2020/074908 (PCT/GB2019/052885), dated Apr. 8, 2020, pp. 1-22.
UK Search Report for GB 1816542.3, dated Mar. 29, 2019, pp. 1-4.
Alanine Daniel G W et al: "Human Antibodies that Slow Erythrocyte Invasion Potentiate Malaria-Neutralizing Antibodies", Cell, vol. 178, No. 1, Jun. 27, 2019 (Jun. 27, 2019) , p. 216.
Williams AR et al: "Enhancing blockade of Plasmodium falciparum erythrocyte invasion: assessing combinations of antibodies against PfRH5 and other merozoite antigens", PLOS Pathogens, Public Library of Science, US, vol. 8, No. 11, Jan. 1, 2012 (Jan. 1, 2012), pp. e1002991-1.
Volz Jennifer C et al: "Essential Role of the PfRh5/PfRipr/CyRPA Complex during Plasmodium falciparum Invasion of Erythrocytes", Cell Host & Microbe, Elsevier, NL, vol. 20, No. 1, Jun. 30, 2016 (Jun. 30, 2016), pp. 60-71.
Proc Natl Acad Sci USA, vol. 112 (2015), Reddy et al., "Multiprotein complex between the GPI-anchored CyRPA with PfRH5 and PfR.ipr is crucial for Plasmodium falciparum erythrocyte invasion", pp. 1179-1184.
PLOS One, vol. 3 (2008), Rodriguez et al., "PfRHS: a novel reticulocyte-binding family homo log of Plasmodium falciparum that binds to the erythrocyte, and an investigation of its receptor", pp. e3300.
Malaria J, vol. 13 (2014), Ord et al., "A malaria vaccine candidate based on an epitope of the Plasmodium falciparum RHS protein", pp. 326.
J Immunol, vol. 192 (2014), Douglas et al., "Neutralization of plasmodium falciparum merozoites by antibodies against PfRHS", pp. 245-258.
Int J Parasitol, vol. 39 (2009), Baum et al., "Reticulocyte-binding protein homologue 5—an essential adhesin involved in invasion of human erythrocytes by Plasmodium falciparum".

(Continued)

*Primary Examiner* — Lei Yao
(74) *Attorney, Agent, or Firm* — Thomas |Horstemeyer, LLP

(57) ABSTRACT

There are provided antibodies and combination thereof, and other binding proteins against malarial antigens, as well as said antigens and vectors encoding the antibodies and antigens. The invention also provides the use of such compounds and combinations thereof in the prevention or treatment of malaria. In particular, synergistic combinations of non-neutralising antibodies directed towards an epitope on Reticulocyte-binding protein Homologue 5 (PfRH5) and neutralising antibodies directed towards *Plasmodium* merozoite antigens are provided.

8 Claims, 21 Drawing Sheets

Specification includes a Sequence Listing.

(56) References Cited

OTHER PUBLICATIONS

Proc Natl Acad Sci USA, vol. 114 (2017), Campeotto et al., "One-step design of a stable variant of the malaria invasion protein RHS for use as a vaccine immunogen", pp. 998-1002.
Cell Host & Microbe, vol. 17 (2015), Douglas et al., "A PfRHS-based vaccine is efficacious against heterologous strain blood-stage Plasmodium falciparum infection in Aotus monkeys".
Am J Trop Med Hyg, vol. 99 (2018), Ouattara et al., "Extent and dynamics of polymorphisms in the malaria vaccine candidate Plasmodium falciparum reticulocyte-binding protein homologue-5 in Kalifabougou, Mali", pp. 43-50.
International Preliminary Report on Patentability for WO WO2020/074908 (PCT/GB2019/052885), dated Apr. 8, 2021, pp. 1-12.

\* cited by examiner

| mAb | VR donor | Chain | Allele usage | Germline change (%) |
|---|---|---|---|---|
| R5.001 | 1019 | Heavy | IGHV1-18*04, IGHD4-17*01, IGHJ5*02 | 1.0 (3/296) |
| | | Light | IGKV1D-16*01, IGKJ4*01 | 1.1 (3/278) |
| R5.002 | 1019 | Heavy | IGHV3-49*04, IGHD1-20*01, IGHJ5*02 | 0.3 (1/301) |
| | | Light | IGLV3-21*02, IGLJ2*01/IGLJ3*01 | 0.3 (1/288) |
| R5.003 | 1019 | Heavy | IGHV1-69*01, IGHD3-22*01, IGHJ4*02 | 2.4 (7/293) |
| | | Light | IGKV3-11*01, IGKJ2*01 | 2.1 (6/287) |
| R5.004 | 1019 | Heavy | IGHV1-69*01, IGHD3-16*01, IGHJ3*02 | 2.4 (7/295) |
| | | Light | IGLV1-44*01, IGLJ3*02 | 1.0 (3/294) |
| R5.006 | 2207 | Heavy | IGHV4-39*01, IGHD6-13*01, IGHJ4*02 | 2.7 (8/298) |
| | | Light | IGLV3-21*01, IGLJ2*01/IGLJ3*01 | 2.1 (6/290) |
| R5.007 | 2207 | Heavy | IGHV3-7*02, IGHD3-16*01, IGHJ5*02 | 1.0 (3/292) |
| | | Light | IGKV4-1*01, IGKJ1*01 | 3.0 (9/300) |
| R5.008 | 1017 | Heavy | IGHV3-33*01, IGHD3-10*01, IGHJ4*02 | 2.4 (7/292) |
| | | Light | IGKV1-39*01, IGKJ4*01 | 2.1 (6/287) |
| R5.009 | 1017 | Heavy | IGHV3-23*04, IGHD3-22*01, IGHJ4*02 | 1.4 (4/295) |
| | | Light | IGLV1-40*01, IGLJ3*02 | 1.0 (3/297) |
| R5.010 | 1017 | Heavy | IGHV3-7*03, IGHD6-25*01, IGHJ6*02 | 1.4 (4/295) |
| | | Light | IGLV3-21*02, IGLJ2*01/IGLJ3*01 | 1.1 (3/285) |
| R5.011 | 1017 | Heavy | IGHV7-4-1*02, IGHD3-22*01, IGHJ4*02 | 1.0 (3/293) |
| | | Light | IGLV3-21*02, IGLJ3*02 | 1.4 (4/289) |
| R5.013 | 1017 | Heavy | IGHV4-39*01, IGHD3-3*01, IGHJ4*02 | 1.7 (5/297) |
| | | Light | IGKV3-11*01, IGKJ3*01 | 1.8 (5/283) |
| R5.014 | 1017 | Heavy | IGHV3-9*01, IGHD2-21*02, IGHJ4*02 | 1.4 (4/296) |
| | | Light | IGLV1-44*01, IGLJ3*02 | 1.4 (4/294) |
| R5.015 | 1017 | Heavy | IGHV1-2*04, IGHD3-10*01, IGHJ6*02 | 1.7 (5/295) |
| | | Light | IGLV3-21*01, IGLJ2*01/IGLJ3*01 | 4.2 (12/288) |
| R5.016 | 1017 | Heavy | IGHV1-18*01, IGHD3-9*01, IGHJ6*02 | 1.7 (5/296) |
| | | Light | IGKV1-5*03, IGKJ2*01 | 3.6 (10/281) |
| R5.017 | 1017 | Heavy | IGHV1-69*02, IGHD5-24*01, IGHJ6*02 | 3.8 (11/291) |
| | | Light | IGLV1-40*01, IGLJ3*02 | 0.3 (1/299) |
| R5.018 | 1017 | Heavy | IGHV3-33*01, IGHD3-22*01, IGHJ4*02 | 1.7 (5/295) |
| | | Light | IGKV1-39*01, IGKJ1*01 | 2.5 (7/284) |
| R5.019 | 1017 | Heavy | IGHV4-31*01, IGHD3-3*01, IGHJ4*02 | 1.3 (4/298) |
| | | Light | IGKV3-20*01, IGKJ2*04 | 1.7 (5/290) |
| c2AC7 | Mouse | Heavy | IGHV5-15*02, IGHD2-4*01, IGHJ1*01 | 3.1 (9/295) |
| | | Light | IGKV3-1*01, IGKJ1*01 | 3.4 (10/296) |
| c4BA7 | Mouse | Heavy | IGHV1-87*01, IGHD1-3*01, IGHJ4*01 | 3.1 (9/292) |
| | | Light | IGKV4-91*01, IGKJ4*01 | 2.1 (6/288) |
| c9AD4 | Mouse | Heavy | IGHV5-15*02, IGHD2-4*01, IGHJ1*01 | 2.0 (6/295) |
| | | Light | IGKV3-1*01, IGKJ1*01 | 3.4 (10/296) |
| QA1 | Mouse | Heavy | IGHV5-4*02, IGHD2-1*01, IGHJ4*01 | 3.4 (10/296) |
| | | Light | IGKV3-7*01, IGKJ2*01 | 2.4 (7/296) |

B
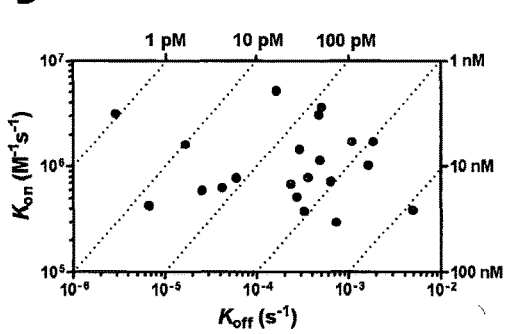

| Parasite | Amino acid position | | | | |
|---|---|---|---|---|---|
| | 147 | 148 | 197 | 203 | 410 |
| 3D7 (Lab-adapted clone, Africa) | Y | H | S | C | I |
| FVO (Lab-adapted line, Vietnam) | Y | H | Y | Y | I |
| Dd2 (Lab-adapted line, Indochina) | Y | H | S | C | M |
| GB4 (Lab-adapted line, Ghana) | Y | H | S | Y | I |
| M-Camp (Patient isolate, Malaysia) | Y | D | S | Y | I |
| Cp806 (Patient isolate, Cambodia) | H | H | S | Y | I |
| Cp845 (Patient isoate, Cambodia) | Y | H | Y | Y | I |

| α-EBOV | | | |
|---|---|---|---|
| | Pre-penetration | Penetration | Total invasion time |
| Median (s) | 15.2 | 10.1 | 25.2 |
| Mean (s) | 17.9 | 10.7 | 28.6 |
| R5.011 | | | |
| | Pre-penetration | Penetration | Total invasion time |
| Median (s) | 61.5 | 11.8 | 75.0 |
| Mean (s) | 62.8 | 17.0 | 79.8 |

B

TREATMENT AND PREVENTION OF MALARIA

CROSS-REFERENCE TO RELATED APPLICATIONS

This application is the National Stage of International Application No. PCT/GB2019/052885, filed Oct. 10, 2019, which claims priority to GB 1816542.3, filed Oct. 10, 2018 and GB 1907609.0, filed May 29, 2019, which are entirely incorporated herein by reference.

FIELD OF THE INVENTION

The present invention relates to antigens, antibodies and vaccines for treatment or prevention of malaria.

BACKGROUND OF THE INVENTION

Malaria places the gravest public-health burden of all parasitic diseases, leading to ~215 million human clinical cases and ~440,000 deaths annually, with the majority of deaths in children. The infection of red blood cells (RBCs) by the blood-stage form of the *Plasmodium* parasite is responsible for the clinical manifestations of malaria. Examples of *Plasmodium* parasite include the species *P. falciparum, P. vivax, P. ovale* and *P. malariae*. The most virulent parasite species, *P. falciparum*, is endemic in large parts of sub-Saharan Africa and Latin America. It causes the majority of malaria deaths. It can infect RBCs of all ages and is not limited to immature RBCs. *P. falciparum*, is therefore of particular interest and is a major target for vaccine development, as it would be highly desirable to develop a vaccine.

The most advanced malarial vaccine aiming for licensure is RTS,S/AS01 (Mosquirix™), which is based on the RTS,S protein. The RTS,S protein acts by blocking infection of *P. falciparum* in the liver. However, this vaccine has achieved only partial efficacy (~30-50% in phase II/III clinical trials). There is therefore an urgent need for a vaccine which can protect against the disease-causing blood-stage *Plasmodium* parasite, potentially by emulating natural immunity or by other immune mechanisms.

Previous studies have investigated the potential for antigens to induce antibodies which are effective against blood-stage malaria parasites in vitro, using the standard growth inhibitory activity (GIA) assay. One such antigen is apical membrane antigen 1 (PfAMA1).

GIA assay investigations into other protein families involved in blood-stage *Plasmodium* parasite invasion of RBCs have found them to be ineffective or less effective than PfAMA1.

PfAMA1 has therefore been a major focus of research on countering blood-stage malarial parasites, with ongoing clinical trials. However, antibodies against PfAMA1 appear only to be effective at an extremely high concentration. In addition, PfAMA1 induces strain-specific antibodies which are not effective against genetically diverse strains of the *Plasmodium* parasite (A. L. Goodman, S. J. Draper, *Ann. Trop. Med. Parasitol.* 104, 189 (2010)). In addition, vaccine development has been hampered by the requirement for potentially reactogenic chemical adjuvants in addition to the antigen to induce sufficient antibody responses in human subjects.

Research has also been ongoing to identify other candidate malarial antigens for vaccines. In particular, the present inventors have previously identified Reticulocyte-binding protein Homologue 5 (PfRH5) as a potential antigen candidate for malarial vaccines (WO 2012/114125).

The Reticulocyte binding Homologue (PfRH) family comprises six members (PfRH1, PfRH2a, PfRH2b, PfRH3, PfRH4 and PfRH5), each of which is involved in the binding of the *Plasmodium* parasite to RBCs, with the possible exception of PfRH3 which may be a non-expressed pseudogene. The PfRH family has been identified as adhesins on the surface of the merozoite form of the *Plasmodium* parasite, which bind to receptors on the surface of the erythrocyte and hence permit invasion of RBCs by the parasite in its blood-stage. The PfRH5 antigen has an approximate molecular weight of 63 KDa. In vitro cleaved fragments of approximately 45 KDa and 28 KDa have been reported.

The present inventors have previously demonstrated that PfRH5 induces antibodies which are highly effective in the GIA assay against the blood-stage *Plasmodium falciparum* parasite and which neutralise parasites more effectively than PfAMA1 and remain effective at lower concentrations of immunoglobulin. In addition, PfRH5 induces antibodies which are effective against genetically diverse strains of the *Plasmodium* parasite. Therefore, PfRH5 is a promising candidate antigen for a malarial vaccine.

Earlier work by the present inventors has improved upon the full-length PfRH5 as a vaccine candidate by the development of rationally designed PfRH5 fragments, which contain regions or amino acid residues from within PfRH5 that give rise to protective antibodies, whilst excluding other regions of the full-length PfRH5 sequence which may be associated with unwanted side effects. In addition, rationally designed PfRH5 antigens have been developed with improved expression profiles and thermal stability without compromising immunological efficacy.

However, there is an ongoing need for the development of antibodies against PfRH5 with improved activity, and to develop rationally designed antigens capable of stimulating the production of such antibodies. In particular, there is a need for improved antibodies that are effective at low concentrations, and that can be used in concert to bolster the immune defence without unwanted interference or competition between said antibodies, and for improved antigens that will induce such antibodies. At the same time, it is necessary for said antibodies to be effective against genetically diverse strains of the *Plasmodium* parasite, with a view to future elimination campaigns, where they would be used alongside conventional antimalarial drugs.

The present invention addresses one or more of the above needs by providing combinations of non-neutralising antibodies for PfRH5 and neutralising antibodies for PfRH5 and other merozoite antigens, which together provide a synergistic effect. The invention also provides antigens which induce such antibodies, vectors encoding the antibodies and antigens, and antibody-like molecules including aptamers and peptides raised against the same antigen, together with the use thereof (either alone or in combination) in the prevention or treatment of malaria.

SUMMARY OF THE INVENTION

The present inventors have for the first time now shown that a class of antibodies which bind to PfRH5 and which in and of themselves have no neutralising activity in vitro but which significantly reduce the speed of red blood cell invasion by the merozoite form of the malarial parasite. Therefore, these non-neutralising antibodies can, when combined, potentiate all neutralising antibodies directed to PfRH5, as well as synergising with antibodies against other malaria invasion proteins. In particular, the present inventors have shown that non-neutralising antibodies which bind to a region near the N-terminus of the α-helical core are capable of potentiating the growth inhibitory activity of neutralising anti-PfRH5 antibodies and neutralising antibodies which bind to PfAMA1, PfCyRPA and PfRipr.

Accordingly, the present invention provides a non-neutralising antibody, or binding fragment thereof, that specifically binds an epitope corresponding to residues Ser153 to Ile163 and Aps305 to Lys319 of PfRH5 (SEQ ID NO:1). Said non-neutralising antibody, or binding fragment thereof, of claim 1, may comprise: (a) a heavy chain with a CDR1 sequence of SEQ ID NO: 11; a CDR2 sequence of SEQ ID NO: 12 and a CDR3 sequence of SEQ ID NO: 13, and a light chain with a CDR1 sequence of SEQ ID NO: 20; a CDR2 sequence of SEQ ID NO: 21 and a CDR3 sequence of SEQ ID NO: 22; (b) a heavy chain with a CDR1 sequence of SEQ ID NO: 14; a CDR2 sequence of SEQ ID NO: 14 and a CDR3 sequence of SEQ ID NO: 16, and a light chain with a CDR1 sequence of SEQ ID NO: 23; a CDR2 sequence of SEQ ID NO: 24 and a CDR3 sequence of SEQ ID NO: 25; or (c) a heavy chain with a CDR1 sequence of SEQ ID NO: 17; a CDR2 sequence of SEQ ID NO: 18 and a CDR3 sequence of SEQ ID NO: 19, and a light chain with a CDR1 sequence of SEQ ID NO: 26; a CDR2 sequence of SEQ ID NO: 21 and a CDR3 sequence of SEQ ID NO: 27. Preferably, said non-neutralising antibody, or binding fragment thereof comprises: (a) a heavy chain variable region sequence of SEQ ID NO: 47 and a light chain variable region sequence of SEQ ID NO: 48; (b) a heavy chain variable region sequence of SEQ ID NO: 49 and a light chain variable region sequence of SEQ ID NO: 50; or (c) a heavy chain variable region sequence of SEQ ID NO: 51 and a light chain variable region sequence of SEQ ID NO: 52. Said non-neutralising antibody, or binding fragment thereof may be: (a) a monoclonal or polyclonal antibody; or (b) an Fab, F(ab')2, Fv, scFv, Fd or dAb.

The invention further provides a composition comprising: (a) one or more non-neutralising antibody, or binding fragment thereof as defined herein; and (b) one or more neutralising antibody, or binding fragment thereof, that specifically binds a *Plasmodium* merozoite antigen. The *Plasmodium* merozoite antigen may be selected from: (a) PfRH5; (b) a non-PfRH5 antigen within the PfRH5 invasion complex; and/or (c) a target closely linked to the PfRH5-basigin interaction. Typically said *Plasmodium* merozoite antigen is selected from PfRH5, PfRipr, PfCyRPA, PfP113, PfRhopH3, PfRAP2, PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP. The *Plasmodium* merozoite antigen may be PfRH5 and the one or more neutralising antibody, or binding fragment thereof, specifically binds an epitope within SEQ ID NO: 3 (RH5ΔN) or SEQ ID NO: 7 (RH5ΔNL); and preferably the one or more neutralising antibody, or binding fragment thereof, specifically binds an epitope corresponding to: (a) residues Lys196 to Ser197; Asn347 to Asn352; Arg357 to His365; and Lys443 to Arg448 of PfRH5 (SEQ ID NO: 1); (b) residues Gly201 to Lys219; and Lys327 to Tyr335 of PfRH5 (SEQ ID NO: 1); (c) residues Gly201 to Lys219 and Lys327 to Gln342 of PfRH5 (SEQ ID NO: 1); or (d) residues Lys196, Ser197, Tyr346 to Asn354 and Lys443 to Lys452PfRH5 (SEQ ID NO: 1); preferably the epitope of (a) or (b). In some preferred embodiments, the one or more neutralising antibody, or binding fragment thereof; comprises: (a) a heavy chain with a CDR1 sequence of SEQ ID NO: 54; a CDR2 sequence of SEQ ID NO: 55 and a CDR3 sequence of SEQ ID NO: 56, and a light chain with a CDR1 sequence of SEQ ID NO: 60; a CDR2 sequence of SEQ ID NO: 61 and a CDR3 sequence of SEQ ID NO: 62; or (b) a heavy chain with a CDR1 sequence of SEQ ID NO: 57; a CDR2 sequence of SEQ ID NO: 58 and a CDR3 sequence of SEQ ID NO: 59, and a light chain with a CDR1 sequence of SEQ ID NO: 63; a CDR2 sequence of SEQ ID NO: 64 and a CDR3 sequence of SEQ ID NO: 65; wherein optionally the one or more neutralising antibody, or binding fragment thereof; comprises: (i) a heavy chain variable region sequence of SEQ ID NO: 81 and a light chain variable region sequence of SEQ ID NO: 82; or (ii) a heavy chain variable region sequence of SEQ ID NO: 83 and a light chain variable region sequence of SEQ ID NO: 84. In the compositions of the invention each of the one or more non-neutralising antibodies and the one or more neutralising antibodies, or binding fragment thereof, is independently selected from: (a) a monoclonal or polyclonal antibody; or (b) an Fab, F(ab')2, Fv, scFv, Fd or dAb.

The invention also provides a neutralising antibody, or binding fragment thereof, which comprises: (a) a heavy chain with a CDR1 sequence of SEQ ID NO: 54; a CDR2 sequence of SEQ ID NO: 55 and a CDR3 sequence of SEQ ID NO: 56, and a light chain with a CDR1 sequence of SEQ ID NO: 60; a CDR2 sequence of SEQ ID NO: 61 and a CDR3 sequence of SEQ ID NO: 62; or (b) a heavy chain with a CDR1 sequence of SEQ ID NO: 57; a CDR2 sequence of SEQ ID NO: 58 and a CDR3 sequence of SEQ ID NO: 59, and a light chain with a CDR1 sequence of SEQ ID NO: 63; a CDR2 sequence of SEQ ID NO: 64 and a CDR3 sequence of SEQ ID NO: 65; wherein optionally the one or more neutralising antibody, or binding fragment thereof; comprises: (i) a heavy chain variable region sequence of SEQ ID NO: 81 and a light chain variable region sequence of SEQ ID NO: 82.

The invention further provides a bispecific dual variable domain molecule comprising a non-neutralising antibody of the invention, or binding fragment thereof and a neutralising antibody of the invention, or binding fragment.

The invention also provides a composition comprising: (a) an oligonucleotide aptamer that specifically binds an epitope corresponding to residues Ser153 to Ile163 and Aps305 to Lys319 of PfRH5 (SEQ ID NO: 1); and (b) an oligonucleotide aptamer that specifically binds to a *Plasmodium* merozoite antigen of the invention.

The invention also provides a viral vector, RNA vaccine or DNA plasmid that expresses one or more non-neutralising antibody of the invention, or binding fragment thereof; or one or more neutralising antibody of the invention.

The invention also provides a viral vector, RNA vaccine or DNA plasmid that expresses: (a) one or more non-neutralising antibody of the invention, or binding fragment thereof; and (b) one or more neutralising antibody of the invention, or binding fragment thereof; wherein the one or more non-neutralising and neutralising antibodies or binding-fragments thereof are expressed by: (i) the same viral vector, RNA vaccine or DNA plasmid; or (ii) by two separate viral vectors, RNA vaccines or DNA plasmids; or (iii) a viral vector, RNA vaccine or DNA plasmid that expresses a bispecific dual variable domain molecule of the invention.

The invention also provides a vector that: (a) expresses or displays an epitope corresponding to residues Ser153 to Ile163 and Aps305 to Lys319 of PfRH5 (SEQ ID NO: 1); or a *Plasmodium* merozoite antigen as defined herein; or (b) induces a non-neutralising antibody or binding fragment thereof of the invention, or a neutralising antibody of the invention; wherein optionally said vaccine is selected from a viral vector, RNA vaccine, DNA plasmid, virus-like particle or a protein-based vaccine.

The invention further provides a vaccine that: (a) expresses or displays (i) an epitope corresponding to residues Ser153 to Ile163 and Aps305 to Lys319 of PfRH5 (SEQ ID NO: 1) and (ii) a *Plasmodium* merozoite antigen of the invention; or (b) induces (i) a non-neutralising antibody of the invention or binding fragment thereof, and (ii) a neutralising antibody, or binding fragment thereof, that specifically binds a *Plasmodium* merozoite antigen as defined herein, preferably a neutralising antibody of the invention; and optionally (c) (i) expresses or displays one or more additional antigen selected from PfRipr, PfCyRPA, PfP113, PfRhopH3, PfRAP2, PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP, or a fragment thereof, or (ii) induces an antibody that specifically binds to said one or more additional antigen; wherein optionally: (i) said vaccine is selected from a viral vector, RNA vaccine, DNA plasmid, virus-like particle or a protein-based vaccine; and/or (ii) wherein the epitope of (a)(i), the *Plasmodium* merozoite antigen of (a)(ii) and optionally the one or more additional antigen of (c)(i) are expressed or displayed by; or the non-neutralising antibody or binding fragment thereof of (b)(i), the neutralising antibody of (b)(ii) and optionally the one or more additional antigen of (c)(ii) are induced by: (i) the same vaccine, preferably the same viral vector, RNA vaccine, DNA plasmid, virus-like particle or a protein-based vaccine, even more preferably as a fusion protein; or (ii) by separate vaccines, preferably separate viral vectors, RNA vaccines, DNA plasmids, virus-like particles or proteins.

In some embodiments: (a) the one or more non-neutralising antibody, or binding fragment thereof, and the one or more neutralising antibody, or binding fragment thereof, or the bispecific dual variable domain molecule, or epitope each further comprise a signal peptide; wherein optionally the signal peptides direct secretion from human cells, and preferably said signal peptide is a mammalian signal peptide from tissue plasminogen activator; and/or (b) the viral vector, RNA vaccine, DNA plasmid or vaccine is capable of expression in a mammalian cell; and/or (c) the DNA plasmid is capable of expression in a heterologous protein expression system; and optionally the viral vector is a human or simian adenovirus, an adeno-associated virus (AAV), or a pox virus, preferably an AdHu5, ChAd63, ChAdOX1, ChAdOX2 or modified vaccinia Ankara (MVA) vector.

The invention also provides a vaccine composition comprising: (i) a composition of the invention; (ii) a non-neutralising antibody of the invention, or binding fragment thereof and optionally a neutralising antibody, or binding fragment thereof as described herein; (iii) a bispecific dual variable domain molecule of the invention; or (iv) a vaccine, RNA vaccine, DNA plasmid, virus-like particle or a protein-based vaccine of the invention.

The invention further provides a vaccine composition comprising: (i) a composition of the invention; (ii) a non-neutralising antibody of the invention, or binding fragment thereof and optionally a neutralising antibody as described herein, or binding fragment thereof; (iii) a bispecific dual variable domain molecule of the invention; or (iv) a vaccine, RNA vaccine, DNA plasmid, virus-like particle or a protein-based vaccine of the invention, for use in a method of treating and/or preventing malaria.

The invention also provides the use of a vaccine composition comprising: (i) a composition of the invention; (ii) a non-neutralising antibody of the invention, or binding fragment thereof and optionally a neutralising antibody as described herein, or binding fragment thereof; (iii) a bispecific dual variable domain molecule of the invention; or (iv) a vaccine, RNA vaccine, DNA plasmid, virus-like particle or a protein-based vaccine of the invention in the manufacture of a medicament for the prevention and/or treatment of malaria.

The invention also provides the vaccine composition for use as described herein, or the use of a vaccine composition as described herein, wherein: (a) the non-neutralising antibody is provided in the form of (i) an antibody as defined herein; (ii) a viral vector, RNA vaccine or DNA plasmid as described herein; or (iii) a vaccine of the invention; and/or (b) the neutralising antibody is provided by (i) an antibody as described herein; (ii) a viral vector, RNA vaccine or DNA plasmid which expresses said neutralising antibody, said viral vector, RNA vaccine or DNA plasmid optionally as defined herein; (iii) a malarial vaccine comprising a *Plasmodium* merozoite antigen as defined herein; or (iv) a malarial vaccine comprising a vector expressing said *Plasmodium* merozoite antigen, or which induces said neutralising antibody, wherein optionally said vaccine is a vaccine as described herein.

The invention also provides a composition of the invention; a non-neutralising antibody of the invention, or binding fragment and optionally a neutralising antibody, or binding fragment thereof as described herein; a bispecific dual variable domain molecule of the invention; or a vaccine, RNA vaccine, DNA plasmid, virus-like particle or a protein-based vaccine of the invention, or a vaccine composition of the invention for use in immunising a subject, which has a growth inhibitory activity (GIA) of at least 50% against the blood-stage *Plasmodium* parasite; wherein optionally: (a) the growth inhibitory activity (GIA) of at least 50% is against a plurality of genetic strains of the blood-stage *Plasmodium* parasite; and/or (b) the *Plasmodium* parasite is *Plasmodium falciparum*.

The invention also provides a host cell containing one or more recombinant expression vector which encodes for: (a)(i) one or more non-neutralising antibody, or binding fragment thereof, that specifically binds an epitope within residues corresponding to residues Ser153 to Ile163 and Aps305 to Lys319 of PfRH5 (SEQ ID NO: 1); and (ii) one or more neutralising antibody, or binding fragment thereof, that specifically binds a *Plasmodium* antigen as described herein; or (b)(i) an epitope corresponding to residues Ser153 to Ile163 and Aps305 to Lys319 of PfRH5 (SEQ ID NO: 1); and (ii) one or more *Plasmodium* merozoite antigen as described herein.

DESCRIPTION OF FIGURES

FIG. 2: Growth inhibitory properties of human PfRH5-specific mAbs. (A) In vitro GIA of each mAb tested at 3 mg/mL against 3D7 clone *P. falciparum*. Data points are coded to reflect potency ("GIA-high" (≥75%) as squares, "GIA-low" (75%>GIA>25%) as triangles and "GIA-negative" (≤25%) as circles). (B) In vitro GIA dilution series against the 3D7 reference clone. EC50 values were determined by interpolation after fitting the data to a four-parameter dose-response curve. (C) In vitro GIA dilution series of GIA-high mAbs against heterologous parasite laboratory lines and isolates. (D) Table of amino acids at the five most common polymorphic sites of PfRH5 for the seven parasite lines used in the GIA assays. Deviations from the 3D7 reference sequence are in bold. All GIA data points are the mean of duplicate wells.

Figure 3:
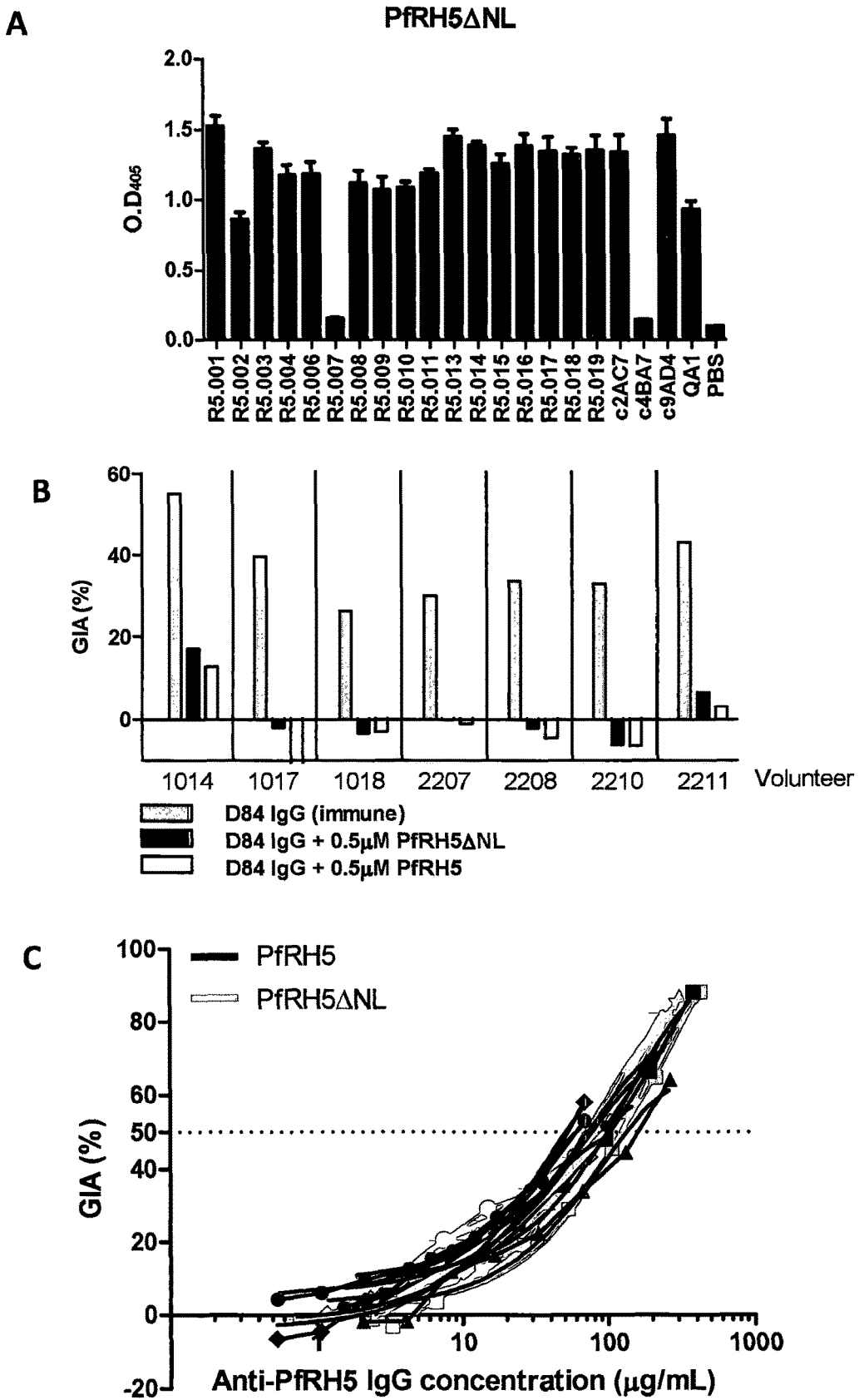
Figure 3:
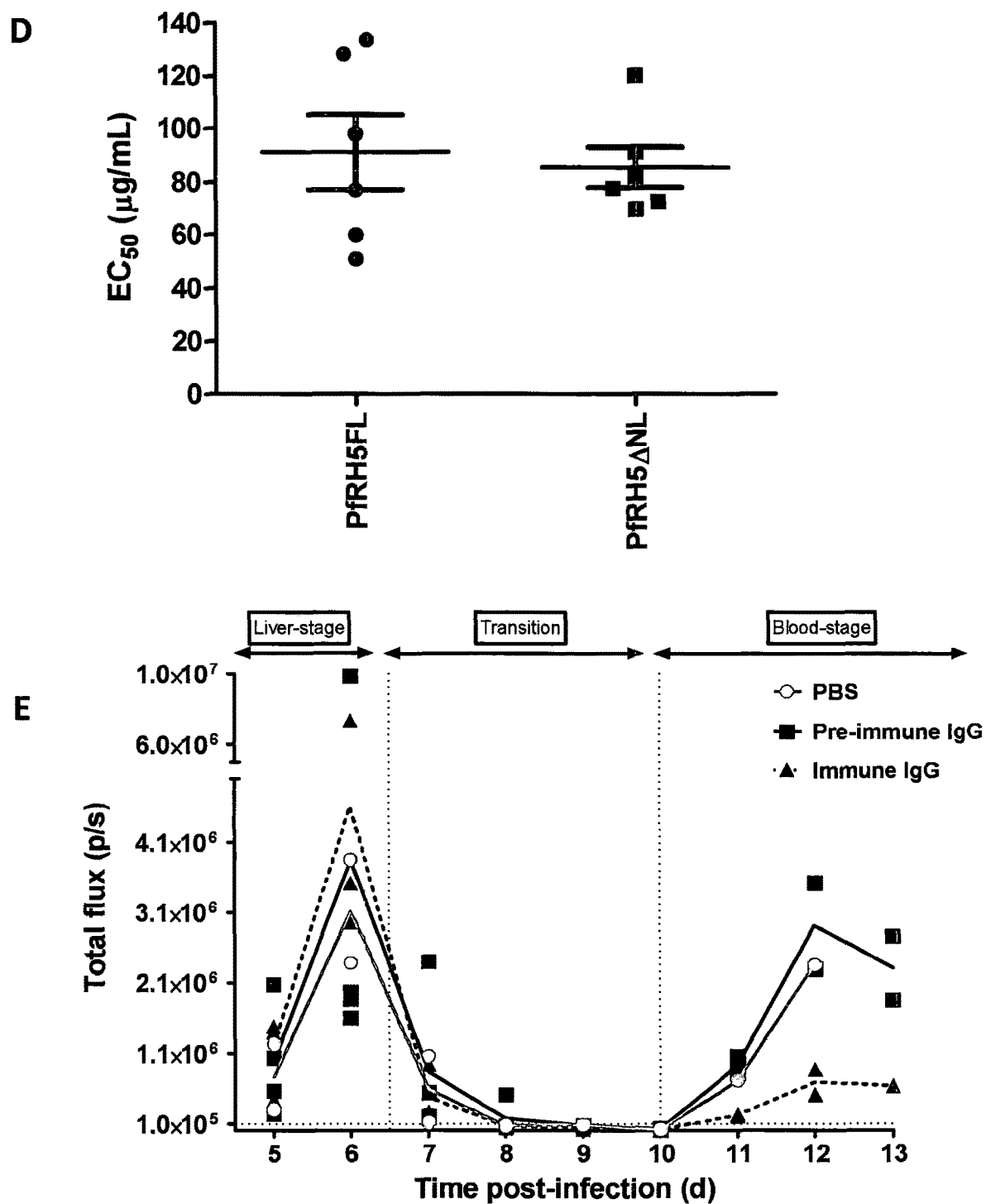
Figure 3:
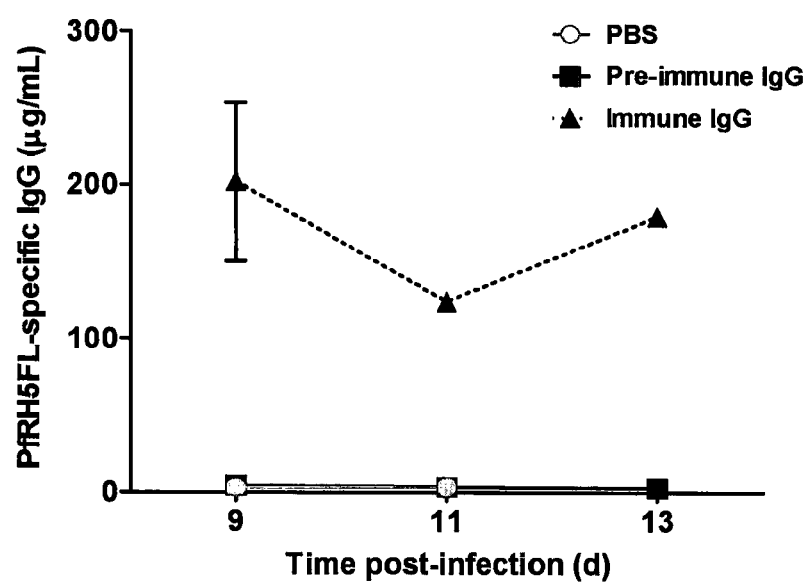

FIG. 3: Anti-PfRH5ΔNL IgG recapitulates the growth inhibitory properties of anti-PfRH5FL IgG. (A) Binding of anti-PfRH5 mAbs to PfRH5ΔNL by ELISA. Bars show the mean and standard deviation of 4 replicate wells. (B) GIA of purified total IgG from seven different PfRH5FL-vaccinated human volunteers alone or in the presence of 0.5 μM of PfRH5FL or PfRH5ΔNL protein (30 μg/mL and 20 μg/mL, respectively). Bars represent the mean of duplicate wells. (C) GIA of purified total IgG from rabbits immunized with PfRH5FL or PfRH5ΔNL (n=6 rabbits per group). The concentration of PfRH5FL-specific polyclonal IgG in each test sample is plotted on the x-axis and was measured by ELISA using a readout with a μg/mL conversion factor determined by calibration-free concentration analysis. (D) GIA $EC_{50}$ comparison between both groups. $EC_{50}$ values were determined by interpolation after fitting the data from panel C to a four-parameter dose-response curve. Black horizontal bars represent the mean and error bars are standard deviation. All GIAs were carried out using 3D7 clone *P. falciparum*. (E) Intravital luminescence signal of humanized mice infected with transgenic *P. falciparum* (NF54-luciferase) following passive transfer of 15 mg of pre-vaccination or PfRH5ΔNL-vaccinated rabbit IgG at d6 post-infection. Starting group sizes were n=2 for the PBS group and n=4 for the two IgG passive transfer groups. Mice which died before the experiment endpoint (d13) were: one at d7 and another at d13 in the PBS group, one at d9 and another at d12 in the pre-vaccination IgG group and one at d6, one at d10 and another at d12 in the vaccinated IgG group. Individual data points are plotted with a connecting line representative of the mean. (F) Concentration time-course of PfRH5-specific rabbit IgG in the passive transfer experiment shown in panel E, as determined by ELISA binding to PfRH5FL. Data points are the mean, error bars are the standard deviation.

Figure 4:
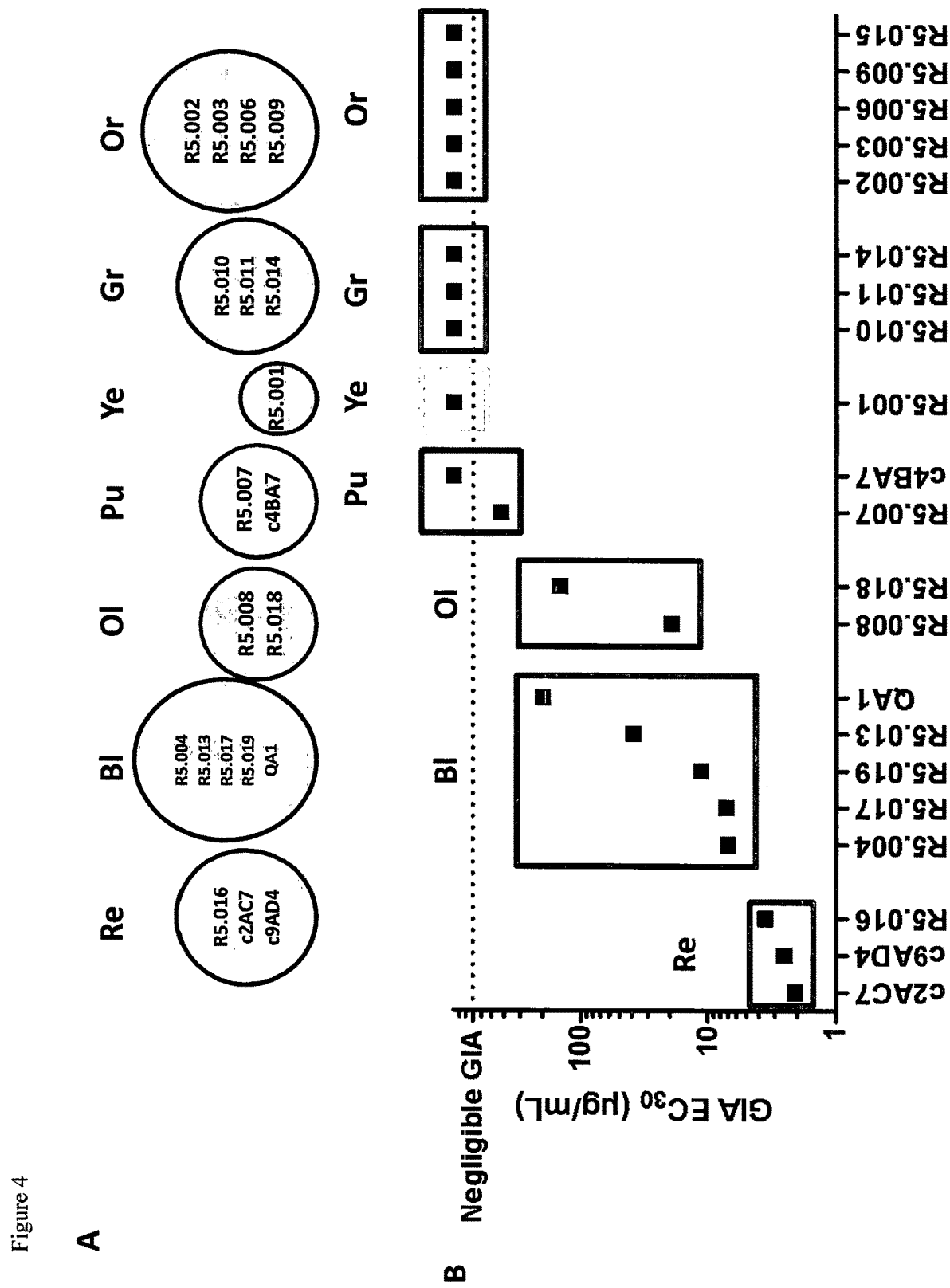
Figure 4:
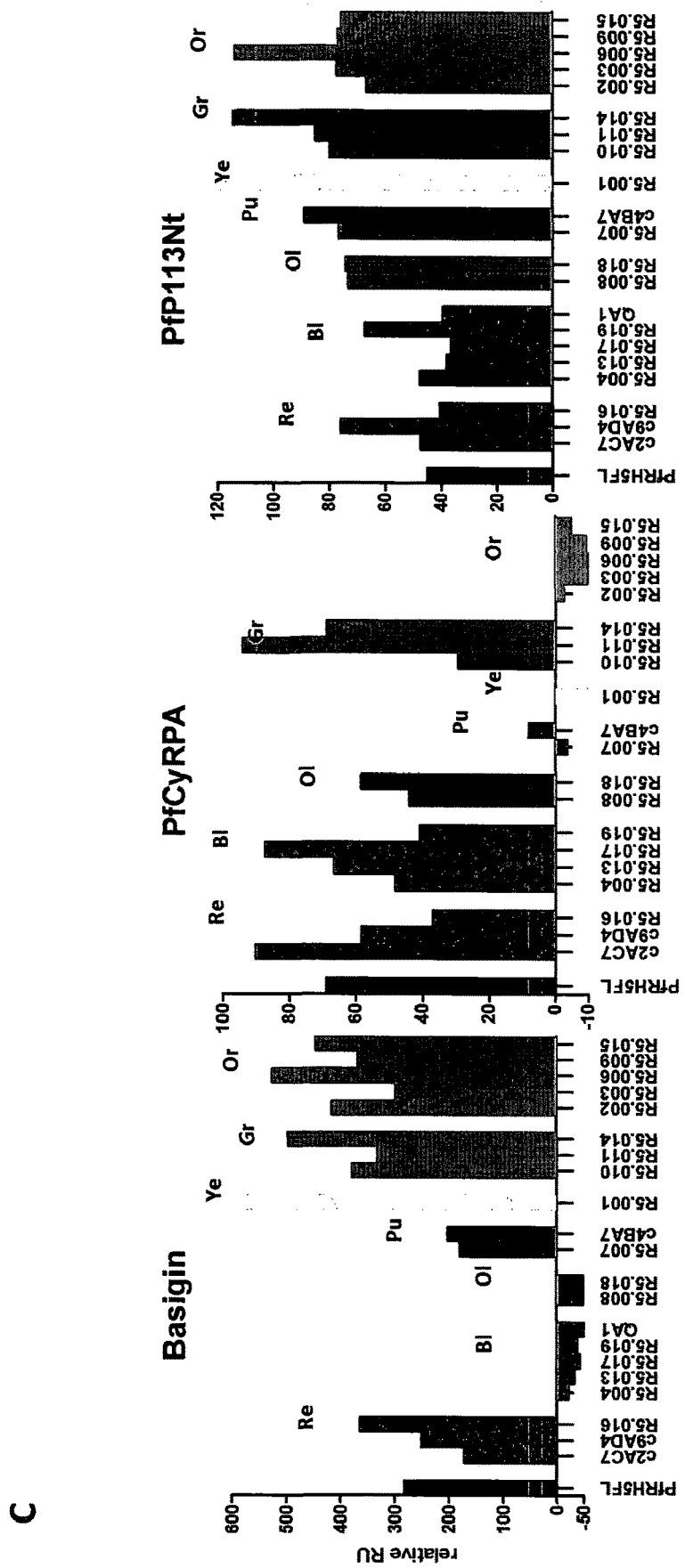
Figure 4:
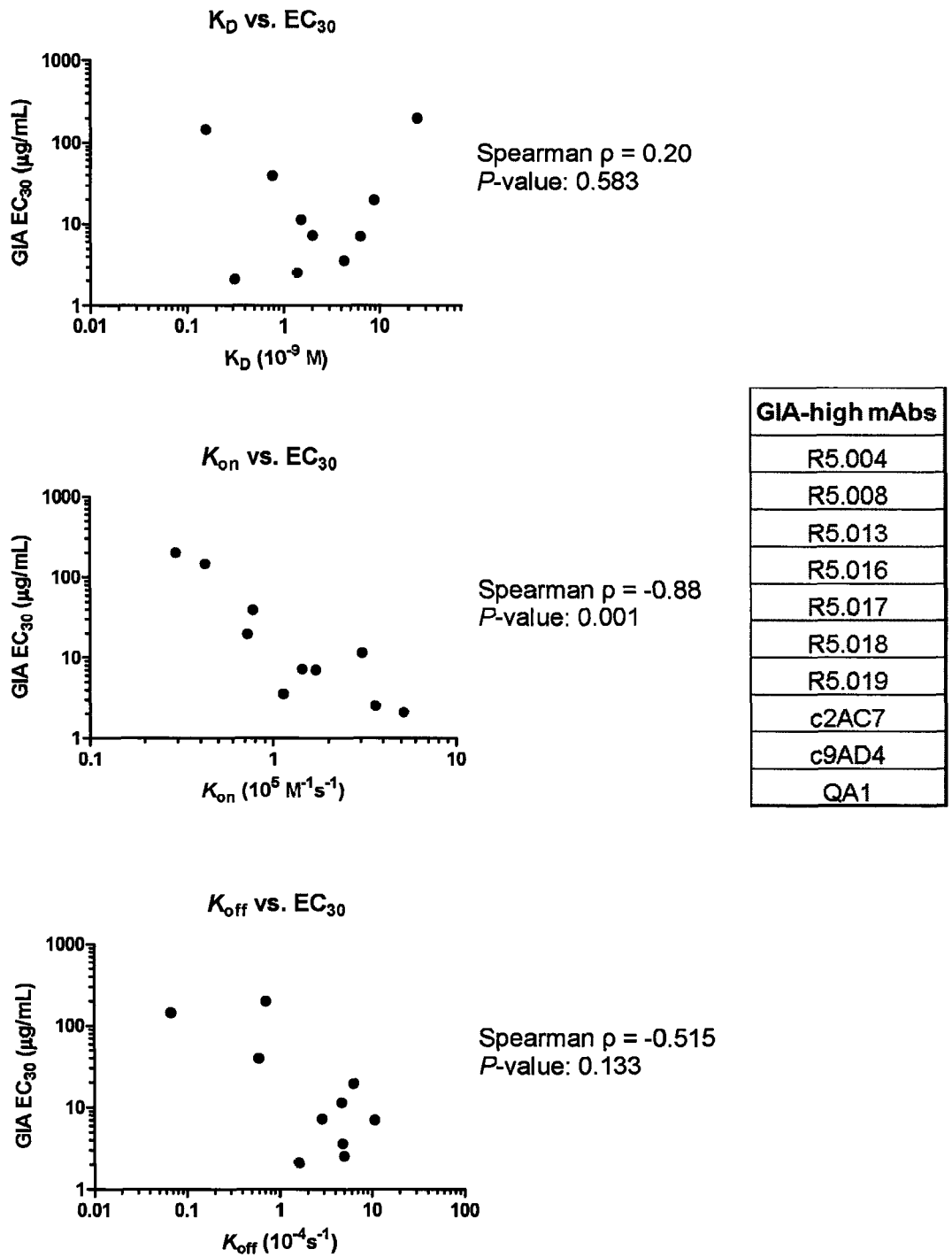

FIG. 4: Epitope-binning groups mAbs by functional phenotype and the correlation between nAb kinetic binding parameters and GIA. (A) Epitope bins determined by a matrix of sequential PfRH5FL-binding assays for different mAbs as measured by BLI. Re=red bin, Bl=blue bin; Ol=olive bin; Pu=purple bin; Ye=yellow bin; Gr=green bin; and Or=orange bin. (B) Potency of anti-PfRH5 mAb invasion inhibition grouped by epitope bin. $EC_{30}$ values were interpolated from data in FIG. 2B. (C) The effect of mAbs on the binding of PfRH5FL to its receptor basigin and to its binding partners PfCyRPA and PfP113 (PfP113Nt used here), as determined by SPR assays. Binding of PfRH5FL to PfCyRPA, PfP113Nt and basigin in the absence of mAb is shown by the black bars in each assay as a control (far left). The colours used in B and C correspond to those of the epitope bins in panel A. (D) The binding parameters of nAbs (Kon, Koff and KD) were correlated with growth inhibition using the GIA $EC_{30}$ as a measure of potency. Only GIA-high nAbs were included in this analysis because of their overt ability to bind merozoite-bound PfRH5, as evidenced by their growth inhibitory properties. $EC_{30}$ values were calculated from data shown in FIG. 2B. The reported P-value is two-tailed.

Figure 5:
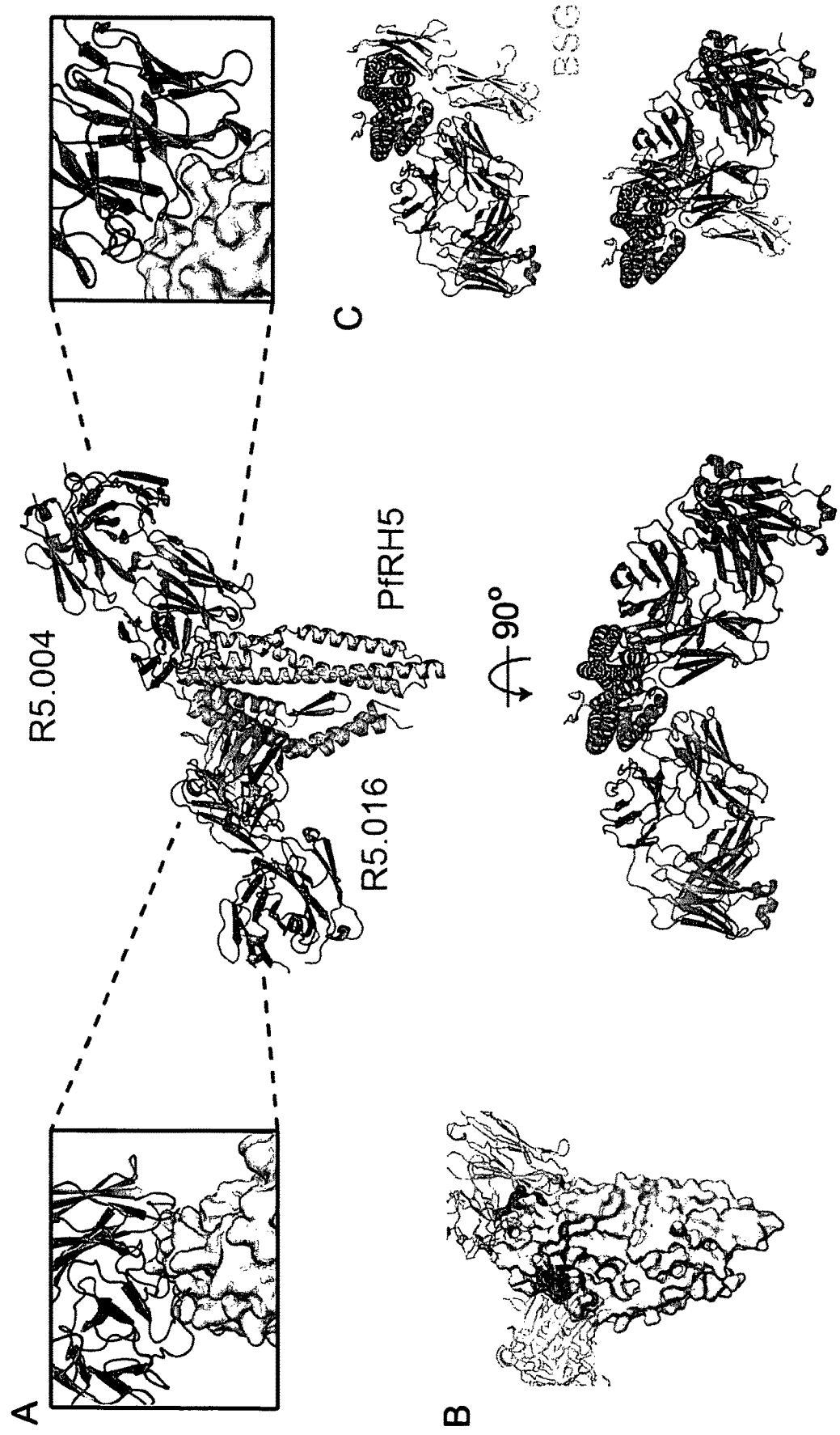

FIG. 5: Identification of the R5.004 and R5.016 mAb epitopes. (A) Crystal structure of the complex of PfRH5ΔNL bound to R5.004 and R5.016 Fab fragments. Insets show close-up views of the epitopes. (B) The top PfRH5 peptides identified as protected by HDX-MS upon binding to R5.004 mAb (blue) and R5.016 mAb (red), respectively, are highlighted on the structure of PfRH5ΔNL. The positions of the Fab fragments in the crystal structure are overlaid as faded cartoons. (C) Overlay of PfRH5ΔNL:BSG co-complex from PDB entry 4U0Q (BSG coloured in teal) with R5.004 Fab or R5.016 Fab structures at their respective binding sites in the PfRH5ΔNL:R5.004:R5.016 co-complex. Fab fragments are color-coded according to their respective epitope bin colour as defined in FIG. 4A.

Figure 6:
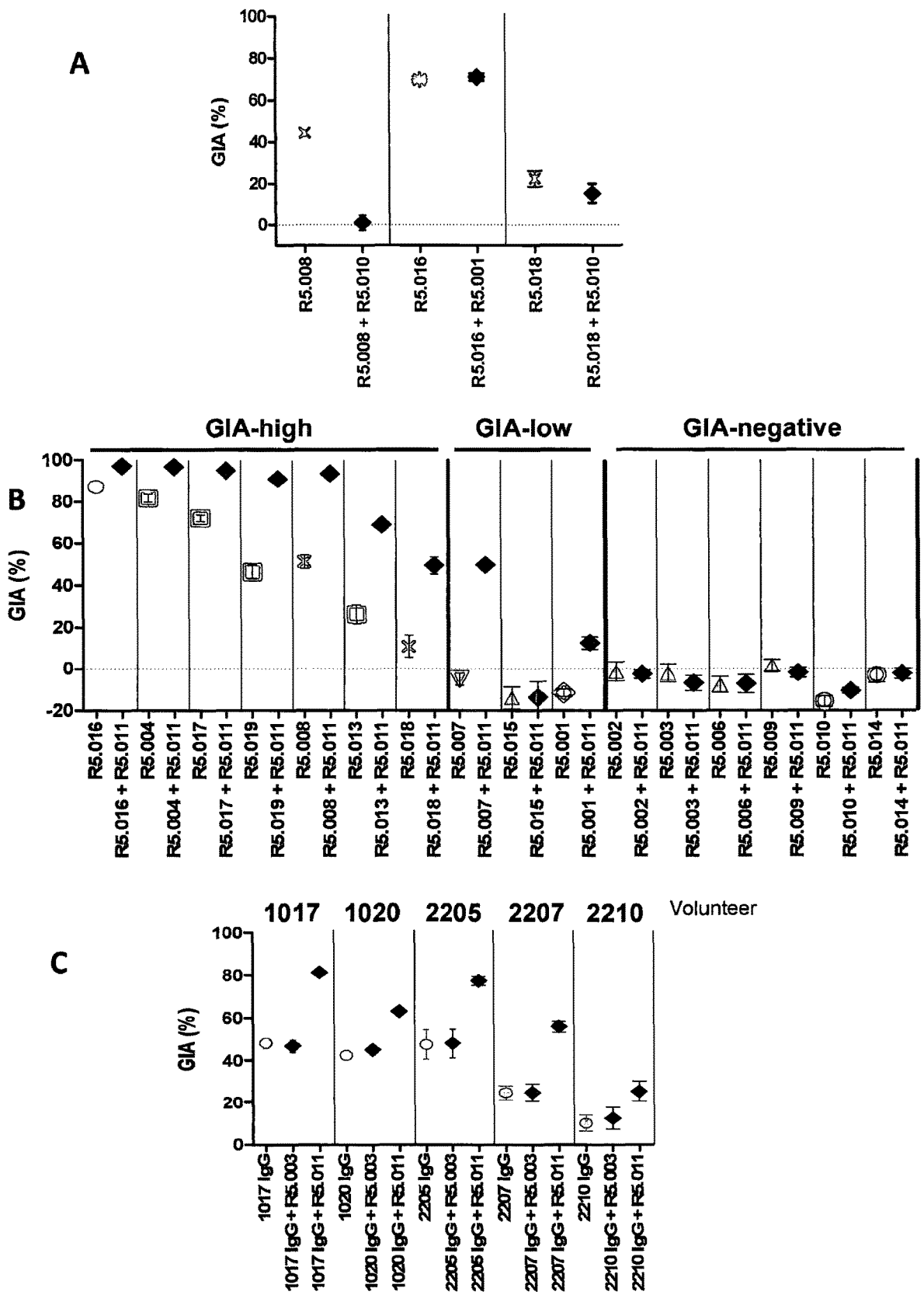
Figure 6:
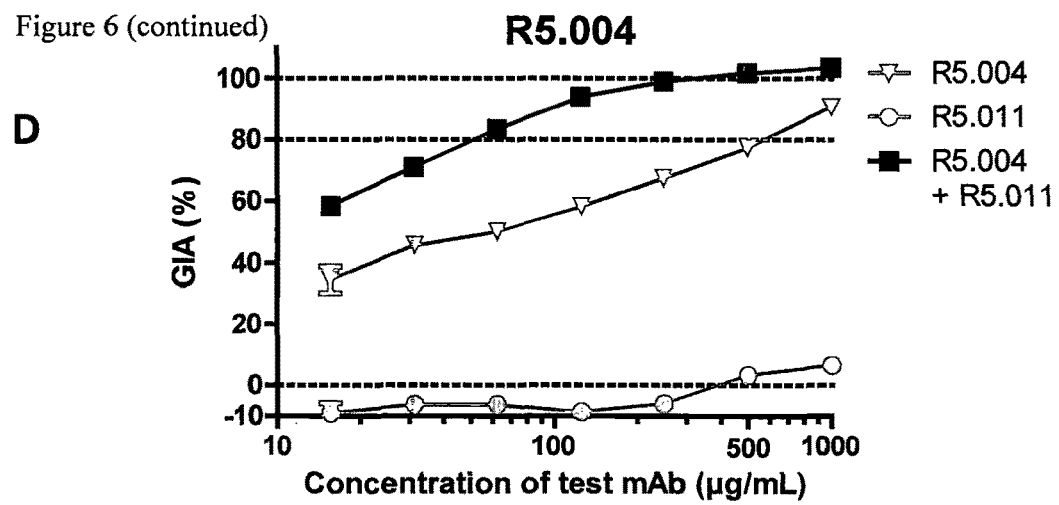
Figure 6:
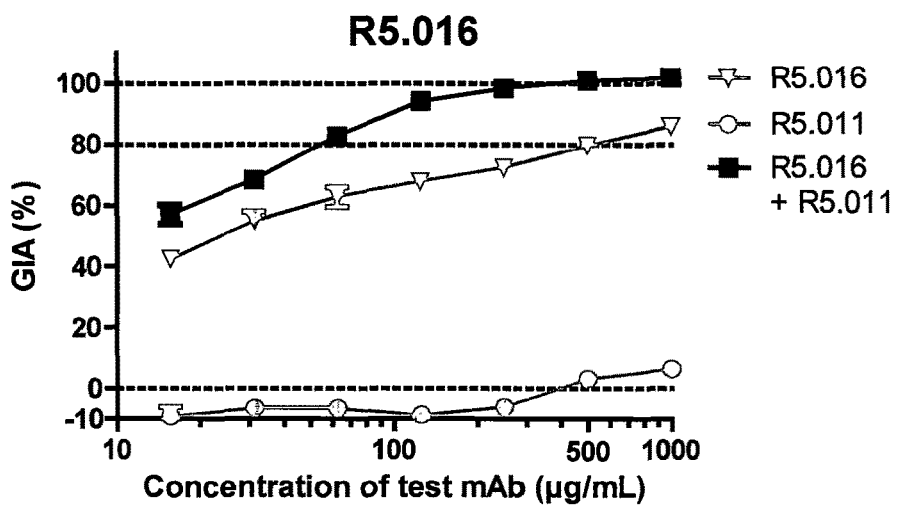
Figure 6:
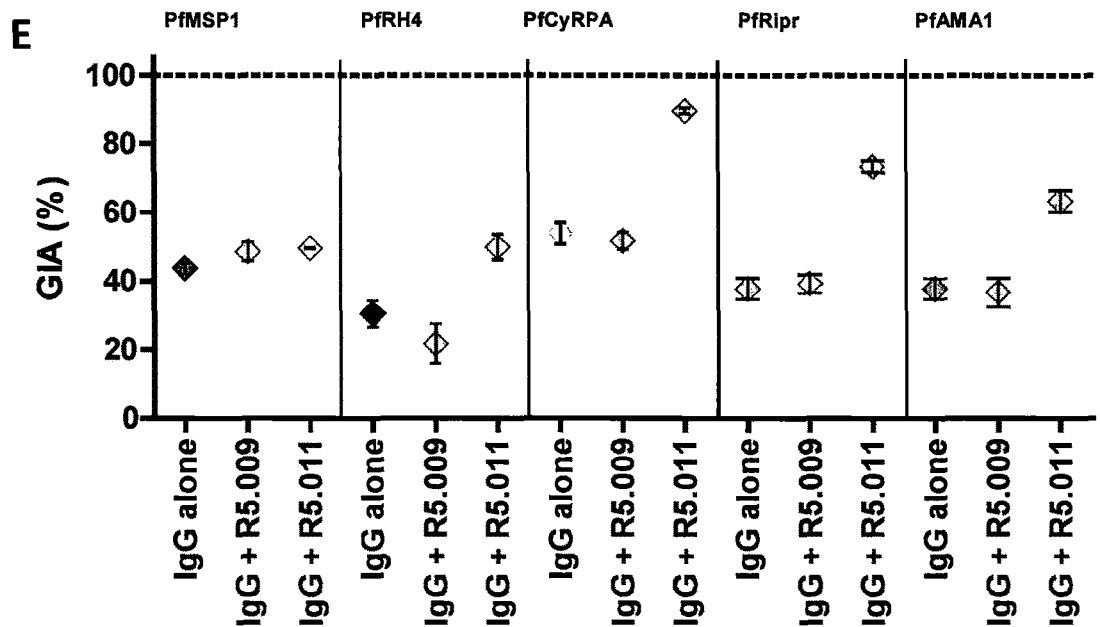
Figure 6:
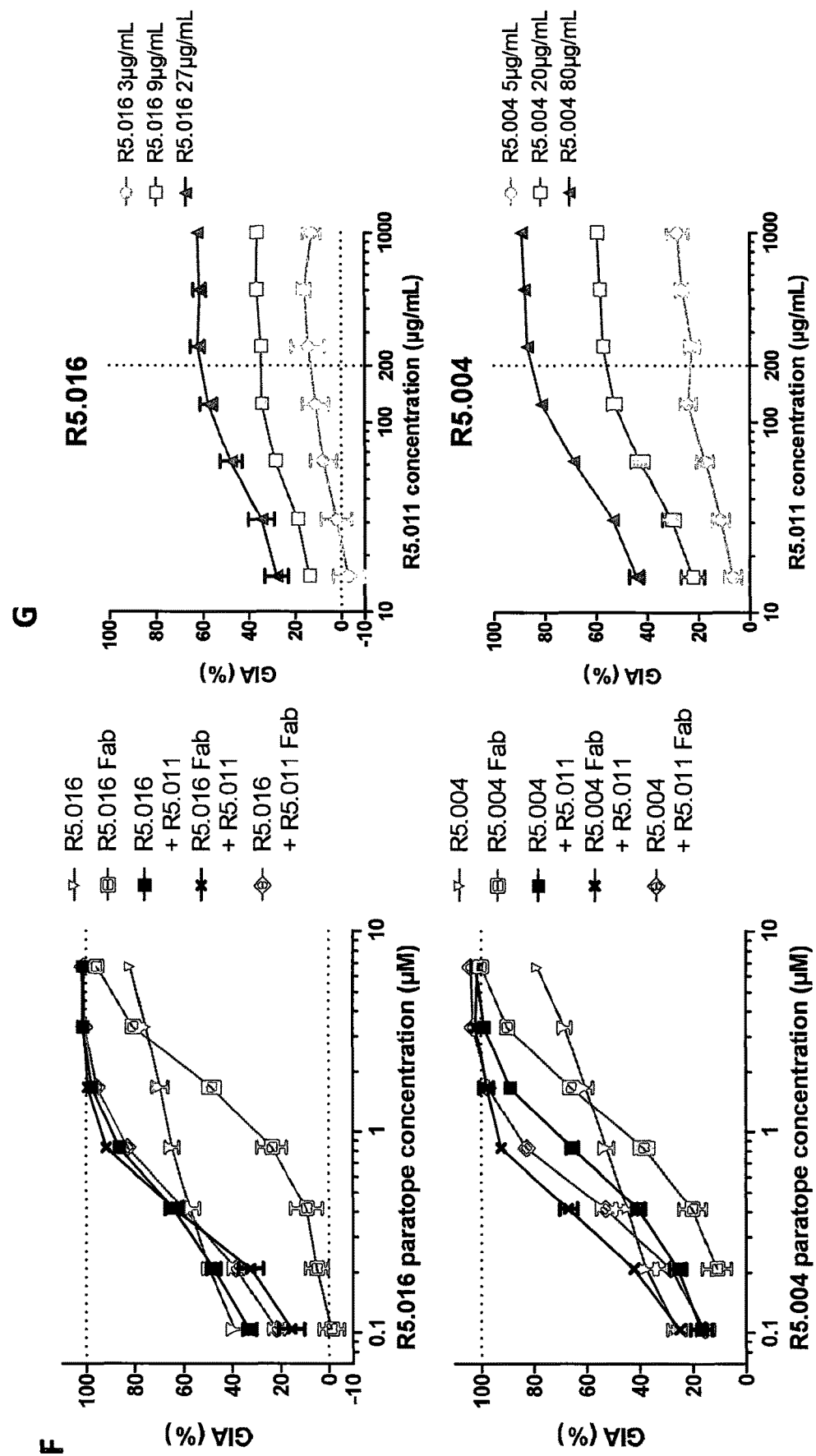
Figure 6:
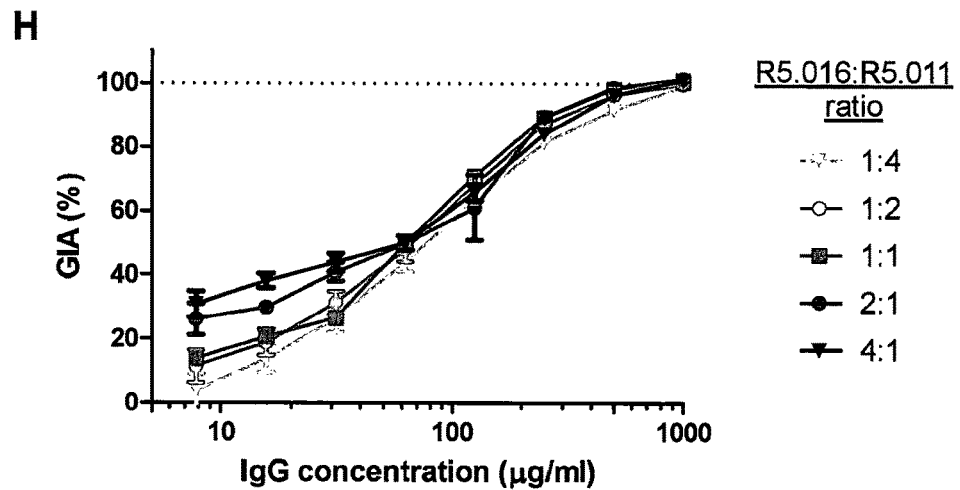
Figure 6:
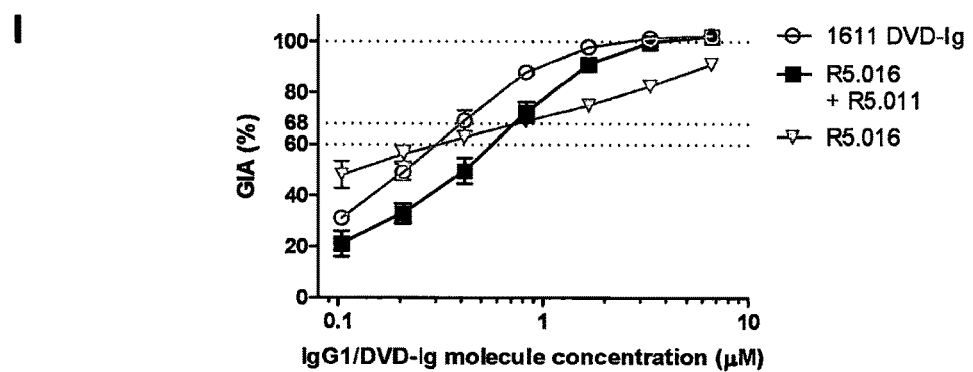
Figure 6:
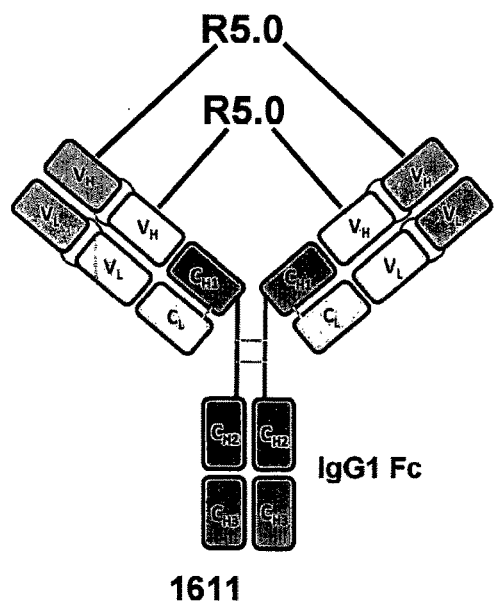

FIG. 6: Non-neutralizing mAb R5.011 potentiates the effect of anti-PfRH5 nAbs against 3D7 clone *P. falciparum*. (A) GIA of nAbs R5.008, R5.016 and R5.018 alone (grey data points) or in the presence of an equimolar concentration of a mAb which blocks binding to PfRH5FL in vitro (black data points). R5.008 was used at 300 μg/mL, R5.016 was used at 150 μg/mL and R5.018 was used at 400 μg/mL. (B) GIA of human anti-PfRH5 mAbs at 150 μg/mL alone (grey data points) or in the presence of 150 μg/mL R5.011 (black data points). (C) GIA of total human IgG from five PfRH5FL-vaccinated volunteers (1017, 1020, 2205, 2207 and 2210) at a concentration of 5 mg/mL alone (grey data points) or in the presence of 300 μg/mL of R5.011 or R5.003 (black data points). (D) GIA of a dilution series of mAbs R5.004, R5.016 and R5.011 alone (triangle, triangle and circle respectively) as well as a dilution series of the R5.004 and R5.016 nAbs in the presence of an excess of R5.011 (500 μg/mL) (square) to determine the maximal effect of R5.011. "Concentration of test mAb" refers to the concentration of nAb in mAb combinations. (E) GIA of total IgG from rabbits immunized with PfMSP1, PfRH4, PfCyRPA, PfRipr or PfAMA1 (left most data point for each immunisation antigen as indicated) with the addition of 300 μg/mL of R5.011 or R5.009 (middle and right data points for each antigen as indicated). The concentrations of vaccinated IgG used were 10 mg/mL for PfRH4 and PfRipr, 5 mg/mL for PfMSP1 and PfCyRPA and 3.25 mg/mL for PfAMA1 to achieve approximately 30-60% GIA in the absence of mAb. All data points are the mean of 3 replicate wells, error bars are standard deviation. Parasites used were 3D7 clone *P. falciparum*. (F) GIAs of nAbs R5.004 and R5.016 alone or with R5.011 as various mAb+Fab fragment combinations. Neither bivalency nor the Fc is necessary for the potentiating effect of R5.011. X-axis concentration values are plotted as the concentration of nAb binding site. mAb-mAb combinations are equimolar and mAb-Fab combinations are equimolar in terms of binding sites. (G) mAb R5.011 is titrated in increasing concentrations into three fixed concentrations of nAb R5.004 or R5.016 to determine the concentration at which R5.011 enhancement reaches a maximum. (H) GIA of titration curves of R5.016+R5.011 combinations in different molar ratios. (I) GIA of the most potent single human anti-PfRH5 mAb (R5.016), the most potent combination of two human anti-PfRH5 mAbs (R5.016+R5.011) and of a 1611 bispecific DVD-Ig™. The cartoon below is a schematic of the 1611 DVD-Ig™ comprising R5.011 and R5.016 variable regions. All data points are the mean of 3 replicate wells, error bars are standard deviation. Parasites used were 3D7 clone *P. falciparum*.

Figure 7:
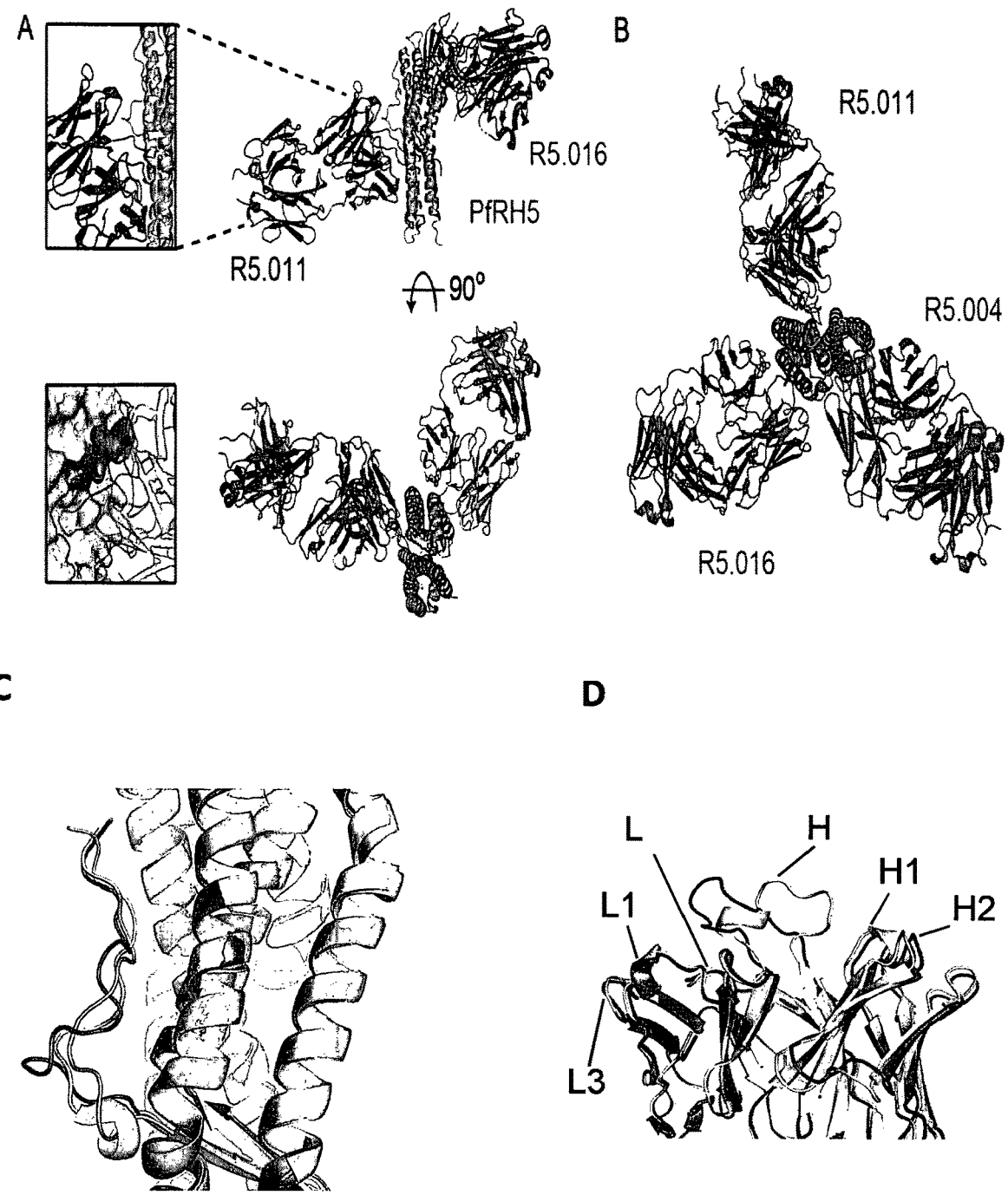

FIG. 7: Potentiating mAb binding site analysis: PfRH5ΔNL in complex with R5.011 and R5.016 Fab fragments. (A) Crystal structure of a complex of PfRH5ΔNL bound to Fab fragments from R5.011 and R5.016. The top left inset box shows a close-up of the R5.011 epitope. The PfRH5 peptide most protected upon R5.011 mAb binding as determined by HDX-MS (green) is highlighted on a close-up of the R5.011 binding site in the bottom left inset box. The position of the R5.011 Fab fragment in the crystal structure is overlaid as a faded cartoon. (B) Overlay of R5.004, R5.011 and R5.016 Fab fragment structures on PfRH5ΔNL. All Fabs are color-coded according to their respective epitope bin colour as defined in FIG. 4A. (C) Structural alignment of PfRH5 from the PfRH5ΔNL:R5.004:R5.016 co-complex (in beige), the PfRH5ΔNL:R5.011:R5.016 co-complex (in magenta) and the PfRH5 from PDB entry 4WAT (in light purple), to highlight differences in conformation of the N-terminus. (D) Structural alignment of R5.011 Fab fragment unbound (white) and bound to PfRH5ΔNL (green). Light chain and heavy chain CDR loops are annotated.

Figure 8:
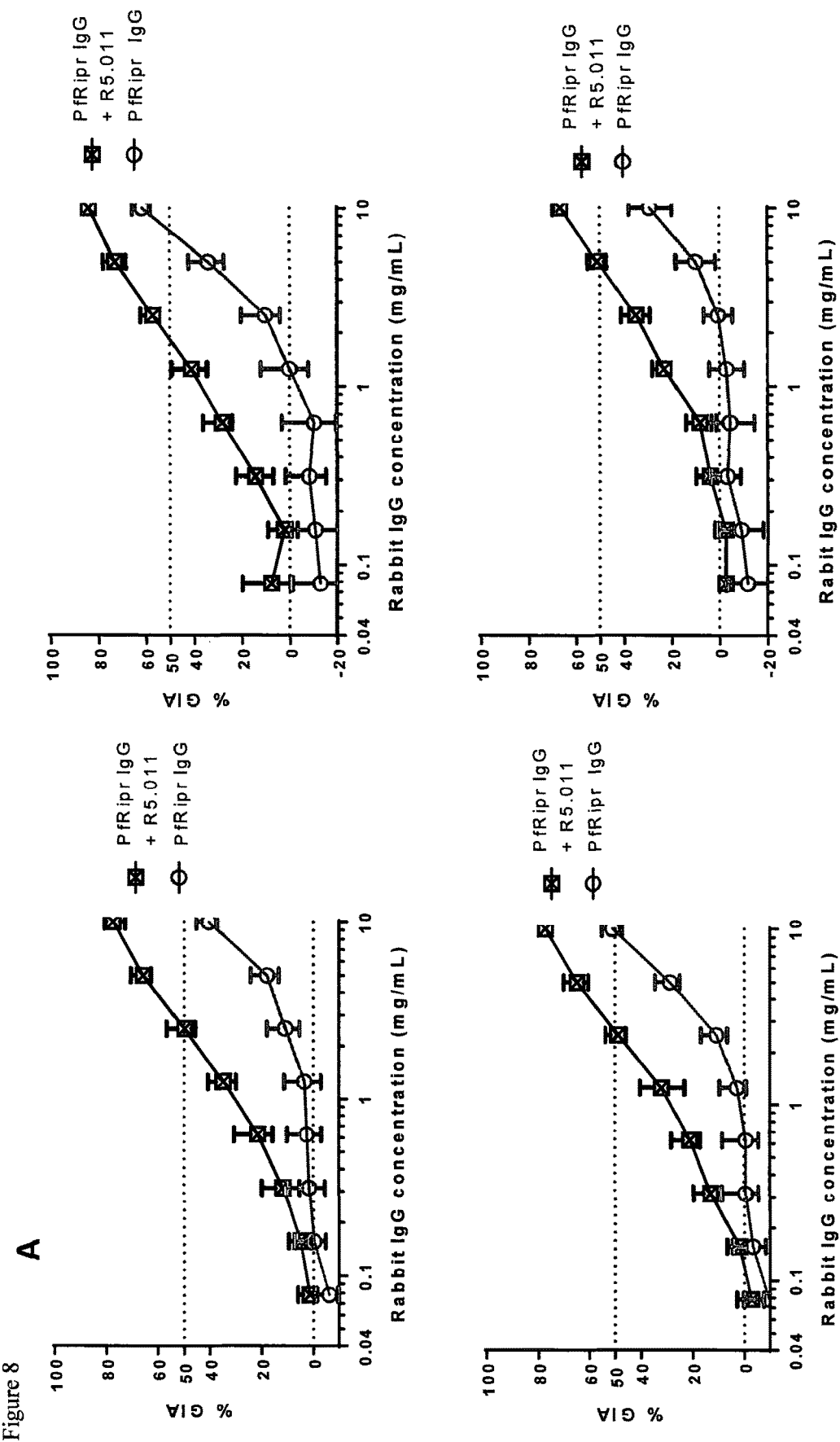
Figure 8:
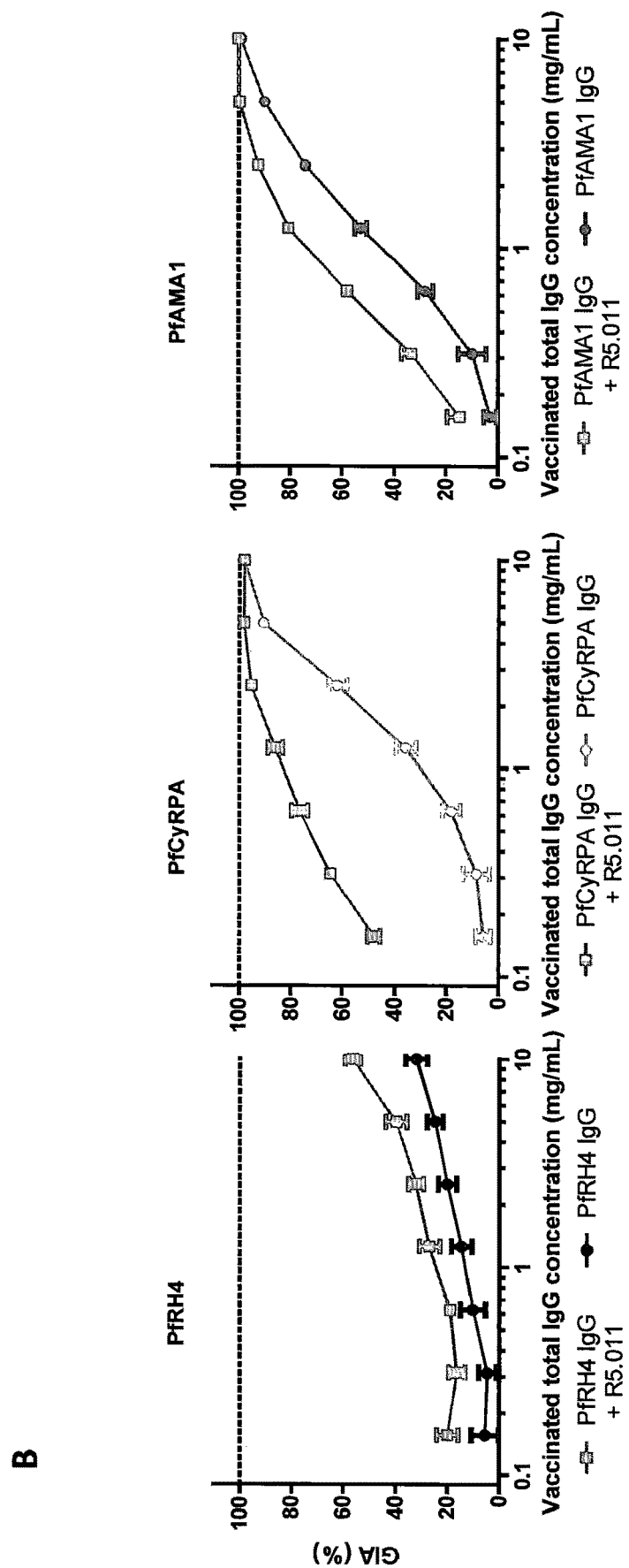

FIG. 8: Non-neutralizing mAb R5.011 potentiates the effect of anti-PfRipr nAbs against 3D7 clone *P. falciparum*. (A) GIA of total IgG from PfRipr-vaccinated rabbits alone (open circles, grey) or in the presence of 1 mg/mL of R5.011 mAb (crossed squares, black). The x-axis shows the concentration of animal-derived IgG only and does not include the R5.011 concentration. Each panel represents the GIA of one rabbit's IgG. All data points show the mean+standard deviation of three replicate wells. (B) GIA of total IgG from a PfRH4-vaccinated rabbit (left), a PfCyRPA-vaccinated rat (centre), and a PfAMA1-vaccinated rabbit (right) in the presence of an excess of R5.011 mAb (1.5 mg/mL, all square data points) showing the maximal extent of R5.011-mediated synergy. The x-axis shows the concentration of animal-derived IgG only and does not include the R5.011 concentration.

Figure 9:
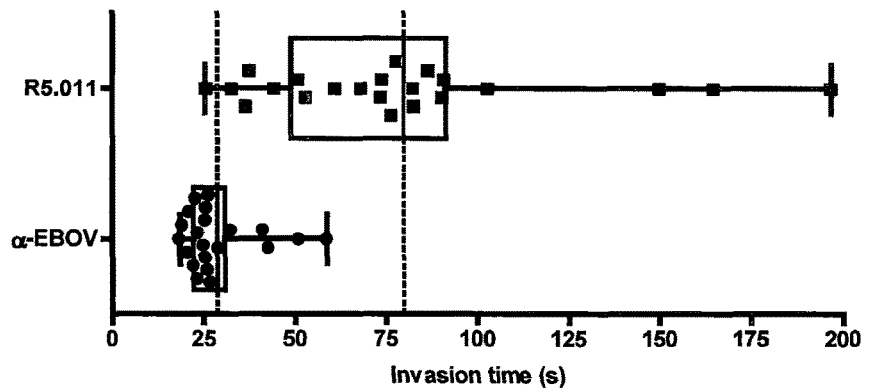
Figure 9:
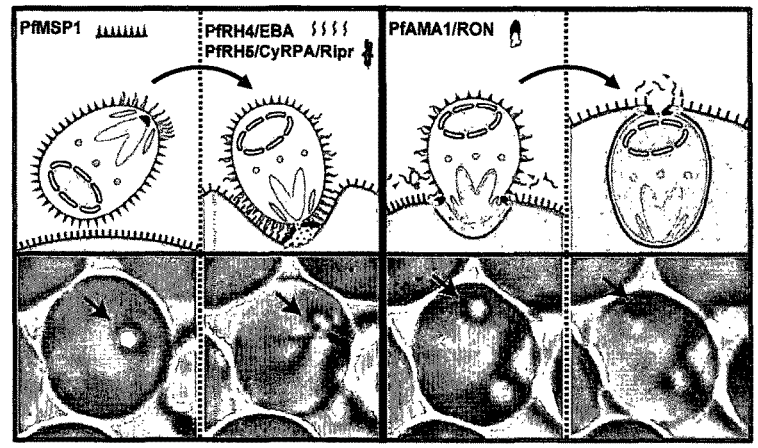
Figure 9:
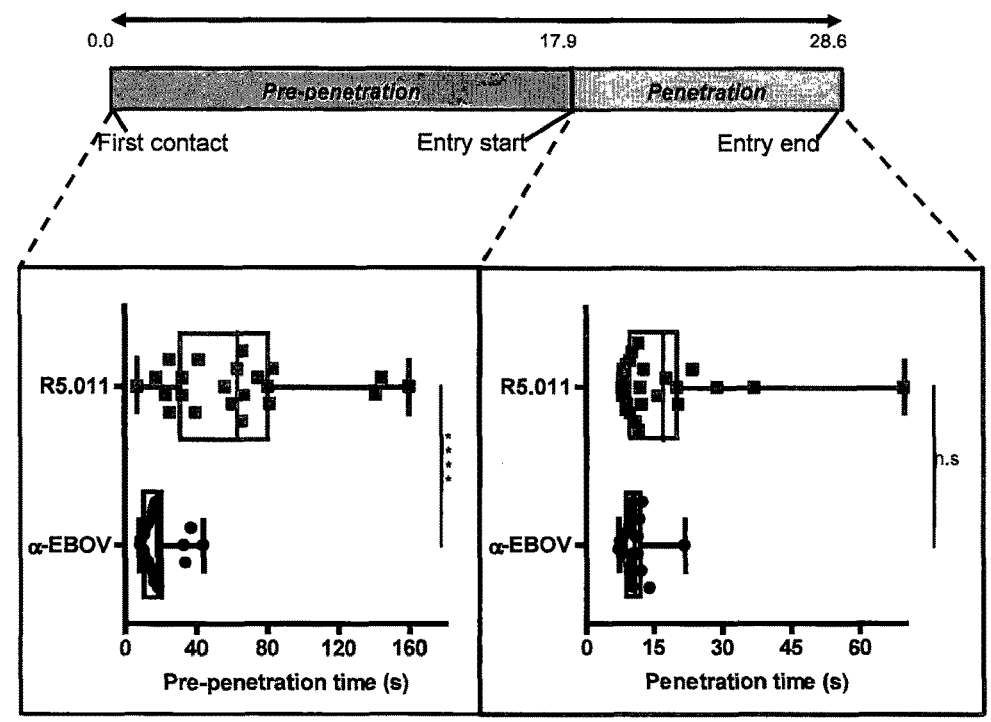

FIG. 9: Influence of R5.011 on parasite invasion time as determined by live-cell microscopy. (A) Total invasion time required for RBC invasion in the presence of R5.011 or an irrelevant isotype-matched antibody control (α-EBOV). (B) Invasion time required in early invasion (pre-penetration) and late invasion (penetration). Data are presented as box-and-whiskers plots showing the interquartile range and total range overlaid on individual data points. Solid black lines show the mean for each group. 3D7 clone *P. falciparum* parasites were used. Both mAbs were used at a concentration of 500 μg/mL and 21 and 22 invasion events were recorded for α-EBOV and R5.011, respectively. **** signifies P<0.0001 and n.s.=non-significant.

FIG. 10: Additional information from live-cell microscopy experiments. (A) Mean and median early (pre-penetration), late (penetration) and total invasion times of merozoites incubated with 500 μg/mL of R5.011 or α-EBOV. (B) Total invasion times of merozoites in the presence of neutralizing mAb R5.016, synergistic mAb combination R5.011+R5.016, non-neutralizing, non-potentiating mAb R5.009 or α-EBOV mAb at the concentrations indicated. Data are representative of n=9 invasions for R5.009, R5.016 10 μg/mL and R5.016+R5.011, n=12 for R5.016 500 μg/mL, n=21 for α-EBOV and are presented as box-and-whiskers plots showing the interquartile range and total range overlaid on individual data points. Solid black lines show the mean for each group. 3D7 clone *P. falciparum* parasites were used. n.s=non-significant.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

PfRH5 Antibodies

The following definitions are generally applicable to all antibodies of the invention, including the non-neutralising antibodies (non-nAb) and neutralising antibodies (nAb) discussed below.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody entities are known in the art, non-limiting embodiments of which are discussed below.

In a full-length antibody, each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Antibodies may be polyclonal (pAb) or monoclonal (mAb). Typically the antibodies of the invention are mAbs.

Antibodies of the invention can be of any type (e.g., IgG, IgE, IgM, IgD, IgA and IgY), class (e.g., IgG1, IgG2, IgG3, IgG4, IgA1 and IgA2) or subclass and may be from any species (e.g., mouse, human, chicken, rat, rabbit, sheep, shark and camelid).

The term "antigen-binding fragment" of an antibody (or simply "binding fragment"), as used herein, refers to one or more fragments of an antibody that retain the ability to specifically bind to an antigen. It has been shown that the antigen-binding function of an antibody can be performed by one or more fragments of a full-length antibody. Single chain antibodies are also encompassed. Such antigen-binding fragments may also be bispecific, dual specific, or multi-specific, specifically binding to two or more different antigens. Thus, examples of binding fragments encompassed within the term "antigen-binding fragment" of an antibody include Fab, Fv, scFv, dAb, Fd, Fab' or F(ab')2, tandem scFv and diabodies.

Also encompassed are antibody constructs, defined as a polypeptide comprising one or more the antigen binding fragment of the invention linked to a linker polypeptide or an immunoglobulin constant domain. Linker polypeptides comprise two or more amino acid residues joined by peptide bonds and are used to link one or more antigen binding portions.

An antibody of the invention may be a "human antibody"; defined as an antibody having variable and constant regions derived from human germline immunoglobulin sequences, but which may include amino acid residues not encoded by human germline immunoglobulin sequences (e.g., mutations introduced by random or site-specific mutagenesis in vitro or by somatic mutation in vivo), for example in the CDRs and in particular CDR3. Recombinant human antibodies are also encompassed by the present invention.

An antibody of the invention may be a "chimeric antibody"; defined as an antibody which comprises heavy and light chain variable region sequences from one species and constant region sequences from another species. The present invention encompasses chimeric antibodies having, for example, murine heavy and light chain variable regions linked to human constant regions.

An antibody of the invention may be a "CDR-grafted antibody"; defined as an antibody which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3 or all three CDRs) has been replaced with human CDR sequences.

An antibody of the invention may be a "humanized antibody"; defined as an antibody which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad. Sci. 190:382-391 and Kabat, E. A., et al. (1991) Sequences of Proteins of Immunological Interest, Fifth Edition, U.S. Department of Health and Human Services, NIH Publication No. 91-3242).

Antibodies of the invention are not limited to a particular method of generation or production. Thus, the invention provides antibodies which have been manufactured from a hybridoma that secretes the antibody, as well as antibodies produced from a recombinantly produced cell that has been transformed or transfected with a nucleic acid or nucleic acids encoding the antibody. Such hybridomas, recombinantly produced cells, and nucleic acids form part of the invention.

An antibody, or antigen-binding fragment thereof, of the invention is selective or specific for PfRH5, or a particular epitope of PfRH5 as described herein. By specific, it will be understood that the antibody binds to the molecule of interest, in this case the PfRH5 fragment of the invention, with no significant cross-reactivity to any other molecule, particularly any other protein. For example, a binding compound or antibody of the invention that is specific for a particular PfRH5 epitope of the invention will show no significant cross-reactivity with other PfRH5 epitopes. As another example, a binding compound or antibody of the invention that is specific for PfRH5 will show no significant cross-reactivity with other malarial invasion proteins. Cross-reactivity may be assessed by any suitable method. Cross-reactivity of a binding compound (e.g. antibody) for a PfRH5 epitope with another PfRH5 epitope or non-PfRH5 protein may be considered significant if the binding compound (e.g. antibody) binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the PfRH5 epitope. A binding compound (e.g. antibody) that is specific for the PfRH5 fragment may bind to another molecule such as PfAMA1 at less than 90%, 85%, 80%, 75%, 70%, 65%, 60%, 55%, 50%, 45%, 40%, 35%, 30%, 25% or 20% the strength that it binds to the PfRH5 epitope. Preferably, the binding compound (e.g. antibody) binds to the other molecule at less than 20%, less than 15%, less than 10% or less than 5%, less than 2% or less than 1% the strength that it binds to the PfRH5 epitope. Binding affinity may be quantified in any suitable way, e.g. by $K_D$.

The binding affinity of a PfRH5 antibody (neutralising or non-neutralising) of the invention for PfRH5 may be quantified in terms of dissociation constant ($K_D$). $K_D$ may be determined using any appropriate technique, but SPR is generally preferred in the context of the present invention. A PfRH5 antibody of the invention may bind to PfRH5 with a $K_D$ of less than 1 µM, less than 100 nM, less than 50 nM, less than 25 nM, less than 10 nM, less than 1 nM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 10 pM, less than 5 pM, or less. Typically a PfRH5 antibody of the invention binds to PfRH5 with a $K_D$ of less 50 nM, less than 10 nM or less than 1 nM.

Further antibodies which bind to the epitopes/antigens of the invention may be generated by producing variants of the antibodies of the invention. Such variants may have CDRs sharing a high level of identity with the CDRs of an antibody of the invention, for example may have CDRs each of which independently may differ by one or two amino acids from the antibody of the invention from which the variant antibody is derived, and wherein the variant retains the binding and functional properties of the antibody of the invention. Additionally, such antibodies may have one or more variations (e.g. a conservative amino acid substitution) in the framework regions. By way of a non-limiting example, variants of antibody mAb11 or mAb16 may have CDRs that differ by 1 or 2 amino acid residues in any one or more of the CDRs of antibody mAb11 or mAb16. Conservative amino acid substitutions are particularly contemplated (see the disclosure herein in relation to PfRH5 antigen variants, which applies equally to variants of antibodies of the invention). The variations in the amino acid sequences of the antibodies of the invention should maintain at least 75%, at least 80%, at least 85%, at least 90%, at least 95% and up to 99% sequence identity. Variants having at least 90% sequence identity with the antibodies of the invention, particularly the specific antibodies exemplified herein are specifically contemplated. Variation may or may not be limited to the framework regions and not present in the CDRs.

A particular exemplified antibody of the invention may be interchangeably referred to as mAbX (where X is an identification number) or as R5.X (where X is the same identification number).

DNA oligonucleotide aptamers, RNA oligonucleotide aptamers, and other engineered biopolymers against a PfRH5 antigen of the invention may also be able to replicate the activity of the antibodies and combinations thereof described here. As a vaccine, PfRH5 antigens of the invention are likely amenable to expression by recombinant viral vectored vaccines, as well as nucleic acid-based vaccines such as RNA or DNA; and recombinant protein or virus-like particles (VLPs) expressed in mammalian expression systems or insect cell systems. It is also possible to express the PfRH5 antigens of the invention as proteins or VLPs in bacteria or yeast, as well as plant/algae systems.

Non-Neutralising Antibodies

The present inventors have identified a novel epitope on PfRH5 which elicits antibodies which themselves possess no neutralising activity. However, the inventors have surprisingly shown that non-neutralising antibodies which bind to this epitope on PfRH5 potentiate the activity of all neutralising antibodies directed to PfRH5. In addition, these non-neutralising antibodies (non-nAb) also synergise with antibodies against other malarial invasion proteins.

Figure 1:
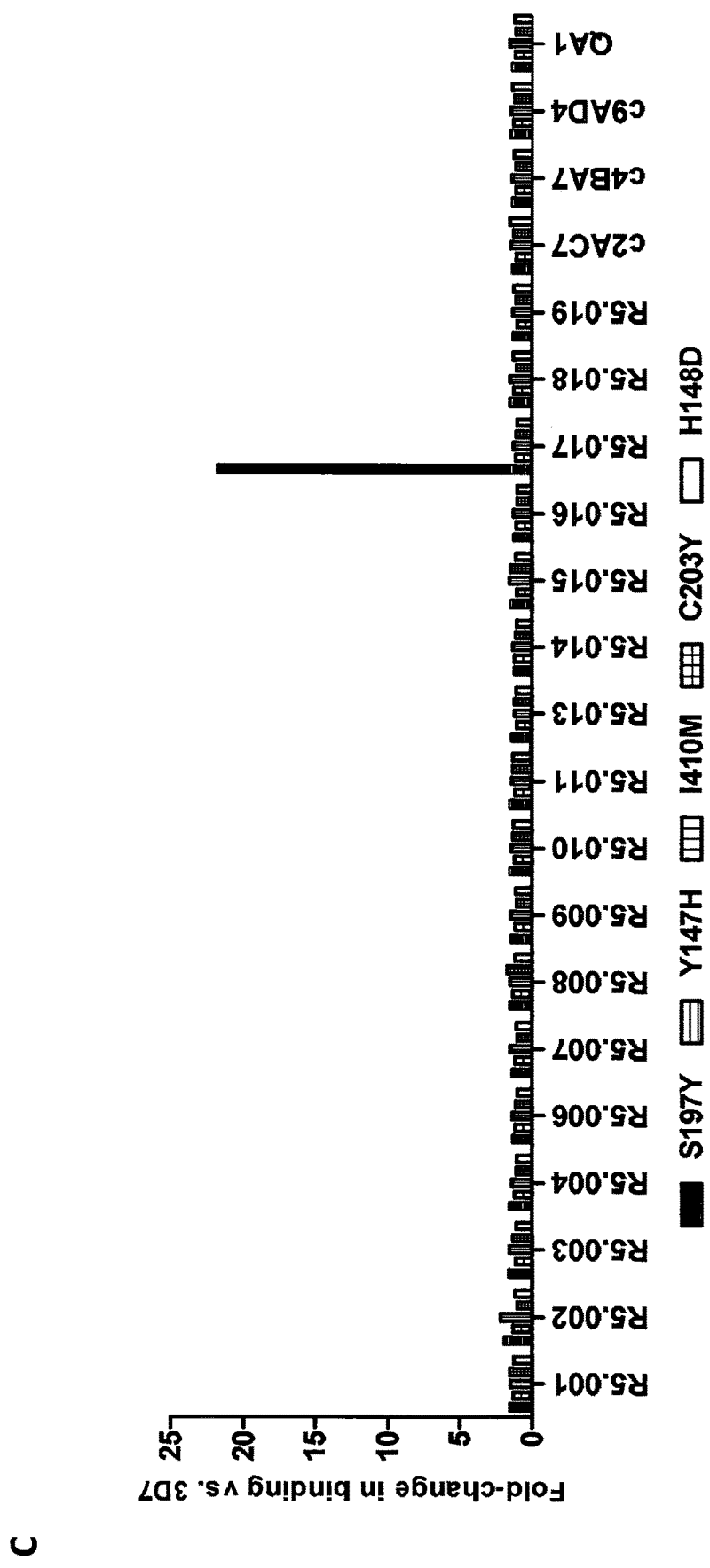
FIG. 1: Description and binding characteristics of anti-PfRH5 mAbs. (A) Genetic lineage of variable regions from PfRH5-specific mAbs and their donor origin. The percentage of nucleotide substitutions relative to germline is shown. (B) Iso-affinity plot showing the kinetic rate constants of binding for all 21 mAbs to PfRH5FL as determined by SPR. Diagonal dotted lines represent equal affinity at equilibrium. (C) Real-time analysis by Bio-Layer Interferometry (BLI) of mAb binding to PfRH5FL variants with the five most common naturally-occurring amino acid substitutions. Bars represent fold change compared to wild type PfRH5FL (3D7 sequence) binding.
Figure 2:
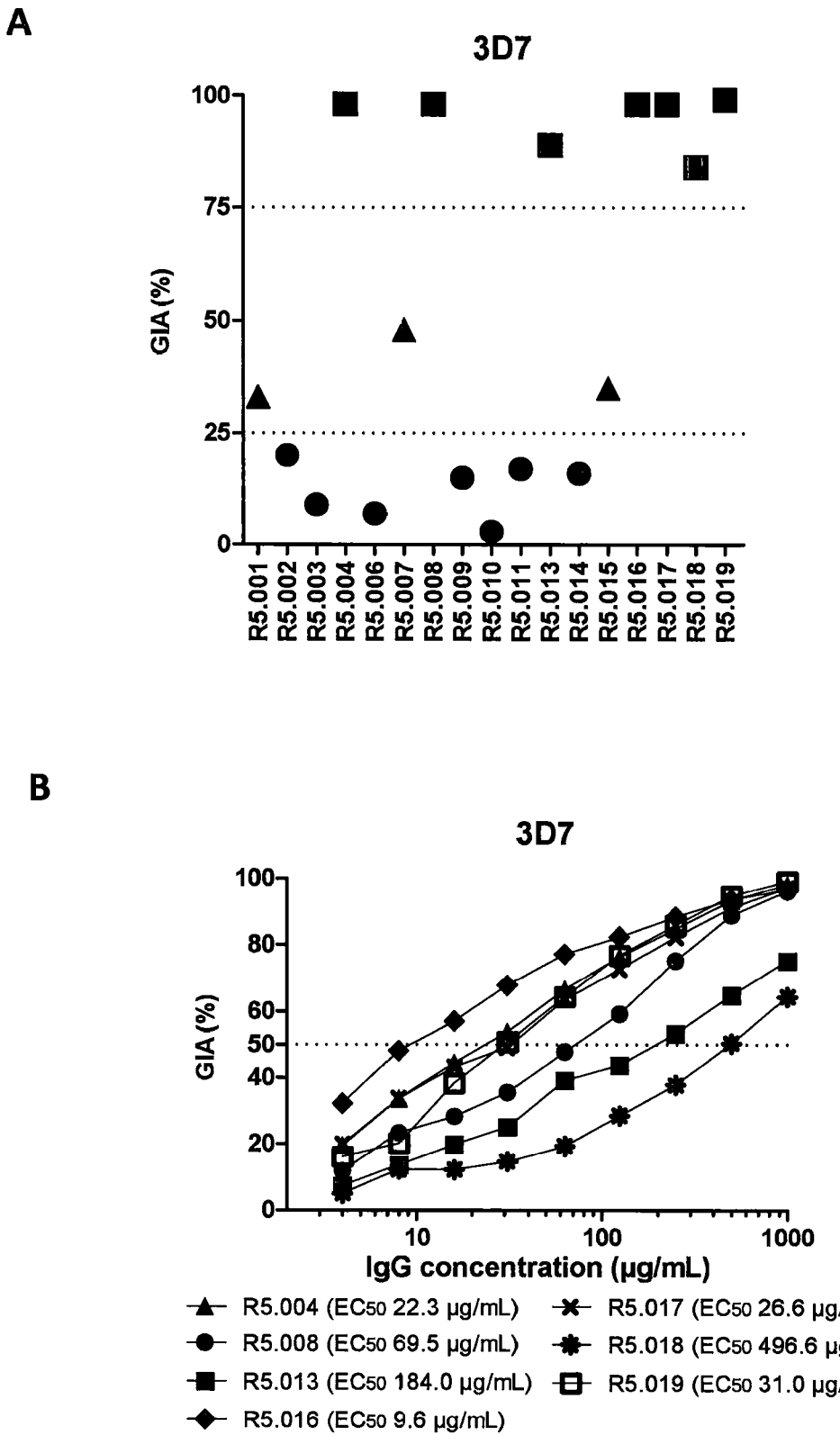
Figure 2:
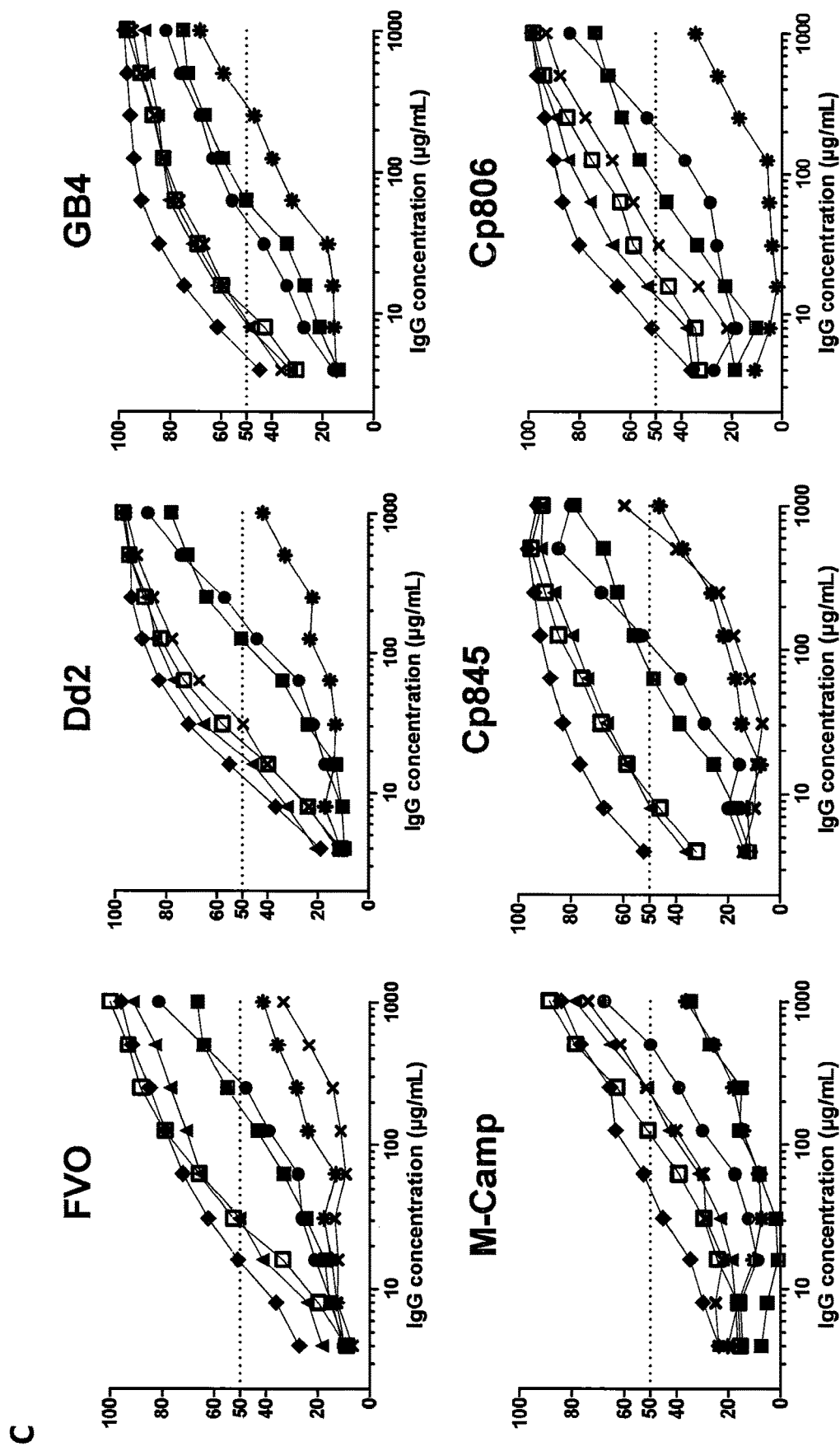

The present inventors have previously solved the crystal structure of PfRH5 (see WO2016/016651, which is incorporated by reference in its entirety, particularly Example 1 and FIGS. 1 and 2A and 2B thereof). The present inventors have now demonstrated in the Examples herein, the non-neutralising antibodies of the present invention bind to an epitope in the vicinity of the interface between the disordered N-terminus and the rigid α-helical core of the full-length PfRH5 protein. Thus, this epitope is situated at the N-terminus of both the PfRH5ΔN fragment (which lacks the signal peptide (corresponding to residues 1 to 23 of SEQ ID NO: 1 or 2) and the flexible/disordered N-terminal region (corresponding to residues 24 to 139 or 24 to 159 (preferably 24 to 139) of SEQ ID NO: 1 or 2) of PfRH5), as exemplified by SEQ ID NOs: 3 to 6; and the PfRH5ΔNL fragment (which lacks both the signal peptide and flexible/disordered N-terminal region identified above and the flexible loop region corresponding to amino acid residues 248 to 296 of SEQ ID NO: 1 or 2), as exemplified by SEQ ID NOs: 7 to 10. Accordingly, the invention provides a novel epitope defined by amino acids Ser153 to Ile163 and Aps305 to Lys319 of PfRH5. In particular, the invention provides an epitope corresponding to residues Ser153 to Ile163 and Aps305 to Lys319 of SEQ ID NO: 1, or the corresponding amino acid residues of another PfRH5 sequence (SEQ ID NO: 2) or fragment (such as any one of SEQ ID NOs: 3 to 10). More particularly, the epitope comprises or consists of amino acid residues corresponding to Ser153 to Asn156; Asn159; Ile161; Ile163; Asp305; Asn308; Lys312; Lys316 and Lys 319 of PfRH5 as defined above. With regards to PfRH5 fragments, the numbering of the amino acids of the epitope may differ from the residues indicated above (as these are defined by reference to the full-length sequence of PfRH5, typically SEQ ID NO: 1 or 2). However, the corresponding residues within a PfRH5 fragment may be readily identified using only routine skill and methods (e.g. sequence alignment). Indeed, by way of example, these epitopes are identified in the fragments of SEQ ID NOs: 3 to 10 in the sequence information section herein. More particularly, the epitope comprises or consists of amino acid residues corresponding to Ser153 to Asn156; Asn159; Ile161; Ile163; Asp305; Asn308; Lys312; Lys316 and Lys319 of PfRH5 or fragments thereof as defined above. Typically the epitopes described above give rise to (induce) non-neutralising antibodies of the invention, such as those exemplified herein.

A non-neutralising antibody or binding fragment thereof of the invention may comprise three heavy chain CDRs having sequences: (a) a CDR1 sequence of SEQ ID NO: 11; a CDR2 sequence of SEQ ID NO: 12 and a CDR3 sequence of SEQ ID NO: 13; (b) a CDR1 sequence of SEQ ID NO: 14; a CDR2 sequence of SEQ ID NO: 15 and a CDR3 sequence of SEQ ID NO: 16; or (c) a CDR1 sequence of SEQ ID NO: 17; a CDR2 sequence of SEQ ID NO: 18 and a CDR3 sequence of SEQ ID NO: 19.

A non-neutralising antibody or binding fragment thereof of the invention may comprise three light chain CDRs having sequences: (a) a CDR1 sequence of SEQ ID NO: 20; a CDR2 sequence of SEQ ID NO: 21 and a CDR3 sequence of SEQ ID NO: 22; a CDR1 sequence of SEQ ID NO: 23; a CDR2 sequence of SEQ ID NO: 24 and a CDR3 sequence of SEQ ID NO: 25; or (c) a CDR1 sequence of SEQ ID NO: 26; a CDR2 sequence of SEQ ID NO: 21 and a CDR3 sequence of SEQ ID NO: 27.

In a preferred embodiment, a non-neutralising antibody or binding fragment thereof of the invention may comprise: (a) a heavy chain with a CDR1 sequence of SEQ ID NO: 11; a CDR2 sequence of SEQ ID NO: 12 and a CDR3 sequence of SEQ ID NO: 13, and a light chain with a CDR1 sequence of SEQ ID NO: 20; a CDR2 sequence of SEQ ID NO: 21 and a CDR3 sequence of SEQ ID NO: 22; (b) a heavy chain with a CDR1 sequence of SEQ ID NO: 14; a CDR2 sequence of SEQ ID NO: 15 and a CDR3 sequence of SEQ ID NO: 16, and a light chain with a CDR1 sequence of SEQ ID NO: 23; a CDR2 sequence of SEQ ID NO: 24 and a CDR3 sequence of SEQ ID NO: 25; or (c) a heavy chain with a CDR1 sequence of SEQ ID NO: 17; a CDR2 sequence of SEQ ID NO: 18 and a CDR3 sequence of SEQ ID NO: 19, and a light chain with a CDR1 sequence of SEQ ID NO: 26; a CDR2 sequence of SEQ ID NO: 21 and a CDR3 sequence of SEQ ID NO: 27. In a more preferred embodiment, a non-neutralising antibody or binding fragment thereof of the present invention comprises the CDRs of mAb11 or the CDRs of mAb14.

A non-neutralising antibody or binding fragment thereof of the invention may comprise four heavy chain framework regions (FRs) having sequences: (a) a FR1 sequence of SEQ ID NO: 28; a FR2 sequence of SEQ ID NO: 29; a FR3 sequence of SEQ ID NO: 30; and a FR4 sequence of SEQ ID NO: 31; (b) a FR1 sequence of SEQ ID NO: 32; a FR2 sequence of SEQ ID NO: 33; a FR3 sequence of SEQ ID NO: 34; and a FR4 sequence of SEQ ID NO: 31; or (c) a FR1 sequence of SEQ ID NO: 35; a FR2 sequence of SEQ ID NO: 36; a FR3 sequence of SEQ ID NO: 37; and a FR4 sequence of SEQ ID NO: 38.

A non-neutralising antibody or binding fragment thereof of the invention may comprise four light chain framework regions (FRs) having sequences: (a) a FR1 sequence of SEQ ID NO: 39; a FR2 sequence of SEQ ID NO: 40; a FR3 sequence of SEQ ID NO: 41; and a FR4 sequence of SEQ ID NO: 42; (b) a FR1 sequence of SEQ ID NO: 43; a FR2 sequence of SEQ ID NO: 44; a FR3 sequence of SEQ ID NO: 41; and a FR4 sequence of SEQ ID NO: 42; or (c) a FR1 sequence of SEQ ID NO: 45; a FR2 sequence of SEQ ID NO: 40; a FR3 sequence of SEQ ID NO: 46; and a FR4 sequence of SEQ ID NO: 42.

Preferably a non-neutralising antibody of the invention has the heavy and light chain CDRs of the mAb11 and the corresponding heavy and light chain FRs of the mAb11 antibody; the heavy and light chain CDRs of the mAb14 and the corresponding heavy and light chain FRs of the mAb14 antibody; or the heavy and light chain CDRs of the mAb10 and the corresponding heavy and light chain FRs of the mAb10 antibody; as identified above. In a preferred embodiment, a non-neutralising antibody of the invention, or binding fragment thereof, comprises: (a) a heavy chain variable region sequence of SEQ ID NO: 47 and/or a light chain variable region sequence of SEQ ID NO: 48; (b) a heavy chain variable region sequence of SEQ ID NO: 49 and/or a light chain variable region sequence of SEQ ID NO: 50; or (c) a heavy chain variable region sequence of SEQ ID NO: 51 and/or a light chain variable region sequence of SEQ ID NO: 52. Particularly preferred are antibodies with both the VH and VL sequences listed above. In a more preferred embodiment, a non-neutralising antibody or binding fragment thereof of the present invention comprises the VH and VL sequences of mAb11 or mAb14.

The term "non-neutralising antibody" is defined herein to mean an antibody which by itself (in the absence of any other PfRH5 antibody or other antibody against a malarial invasion protein) lacks the ability, or has negligible ability, to inhibit the growth of Plasmodium falciparum parasites, and more preferably across a plurality of strains of blood-stage P. falciparum parasites.

This activity or lack thereof may be quantified using any appropriate technique and measured in any appropriate units. For example, the activity of PfRH5 antibodies of the invention may be given in terms of their growth inhibitory activity (GIA), half maximal effective concentration ($EC_{50}$), antibody titre stimulated (in terms of antibody units, AU) and/or $EC_{50}$ in terms of AU. The latter of these gives an indication of the quality of the response elicited by the PfRH5 antibody of the invention. Any appropriate technique may be used to determine the GIA, $EC_{50}$, AU or $EC_{50}$/AU. Typically the activity of polyclonal antibodies is quantified using $EC_{50}$/AU, and the activity of monoclonal antibodies is quantified using $EC_{50}$. Exemplary techniques are described in the examples and conventional techniques are known in the art.

Typically non-neutralising antibodies of the invention have a GIA of less than 25%, less than 20%, less than 15%, less than 10%, less than 5%, less than 4%, less than 3%, less than 2%, less than 1%, or less against Plasmodium parasites, down to zero GIA against Plasmodium parasites.

The growth inhibitory activity (GIA) may be measured at any appropriate concentration of the antibodies, for example the GIA may be measured at 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml or 3 mg/ml of purified IgG antibody.

As described herein, without being bound by theory, the evidence suggests that non-neutralising antibodies of the invention slow the invasion of host red blood cells by the merozoite form of the Plasmodium parasite (referred to interchangeably herein as increasing invasion time), giving longer for neutralising antibodies to bind to their epitope on the merozoite. A non-neutralising antibody of the invention may increase invasion time by at least 1.5 times, at least 2 times, at least 2.5 times, at least 3 times or more, preferably at least 2 times and more preferably at least 3 times, compared with the time taken for red blood cell invasion by merozoites (typically a merozoite from the same malarial strain) in the absence of said non-neutralising antibody. By way of non-limiting example, a non-neutralising antibody of the invention may increase invasion time by at least 10 seconds, at least 15 seconds, at least 20 seconds, at least 30 seconds or more compared with the time taken for red blood cell invasion by merozoites (typically a merozoite from the same malarial strain) in the absence of said non-neutralising antibody. Typically, a non-neutralising antibody of the invention increases the phase of invasion immediately preceding merozoite penetration of a red blood cell (see schematic in FIG. 9B). Any disclosure herein in relation to non-neutralising antibodies increasing invasion time may also more specifically relate to increasing the time for the phase of invasion immediately preceding merozoite penetration of a red blood cell.

Neutralising Antibodies

The present inventors have further identified three novel epitopes on PfRH5 which elicits antibodies which possess significant neutralising activity. The inventors have also shown the effects of these neutralising antibodies (nAb) are potentiated when used in combination with the non-neutralising antibodies of the invention.

All the novel neutralising antibodies identified by the present inventors bind to the PfRH5ΔNL fragment. As indicated above, this fragment lacks both the signal peptide (corresponding to residues 1 to 23 of SEQ ID NO: 1 or 2); the flexible/disordered N-terminal region (corresponding to residues 24 to 139 or 24 to 159 (preferably 24 to 139) of SEQ ID NO: 1 or 2) of PfRH5) and the flexible loop region corresponding to amino acid residues 248 to 296 of SEQ ID NO: 1 or 2). The PfRH5ΔNL fragment is exemplified by SEQ ID NOs: 7 to 10.

Notably, the PfRH5ΔNL fragment lacks resides K33 to K51 of the full-length PfRH5 protein, which have previously been reported as the minimal PfP113 binding region, and which was thought to be a potential site for antibody-mediated neutralisation In particular, the inventors identified three epitope bins which contain potent neutralising antibodies. The binding sites of mAb16 and mAb4 as defined herein both have significant overlap with the basigin binding site of PfRH5 (as defined in WO2016/016651, particularly in Example 1 which is incorporated by reference in its entirety, particularly Example 1 and FIGS. 3A and 3D thereof). mAb4 binds PfRH5 towards the tip of the "kite-like" structure, contacting the N-terminus of helix 4 and each of the three loops that link the converging helices at this apex of PfRH5. These interactions are mediated by five of the CDR loops of the antibody, with only light chain CDR2 (L2) not participating. mAb16 binds predominantly to the N-terminus of helix 2 of PfRH5. The major contact is mediated by the heavy chain CDR3 (H3) loop, which lies along the groove between helices 2 and 3. Additional interactions are mediated by the heavy chain CDR1 (H1) and CDR2 (H2) and L2 loops.

Accordingly, the invention provides a novel epitope within RH5ΔN (as exemplified by SEQ ID NOs: 3 to 6) or RH5ΔNL as exemplified by SEQ ID NOs: 7 to 10). In particular, the invention provides novel epitopes corresponding to (a) (i) residues Lys196 to Ser197; Asn347 to Asn352; Arg357 to His365; and Lys443 to Arg448 of PfRH5 (SEQ ID NO: 1); or (ii) residues Gly201 to Lys219; and Lys327 to Tyr335 of PfRH5 (SEQ ID NO: 1); (b) residues Gly201 to Lys219 and Lys327 to Gln342 of PfRH5 (SEQ ID NO: 1); or (c) residues Lys196, Ser197; Tyr346 to Asn354 and Lys443 to Lys452 of PfRH5 (SEQ ID NO: 1). In a preferred embodiment, the invention provides novel epitopes corresponding to (i) residues Lys196 to Ser197; Asn347 to Asn352; Arg357 to His365; and Lys443 to Arg448 of PfRH5 (SEQ ID NO: 1); or (ii) residues Gly201 to Lys219; and Lys327 to Tyr335 of PfRH5 (SEQ ID NO: 1). Alternatively, said epitopes may be defined in terms of the corresponding amino acid residues of another PfRH5 sequence (SEQ ID NO: 2) or fragment (such as any one of SEQ ID NOs: 3 to 10). With regards to PfRH5 fragments, the numbering of the amino acids of the epitope may differ from the residues indicated above (as these are defined by reference to the full-length sequence of PfRH5, typically SEQ ID NO: 1 or 2). However, the corresponding residues within a PfRH5 fragment may be readily identified using only routine skill and methods (e.g. sequence alignment). Indeed, by way of example, these epitopes are identified in the fragments of SEQ ID NOs: 3 to 10 in the sequence information section herein. More particularly, the epitope comprises or consists of amino acid residues corresponding to (a) Lys196; Ser197; Asn347; Asn352; Arg357; Asp361; Glu362; His365; Lys443; Trp447 and Arg448; or (b) Gly201; Lys202; Ile204; Asp207 to Phe209; Lys211; Lys212; Glu215; Lys219; Lys327, Asp331 and Tyr335 of PfRH5 or fragments thereof as defined above. Typically the epitopes described above give rise to (induce) neutralising antibodies of the invention, such as those exemplified herein.

A neutralising antibody or binding fragment thereof of the invention may comprise three heavy chain CDRs having sequences: (a) a CDR1 sequence of SEQ ID NO: 54; a CDR2 sequence of SEQ ID NO: 55 and a CDR3 sequence of SEQ ID NO: 56; or (b) a CDR1 sequence of SEQ ID NO: 57; a CDR2 sequence of SEQ ID NO: 58 and a CDR3 sequence of SEQ ID NO: 59.

A neutralising antibody or binding fragment thereof of the invention may comprise three light chain CDRs having sequences: (a) a CDR1 sequence of SEQ ID NO: 60; a CDR2 sequence of SEQ ID NO: 61 and a CDR3 sequence of SEQ ID NO: 62; or (b) a CDR1 sequence of SEQ ID NO: 63; a CDR2 sequence of SEQ ID NO: 64 and a CDR3 sequence of SEQ ID NO: 65.

In a preferred embodiment, a neutralising antibody or binding fragment thereof of the invention may comprise: (a) a heavy chain with a CDR1 sequence of SEQ ID NO: 54; a CDR2 sequence of SEQ ID NO: 55 and a CDR3 sequence of SEQ ID NO: 56, and a light chain with a CDR1 sequence of SEQ ID NO: 60; a CDR2 sequence of SEQ ID NO: 61 and a CDR3 sequence of SEQ ID NO: 62; or (b) a heavy chain with a CDR1 sequence of SEQ ID NO: 57; a CDR2 sequence of SEQ ID NO: 58 and a CDR3 sequence of SEQ ID NO: 59, and a light chain with a CDR1 sequence of SEQ ID NO: 63; a CDR2 sequence of SEQ ID NO: 64 and a CDR3 sequence of SEQ ID NO: 65.

A neutralising antibody or binding fragment thereof of the invention may comprise four heavy chain framework regions (FRs) having sequences: (a) a FR1 sequence of SEQ ID NO: 66; a FR2 sequence of SEQ ID NO: 67; a FR3 sequence of SEQ ID NO: 68; and a FR4 sequence of SEQ ID NO: 69; or (b) a FR1 sequence of SEQ ID NO: 70; a FR2 sequence of SEQ ID NO: 67; a FR3 sequence of SEQ ID NO: 71; and a FR4 sequence of SEQ ID NO: 72.

A neutralising antibody or binding fragment thereof of the invention may comprise four light chain framework regions (FRs) having sequences: (a) a FR1 sequence of SEQ ID NO: 73; a FR2 sequence of SEQ ID NO: 74; a FR3 sequence of SEQ ID NO: 75; and a FR4 sequence of SEQ ID NO: 76; or (b) a FR1 sequence of SEQ ID NO: 77; a FR2 sequence of SEQ ID NO: 78; a FR3 sequence of SEQ ID NO: 79; and a FR4 sequence of SEQ ID NO: 80.

Typically a neutralising antibody of the invention has both the heavy and light chain CDRs of the same antibody of the invention (e.g. the heavy and light chain CDRs of mAb16) and the heavy and light chain FRs from this same antibody (e.g. the heavy and light chain FRs of mAb16). Preferably a neutralising antibody of the invention comprises the heavy and light chain CDRs of the mAb16 antibody and the corresponding heavy and light chain FRs of the mAb16 antibody; or the heavy and light chain CDRs of the mAb4 antibody and the corresponding heavy and light chain FRs of the mAb4 antibody; as identified above.

In a preferred embodiment, a neutralising antibody of the invention, or binding fragment thereof, comprises: (a) a heavy chain variable region sequence of SEQ ID NO: 81 and/or a light chain variable region sequence of SEQ ID NO: 82; or (b) a heavy chain variable region sequence of SEQ ID NO: 83 and/or a light chain variable region sequence of SEQ ID NO: 84. Particularly preferred are neutralising antibodies with both the VH and VL sequences listed above. In a more preferred embodiment, a neutralising antibody or binding fragment thereof of the present invention comprises the VH and VL sequences of mAb16 or mAb4.

The term "neutralising antibody" is defined herein to mean an antibody which by itself (in the absence of any other PfRH5 antibody or other antibody against a malarial invasion protein) has the ability to inhibit the growth of *Plasmodium falciparum* parasites, and more preferably across a plurality of strains of blood-stage *P. falciparum* parasites.

This activity may be quantified using any appropriate technique and measured in any appropriate units as discussed above in relation to non-neutralising antibodies. This disclosure applies equally to neutralising antibodies of the invention (and to other binding compounds as described herein).

Typically, the neutralising PfRH5 antibodies of the invention have a GIA of at least at least 40%, at least 50%, at least 60%, at least 70%, at least 80%, at least 90% or more against *Plasmodium* parasites. In a preferred embodiment, the PfRH5 fragments of the invention induce antibodies that have a growth inhibitory activity (GIA) of at least 70%, at least 75%, at least 80%, at least 90% or more against *Plasmodium* parasites.

The growth inhibitory activity (GIA) may be measured at any appropriate concentration of the antibodies (again, as described in relation to non-neutralising antibodies and which equally applies to neutralising antibodies). For example, the neutralising antibodies of the invention may give a GIA of at least 40%, at least 50% and preferably at least 70% or more against the blood-stage *Plasmodium* parasite, at an IgG concentration of 1 mg/ml IgG, of the purified neutralising antibody.

Preferably the neutralising PfRH5 antibodies of the invention exert similarly high levels of GIA against both the vaccine-homologous clone, 3D7, and against a vaccine-heterologous strain, FVO. A neutralising PfRH5 antibody of the invention has an $EC_{50}$ which is at least comparable to total IgG against full length PfRH5, and preferably significantly lower than the $EC_{50}$ against full-length PfRH5 of the $EC_{50}$ of known anti-PfRH5 antibodies. A neutralising antibody of the invention preferably has an $EC_{50}$ significantly lower than that of the anti-PfAMA1 BG98 standard (Faber, B. W., et al., Infection and immunity, 2013; incorporated herein by reference). Typically a neutralising PfRH5 antibody of the invention has an $EC_{50}$ value of less than 500 µg/ml, less than 400 µg/ml, less than 300 µg/ml, less than 200 µg/ml, less than 150 µg/ml, less than 100 µg/ml, less than 90 µg/ml, less than 80 µg/ml, less than 70 µg/ml, less than 60 µg/ml, less than 50 µg/ml, less than 40 µg/ml, less than 30 µg/ml, less than 25 µg/ml, less than 20 µg/ml, less than 15 µg/ml, less than 10 µg/ml, less than 9 µg/ml, less than 8 µg/ml, less than 7 µg/ml, less than 6 µg/ml, less than 5 µg/ml, less than 4 µg/ml, less than 3 µg/ml, less than 2 µg/ml, less than 1 µg/ml, or less.

Typically the neutralising antibodies of the invention result in a GIA of at least 50%, at least 60%, at least 70%, at least 80%, at least 90% or more against the blood-stage *Plasmodium* parasite. In a preferred embodiment, the neutralising antibodies of the invention will raise antibodies that result in a GIA of at least 70% against the blood-stage *Plasmodium* parasite measured at any appropriate concentration as described herein.

Typically the PfRH5 neutralising antibodies of the invention are effective against genetically diverse strains of the *Plasmodium* parasite. This is likely to be of importance in achieving protection against the variety of strains circulating in the natural environment. Accordingly, in a preferred embodiment, the neutralising antibodies of the invention will result in a GIA of at least at least 50%, at least 60%, at least 70%, at least 80%, at least 90% or more against a plurality of genetic strains of the blood-stage *Plasmodium* parasite. In a preferred embodiment, the neutralising antibodies of the invention will result in a GIA of at least 70% or more against a plurality of genetic strains of the blood-stage *Plasmodium* parasite.

The PfRH5 fragment of the invention may have a comparable immunogenicity when compared with the full length PfRH5 antigen.

Antibody Combinations

As outlined above and as demonstrated in the Examples below, the present inventors have surprisingly shown that non-neutralising antibodies which bind to a particular epitope on PfRH5 potentiate the activity of all neutralising antibodies directed to PfRH5, and also synergise with antibodies against other malarial invasion proteins.

Accordingly, the present invention provides a composition comprising: (a) one or more non-neutralising antibody, or binding fragment thereof, that specifically binds a non-neutralising antibody epitope of the invention, particularly, an epitope corresponding to residues Ser153 to Ile163 and Asp305 to Lys319 of PfRH5 (SEQ ID NO: 1); and (b) one or more neutralising antibody, or binding fragment thereof, that specifically binds a *Plasmodium* merozoite antigen.

The one or more non-neutralising antibody may be any non-neutralising antibody as described herein. The disclosure of non-neutralising antibodies of the invention is generally applicable to all disclosure herein in relation to the compositions of the invention.

The one or more neutralising antibody may bind to any *Plasmodium* merozoite antigen, also referred to interchangably herein as a malarial invasion protein (or a fragment thereof), including malarial invasion proteins already known in the art. The one or more neutralising antibody typically binds to: (a) PfRH5; (b) a non-PfRH5 *Plasmodium* merozoite antigen that is within the PfRH5 invasion complex; or (c) a *Plasmodium* merozoite antigen that is closely linked to PfRH5. Closely linked *Plasmodium* merozoite antigens may act either prior to PfRH5 engagement (upstream of PfRH5) or after PfRH5 engagement (downstream of PfRH5).

In particular, the one or more neutralising antibody may bind to a *Plasmodium* merozoite antigen selected from: (a) PfRH5; (b) a non-PfRH5 antigen within the PfRH5 invasion complex; and/or (c) a target upstream or downstream of the PfRH5-basigin interaction.

As used herein, a non-PfRH5 antigen within the PfRH5 invasion complex is any malarial protein which associates with PfRH5 to form a complex essential for the invasion of red blood cells by the *Plasmodium* merozoites. Accordingly, non-PfRH5 antigens within the PfRH5 invasion complex include PfRipr, PfCyRPA, PfP113, PfRhopH3 and PfRAP2.

Non-limiting examples of *Plasmodium* merozoite antigens that are closely linked to PfRH5 include PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP, or a fragment thereof Antibodies to one or more of these antigens, or any combination thereof, may be used according to the invention.

In some preferred embodiments the one or more neutralising antibody is an anti-PfRH5 neutralising antibody as defined herein. The disclosure of neutralising PfRH5 antibodies of the invention is generally applicable to all disclosure herein in relation to the compositions of the invention.

Any combinations of neutralising antibodies of the invention (e.g. any two, three, four or more neutralising antibodies to one or more of the *Plasmodium* merozoite antigens described herein) may be used in combination with a non-neutralising antibody. By way of a non-limiting example, a non-neutralising antibody of the invention may be used in combination with a neutralising antibody (or binding fragment thereof) to PfRH5 together with a neutralising antibody (or binding fragment thereof) against a PfCyRPA antigen, a neutralising antibody (or binding fragment thereof) against a PfAMA1 antigen and/or a neutralising antibody (or binding fragment thereof) against a PfRipr antigen. Such a combination may be equally effective against both the vaccine-homologous 3D7 clone and the vaccine-heterologous FVO strain. One or more additional neutralising antibodies to other *Plasmodium* merozoite antigen(s) can be used in combination with the non-neutralising antibody (or binding fragment thereof), neutralising PfRH5 antibody and other merozoite antigen neutralising antibody combination. One exemplary preferred combination is a non-neutralising antibody of the invention together with a neutralising antibody (or binding fragment thereof) to PfRH5 and with a neutralising antibody (or binding fragment thereof) against a PfCyRPA antigen, a PfAMA1 antigen or a PfRipr antigen.

The combination of a non-neutralising antibody of the invention and a neutralising antibody of the invention may be in the form of two separate antibody molecules or binding fragments thereof. In which case, the antibodies may be used or administered (or in the case of a therapeutic indication) sequentially or simultaneously, with simultaneous use or administration being preferred. If the use/administration is sequential, preferably the non-neutralising antibody is used/administered first.

Alternatively, the non-neutralising antibody or binding fragment thereof and the neutralising antibody or binding fragment thereof may be in the form of a single molecule. Thus, the invention provides bispecific molecules comprising both a non-neutralising antibody or binding fragment thereof and a neutralising antibody or binding fragment thereof Such bispecific molecules include fusion proteins, trifunctional antibodies, F(ab')$_2$, bispecific T-cell engager molecules, dual-variable-domain immunoglobulins (DVD-Ig™, in which the antigen-binding variable domains of two monoclonal antibodies are combined via linkers (typically naturally occurring linkers) to create a tetravalent, dual-targeting single agent). Examples of bispecific antibody structures are well known in the art, as are methods for their production, including the so-called "Knobs-into-Holes" (KiH) approach, the controlled Fab arm exchange method (cFAE) and using scFvs.

As well as use or administration of the non-neutralising antibodies and neutralising antibodies of the invention in protein (i.e. antibody) form as discussed above, the non-neutralising and neutralising antibodies of the invention may be used or administered in any other appropriate form.

In some embodiments, one or more non-neutralising antibody and/or one or more neutralising antibody is generated in vivo. In vivo generation of said antibodies may be via the administration of one or more vector (e.g. a viral vector, RNA vaccine or DNA plasmid) which encodes and expresses said one or more non-neutralising antibody and/or one or more neutralising antibody. Alternatively, in vivo generation of said antibodies may be by the administration of a vector or vaccine which (i) delivers an antigen which will induce the immune system to make said one or more non-neutralising antibody and/or one or more neutralising antibody, or (ii) encodes or expresses an antigen which will then induce the immune system to make said one or more non-neutralising antibody and/or one or more neutralising antibody; or (iii) natural exposure to malaria (particularly in the case of said one or more neutralising antibody).

Any combination of delivery of said one or more non-neutralising antibody and/or one or more neutralising antibody in protein form or in vivo generation of said one or more non-neutralising antibody and/or one or more neutralising antibody may be used.

For example, in some embodiments non-neutralising antibodies are used or administered in protein form (i.e. as antibodies), and the neutralising antibodies are generated in vivo.

The in vivo generation of the neutralising antibodies may be via the use or administration of a malarial vaccine encoding a *Plasmodium* merozoite antigen as described herein to a subject to be treated, by natural exposure to malaria, or by the use or administration of a vector or plasmid encoding the neutralising antibody (as exemplified herein).

In embodiments where the in vivo generation of the neutralising antibodies is via the use or administration of a malarial vaccine to a subject to be treated, the non-neutralising antibody or binding fragment thereof may be described as being used in combination with the antibodies generated in vivo in response to the malarial vaccine. The malarial vaccine may comprise any *Plasmodium* merozoite antigen as described herein. All the disclosure herein in relation to *Plasmodium* merozoite antigens to which neutralising antibodies of the invention specifically binds also applies to the *Plasmodium* antigens themselves as included in a malarial vaccine for use in combination with a non-neutralising antibody (or binding fragment thereof) of the invention. Thus, the malaria vaccine may contain one or more of: (a) PfRH5; (b) a non-PfRH5 *Plasmodium* merozoite antigen that is within the PfRH5 invasion complex; or (c) a *Plasmodium* merozoite antigen that is closely linked to PfRH5; or may contain a vector which encodes one or more of said antigens. Examples of such antigens are described herein. Typically the malarial vaccine comprises or encodes a PfRH5 antigen, preferably comprising or encoding an epitope for a neutralising antibody as described herein. Non-limiting examples of vaccine vectors are described herein.

The combination of a non-neutralising antibody of the invention and a malarial vaccine may be used or administered (or in the case of a therapeutic indication) sequentially or simultaneously. If the use/administration is sequential, preferably the malarial vaccine is used/administered first.

Alternatively, the neutralising antibodies may be generated in vivo naturally via exposure to malaria.

The non-neutralising antibodies may be used or administered as a vector encoding said non-neutralising antibody. In such embodiments, the neutralising antibodies may be generated in vivo as described above (e.g. induced by a vaccine, including protein, VLP or other vaccine, or expressed by an expression vector) or used or administered in protein (i.e. antibody) form. The antibodies (in whatever form) may be used or administered (or in the case of a therapeutic indication) sequentially or simultaneously. If the use/administration is sequential, preferably the non-neutralising antibody (in whatever form) is used/administered first.

Any combination of delivery method may be used for the non-neutralising antibodies and neutralising antibodies of the invention. In particular, the non-neutralising antibody may be delivered by a means selected from vaccine induction, in vivo vector generation or direct antibody protein delivery as described herein, or a combination thereof, and independently the neutralising antibody of may be also delivered by a means selected from vaccine induction, in vivo vector generation or direct antibody protein delivery as described herein, or a combination thereof. In some preferred embodiments: (i) the neutralising antibody is induced in vivo by a vaccine and the non-neutralising antibody is given directly as a protein antibody; (ii) both the neutralising and non-neutralising antibodies are given directly as protein antibodies; or (iii) both the neutralising and non-neutralising antibodies are induced by vaccines.

Regardless of how the non-neutralising antibody is delivered (e.g. as a protein antibody, expressed in vivo by a vector or plasmid of the invention or generated in vivo by the administration of a malarial vaccine (protein, virus-like particle or any other type of vaccine, examples of which are described herein)), or how the neutralising antibody is delivered (e.g. generated in vivo by administration of a malarial vaccine (protein, virus-like particle or any other type of vaccine, examples of which are described herein), by exposure to malaria, as a protein antibody or expressed in vivo by a vector or plasmid of the invention), a non-neutralising antibody of the invention can synergise the activity of the neutralising antibodies as described herein.

The non-neutralising antibodies of the invention are able to potentiate or synergise the activity of the neutralising antibodies. The terms potentiate and synergise (or variants thereof) are used interchangeably herein.

By potentiation, it is meant that the non-neutralising antibody increases the effect of the neutralising antibody beyond the effect obtained using the non-neutralising antibody alone. This can be quantified in any suitable way and measured using conventional means, as exemplified in the Examples herein.

Typically a non-neutralising antibody of the invention or binding fragment thereof reduces the amount or concentration of neutralising antibody required to obtain the desired inhibitory effect on the *Plasmodium* parasite. As a non-limiting example, a non-neutralising antibody or binding fragment thereof of the invention may decrease the $EC_{50}$ value of a neutralising antibody or binding fragment thereof by at least two-fold, at least three-fold, at least four-fold, at least five-fold, at least six-fold, at least seven-fold, at least eight-fold, at least nine-fold, at least ten-fold or more compared with the $EC_{50}$ value of the neutralising antibody or binding fragment thereof alone. In some preferred embodiments, the non-neutralising antibody or binding fragment thereof decreases the $EC_{80}$ value of the neutralising antibody or binding fragment thereof by at least five-fold, more preferably at least seven-fold, even more preferably at least nine-fold or more compared with the $EC_{80}$ value of the neutralising antibody or binding fragment thereof alone.

Typically the maximum synergistic effect of a non-neutralising antibody of the invention or binding fragment thereof is achieved using a concentration of greater than 1 µg/ml, greater than 10 µg/ml, greater than 50 µg/ml, greater than 100 µg/ml, greater than 150 µg/ml, greater than 200 µg/ml, greater than 250 µg/ml, greater than 300 µg/ml, or more of the non-neutralising antibody or binding fragment thereof. In some preferred embodiments, the maximum synergistic effect of a non-neutralising antibody of the invention or binding fragment thereof is achieved using a concentration of greater than 150 µg/ml, even more preferably greater than 200 µg/ml of the non-neutralising antibody or binding fragment thereof.

The ratio of a neutralising antibody or binding fragment thereof to non-neutralising antibody or binding fragment thereof (nAb:non-nAb) may be about 2:1, about 2.5:1, about 3:1, about 3.5:1, about 4:1 or about 4.5:1. Typically the nAb:non-nAb ratio is about 4:1. The lower the concentration of neutralising antibody or binding fragment thereof, the greater the effect of nAb-biased ratios. Thus, for concentrations of neutralising antibody (or binding fragment thereof) below 100 µg/ml, a nAb:non-nAb ratio of 4:1 is preferred. However, at neutralising antibody (or binding fragment thereof) concentrations above 100 µg/ml, the nAb:non-nAb has less effect, with nAb:non-nAb ratios in the range of 1:4 to 4:1 being roughly equivalent.

Other Binding Compounds

PfRH5 is a component of the mechanism by which the *Plasmodium* parasite invades RBCs. Compounds that specifically bind to PfRH5 inhibit this process and prevent the invasion of RBCs.

Accordingly, other binding compounds and combinations thereof may be used as alternatives to the non-neutralising antibody and neutralising antibody combinations described herein, provided that these combinations of other binding compounds include a non-neutralising binding compound to the epitope identified herein for the non-neutralising antibodies of the invention, and a neutralising binding compound to a *Plasmodium* merozoite antigen as defined herein, and that the non-neutralising binding compound synergises the activity of the neutralising binding compound as for the non-neutralising antibody/neutralising antibody combinations described herein.

Thus, the invention provides a composition comprising: (a) an oligonucleotide aptamer that specifically binds to the non-neutralising epitope of the invention, particularly, an epitope corresponding to residues Ser153 to Ile163 and Aps305 to Lys319 of PfRH5 (SEQ ID NO: 1); and (b) an oligonucleotide aptamer that specifically binds to a *Plasmodium* merozoite antigen as defined herein.

Any of the disclosure herein in relation to non-neutralising antibodies/neutralising antibodies and combinations thereof of the invention applies equally to other binding compounds and combinations thereof.

The non-neutralising and/or neutralising binding compounds of the invention may be oligonucleotide aptamers which bind to the respective epitopes/antigens as defined herein in relation to the corresponding non-neutralising and neutralising antibodies of the invention. The aptamer(s) may specifically bind to the respective epitopes/antigens as defined herein in relation to the corresponding non-neutralising and neutralising antibodies of the invention. Specificity is discussed herein in relation to the antibodies of the invention and applies equally to aptamers (or other binding compounds of the invention).

The activity of neutralising aptamers and the synergistic effect of non-neutralising aptamers may be assessed using a GIA assay. Such aptamers can be found by known methods (e.g. as set out in D. H. J. Bunka, P. G. Stockley, *Nature Reviews Microbiology* 4, 588 (2006)). An aptamer of the invention may be optimised to render it suitable for therapeutic use, e.g. it may be conjugated to a monoclonal antibody to modify its pharmacokinetics (e.g. half-life and biodistribution) and/or recruit Fc-dependent immune functions.

Vectors and Plasmids

The present invention provides vectors that express a non-neutralising antibody of the invention (or other non-neutralising binding compound as defined herein) and a neutralising antibody of the invention (or other neutralising binding compound as defined herein). Typically the vector is present in the form of a vaccine formulation.

The one or more non-neutralising and neutralising antibodies or binding-fragments thereof (or other binding compounds as defined herein) may be expressed by: (i) the same vector; or (ii) by two (or more in the case of multiple antibodies/binding proteins) separate vectors; or (iii) a vector that expresses a bispecific molecule (such as a bispecific dual variable domain molecule as defined herein). The vector(s) may be present in the form of a vaccine formulation.

The invention also provides a vector that expresses the non-neutralising antibody epitope, a vector that expresses one or more neutralising antibody epitope and a vector that expresses the non-neutralising antibody epitope and one or more neutralising antibody epitope of the invention. The vector(s) may be present in the form of a vaccine formulation.

The invention provides a vector that expresses: (a) a non-neutralising antibody epitope of the invention, particularly, an epitope corresponding to residues Ser153 to Ile163 and Aps305 to Lys319 of PfRH5 (SEQ ID NO: 1); and (b) a *Plasmodium* merozoite antigen as defined herein; and optionally (c) one or more additional antigen selected from PfRipr, PfCyRPA, PfP113, PfRhopH3, PfRAP2, PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP, or a fragment thereof; wherein the epitope of (a), the *Plasmodium* merozoite antigen of (b) and optionally the one or more additional antigen of (c) are expressed by: (i) the same vector; or (ii) by separate vectors. The vector(s) may be present in the form of a vaccine formulation.

The vector(s) may be a viral vector. Such a viral vector may be an adenovirus (of a human serotype such as AdHu5, a simian serotype such as ChAd63, ChAdOX1 or ChAdOX2, or another form), an adeno-associated virus (AAV), or poxvirus vector (such as a modified vaccinia Ankara (MVA)). ChAdOX1 and ChAdOX2 are disclosed in WO2012/172277 (herein incorporated by reference in its entirety). ChAdOX2 is a BAC-derived and E4 modified AdC68-based viral vector. Preferably said viral vector is an AAV vector.

Viral vectors are usually non-replicating or replication impaired vectors, which means that the viral vector cannot replicate to any significant extent in normal cells (e.g. normal human cells), as measured by conventional means—e.g. via measuring DNA synthesis and/or viral titre. Non-replicating or replication impaired vectors may have become so naturally (i.e. they have been isolated as such from nature) or artificially (e.g. by breeding in vitro or by genetic manipulation). There will generally be at least one cell-type in which the replication-impaired viral vector can be grown—for example, modified vaccinia Ankara (MVA) can be grown in CEF cells. In one embodiment, the vector is selected from a human or simian adenovirus or a poxvirus vector.

Typically, the viral vector is incapable of causing a significant infection in an animal subject, typically in a mammalian subject such as a human or other primate.

The vector(s) may be a DNA vector, such as a DNA plasmid. In one embodiment the DNA vector(s) is capable of expression in a mammalian cell expression system, such as an immunised cell. The vector may be suitable for expression in a bacterial and/or insect host cell or expression system, such as any of those exemplified herein. A non-limiting example of a suitable expression vector is a pET15b vector, which may be optionally modified to encode an N-terminal tag, such as a hexa-histidine tag and/or a protease cleavage site, such as a TEV protease cleavage site.

The vector(s) may be a RNA vector, such as a self-amplifying RNA vaccine (Geall, A. J. et al., Proc Natl Acad Sci USA 2012; 109(36) pp. 14604-9; incorporated herein by reference).

The present invention may be a phage vector, such as an AAV/phage hybrid vector as described in Hajitou et al., Cell 2006; 125(2) pp. 385-398; herein incorporated by reference.

Vectors of the present invention also include virus-like particles (VLP), soluble proteins and/or fusion proteins comprising non-neutralising antibodies and neutralising antibodies (or other binding compounds), as described herein, or PfRH5 epitopes or *Plasmodium* merozoite antigens as described herein. Typically these comprise or express PfRH5 epitopes or *Plasmodium* merozoite antigens as described herein. Methods for generating VLPs are known in the art (see, for example, Brune et al. Sci. Rep. (2016), 19(6):19234, which is incorporated by reference in its entirety) and can readily be applied to the present invention. References herein to vectors of the invention may apply equally to VLP, soluble proteins and/or fusion proteins of the invention.

The antibodies/binding compounds or epitopes/antigens of the invention may be expressed by in a single vector. Wherein the vector of the invention expresses epitopes/antigens of the invention, the expressed epitopes/antigens are capable of inducing both non-neutralising and neutralising antibodies (or other binding proteins) as described herein. Alternatively, the modified PfRH5 antigen and the one or more additional antigen or fragment thereof may be delivered using a mixture of vectors expressing the individual non-neutralising and neutralising antibodies or epitopes/antigens which induce said antibodies (Forbes, E. K., et al., J Immunol, 2011. 187(7): p. 3738-50; and Sheehy, S. H., et al., Mol Ther, 2012. 20(12): p. 2355-68; both of which are incorporated herein by reference). Where the non-neutralising and neutralising antibodies or epitopes/antigens which induce said antibodies are co-expressed, this may be in the form of a fusion protein (Porter, D. W., et al., Vaccine, 2011. 29(43): p. 7514-22; incorporated herein by reference), or the non-neutralising and neutralising antibodies or epitopes/antigens which induce said antibodies expressed as separate transcripts under the control of separate promoters (Bruder, J. T., et al., Vaccine, 2010. 28(18): p. 3201-10; and Tine, J. A., et al., Infect Immun, 1996. 64(9): p. 3833-44; both of which are incorporated herein by reference), or the non-neutralising and neutralising antibodies or epitopes/antigens which induce said antibodies translated as a single polypeptide which undergoes cleavage to yield two separate antigens (Ibrahimi, A., et al., *Hum Gene Ther,* 2009. 20(8): p. 845-60; incorporated herein by reference).

The antibodies/binding compounds or epitopes/antigens of the invention may include a leader sequence, for example to assist in recombinant production and/or secretion. Any suitable leader sequence may be used, including conventional leader sequences known in the art. Suitable leader sequences include Bip leader sequences, which are commonly used in the art to aid secretion from insect cells and human tissue plasminogen activator leader sequence (tPA), which is routinely used in viral and DNA based vaccines and for protein vaccines to aid secretion from mammalian cell expression platforms. By way of a non-limiting example, the antibodies/binding compounds or epitopes/antigens of the invention may include the secretory signal from bovine tissue plasminogen activator, or may include another signal to direct the subcellular trafficking of the antibodies/binding compounds or epitopes/antigens. Alternatively, the antibodies/binding compounds or epitopes/antigens of the invention may be the mature form in which the N-terminal signal peptide has been removed.

The antibodies/binding compounds or epitopes/antigens of the invention may additionally comprise an N- or C-terminal tag, for example to assist in recombinant production and/or purification. Any N- or C-terminal tag may be used, including conventional tags known in the art. Suitable tags sequences include C-terminal hexa-histidine tags and the "C-tag" (the four amino acids EPEA at the C-terminus), which are commonly used in the art to aid purification from heterologous expression systems, e.g. insect cells, mammalian cells, bacteria, or yeast. Other examples of suitable tags include GST and MBP tags, or any other conventional tag which may be used to facilitate increased expression. In other embodiments, the antibodies/binding compounds or epitopes/antigens of the invention are purified from heterologous expression systems without the need to use a purification tag.

PfRH5 Antigens

The present invention provides PfRH5 antigens that give rise to non-neutralising antibodies as defined herein. The invention also provides PfRH5 antigens which give rise to neutralising antibodies as defined herein. The invention further relates to the use of other *Plasmodium* merozoite antigens which give rise to neutralising antibodies that can be used according to the present invention.

In particular, the invention provides PfRH5 antigens which comprise an epitope within residues corresponding to amino acid residues Ser153 to Ile163 and Aps305 to Lys319 of PfRH5 (SEQ ID NO: 1). As described herein, said antigens give rise to antibodies which are themselves non-neutralising, but which potentiate the activity of neutralising PfRH5 antibodies, and which also synergise with the activity of neutralising antibodies directed to other *Plasmodium* merozoite antigens as defined herein. The structure of such a PfRH5 antigen of the invention is not limited, provided that the epitope is held in the correct confirmation to give rise to non-neutralising antibodies according to the invention.

Full-length PfRH5 is defined by SEQ ID NO: 1 or 2. The mature form of PfRH5 in which the N-terminal signal peptide has been removed may comprise or consist of amino acid residues 26 to 526 of SEQ ID NO: 1 or 2. Said fragments may comprise or consist of at least 21, at least 30, at least 40, at least 50, at least 60, at least 70, at least 80, at least 90, at least 100, 110, 120, 130 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520 or more consecutive amino acid residues in length. Such fragments may have a common antigenic cross-reactivity with said unmodified (full-length) PfRH5 antigen. Unmodified PfRH5 antigens are described in detail in WO2012/114125 (herein incorporated by reference in its entirety).

The inventors have previously described rationally designed fragments of PfRH5 lacking some of the internal disorganised regions. These fragments, including fragments lack the flexible N-terminal domain and/or a flexible central linker. Said flexible N-terminal region of PfRH5 typically comprises amino acid residues corresponding to amino acid residues 1 to 139 or 1 to 159 of SEQ ID NO: 1 or 2. Amino acid residues corresponding to amino acid residues 1 to 23 of SEQ ID NO: 1 or 2 are typically a signal peptide that is cleaved from the mature PfRH5 protein. As used herein, the term flexible N-terminal region may include or exclude the signal peptide. Thus, the term flexible N-terminal region may include the signal peptide and so refer to the amino acids corresponding to amino acid residues 1 to 139 or 1 to 159 of SEQ ID NO: 1 or 2. Alternatively, the term flexible N-terminal region may exclude the signal peptide and so refer to the amino acids corresponding to amino acid residues 24 to 139 or 24 to 159 of SEQ ID NO: 1 or 2. Said flexible disordered central linker region of PfRH5 typically corresponds to amino acid residues 248 to 296 of SEQ ID NO: 1 or 2. The terms "flexible disordered central linker region", "flexible central linker region" and "flexible central linker" are used interchangeable herein. The flexible central linker of PfRH5 as defined herein may comprise or consist of one of the recited sequences or variants thereof. Such rationally designed PfRH5 fragments may be discontinuous (i.e. contain consecutive runs of amino acid sequences that would be separated by additional amino acids in the full-length wild-type PfRH5). These rationally designed fragments are described in detail in WO 2016/016651 (herein incorporated by reference in its entirety).

Optimised PfRH5 fragments, derived from either unmodified PfRH5 or rationally designed PfRH5 fragments have also previously been developed, as described in WO 2018/055331 (herein incorporated by reference in its entirety). Such optimised fragments are typically more stable than the corresponding unmodified PfRH5 antigens, and also have improved expression profiles.

The PfRH5 antigens of the invention which give rise to non-neutralising antibodies of the invention may be derived from unmodified PfRH5 fragments, from rationally designed PfRH5 fragments, or from optimised PfRH5 fragments, provided they retain the epitope corresponding to amino acid residues Ser153 to Ile163 and Asp305 to Lys319 of PfRH5 (SEQ ID NO: 1) in the correct confirmation to give rise to non-neutralising antibodies with the synergistic activity described herein.

The invention provides PfRH5 antigens which comprise an epitope within SEQ ID NO: 3 (RH5ΔN) or SEQ ID NO: 7 (RH5ΔNL). As described herein, said antigens give rise to antibodies which are themselves neutralising, and the activity of which is potentiated by the non-neutralising PfRH5 antibodies of the invention as described herein. Typically, said PfRH5 antigens which give rise to neutralising PfRH5 antibodies of the invention comprise an epitope having residues corresponding to (i) amino acid residues Lys196 to Ser197; Asn347 to Asn352; Arg357 to His365; and Lys443 to Arg448 of PfRH5 (SEQ ID NO: 1); (ii) residues Gly201 to Lys219; and Lys327 to Tyr335 of PfRH5 (SEQ ID NO: 1); residues Gly201 to Lys219 and Lys327 to Gln342 of PfRH5 (SEQ ID NO: 1); or residues Lys196, Ser197, Tyr346 to Asn354 and Lys443 to Lys452 of PfRH5 (SEQ ID NO: 1). The structure of such a PfRH5 antigen of the invention is not limited, provided that the epitope is held in the correct confirmation to give rise to neutralising antibodies according to the invention.

The PfRH5 antigens of the invention which give rise to neutralising anti-PfRH5 antibodies of the invention may be derived from unmodified PfRH5 fragments, from rationally designed PfRH5 fragments, or from optimised PfRH5 fragments (as described above in relation to antigens which give rise to non-neutralising antibodies), provided they retain the epitope within SEQ ID NO: 3 (RH5ΔN) or SEQ ID NO: 7 (RH5ΔNL), and more particularly an epitope corresponding to (i) amino acid residues amino acid residues Lys196 to Ser197; Asn347 to Asn352; Arg357 to His365; and Lys443 to Arg448 of PfRH5 (SEQ ID NO: 1); (ii) residues Gly201 to Lys219; and Lys327 to Tyr335 of PfRH5 (SEQ ID NO: 1); residues Gly201 to Lys219 and Lys327 to Gln342 of PfRH5 (SEQ ID NO: 1); or residues Lys196, Ser197, Tyr346 to Asn354 and Lys443 to Lys452 of PfRH5 (SEQ ID NO: 1) in the correct confirmation to give rise to neutralising antibodies with the activity described herein.

The PfRH5 antigens of the invention (either which give rise to non-neutralising antibodies or to neutralising antibodies) may have variant sequences compared with the PfRH5 sequence (be it a wild-type/unmodified PfRH5 sequence, a rationally designed fragment or optimised PfRH5 sequence) from which it is derived. Such variants may exhibit at least 80%, at least 85%, at least 90%, at least 91%, at least 92%, at least 93%, at least 94%, at least 95%, at least 96%, at least 97% at least 98%, at least 99% or more identity with the PfRH5 sequence from which they are derived.

Conventional methods for determining amino acid sequence identity are known in the art. The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (e.g. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes.

The percent identity is calculated as:

$$\frac{\text{(Total number of identical matches)}}{[\text{length of the longer sequence plus the number of gaps Introduced into the longer sequence in order to align the two sequences}]} \times 100$$

```
BLOSUM62 table
  A  R  N  D  C  Q  E  G  H  I  L  K  M  F  PST W  Y  V

A 4

R-1 5

N-2 0 6

D-2-2 1 6

C 0-3-3-3 9

Q-1 1 0 0-3 5

E-1 0 0 2-4 2 5

G 0-2 0-1-3-2-2 6

H-2 0 1-1-3 0 0-2 8

I-1-3-3-3-1-3-3-4-3 4

L-1-2-3-4-1-2-3-4-3 24

K-1 2 0-1-3 1 1-2-1-3-2 5

M-1-1-2-3-1 0-2-3-2 1 2-1 5

F-2-3-3-3-2-3-3-3-1 0 0-3 0 6

P-1-2-2-1-3-1-1-2-2-3-3-1-2-4 7

S 1-1 1 0-1 0 0 0-1-2-2 0-1-2-1 4

T 0-1 0-1-1-1-1-2-2-1-1-1-1-2-1 1 5

W-3-3-4-4-2-2-3-2-2-3-2-3-1 1-4-3-2 11

Y-2-2-2-3-2-1-2-3 2-1-1-2-1 3-3-2-2 2 7

V 0-3-3-3-1-2-2-3-3 3 1-2 1-1-2-2 0-3-1 4
```

In a homology comparison, the identity may exist over a region of the sequences that is at least 10 amino acid residues in length (e.g. at least 15, 20, 30, 40, 50, 75, 100, 150, 200, 250, 300, 350, 400, 450, 500 or 520 amino acid residues in length)—e.g. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

Typically a PfRH5 antigen of the invention (either which give rise to non-neutralising antibodies or to neutralising anti-PfRH5 antibodies) is at least 12, at least 13, at least ILL at least 15 at least 16 at least 17 at least 18 at least 19 at least 20 at least 21, at least 30, at least 40, at least 50, at least 60, at least 70, at least 80, at least 90, at least 100, 110, 120, 130 140, 150 or more consecutive amino acids in length. The PfRH5 antigens of the invention may be linear or branched, preferably linear.

The PfRH5 antigens of the invention may have substitutions at amino acid residues corresponding to amino acid residue 40 and/or amino acid residue 216 and/or amino acid residue 286 and/or amino acid residue 299 of SEQ ID NO: 1 or 2, wherein the amino acid T is replaced by an amino acid other than T. In one embodiment amino acid residues corresponding to amino acid residues 40, 216, 286 and/or 299 of SEQ ID NO: 1 or 2 are replaced with A. Typically, amino acid residues corresponding to amino acid residues 40, 216, 286 and 299 of SEQ ID NO: 1 or 2 are each replaced with A.

A PfRH5 antigen of the invention may be modified relative to the PfRH5 antigen from which it is derived, provided that: (i) in the case of a PfRH5 antigen that gives rise to a non-neutralising antibody of the invention, the epitope defined herein is retained and the antigen still gives rise to a non-neutralising antibody; or (ii) in the case of a PfRH5 antigen that gives rise to a neutralising antibody of the invention, the epitope defined herein is retained and the antigen still gives rise to a neutralising antibody.

An amino acid modification according to the invention may be a substitution, deletion, addition or other modification, including post-translational modification, unless the relevant disclosure explicitly says otherwise. Preferably said modifications are amino acid substitutions. In other words, the amino acid at a specified position within the PfRH5 antigen of the invention is substituted by a naturally occurring or non-naturally occurring amino acid that is different to the amino acid present at that position in the PfRH5 sequence from which the PfRH5 antigen of the invention is derived. Alternatively, the amino acid at a specified position within the PfRH5 antigen of the invention may be modified post-translationally. Post-translational modifications include glycosylations, acetylations, acylations, de-aminations, phosphorylisations, isoprenylisations, glycosyl phosphatidyl inositolisations and further modifications known to a person skilled in the art.

The modification of one or more amino acid position as described herein may be performed, for example, by specific mutagenesis, or any other method known in the art.

In embodiments in which one or more amino acid position is substituted relative to the corresponding PfRH5 antigen from which the antigen of the invention is derived, the substitution may be a conservative substitution or a non-conservative substitution. A conservative substitution is defined as substitution by an amino acid pertaining to the same physiochemical group to the amino acid present in the PfRH5 antigen from which the antigen of the invention is derived. A non-conservative amino acid substitution is defined as substitution by an amino acid pertaining to a different physiochemical group to the amino acid present in the PfRH5 antigen from which the antigen of the invention is derived. In more detail, amino acids are, in principle, divided into different physiochemical groups. Aspartate and glutamate belong to the negatively-charged amino acids. Histidine, arginine and lysine belong to the positively-charged amino acids. Asparagine, glutamine, serine, threonine, cysteine and tyrosine belong to the polar amino acids. Glycine, alanine, valine, leucine, isoleucine, methionine, proline, phenylalanine and tryptophan belong to the non-polar amino acids. Aromatic side groups are to be found among the amino acids histidine, phenylalanine, tyrosine and tryptophan. Thus, as a non-limiting example, a conservative substation may involve the substitution of a non-polar amino acid by another non-polar amino acid, such as substituting leucine with isoleucine. As another non-limiting example, a non-conservative substitution may involve the substation of a non-polar amino acid (e.g. leucine) with a negatively-charged amino acid (e.g. aspartate), a positively-charged amino acid (e.g. arginine), or a polar amino acid (e.g. asparagine).

Expression Systems

A PfRH5 antibody, binding compound or antigen of the invention may be expressed using any suitable systems.

Generation of antibodies once an epitope has been identified can be carried out using known methods in the art. The antibodies per se can be generated using such methods as mouse hybridomas, phage display or ribosome display. Other methods known to the person skilled in the art may also be used. The resultant functional antibodies from a mouse immunisation or a phage display screen can then have their binding confirmed by epitope mapping. Accordingly, the invention provides a hybridoma expressing any antibody (non-neutralising or neutralising) of the invention.

For example, one could readily determine whether an antibody binds to the epitope of the invention via a reference antibody such as the mAb11 antibody of the invention (for a non-neutralising antibody), or the mAb16 or mAb4 antibodies (for a neutralising antibody).

Such methods are a matter of routine in the art. By way of a non-limiting example, to determine whether a given antibody binds to the same epitope as antibody mAb11, the antibody mAb11 can be bound to PfRH5 under saturating conditions. Subsequently, the antibody of interest can be assessed for binding to PfRH5. If this antibody is capable of binding to PfRH5 following saturation binding with antibody mAb11, it is clear that the two antibodies are binding to different epitopes. If the antibody is not capable of binding to PfRH5 following saturation binding with antibody mAb11, then the antibody may be binding to the epitope of the invention. The binding profile of the antibody of interest should also be taken into consideration: if it binds with similar affinity ($K_D$) and/or potency (GIA) to PfRH5 as antibody mAb11, then this makes it far more likely that it is binding to the epitope of the invention. Conversely, if the binding profiles are very different, this suggests that it is not binding to the epitope of the invention. Additional routine experimentation (such as peptide mutation and binding analyses) can be carried out to confirm whether the observed lack of binding in this situation is in fact due to binding the epitope of the invention or if some other phenomenon (such as steric hindrance) is responsible. Such experiments can be carried out using ELISA, RIA, Biacore, flow cytometry or other known antibody binding assays.

Antigens of the invention may be expressed using conventional systems. Such a system may be a prokaryotic or a eukaryotic system. Examples of such systems are well-known in the art. Non-limiting examples of suitable host systems include *Escherichia coli, Saccharomyces cerevisiae, Pichia pastoris*, non-lytic insect cell expression systems such as Schneider 2 (S2) and Schneider 3 (S3) cells from *Drosophila melanogaster* and Sf9 and Sf21 cells from *Spodoptera frugiperda*, and mammalian expression systems such as CHO cells and human embryonic kidney (HEK/HEK293) cells.

Accordingly, the invention provides a host cell containing a recombinant expression vector which encodes for a PfRH5 antigen of the invention. In a preferred embodiment the host cell is an insect cell, preferably a *Drosophila melanogaster* cell, or a *Pichia* yeast cell, or an *Escherichia coli* cell.

The term antigen as used herein refers to any peptide-based sequence that can be recognised by the immune system and/or that stimulates a cell-mediated immune response and/or stimulates the generation of antibodies. The PfRH5 antigens of the invention may be present in the form of a vaccine composition or vaccine formulation.

As described herein, the PfRH5 antigens of the invention raise non-neutralising or neutralising antibodies as described herein. The neutralising antibodies raised by PfRH5 antigens of the invention inhibit the growth of malarial parasites, i.e. *Plasmodium* parasites, preferably across a plurality of strains of blood-stage *Plasmodium* parasites. In a more preferred embodiment, the PfRH5 antigens of the invention raise neutralising antibodies that inhibit the growth of *Plasmodium falciparum* parasites, and more preferably across a plurality of strains of blood-stage *P. falciparum* parasites. The effectiveness of the PfRH5 antigens of the invention may be quantified using any appropriate technique and measured in any appropriate units. For example, the effectiveness of the PfRH5 antigens of the invention may be given in terms of their growth inhibitory activity (GIA), half maximal effective concentration ($EC_{50}$), antibody titre stimulated (in terms of antibody units, AU) and/or $EC_{50}$ in terms of AU (described herein in relation to antibodies of the invention). The latter of these gives an indication of the quality of the antibody response stimulated by the PfRH5 antigen of the invention. Any appropriate technique may be used to determine the GIA, $EC_{50}$, AU or $EC_{50}$/AU. Exemplary techniques are described in the examples and conventional techniques are known in the art. The disclosure herein in relation to quantifying the effectiveness of the antibodies of the invention applies equally to antibodies raised by PfRH5 antigens or epitopes of the invention.

The antibodies/binding compounds or epitopes/antigens of the invention may be expressed by in a single vector. Wherein the vector of the invention expresses epitopes/antigens of the invention, the expressed epitopes/antigens are capable of inducing both non-neutralising and neutralising antibodies (or other binding proteins) as described herein. Alternatively the combination of the non-neutralising and neutralising antibodies of the invention, or the combination of the corresponding epitopes/antigens, can be effected by mixing two separate recombinant protein vaccines (Pichyangkul, S., et al., Vaccine, 2009. 28(2): p. 452-62; and Ellis, R. D., et al., PLoS One, 2012. 7(10): p. e46094; both of which are incorporated herein by reference), or by co-delivery using vaccine platforms such as particle-based protein vaccine delivery (Bachmann, M. F., et al., Nat Rev Immunol, 2010. 10(11): p. 787-96; incorporated herein by reference), or virus-like particles (VLP), or by fusing or conjugating the PfRH5 epitopes/antigens to a construct or constructs that allow for particle formation and/or enhanced immunogenicity (Spencer, A. J., et al., PLoS One, 2012. 7(3): p. e33555; and Wu, Y., et al., Proc Natl Acad Sci USA, 2006. 103(48): p. 18243-8; both of which are incorporated herein by reference). In one embodiment, the PfRH5 antigen/epitope that gives rise to a non-neutralising antibody and the PfRH5 antigen/epitope that gives rise to a neutralising antibody may be delivered as a fusion protein (Biswas, S., et al., PLoS One, 2011. 6(6): p. e20977; incorporated herein by reference). Additionally or alternatively, the PfRH5 antigen/epitope that gives rise to a non-neutralising antibody and the PfRH5 antigen/epitope that gives rise to a neutralising antibody (or the non-neutralising antibody and neutralising antibodies themselves) may be delivered using a mixture of viral vectors expressing the individual antigens/epitopes (or antibodies) (Forbes, E. K., et al., J Immunol, 2011. 187(7): p. 3738-50; and Sheehy, S. H., et al., Mol Ther, 2012. 20(12): p. 2355-68; both of which are incorporated herein by reference), or viral vectors co-expressing both the PfRH5 antigen/epitope that gives rise to a non-neutralising antibody and the PfRH5 antigen/epitope that gives rise to a neutralising antibody (or the antibodies themselves). Co-expression may be in the form of a fusion protein (Porter, D. W., et al., Vaccine, 2011. 29(43): p. 7514-22; incorporated herein by reference), or as separate transcripts under the control of separate promoters (Bruder, J. T., et al., Vaccine, 2010. 28(18): p. 3201-10; and Tine, J. A., et al., Infect Immun, 1996. 64(9): p. 3833-44; both of which are incorporated herein by reference), or as a single polypeptide which undergoes cleavage to yield two separate antigens/epitopes (or antibodies) (Ibrahimi, A., et al., *Hum Gene Ther*, 2009. 20(8): p. 845-60; incorporated herein by reference).

Therapeutic Indications

The present invention also provides a method of stimulating or inducing an immune response in a subject comprising administering to the subject a composition of the invention, one or more antibodies of the invention, one or more binding proteins of the invention, one or more vectors of the invention, or one or more epitopes/antigens of the invention (as described above).

Thus, the invention provides a vaccine composition comprising a composition of the invention; a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention.

In one embodiment, the method of stimulating or inducing an immune response in a subject comprises administering a composition of the invention (including a vaccine composition); a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above) to a subject. In the context of the therapeutic uses and methods, a "subject" is any animal subject that would benefit from stimulation or induction of an immune response against a *Plasmodium* parasite. Typical animal subjects are mammals, such as primates, for example, humans.

Thus, the present invention provides a method for treating or preventing malaria.

The present invention also provides a composition of the invention (including a vaccine composition); a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention for use in the prevention or treatment of malaria.

The present invention also provides the use of a composition of the invention (including a vaccine composition); a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention in the manufacture of a medicament for the prevention and/or treatment of malaria.

The one or more epitopes/antigens of the invention may be in the form of a recombinant protein, a protein particle, a virus-like particle, a fusion protein, or a combination thereof as described herein. In addition, the one or more epitopes/antigens of the invention may be used in combination with one or more further antigens selected from the group consisting of PfRipr, PfCyRPA, PfP113, PfRhopH3, PfRAP2, PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP, or a fragment thereof; for use in prevention or treatment of malaria.

The present invention provides the use of a composition of the invention (including a vaccine composition); a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above) for use either alone or in combination in the prevention or treatment of malaria.

In one embodiment, the method for treating or preventing malaria comprises administering a therapeutically effective amount of a composition of the invention (including a vaccine composition); a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above), either alone or in combination, to a subject.

Vaccine compositions of the invention, whilst they may express or display an epitope as defined herein, or induce an antibody as defined herein, typically do not express or display the full-length PfRH5 protein. Instead, such vaccine compositions of the invention express or display rationally designed fragments of PfRH5 which comprise or consist of one or more epitope as defined herein, or otherwise induce an antibody as defined herein. Nor do vaccine compositions of the invention comprise or consist of the full-length PfRH5 protein, but rather such vaccines of the invention comprise or consist of rationally designed fragments of PfRH5 which comprise or consist of one or more epitope as defined herein, or otherwise induce an antibody as defined herein.

As used herein, the term "treatment" or "treating" embraces therapeutic or preventative/prophylactic measures, and includes post-infection therapy and amelioration of malaria.

As used herein, the term "preventing" includes preventing the initiation of malaria and/or reducing the severity or intensity of malaria. The term "preventing" includes inducing or providing protective immunity against malaria. Immunity to malaria may be quantified using any appropriate technique, examples of which are known in the art.

A composition of the invention (including a vaccine composition), a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above) may be administered to a subject (typically a mammalian subject such as a human or other primate) already having malaria, a condition or symptoms associated with malaria, to treat or prevent malaria. For example, the subject may be suspected of having come in contact with *Plasmodium* parasite, or has had known contact with *Plasmodium* parasite, but is not yet showing symptoms of exposure.

When administered to a subject (e.g. a mammal such as a human or other primate) that already has malaria, or is showing symptoms associated with *Plasmodium* parasite infection, a composition of the invention (including a vaccine composition), a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above) can cure, delay, reduce the severity of, or ameliorate one or more symptoms, and/or prolong the survival of a subject beyond that expected in the absence of such treatment.

Alternatively, a composition of the invention (including a vaccine composition), a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (as described above) may be administered to a subject (e.g. a mammal such as a human or other primate) who ultimately may be infected with *Plasmodium* parasite, in order to prevent, cure, delay, reduce the severity of, or ameliorate one or more symptoms of malaria, or in order to prolong the survival of a subject beyond that expected in the absence of such treatment, or to help prevent that subject from transmitting malaria.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The present invention provides vaccine compositions comprising any of the compositions of the invention; non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention (described herein). Said vaccine compositions may further comprise one or more additional malarial antigens as described herein, and/or any further components as described herein.

A vaccine composition of the invention may further comprise one or more additional neutralising antibody to, a bispecific dual variable domain molecule binding to; a viral vector, RNA vaccine or DNA plasmid expressing such an antibody or binding molecule, or one or more epitopes/antigens (or vectors expressing) one or more additional antigen selected from the group consisting of PfRipr, PfCyRPA, PfP113, PfRhopH3, PfRAP2, PfAMA1, PfRON2, PfEBA175, PfRH1, PfRH2a, PfRH2b, PfRH4, PfRAP1, PfRAP3, PfMSRP5, PfRAMA, PfSERA9, PfEBA181 and PfAARP, or a fragment thereof. These may be expressed in any suitable form. As a non-limiting example, expression may be as a virus like particle (VLP). Recombinant particulate vaccines are well known in the art. They may be, for example, either fusion proteins or proteins chemically conjugated to particles. Examples of fusion proteins are hepatitis B surface antigen fusions (e.g. as in the RTS,S malaria vaccine candidate), hepatitis B core antigen fusions, or Ty-virus like particles. Examples of chemical fusion particles are the Q-beta particles under development by the biotechnology company Cytos (Zurich, Switzerland) and as in Brune et al. Sci. Rep. (2016), 19(6):19234.

The present invention further provides a vaccine composition comprising a PfRH5 epitope of the invention (which gives rise to a non-neutralising but synergistic antibody) and a *Plasmodium* merozoite antigen of the invention (which gives rise to a neutralising antibody synergised by the non-neutralising antibody of the invention). Optionally said vaccine may further comprise one or more additional antigen or a fragment thereof to an additional malarial antigen as described herein (particularly PfRipr or PfCyRPA or a fragment thereof), where either or both the PfRH5 epitope, the *Plasmodium* merozoite antigen and/or the one or more additional antigen or fragment thereof may be expressed as a soluble recombinant protein. Recombinant protein-based vaccines are well known in the art. They may be, for example, monomeric soluble proteins or soluble fusion proteins. Such proteins are typically administered or formulated in a vaccine adjuvant. Examples of protein-based vaccines are diphtheria and tetanus toxoids, or soluble malaria protein antigens such as the PfAMA1 protein vaccine candidates developed for blood-stage malaria (Spring, M. D., et al., PLoS ONE, 2009. 4(4): p. e5254; incorporated herein by reference).

The compositions of the invention; non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention (described herein) may be combined to provide a single vaccine product (as described above), e.g. by mixing two separate vaccines, or by co-delivery using vaccine platforms such as particle-based protein vaccine delivery, or by using a mixture of viral vectors expressing the individual components, or viral vectors co-expressing both components.

As used, herein, a "vaccine" is a formulation that, when administered to an animal subject such as a mammal (e.g. a human or other primate) stimulates or provides a protective immune response against *Plasmodium* parasitic infection. The immune response may be a humoral and/or cell-mediated immune response. A vaccine of the invention can be used, for example, to protect a subject from the effects of *P. falciparum* infection (i.e. malaria).

The lack of polymorphism at the PfRH5 locus (five non-synonymous SNP across its entire length in circulating *P. falciparum* parasites) suggest either a lack of substantial immune pressure, or a high degree of functional constraint that prevents mutations from freely occurring. This property makes it highly likely that the vaccine compositions comprising any of the compositions of the invention; non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention (described herein) according to the present invention will have broadly neutralising activity.

Thus, the compositions of the invention; non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention (described herein) typically provide a highly effective cross-strain GIA against the *Plasmodium* parasite. Thus, in one embodiment, the invention provides protection (such as long term protection) against disease caused by *Plasmodium* parasites. Typically, a composition of the invention; a non-neutralising antibody, or binding fragment thereof, of the invention and a neutralising antibody, or binding fragment thereof, of the invention; a bispecific dual variable domain molecule of the invention; a viral vector, RNA vaccine or DNA plasmid of the invention, or one or more epitopes/antigens of the invention (described herein) provides an antibody response (e.g. a neutralising antibody response) to *Plasmodium* parasitic infection. The compositions of the invention; non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention as described herein may be used to confer pre-erythrocytic or transmission-blocking protection against *Plasmodium* parasites.

The treatment and/or prevention of malaria according to the present invention may further comprise boosting a subject. Such "boosting" may comprise the administration of a pox virus, such as MVA.

Pharmaceutical Compositions and Formulations

The term "vaccine" is herein used interchangeably with the terms "therapeutic/prophylactic composition", "formulation" or "medicament".

The vaccine of the invention (as defined above) can be combined or administered in addition to a pharmaceutically acceptable carrier. Alternatively or in addition the vaccine of the invention can further be combined with one or more of a salt, excipient, diluent, adjuvant, immunoregulatory agent and/or antimicrobial compound.

Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations (e.g. vaccines) is generally by conventional routes e.g. intravenous, subcutaneous, intraperitoneal, or mucosal routes. The administration may be by parenteral injection, for example, a subcutaneous, intradermal or intramuscular injection. Formulations comprising neutralizing antibodies may be particularly suited to administration intravenously, intramuscularly, intradermally, or subcutaneously.

Accordingly, immunogenic compositions, therapeutic formulations, medicaments and prophylactic formulations (e.g. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients (such as the non-neutralising antibodies, or binding fragments thereof, of the invention and the neutralising antibodies, or binding fragments thereof, of the invention; the bispecific dual variable domain molecules of the invention; the viral vectors, RNA vaccines or DNA plasmids of the invention, or one or more epitopes/antigens of the invention) are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freund's adjuvant (CFA), Incomplete Freund's adjuvant (IFA), Saponin, a purified extract fraction of Saponin such as Quil A, a derivative of Saponin such as QS-21, lipid particles based on Saponin such as ISCOM/ISCOMATRIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, ASO1, AS03 and ASO4 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

It is within the routine practice of a clinician to determine an effective amount of a vaccine composition of the invention. An effective amount is an amount sufficient to elicit a protective immune response against malaria. A clinician will also be able to determine appropriate dosage interval using routine skill.

Sequence Information

PfRH5 Antigens from which Antigens/Epitopes of the Invention May be Derived

Full Length PfRH5 Amino Acid Sequence (3D7) Including Signal Sequence: SEQ ID NO: 1

```
  1   MIRIKKKLIL TIIYIHLFIL NRLSFENAIK KTKNQENNLT LLPIKSTEEE KDDIKNGKDI

61   KKEIDNDKEN IKTNNAKDHS TYIKSYLNTN VNDGLKYLFI PSHNSFIKKY SVFNQINDGM

121   LLNEKNDVKN NEDYKNVDYK NVNFLQYHFK ELSNYNIANS IDILQEKEGH LDFVIIPHYT

181   FLDYYKHLSY NSIYHKSSTY GKCIAVDAFI KKINETYDKV KSKCNDIKND LIATIKKLEH

241   PYDINNKNDD SYRYDISEEI DDKSEETDDE TEEVEDSIQD TDSNHTPSNK KKNDLMNRTF

301   KKMMDEYNTK KKKLIKCIKN HENDFNKICM DMKNYGTNLF EQLSCYNNNF CNTNGIRYHY

361   DEYIHKLILS VKSKNLNKDL SDMTNILQQS ELLLTNLNKK MGSYIYIDTI KFIHKEMKHI

421   FNRIEYHTKI INDKTKIIQD KIKLNIWRTF QKDELLKRIL DMSNEYSLFI TSDHLRQMLY

481   NTFYSKEKHL NNIFHHLIYV LQMKFNDVPI KMEYFQTYKK NKPLTQ
```

Signal sequence (amino acids 1 to 23) is in bold italics, flexible N-terminal (amino acids 1 to 139) and flexible loop (amino acids 248 to 296) regions are underlined.

The (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

Full Length PfRH5 Amino Acid Sequence (7G8) Including Signal Sequence: SEQ ID NO: 2

```
  1   MIRIKKKLIL TIIYIHLFIL NRLSFENAIK KTKNQENNLT LLPIKSTEEE KDDIKNGKDI

61   KKEIDNDKEN IKTNNAKDHS TYIKSYLNTN VNDGLKYLFI PSHNSFIKKY SVFNQINDGM

121   LLNEKNDVKN NEDYKNVDYK NVNFLQYHFK ELSNYNIANS IDILQEKEGH LDFVIIPHYT

181   FLDYYKHLSY NSIYHKSSTY GKYIAVDAFI KKINETYDKV KSKCNDIKND LIATIKKLEH

241   PYDINNKNDD SYRYDISEEI DDKSEETDDE TEEVEDSIQD TDSNHTPSNK KKNDLMNRTF

301   KKMMDEYNTK KKKLIKCIKN HENDFNKICM DMKNYGTNLF EQLSCYNNNF CNTNGIRYHY

361   DEYIHKLILS VKSKNLNKDL SDMTNILQQS ELLLTNLNKK MGSYIYIDTI KFIHKEMKHI

421   FNRIEYHTKI INDKTKIIQD KIKLNIWRTF QKDELLKRIL DMSNEYSLFI TSDHLRQMLY

481   NTFYSKEKHL NNIFHHLIYV LQMKFNDVPI KMEYFQTYKK NKPLTQ
```

Signal sequence (amino acids 1 to 23) is in bold italics, flexible N-terminal (amino acids 1 to 139) and flexible loop (amino acids 248 to 296) regions are underlined.

The (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

PfRH5 Amino Acid Sequence (3D7) Excluding Signal Sequence and Flexible N-Terminal Region (Amino Acids 1 to 139): SEQ ID NO: 3 (3D7 RH5ΔN)

```
  1 KNVNFLQYHF KELSNYNIAN SIDILQEKEG HLDFVIIPHY TFLDYYKHLS YNSIYHKSST

61 YGKCIAVDAF IKKINETYDK VKSKCNDIKN DLIATIKKLE HPYDINNKND DSYRYDISEE

121 IDDKSEETDD ETEEVEDSIQ DTDSNHTPSN KKKNDLMNRT FKKMMDEYNT KKKKLIKCIK

181 NHENDFNKIC MDMKNYGTNL FEQLSCYNNN FCNTNGIRYH YDEYIHKLIL SVKSKNLNKD

241 LSDMTNILQQ SELLLTNLNK KMGSYIYIDT IKFIHKEMKH IFNRIEYHTK IINDKTKIIQ

301 DKIKLNIWRT FQKDELLKRI LDMSNEYSLF ITSDHLRQML YNTFYSKEKH LNNIFHHLIY

361 VLQMKFNDVP IKMEYFQTYK KNKPLTQ
```

Flexible loop (corresponding to amino acids 248 to 296 of full length PfRH5 of SEQ ID NO: 1) region is underlined.
The (discontinuous) epitope for the non-neutralising antibodies of the invention is shown in broken underline.
The (discontinuous) epitope for the neutralising mAb4 antibody of the invention is shown in double underline.
The (discontinuous) epitope for the neutralising mAb16 antibody of the invention is shown in wavy underline.

PfRH5 Amino Acid Sequence (7G8) Excluding Signal Sequence and Flexible N-Terminal Region (Amino Acids 1 to 139): SEQ ID NO: 4 (7G8 RH5ΔN)

```
  1 KNVNFLQYHF KELSNYNIAN SIDILQEKEG HLDFVIIPHY TFLDYYKHLS YNSIYHKSST

61 YGKYIAVDAF IKKINETYDK VKSKCNDIKN DLIATIKKLE HPYDINNKND DSYRYDISEE

121 IDDKSEETDD ETEEVEDSIQ DTDSNHTPSN KKKNDLMNRT FKKMMDEYNT KKKKLIKCIK

181 NHENDFNKIC MDMKNYGTNL FEQLSCYNNN FCNTNGIRYH YDEYIHKLIL SVKSKNLNKD

241 LSDMTNILQQ SELLLTNLNK KMGSYIYIDT IKFIHKEMKH IFNRIEYHTK IINDKTKIIQ

301 DKIKLNIWRT FQKDELLKRI LDMSNEYSLF ITSDHLRQML YNTFYSKEKH LNNIFHHLIY

361 VLQMKFNDVP IKMEYFQTYK KNKPLTQ
```

Flexible loop (corresponding to amino acids 248 to 296 of full length PfRH5 of SEQ ID NO: 2) region is underlined.
The (discontinuous) epitope for the non-neutralising antibodies of the invention is shown in broken underline.
The (discontinuous) epitope for the neutralising mAb4 antibody of the invention is shown in double underline.
The (discontinuous) epitope for the neutralising mAb16 antibody of the invention is shown in wavy underline.

PfRH5 Amino Acid Sequence (3D7) Excluding Signal Sequence and Flexible N-Terminal Region (Amino Acids 1 to 159): SEQ ID NO: 5

```
  1 SIDILQEKEG HLDFVIIPHY TFLDYYKHLS YNSIYHKSST YGKCIAVDAF IKKINETYDK

61 VKSKCNDIKN DLIATIKKLE HPYDINNKND DSYRYDISEE IDDKSEETDD ETEEVEDSIQ

121 DTDSNHTPSN KKKNDLMNRT FKKMMDEYNT KKKKLIKCIK NHENDFNKIC MDMKNYGTNL

181 FEQLSCYNNN FCNTNGIRYH YDEYIHKLIL SVKSKNLNKD LSDMTNILQQ SELLLTNLNK

241 KMGSYIYIDT IKFIHKEMKH IFNRIEYHTK IINDKTKIIQ DKIKLNIWRT FQKDELLKRI
```

```
301 LDMSNEYSLF ITSDHLRQML YNTFYSKEKH LNNIFHHLIY VLQMKFNDVP IKMEYFQTYK

361 KNKPLTQ
```

Flexible loop (corresponding to amino acids 248 to 296 of full length PfRH5 of SEQ ID NO: 1) region is underlined.

Partial (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

PfRH5 Amino Acid Sequence (7G8) Excluding Signal Sequence and Flexible N-Terminal Region (Amino Acids 1 to 159): SEQ ID NO: 6

```
  1 SIDILQEKEG HLDFVIIPHY TFLDYYKHLS YNSIYHKSST YGKCIAVDAF IKKINETYDK

61 VKSKCNDIKN DLIATIKKLE HPYDINNKND DSYRYDISEE IDDKSEETDD ETEEVEDSIQ

121 DTDSNHTPSN KKKNDLMNRT FKKMMDEYNT KKKKLIKCIK NHENDFNKIC MDMKNYGTNL

181 FEQLSCYNNN FCNTNGIRYH YDEYIHKLIL SVKSKNLNKD LSDMTNILQQ SELLLTNLNK

241 KMGSYIYIDT IKFIHKEMKH IFNRIEYHTK IINDKTKIIQ DKIKLNIWRT FQKDELLKRI

301 LDMSNEYSLF ITSDHLRQML YNTFYSKEKH LNNIFHHLIY VLQMKFNDVP IKMEYFQTYK

361 KNKPLTQ
```

Flexible loop (corresponding to amino acids 248 to 296 of full length PfRH5 of SEQ ID NO: 2) region is underlined.

Partial (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

PfRH5 Amino Acid Sequence (3D7) Excluding Signal Sequence, Flexible N-Terminal (Amino Acids 1 to 139) and Flexible Loop (Amino Acids 248 to 296) Regions: SEQ ID NO: 7 (3D7 RH5ΔNL)

```
  1 KNVNFLQYHF KELSNYNIAN SIDILQEKEG HLDFVIIPHY TFLDYYKHLS YNSIYHKSST

61 YGKYIAVDAF IKKINETYDK VKSKCNDIKN DLIATIKKLE HPYDINNKNR TFKKMMDEYN

121 TKKKKLIKCI KNHENDFNKI CMDMKNYGTN LFEQLSCYNN NFCNTNGIRY HYDEYIHKLI

181 LSVKSKNLNK DLSDMTNILQ QSELLLTNLN KKMGSYIYID TIKFIHKEMK HIFNRIEYHT

241 KIINDKTKII QDKIKLNIWR TFQKDELLKR ILDMSNEYSL FITSDHLRQM LYNTFYSKEK

301 HLNNIFHHLI YVLQMKFNDV PIKMEYFQTY KKNKPLTQ
```

The (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

PfRH5 Amino Acid Sequence (7G8) Excluding Signal Sequence, Flexible N-Terminal (Amino Acids 1 to 139) and Flexible Loop (Amino Acids 248 to 296) Regions: SEQ ID NO: 8 (7G8 RH5ΔNL)

```
  1 KNVNFLQYHF KELSNYNIAN SIDILQEKEG HLDFVIIPHY TFLDYYKHLS YNSIYHKSST

61 YGKYIAVDAF IKKINETYDK VKSKCNDIKN DLIATIKKLE HPYDINNKNR TFKKMMDEYN

121 TKKKKLIKCI KNHENDFNKI CMDMKNYGTN LFEQLSCYNN NFCNTNGIRY HYDEYIHKLI

181 LSVKSKNLNK DLSDMTNILQ QSELLLTNLN KKMGSYIYID TIKFIHKEMK HIFNRIEYHT

241 KIINDKTKII QDKIKLNIWR TFQKDELLKR ILDMSNEYSL FITSDHLRQM LYNTFYSKEK

301 HLNNIFHHLI YVLQMKFNDV PIKMEYFQTY KKNKPLTQ
```

The (discontinuous) epitope for the non-neutralising antibodies of the invention is shown in broken underline.
The (discontinuous) epitope for the neutralising mAb4 antibody of the invention is shown in double underline.
The (discontinuous) epitope for the neutralising mAb16 antibody of the invention is shown in wavy underline.

PfRH5 Amino Acid Sequence (3D7) Excluding Signal Sequence, Flexible N-Terminal (Amino Acids 1 to 159) and Flexible Loop (Amino Acids 248 to 296) Regions: SEQ ID NO: 9

```
  1 SIDILQEKEG HLDFVIIPHY TFLDYYKHLS YNSIYHKSST YGKCIAVDAF IKKINETYDK

61 VKSKCNDIKN DLIATIKKLE HPYDINNKNR TFKKMMDEYN TKKKKLIKCI KNHENDFNKI

121 CMDMKNYGTN LFEQLSCYNN NFCNTNGIRY HYDEYIHKLI LSVKSKNLNK DLSDMTNILQ

181 QSELLLTNLN KKMGSYIYID TIKFIHKEMK HIFNRIEYHT KIINDKTKII QDKIKLNIWR

241 TFQKDELLKR ILDMSNEYSL FITSDHLRQM LYNTFYSKEK HLNNIFHHLI YVLQMKFNDV

301 PIKMEYFQTY KKNKPLTQ
```

Partial (discontinuous) epitope for the non-neutralising antibodies of the invention is shown in broken underline.
The (discontinuous) epitope for the neutralising mAb4 antibody of the invention is shown in double underline.
The (discontinuous) epitope for the neutralising mAb16 antibody of the invention is shown in wavy underline.

PfRH5 Amino Acid Sequence (7G8) Excluding Signal Sequence, Flexible N-Terminal (Amino Acids 1 to 159) and Flexible Loop (Amino Acids 248 to 296) Regions: SEQ ID NO: 10

```
  1 SIDILQEKEG HLDFVIIPHY TFLDYYKHLS YNSIYHKSST YGKCIAVDAF IKKINETYDK

61 VKSKCNDIKN DLIATIKKLE HPYDINNKNR TFKKMMDEYN TKKKKLIKCI KNHENDFNKI

121 CMDMKNYGTN LFEQLSCYNN NFCNTNGIRY HYDEYIHKLI LSVKSKNLNK DLSDMTNILQ

181 QSELLLTNLN KKMGSYIYID TIKFIHKEMK HIFNRIEYHT KIINDKTKII QDKIKLNIWR

241 TFQKDELLKR ILDMSNEYSL FITSDHLRQM LYNTFYSKEK HLNNIFHHLI YVLQMKFNDV

301 PIKMEYFQTY KKNKPLTQ
```

Partial (discontinuous) epitope for the non-neutralising antibodies of the invention is shown in broken underline.

The (discontinuous) epitope for the neutralising mAb4 antibody of the invention is shown in double underline.

The (discontinuous) epitope for the neutralising mAb16 antibody of the invention is shown in wavy underline.

Heavy Chain CDR Sequences for Non-Neutralising Antibodies of the Invention

| Antibody | CDR1 (SEQ ID NO) | CDR2 (SEQ ID NO) | CDR3 (SEQ ID NO) |
|---|---|---|---|
| mAb11 | SYAMN (11) | WINTNTGNPTY AQGFTG (12) | ESPNYYDSSGYY SGYYFDY (13) |
| mAb14 | DYAMH (14) | GISWNSASMDY ADSVKG (15) | DPAPPYCGGDCY PSFDY (16) |
| mAb10 | SYWMS (17) | NIKQDGSEKYY VDSVKG (18) | GASGYYYNYGM DV (19) |

Light Chain CDR Sequences for Non-Neutralising Antibodies of the Invention

| Antibody | CDR1 (SEQ ID NO) | CDR2 (SEQ ID NO) | CDR3 (SEQ ID NO) |
|---|---|---|---|
| mAb11 | GGKNIGSKSVH (20) | DDSDRPS (21) | QVWDSSSDHRV (22) |
| mAb14 | GNNIGSKSVH (23) | YDSDRPS (24) | QVWDSSRDHVV (25) |
| mAb10 | GGNNIGIKSVH (26) | DDSDRPS (21) | QVWDSSSDHPGV (27) |

Heavy Chain Framework Region Sequences Non-Neutralising Antibodies of the Invention

| Antibody | FR1 (SEQ ID NO) | FR2 (SEQ ID NO) | FR3 (SEQ ID NO) | FR4 (SEQ ID NO) |
|---|---|---|---|---|
| mAb11 | EVQLVQSGSDLKKP GASVKVSCKASGYT FT (28) | WVRQAPGQGLEWVG (29) | RFVFSLDTSVSTAY LQISSLKAEDTAVY YCAR (30) | WGQGTLVTVSS (31) |
| mAb14 | EVQLVESGGGLVQP GRSLRLSCAASGFT FD (32) | WVRQAPGKGLEWVS (33) | RFTISRDNAKNSLY LQMNSLRAEDTALY YCAK (34) | WGQGTLVTVSS (31) |
| MAb10 | EVQLVESGGGLVQP GGSLRLSCAASGFT FS (35) | WVRQAPGKGLEWVA (36) | RFTISGDNAKNSLY LQMNSLRAEDTAVY YCAR (37) | WGQGTRVTVSS (38) |

Light Chain Framework Region Sequences Non-Neutralising Antibodies of the Invention

| Antibody | FR1 (SEQ ID NO) | FR2 (SEQ ID NO) | FR3 (SEQ ID NO) | FR4 (SEQ ID NO) |
|---|---|---|---|---|
| mAb11 | SYELTQPPSVSVAPGWYQQKPGQAPVLVVYGIPERFSGSNSGNTA QTATITC (39) | (40) | TLTISRVEAGDEADY YC (41) | FGGGTKLTVLGQP (42) |
| mAb14 | SYELTQPPSMSVAPGWYQQKPGQAPVLVIYGIPERFSGSNSGNTA KTARITCG (43) | (44) | TLTISRVEAGDEADY YC (41) | FGGGTKLTVLGQP (42) |
| mAb10 | QPVLTQPPSVSVAPGWYQQKPGQAPVLVVYGIPERFSGSNSANTA QTARITC (45) | (40) | TLTISRVEAGDEADY FC (46) | FGGGTKLTVLGQP (42) |

VH and VL Sequences for Non-Neutralising Antibodies of the Invention

| Antibody | VH (SEQ ID NO) | VL (SEQ ID NO) |
|---|---|---|
| mAb11 | EVQLVQSGSDLKKPGASVKVSCKASGYTFTS YAMNWVRQAPGQGLEWVGWINTNTGNPTYAQ GFTGRFVFSLDTSVSTAYLQISSLKAEDTAV YYCARESPNYYDSSGYYSGYYFDYWGQGTLV TVSS (47) | SYELTQPPSVSVAPGQTATITCGGKNIGSKS VHWYQQKPGQAPVLVVYDDSDRPSGIPERFS GSNSGNTATLTISRVEAGDEADYYCQVWDSS SDHRVFGGGTKLTVLGQP (48) |

| Antibody | VH (SEQ ID NO) | VL (SEQ ID NO) |
|---|---|---|
| mAb14 | EVQLVESGGGLVQPGRSLRLSCAASGFTFDD YAMHWVRQAPGKGLEWVSGISWNSASMDYAD SVKGRFTISRDNAKNSLYLQMNSLRAEDTAL YYCAKDPAPPYCGGDCYPSFDYWGQGTLVTV SS (49) | SYELTQPPSMSVAPGKTARITCGGNNIGSKS VHWYQQKPGQAPVLVIYYDSDRPSGIPERFS GSNSGNTATLTISRVEAGDEADYYCQVWDSS RDHVVFGGGTKLTVLGQP (50) |
| MAbi0 | EVQLVESGGGLVQPGGSLRLSCAASGFTFSS YWMSWVRQAPGKGLEWVANIKQDGSEKYYVD SVKGRFTISGDNAKNSLYLQMNSLRAEDTAV YYCARGASGYYYYNYGMDVWGQGTRVTVSS (51) | QPVLTQPPSVSVAPGQTARITCGGNNIGIKS VHWYQQKPGQAPVLVVYDDSDRPSGIPERFS GSNSANTATLTISRVEAGDEADYFCQVWDSS SDHPGVFGGGTKLTVLGQP (52) |

Epitope for the Non-Neutralising Antibodies of the Invention: SEQ ID NO: 53

SNYNIANSID IDEYNTKKKK LIKCIK

This is a non-linear epitope corresponding to residues Ser153 to Ile163 and Asp305 to Lys319 of SEQ ID NO: 1 or 2

Heavy Chain CDR Sequences for Neutralising Antibodies of the Invention

| Antibody | CDR1 (SEQ ID NO) | CDR2 (SEQ ID NO) | CDR3 (SEQ ID NO) |
|---|---|---|---|
| mAb16 | SYGIS (54) | WISGYDGNTNY AQKLQG (55) | DGPQVGDFDWQ VYYYYGMDV (56) |
| mAb4 | NYAIN (57) | GIIPIFATTNY AQKFQG (58) | DKHSWSYAFDI (59) |

Light Chain CDR Sequences for Neutralising Antibodies of the Invention

| Antibody | CDR1 (SEQ ID NO) | CDR2 (SEQ ID NO) | CDR3 (SEQ ID NO) |
|---|---|---|---|
| mAb16 | RASQSINTWLA (60) | KASSLES (61) | QQYNSYLYT (62) |
| mAb4 | SGSSSNIGSNTVN (63) | SNNQRPS (64) | AAWDDSLNGWV (65) |

Heavy Chain Framework Region Sequences Neutralising Antibodies of the Invention

| Antibody | FR1 (SEQ ID NO) | FR2 (SEQ ID NO) | FR3 (SEQ ID NO) | FR4 (SEQ ID NO) |
|---|---|---|---|---|
| mAb16 | AIRMTQSP STLSASVG DRVTITC (73) | WYQQKPGK APNLLIS (74) | GVPSRFSG SGSGTEF TLTISSL QPDDFAT YFC (75) | FGQGTKV EIRRTV (76) |
| mAb4 | QSVLTQPP SASGTPG LRVTISC (77) | WYQHLPG TAPKLLIH (78) | GVPDRFSG SKSGTSAS LAISGLQS EDEADYYC (79) | FGGGTKL TVLGQP (80) |

Light Chain Framework Region Sequences Neutralising Antibodies of the Invention

| Antibody | FR1 (SEQ ID NO) | FR2 (SEQ ID NO) | FR3 (SEQ ID NO) | FR4 (SEQ ID NO) |
|---|---|---|---|---|
| mAb16 | AIRMTQSP STLSASVG DRVTITC (73) | WYQQKPGK APNLLIS (74) | GVPSRFSG SGSGTEF TLTISSLQ PDDFATY FC (75) | FGQGTKV EIRRTV (76) |
| mAb4 | QSVLTQPP SASGTPG LRVTISC (77) | WYQHLPGT APKLLIH (78) | GVPDRFSG SKSGTSAS LAISGLQS EDEADYYC (79) | FGGGTKL TVLGQP (80) |

VH and VL Sequences for Neutralising Antibodies of the Invention

| Antibody | VH (SEQ ID NO) | VL (SEQ ID NO) |
|---|---|---|
| mAb 16 | QVQLVQSGAEVKKPG ASVRVSCKASGYTFT SYGISWVRQAPGQGL EWMGWISGYDGNTNY AQKLQGRVTMTTDTS TSTAYMELRSLRSDD TAVYYCARDGPQVGD FDWQVYYYYGMDWGQ GTTVTVSS (81) | AIRMTQSPSTLSASV GDRVTITCRASQSIN TWLAWYQQKPGKAPN LLISKASSLESGVPS RFSGSGSGTEFTLTI SSLQPDDFATYFCQQ YNSYLYTFGQGTKVE IRRTV (82) |
| mAb 4 | EVQLVQSGAEVKKPG SSVKVSCKASGGTFS NYAINWVRQAPGQGL EWMGGIIPIFATTNY AQKFQGRVTITADES TSTAYMELSSLRSED TAVYFCARDKHSWSY AFDIWGQGTMVTVSS (83) | QSVLTQPPSASGTPG LRVTISCSGSSSNIG SNTVNWYQHLPGTAP KLLIHSNNQRPSGVP DRFSGSKSGTSASLI SGLQSEDEADYYCAA WDDSLNGWVFGGGTK LTVLGQP (84) |

Epitope for the Neutralising Antibody mAb4 of the Invention: SEQ ID NO: 85

```
KSNNNFCNRY HYDEYIHKLN IWR
```

This is a non-linear epitope corresponding to residues Lys196 to Ser197; Asn347 to Asn352; Arg357 to His365; and Lys443 to Arg448 of SEQ ID NO: 1 or 2
Epitope for the Neutralising Antibody mAb16 of the Invention: SEQ ID NO: 86

```
GKCIAVDAFI KKINETYDKK ICMDMKNY
```

This is a non-linear epitope corresponding to residues Gly201 to Lys219 and Lys327 to Tyr335 of SEQ ID NO: 1 or the corresponding residues in SEQ ID NO: 2
The Neutralising Antibody Red Epitope Bin Sequence: SEQ ID NO: 87

```
GKCIAVDAFI KKINETYDKK ICMDMKNYGT NLFEQ
```

This is a non-linear epitope corresponding to residues Gly201 to Lys219 and Lys327 to Gln342 of SEQ ID NO: 1 or the corresponding residues in SEQ ID NO: 2

The Neutralising Antibody Blue Epitope Bin Sequence: SEQ ID NO: 88

KSYNNNFCNT NKLNIWRTFQ K

This is a non-linear epitope corresponding to residues Lys196, Ser 197, Tyr346 to Asn354 and Lys443 to Lys452 of SEQ ID NO: 1 or the corresponding residues in SEQ ID NO: 2

RH5.1 amino acid sequence—based on residues E26-Q526 of the 3D7 clone reference sequence, together with a C-terminal four-amino acid purification tag (C-tag: EPEA—underlined) and four mutations to delete N-linked glycosylation sequons (T40A, T216A, T286A and T299A, each in bold), i.e. residue 1 corresponds to residues 26 of SEQ ID NO: 1 (SEQ ID NO: 89)

ENAIKKTKNQ ENNLALLPIK STEEEKDDIK NGKDIKKEID NDKENIKTNN AKDHSTYIKS 60
YLNTNVNDGL KYLFIPSHNS FIKKYSVFNQ INDGMLLNEK NDVKNNEDYK NVDYKNVNFL 120
QYHFKELSNY NIANSIDILQ EKEGHLDFVI IPHYTFLDYY KHLSYNSIYH KSSTYGKCIA 180
VDAFIKKINE AYDKVKSKCN DIKNDLIATI KKLEHPYDIN NKNDDSYRYD ISEEIDDKSE 240
ETDDETEEVE DSIQDTDSNH APSNKKKNDL MNRAFKKMMD EYNTKKKKLI KCIKNHENDF 300
NKICMDMKNY GTNLFEQLSC YNNNFCNTNG IRYHYDEYIH KLILSVKSKN LNKDLSDMTN 360
ILQQSELLLT NLNKKMGSYI YIDTIKFIHK EMKHIFNRIE YHTKIINDKT KIIQDKIKLN 420
IWRTFQKDEL LKRILDMSNE YSLFITSDHL RQMLYNTFYS KEKHLNNIFH HLIYVLQMKF 480
NDVPIKMEYF QTYKKNKPLT QEPEA 505

PfRH5 (PfRH5FL) sequence of amino acids E26-Q526 of the 3D7 clone *P. falciparum* reference sequence, with two mutations to delete N-linked glycosylation (N38Q and N214Q, shown in bold) and with an additional C-terminal AviTag™ and Strep-II® tag in tandem (SEQ ID NO: 90)

ENAIKKTKNQ ENQLTLLPIK STEEEKDDIK NGKDIKKEID NDKENIKTNN AKDHSTYIKS 60
YLNTNVNDGL KYLFIPSHNS FIKKYSVFNQ INDGMLLNEK NDVKNNEDYK NVDYKNVNFL 120
QYHFKELSNY NIANSIDILQ EKEGHLDFVI IPHYTFLDYY KHLSYNSIYH KSSTYGKCIA 180
VDAFIKKIQE TYDKVKSKCN DIKNDLIATI KKLEHPYDIN NKNDDSYRYD ISEEIDDKSE 240
ETDDETEEVE DSIQDTDSNH TPSNKKKNDL MNRTFKKMMD EYNTKKKKLI KCIKNHENDF 300
NKICMDMKNY GTNLFEQLSC YNNNFCNTNG IRYHYDEYIH KLILSVKSKN LNKDLSDMTN 360
ILQQSELLLT NLNKKMGSYI YIDTIKFIHK EMKHIFNRIE YHTKIINDKT KIIQDKIKLN 420
IWRTFQKDEL LKRILDMSNE YSLFITSDHL RQMLYNTFYS KEKHLNNIFH HLIYVLQMKF 480
NDVPIKMEYF QTYKKNKPLT QGSASGLNDI FEAQKIEWHE WSHPQFEK 528

PfRH5ΔNL amino acid sequence based on the 3D7 clone *P. falciparum* reference sequence—residues K140-K247 and N297-Q526 with two mutations to delete N-linked glycosylation sequons (T216A and T299A, each in bold) and with the addition of a C-terminal C-tag (underlined) (SEQ ID NO: 91).

```
KNVNFLQYHF KELSNYNIAN SIDILQEKEG HLDFVIIPHY TFLDYYKHLS YNSIYHKSST  60
YGKCIAVDAF IKKINEAYDK VKSKCNDIKN DLIATIKKLE HPYDINNKNR AFKKMMDEYN 120
TKKKKLIKCI KNHENDFNKI CMDMKNYGTN LFEQLSCYNN NFCNTNGIRY HYDEYIHKLI 180
LSVKSKNLNK DLSDMTNILQ QSELLLTNLN KKMGSYIYID TIKFIHKEMK HIFNRIEYHT 240
KIINDKTKII QDKIKLNIWR TFQKDELLKR ILDMSNEYSL FITSDHLRQM LYNTFYSKEK 300
HLNNIFHHLI YVLQMKFNDV PIKMEYFQTY KKNKPLTQEP EA                    342
```

PfCyRPA based on the 3D7 clone *P. falciparum* sequence and comprised amino acids D29-E362 with three mutations introduced to ablate N-linked glycosylation (S147A, T324A and T340A, in bold) and also included a C-terminal CD4 tag comprising rat domains 3 and 4 (CD4d3+4) tag followed by a hexahistidine (His6) tag (SEQ ID NO: 92)

```
DSRHVFIRTE LSFIKNNVPC IRDMFFIYKR ELYNICLDDL KGEEDETHIY VQKKVKDSWI  60
TLNDLFKETD LTGRPHIFAY VDVEEIIILL CEDEEFSNRK KDMTCHRFYS NDGKEYNNAE 120
ITISDYILKD KLLSSYVSLP LKIENREYFL ICGVSPYKFK DDNKKDDILC MASHDKGETW 180
GTKIVIKYDN YKLGVQYFFL RPYISKNDLS FHFYVGDNIN NVKNVNFIEC THEKDLEFVC 240
SNRDFLKDNK VLQDVSTLND EYIVSYGNDN NFAECYIFFN NENSILIKPE KYGNTAAGCY 300
GGTFVKIDEN RALFIYSSSQ GIYNIHTIYY ANYEGAPSTS ITAYKSEGES AEFSFPLNLG 360
EESLQGELRW KAEKAPSSQS WITFSLKNQK VSVQKSTSNP KFQLSETLPL TLQIPQVSLQ 420
FAGSGNLTLT LDRGILYQEV NLVVMKVTQP DSNTLTCEVM GPTSPKMRLI LKQENQEARV 480
SRQEKVIQVQ APEAGVWQCL LSEGEEVKMD SKIQVLSKGL NSGSLHHILD AQKMLWNHRD 540
RNLPPLAPLG PHHHHHH                                                557
```

PfCyRPA based on the 3D7 clone *P. falciparum* sequence and comprised amino acids D29-E362 with three mutations introduced to ablate N-linked glycosylation (S147A, T324A and T340A, shown in bold) and also included a C-terminal 4-amino acid C-tag (EPEA, underlined) separated from the PfCyRPA sequence by a GGGGS linker (SEQ ID NO: 93)

```
DSRHVFIRTE LSFIKNNVPC IRDMFFIYKR ELYNICLDDL KGEEDETHIY VQKKVKDSWI  60
TLNDLFKETD LTGRPHIFAY VDVEEIIILL CEDEEFSNRK KDMTCHRFYS NDGKEYNNAE 120
ITISDYILKD KLLSSYVSLP LKIENREYFL ICGVSPYKFK DDNKKDDILC MASHDKGETW 180
GTKIVIKYDN YKLGVQYFFL RPYISKNDLS FHFYVGDNIN NVKNVNFIEC THEKDLEFVC 240
SNRDFLKDNK VLQDVSTLND EYIVSYGNDN NFAECYIFFN NENSILIKPE KYGNTAAGCY 300
GGTFVKIDEN RALFIYSSSQ GIYNIHTIYY ANYEGGGGSE PEA                   343
```

PfP113Nt, encoding amino acids Y23-K219 of PfP113 (3D7) was expressed encoding C-terminal tags comprising CD4d3+4, a biotin acceptor peptide and a His6 tag in tandem. Mutations to deleted glycosylation are shown in bold. (SEQ ID NO: 94)

```
YVHNDVIKFG EENSLKCSQG NLYVLHCEVQ CLNGNNEIIH KRCNDDIEKK CNGNNKCIYF  60
FEYELRKKTQ SFRNKNSIEI SECVESEQNE VKTSTTCLLS NSFILDEAFI QYFFFIKNKN 120
EEPVICKDGN INIKSALLHS PFCEIKLKDI SEYIRKKCDN NKECLIDPLD VQKNLLNEED 180
PCYINNAYVS VNVVCNKGAP STSITAYKSE GESAEFSFPL NLGEESLQGE LRWKAEKAPS 240
SQSWITFSLK NQKVSVQKST SNPKFQLSET LPLTLQIPQV SLQFAGSGNL TLTLDRGILY 300
QEVNLVVMKV TQPDSNTLTC EVMGPTSPKM RLILKQENQE ARVSRQEKVI QVQAPEAGVW 360
QCLLSEGEEV KMDSKIQVLS KGLNSGSLHH ILDAQKMLWN HRDRNLPPLA PLGPHHHHHH 420
```

PfRH5Nt encoding amino acids F25-K140 of PfRH5 (3D7) was expressed encoding C-terminal tags comprising CD4d3+4, a biotin acceptor peptide and a His6 tag in tandem. Mutations to deleted glycosylation are shown in bold. (SEQ ID NO: 95)

```
FENAIKKTKN QENNLALLPI KSTEEEKDDI KNGKDIKKEI DNDKENIKTN NAKDHSTYIK  60
SYLNTNVNDG LKYLFIPSHN SFIKKYSVFN QINDGMLLNE KNDVKNNEDY KNVDYKGAPS 120
TSITAYKSEG ESAEFSFPLN LGEESLQGEL RWKAEKAPSS QSWITFSLKN QKVSVQKSTS 180
NPKFQLSETL PLTLQIPQVS LQFAGSGNLT LTLDRGILYQ EVNLVVMKVT QPDSNTLTCE 240
VMGPTSPKMR LILKQENQEA RVSRQEKVIQ VQAPEAGVWQ CLLSEGEEVK MDSKIQVLSK 300
GLNSGSLHHI LDAQKMLWNH RDRNLPPLAP LGPHHHHHH
```

The present invention will now be described with reference to the following non-limiting Examples.

EXAMPLES

Materials and Methods

Generation of Monoclonal Antibodies
Plasmablast Isolation and Sorting

Volunteers from a Phase Ia safety and immunogenicity clinical trial were bled seven days after the second immunization using MVA (modified vaccinia virus Ankara) encoding PfRH5FL. Blood was collected from volunteers in heparinized tubes and centrifuged in Leucosep tubes (Greiner Bio one) to separate the peripheral blood mononuclear cells (PBMC). The PBMC were enriched for B cells using a human pan-B cell enrichment kit (Easysep) and resuspended in DMEM before staining with a CD19+, CD10-, CD21-, CD27+, CD20-, CD38+, IgG fluorophore-conjugated antibody panel. Plasmablasts were single-cell sorted using a MoFlo cell sorter (Dako cytomation) into 96-well PCR plates containing 10 µL of 10 mM Tris HCl buffer containing 40 U/mL of RNase inhibitor (Promega). The study received ethical approval from the Oxfordshire Research Ethics Committee A in the UK (REC reference 14/SC/0120). The volunteers signed written consent forms and consent was verified before each vaccination.

Antibody Variable Gene Amplification

In each well of a 96-well plate containing a single antibody-secreting cell (ASC), a two-step RT-PCR was carried out with a first reverse transcription (RT) step using a Sensiscript RT kit (Qiagen) and degenerate primers 1-17 (see Table 1).

Next, a first PCR was performed on 1 µL of the RT reaction product using the same set of primers used before (1-17) which cover the diversity of all Vγ, Vκ and Vλ sequences using Phusion HF master mix (New England Biolabs). Following this, a nested PCR was performed using primers 18-51, also using Phusion HF master mix, (see Table 1) on 1 µL of the previous product diluted 1:100 to amplify inserts which contain plasmid-homologous extensions designed for circular polymerase extension cloning (CPEC).

TABLE 1

| primers for antibody variable gene amplification | |
|---|---|
| Primer number (SEQ ID NO) | Primer sequence (5' to 3') |
| 1 (96) | ACAGGTGCCCACTCCCAGGT GCAG |
| 2 (97) | AAGGTGTCCAGTGTGARGTG CAG |
| 3 (98) | CCCAGATGGGTCCTGTCCCA GGTGCAG |
| 4 (99) | CAAGGAGTCTGTTCCGAGGT GCAG |
| 5 (100) | GGAAGGTGTGCACGCCGCTG GTC |
| 6 (101) | ATGAGGSTCCCYGCTCAGCT GCTGG |
| 7 (102) | CTCTTCCTCCTGCTACTCTG GCTCCCAG |
| 8 (103) | ATTTCTCTGTTGCTCTGGAT CTCTG |
| 9 (104) | GTTTCTCGTAGTCTGCTTTG CTCA |
| 10 (105) | GGTCCTGGGCCCAGTCTGTG CTG |

TABLE 1-continued primers for antibody variable gene amplification

| Primer number (SEQ ID NO) | Primer sequence (5' to 3') |
|---|---|
| 11 (106) | GGTCCTGGGCCCAGTCTGCCCTG |
| 12 (107) | GCTCTGTGACCTCCTATGAGCTG |
| 13 (108) | GGTCTCTCTCSCAGCYTGTGCTG |
| 14 (109) | GTTCTTGGGCCAATTTTATGCTG |
| 15 (110) | GGTCCAATTCYCAGGCTGTGGTG |
| 16 (111) | GAGTGGATTCTCAGACTGTGGTG |
| 17 (112) | CACCAGTGTGGCCTTGTTGGCTTG |
| 18 (113) | CTTTTTCTAGTAGCAACTGCAACCGGTGTACATTCCGAGGTGCAGCTGGTGCAG |
| 19 (114) | CTTTTTCTAGTAGCAACTGCAACCGGTGTACATTCTGAGGTGCAGCTGGTGGAG |
| 20 (115) | CTTTTTCTAGTAGCAACTGCAACCGGTGTACATTCCCAGGTGCAGCTGCAGGAG |
| 21 (116) | CTTTTTCTAGTAGCAACTGCAACCGGTGTACATTCTGAGGTGCAGCTGTTGGAG |
| 22 (117) | CTTTTTCTAGTAGCAACTGCAACCGGTGTACATTCCCAGGTGCAGCTACAGCAGTG |
| 23 (118) | CTTTTTCTAGTAGCAACTGCAACCGGTGTACATTCCCAGGTTCAGCTGGTGCAG |
| 24 (119) | CTTTTTCTAGTAGCAACTGCAACCGGTGTACATTCCCAGGTCCAGCTGGTACAG |
| 25 (120) | CTTTTTCTAGTAGCAACTGCAACCGGTGTACATTCTGAAGTGCAGCTGGTGGAG |
| 26 (121) | CTTTTTCTAGTAGCAACTGCAACCGGTGTACATTCCCAGGTACAGCTGCAGCAG |
| 27 (122) | CTTTTTCTAGTAGCAACTGCAACCGGTGTACATTCCCAGCTGCAGCTGCAGGAG |
| 28 (123) | CTTTTTCTAGTAGCAACTGCAACCGGTGTACATTCTCAGGTGCAGCTGGTGGAG |
| 29 (124) | GATGGGCCCTTGGTCGACGCTGAGGAGACGGTGACCAG |
| 30 (125) | GATGGGCCCTTGGTCGACGCTGAAGAGACGGTGACCATTG |
| 31 (126) | GATGGGCCCTTGGTCGACGCTGAGGAGACGGTGACCGTG |
| 32 (127) | CTTTTTCTAGTAGCAACTGCAACCGGTGTACATTCTGACATCCAGATGACCCAGTC |
| 33 (128) | CTTTTTCTAGTAGCAACTGCAACCGGTGTACATTCAGACATCCAGTTGACCCAGTCT |
| 34 (129) | CTTTTTCTAGTAGCAACTGCAACCGGTGTACATTGTGCCATCCGGATGACCCAGTC |
| 35 (130) | CTTTTTCTAGTAGCAACTGCAACCGGTGTACATGGGGATATTGTGATGACCCAGAC |
| 36 (131) | CTTTTTCTAGTAGCAACTGCAACCGGTGTACATGGGGATATTGTGATGACTCAGTC |
| 37 (132) | CTTTTTCTAGTAGCAACTGCAACCGGTGTACATTCAGAAATTGTGTTGACACAGTC |
| 38 (133) | CTTTTTCTAGTAGCAACTGCAACCGGTGTACATTCAGAAATAGTGATGACGCAGTC |
| 39 (134) | CTTTTTCTAGTAGCAACTGCAACCGGTGTACATTCAGAAATTGTGTTGACGCAGTCT |
| 40 (135) | CTTTTTCTAGTAGCAACTGCAACCGGTGTACATTCGGACATCGTGATGACCCAGTC |
| 41 (136) | ATGGTGCAGCCACCGTACGTTTGATYTCCACCTTGGTC |
| 42 (137) | ATGGTGCAGCCACCGTACGTTTGATATCCACTTTGGTC |
| 43 (138) | ATGGTGCAGCCACCGTACGTTTAATCTCCAGTCGTGTC |
| 44 (139) | ATGGTGCAGCCACCGTACGTCTGATTTCCACCTTGGTC |
| 45 (140) | CTTTTTCTAGTAGCAACTGCAACCGGTTCCTGGGCCAGTCTGTGCTGACKCAG |
| 46 (141) | CTTTTTCTAGTAGCAACTGCAACCGGTTCCTGGGCCCAGTCTGCCCTGACTCAG |
| 47 (142) | CTTTTTCTAGTAGCAACTGCAACCGGTTCTGTGACCTCCTATGAGCTGACWCAG |
| 48 (143) | CTTTTTCTAGTAGCAACTGCAACCGGTTCTCTCTCSCAGCYTGTGCTGACTCA |
| 49 (144) | CTTTTTCTAGTAGCAACTGCAACCGGTTCTTGGGCCAATTTTATGCTGACTCAG |

TABLE 1-continued primers for antibody variable
gene amplification

| Primer number (SEQ ID NO) | Primer sequence (5' to 3') |
|---|---|
| 50 (145) | CTTTTTCTAGTAGCAACTGC AACCGGTTCCAATTCYCAGR CTGTGGTGACYCAG |
| 51 (146) | GGCTTGAAGCTCCTCACTCG AGGGYGGGAACAGAGTG |

Cloning

The AbVec-hIgG1/AbVec-hIgKappa/AbVec-hIgLambda expression plasmids were a kind gift from Patrick C. Wilson (University of Chicago). These plasmids were 5' digested using BshTI and at the 3' using SalI (AbVec-hIgG1), XhoI (AbVec-hIgLambda) and Pfl23II (AbVec-hIgKappa) to yield linear products. CPEC assembly was done by mixing 100 ng of a 1:1 molar ratio of insert:plasmid in 20 μL containing 1× Phusion HF polymerase master mix and assembled using an 8-cycle CPEC protocol (8 cycles: 98° C. 10 s, slow ramp anneal 70° C. → 55° C. at 0.1° C./s, 72° C. 35 s). Full nicked plasmids were subsequently transformed into Zymo 5α Mix & go competent *Escherichia coli* (Zymo Research) according to manufacturer's instructions, streaked on LB agar petri dishes containing 100 μg/mL carbenicillin and grown at 37° C. overnight in a static incubator. Colonies were screened by PCR for inserts of the correct size.

Screening

Exponential growth-phase adherent HEK293 cells were resuspended in DMEM (Sigma-Aldrich) supplemented with 2 mM L-glutamine, 1 mM sodium pyruvate, 100 U/mL penicillin, 0.1 mg/mL streptomycin and 10% ultra-low IgG foetal bovine serum (FBS) (all from Thermo Fischer Scientific) and seeded at 4×10$^4$ cells/well in 100 μL 24 h prior to transfection in Costar 96-well cell culture plates (Corning). On the day of transfection, for each well, 50 μL of 60 μg/mL linear 25 kDa PEI (Alfa Aesar) was mixed with 200 ng of cognate heavy- and light-chain coding plasmid in a volume of 50 μL and shaken at 20° C. for 30 min. The DNA-PEI complexes were then added to the HEK293 cells. The next day, an additional 50 μL of supplemented DMEM (as described above) was added to each well. Supernatants were screened for PfRH5FL binding by indirect ELISA as described in the ELISA methods section.

Recombinant Protein Constructs, Expression and Purification

The recombinant PfRH5 sequence used in all experiments except for those involving BLI (FIGS. 1C and 4A) was based on the 3D7 clone *P. falciparum* reference sequence and encoded amino acids E26-Q526. The sequence also encoded a C-terminal four-amino acid purification tag (C-tag: EPEA) and four mutations to delete N-linked glycosylation sequons (T40A, T216A, T286A and T299A) and was named "PfRH5FL" (this recombinant protein is also known as "RH5.1", SEQ ID NO: 89). This protein was expressed as secreted protein by a stable monoclonal *Drosophila* S2 cell line and affinity purified using CaptureSelect™ C-tag affinity matrix (Thermo Fischer Scientific). A further size-exclusion chromatography (SEC) polishing step was done on a HiLoad 16/60 Superdex 200 pg column (GE Healthcare) to separate monomers from oligomers and contaminants as well as to buffer-exchange the protein into 20 mM Tris, 150 mM NaCl, pH 7.5.

The recombinant PfRH5 sequence (also named "PfRH5FL" for simplicity) used in BLI experiments (FIGS. 1C and 4A) also encoded amino acids E26-Q526 of the 3D7 clone *P. falciparum* reference sequence, with only two mutations to delete N-linked glycosylation (N38Q and N214Q). This sequence is identical to the vaccine sequence and was expressed with an additional C-terminal AviTag™ and Strep-II® tag in tandem (SEQ ID NO: 90). This protein was expressed in HEK293F cells as a secreted, monobiotinylated protein as described previously by Bushell et al., 2008 (Genome research, 18(4), pp. 622-630).

The recombinant PfRH5ΔNL sequence used was based on the 3D7 clone *P. falciparum* reference sequence and encoded amino acids K140-K247 and N297-Q526 with two mutations to delete N-linked glycosylation sequons (T216A and T299A) and with the addition of a C-terminal C-tag (SEQ ID NO: 91). PfRH5ΔNL was expressed as secreted protein from stably-transfected polyclonal *Drosophila* S2 cells. Its purification is detailed in the X-ray crystallography experimental procedures section.

The expression construct used for monomeric PfCyRPA production in FIG. 4C and for rat vaccination in FIG. 6I was based on the 3D7 clone *P. falciparum* sequence and comprised amino acids D29-E362 with three mutations introduced to ablate N-linked glycosylation (S147A, T324A and T364A) and also included a C-terminal GGGS linker followed by a 4-amino acid C-tag (EPEA), SEQ ID NO: 93. The PfCyRPA immunogen sequence used for rabbit vaccination in FIG. 6E was identical to that described above with the C-tag replaced by a C-terminal CD4 tag comprising rat domains 3 and 4 (CD4d3+4) tag followed by a hexahistidine (His6) tag (SEQ ID NO: 92). The protein was expressed as secreted protein from HEK293F cells using the Expi293™ Expression System (Thermo Fischer Scientific) according to the manufacturer's recommendations and purified by C-tag affinity chromatography followed by SEC on a HiLoad 16/60 Superdex 200 pg column (GE Healthcare). Basigin protein comprised of immunoglobulin domains 1 and 2 of the short isoform (residues A22-H205) and was expressed from *E. coli* and purified by Ni$^{2+}$-affinity and size exclusion chromatography.

PfP113Nt, encoding amino acids Y23-K219 of PfP113 (3D7) (SEQ ID NO: 94) and PfRH5Nt encoding amino acids F25-K140 of PfRH5 (3D7) (SEQ ID NO: 95), were expressed encoding C-terminal tags comprising CD4d3+4, a biotin acceptor peptide and a His6 tag in tandem.

Recombinant monoclonal antibodies were transiently expressed in HEK293F cells using the Expi293™ Expression System (Thermo Fischer Scientific) according to the manufacturer's recommendations. Cognate heavy and light chain-coding plasmids were co-transfected at a 1:1 ratio. Supernatants were harvested by centrifuging the culture at 2500×g for 15 min and filtering the supernatant with a 0.22 μm vacuum filter. All mAbs were purified using a 5 mL Protein G HP column (GE Healthcare) on an ÄKTA start FPLC system or an AKTA Pure FPLC system (both GE Healthcare). Equilibration and wash steps were performed with Dulbecco's PBS and mAbs were eluted in 0.1 M glycine pH 2.7. The eluates were pH equilibrated to 7.4 using 1.0 M Tris HCl pH 9.0 and immediately buffer-exchanged into Dulbecco's PBS and concentrated using an Amicon® ultra centrifugal concentrator (Millipore) with a molecular weight cut-off of 30 kDa.

IgG from serum in FIGS. 3B, C, D and FIGS. 6C, E was purified on drip columns packed with Pierce Protein G agarose resin (Thermo Fisher Scientific). Pierce protein G IgG binding buffer (Thermo Fisher Scientific) was used to dilute the serum 1:1 before loading as well as for equilibration and wash steps. Bound IgG was subsequently eluted, neutralized and concentrated as above. Bispecific DVD-Ig 1611 was constructed by cloning R5.016 variable regions upstream (5') of R5.011 variable regions, separated by ASTKGPSVFPLAP and TVAAPSVFIFPP linkers for the heavy and light chains, respectively. 1611 DVD-Ig expression and purification was conducted as described above for monospecific mAbs.

X-Ray Crystallography

Complex Preparation

PfRH5ΔNL was purified from *Drosophila* S2 culture supernatant using C-tag affinity chromatography and glycosylated contaminants were removed by a subsequent lectin chromatography step with a HiTrap ConA 4B column (GE Healthcare). Disordered regions were trimmed by an overnight incubation at 20° C. with endoproteinase gluC (New England Biolabs) at a final concentration of 1 μg/mL. Fab fragments were generated by papain digestion using a Pierce™ Fab Preparation Kit (Thermo Fischer Scientific) following the manufacturer's recommendations. Complexes were prepared by mixing each Fab fragment with PfRH5ΔNL at a 1:1 molar ratio and were methylated with 1 M ABC (Borane dimethylamine complex) and 1 M formaldehyde (both Sigma-Aldrich) (Walter et al., 2006). The methylated complexes were subjected to SEC on a HiLoad 16/60 Superdex 200 pg column (GE Healthcare) at 4° C. in 20 mM Tris pH 7.4, 150 mM NaCl. The complex-containing fractions were pooled and concentrated using an Amicon® ultra centrifugal concentrator (Millipore) with a molecular weight cut-off of 30 kDa.

Crystallisation, Data Collection and Processing

Crystallization was achieved using vapour diffusion in sitting drops. Crystals were obtained for the Fab fragments of mAbs R5.004, R5.011 and R5.016 alone, as well as for complexes consisting of PfRH5ΔNER5.004:R5.016 and PfRH5ΔNL:R5.011:R5.016. In each case, a TTP Labtech Mosquito LCP robot was employed to mix 100 nL of each protein complex at a concentration of 10 mg/mL with 100 nL of well solutions from commercially available crystal screens.

Crystals of R5.004 Fab fragments were obtained in the JCSG-plus crystallization screen (Molecular Dimensions) and were optimized with a final well solution of 0.2 M lithium sulfate, 0.1 M NaAc pH 4.5, 30% PEG 8000 and 0.33% hexamminecobalt(III) chloride, 0.06 M MES monohydrate, 0.06 PIPES, 0.02 M HEPES chloride. They were cryo-protected by transfer into well solution supplemented with 25% glycerol, then cryo-cooled by plunging into liquid nitrogen. Data were collected on beamline 1-03 at Diamond Light Source (Harwell, UK), leading to a complete data set at a resolution of 1.7 Å.

Crystals of R5.016 Fab fragments were obtained in the JCSG-plus crystallization screen (Molecular Dimensions), with a final well solution of 0.2 M lithium sulfate, 0.1 M NaAc pH 4.5, 50% PEG 400. Crystals were cryo-cooled directly in the well solution by plunging into liquid nitrogen. Data were collected on beamline I04-1 at Diamond Light Source (Harwell, UK), leading to a complete data set at a resolution of 2.1 Å.

Crystals of R5.011 Fab fragments were obtained in the JCSG-IV crystallization screen (Qiagen), with a final well solution of 0.16 M ZnAc, 0.108 M Na cacodylate pH 6.5, 14.4% PEG 8000, 20% glycerol. They were cryo-protected by transfer into well solution supplemented with 25% glycerol, then cryo-cooled by plunging into liquid nitrogen. Data were collected on beamline PROXIMA-1 at SOLEIL (Saint-Aubin, France), leading to a complete data set at a resolution of 2.3 Å.

Crystals of the PfRH5ΔNL:R5.004:R5.016 complex were obtained in the JCSG-plus crystallization screen (Molecular Dimensions), with a final well solution of 0.15 M DL malic acid, 20% PEG 3350. They were cryo-protected by transfer into well solution supplemented with 25% glycerol, then cryo-cooled by plunging into liquid nitrogen. Data were collected on beamline I04 at Diamond Light Source (Harwell, UK), leading to a complete data set at a resolution of 4.0 Å.

Crystals of the PfRH5ΔNL:R5.011:R5.016 complex were obtained in the Morpheus crystallization screen (Molecular Dimensions), with a final well solution of 10% PEG 20000, 20% PEG 550 MME, 0.02 M amino acids, 0.1 M MES/imidazole pH 6.5. Crystals were cryo-cooled directly in the well solution by plunging into liquid nitrogen. Data were collected on beamline ID23 at the European Synchrotron Radiation Facility (Grenoble, France), leading to a complete data set at a resolution of 3.6 Å.

In each case, data reduction was performed using XDS. Molecular replacement solutions were found for each individual Fab fragment, using PHASER with the most closely related Fab fragment structure in the PDB, split into their constant and variable domains, as search models (4KQ3 for R5.004, 4HK0 for R5.011 and 5K90 for R5.016). This led to a cycle of model building and refinement using COOT and BUSTER. For R5.004, this resulted in a complete model for the Fab fragment. For R5.011, this resulted in a complete model for the Fab fragment, with the exception of residues 143-148 in the heavy chain, which were disordered in the electron density map. For R5.016, this resulted in a complete model for the Fab fragment, with the exception of residues 103-108 in the heavy chain and 1-7, 25-29 and 55-58 in the light chain, all of which were disordered in the electron density map.

The structure of the PfRH5ΔNL:R5.011:R5.016 complex was obtained to 3.6 Å resolution using PHASER with the structure of PfRH5ΔNL (PDB code: 4U0R) and those of Fab fragments obtained above, split into their constant and variable domains, as search models. All domains were well resolved, although significant changes in conformation were observed in CDR H3 of both R5.011 and R5.016, as a result of PfRH5ΔNL binding. COOT and BUSTER were used for refinement, including application of restraints that derived from the higher resolution structures of PfRH5ΔNL and the shared regions of the Fab fragments. This allowed the production of a final model in which all of the Fab fragment domains, and all of the CDR loops, were clearly resolved.

The structure of the PfRH5ΔNL:R5.004:R5.016 complex was obtained at 4 Å resolution, using PHASER. The structure of PfRH5ΔNL bound to the variable domain of R5.016, obtained from the structure of the PfRH5ΔNL:R5.011:R5.016 complex, and the structure of the variable domain of R5.004 obtained above, were used as search models in PHASER. No significant changes were observed in the CDR loops of the Fab fragment of R5.004. Placement of the constant domains of R5.016 and R5.004 was challenging, due to anisotropy resulting from disorder within the crystal. These domains were therefore placed using real space docking after refinement in BUSTER of a structure consisting of PfRH5ΔNL and the variable domains of R5.004 and R5.016. This gave unambiguous electron density for the regions of the constant domains which lie close to the contact with the variable domains, but, after refinement, electron density is still absent for the PfRH5ΔNL-distal parts of the constant domains. Refinement in COOT and BUSTER allowed the production of a final model in which the Fab fragment domains, and all of the CDR loops, were clearly resolved.

Humanized Mouse Passive Transfer

P. falciparum Sporozoite Production and Mouse Infection

The luciferase expressing strain P. falciparum NF54HT-GFP-luc was maintained in RPMI 1640 supplemented with 25 mM HEPES, 2 mM L-glutamine, 50 μM hypoxanthine, 10% human serum and sub-cultured in 5% O+ human erythrocytes. Briefly, asexual cultures were inoculated at 1 parasitemia with no further sub-culturing and daily media changes to induce gametocytogenesis. Mature gametocytes were fed to 4-day old Anopheles stephensi mosquitoes to initiate infection. Mosquitoes were incubated at 27° C. and 75% humidity for 14 d and given 8% dextrose+PABA to foster parasite growth. Liver humanized FRGN KO mice were purchased from Yecuris Corp. and showed human hepatocyte repopulation levels above 70% determined by human serum albumin levels. Liver humanized mice were cycled on NTBC once a month for 3 d at 8 μg/mL in the drinking water to maintain health. Animals did not receive NTBC three weeks prior to and during the infection study. For mosquito bite infection, 3-5 liver humanized FRGN mice were anesthetised and placed on top of a mosquito cage containing 150-250 infected mosquitoes for 20 min.

P. falciparum Liver-to-Blood Stage Transition

On the day of challenge, liver humanized FRGN mice were injected both in the retro-orbital plexus and the peritoneal cavity with 50 μL clodronate-containing liposomes (Clophosome®-A), 100 mg/kg cyclophosphamide (Sigma-Aldrich). Five days after challenge, the animals were bled a volume of approximately 200 μL, and 500 μL hRBC was injected in the retro-orbital plexus (70% O+ human erythrocytes in RPMI 1640 supplemented with 25 mM HEPES, 2 mM L-glutamine, 50 μM hypoxanthine and 10% human serum). The next day, mice were bled 200 μL and received an intraperitoneal injection of 700 μL hRBC. mAb transfer was done on day 6 to precede the establishment of blood-stage infection. Dosage was 15 mg total rabbit IgG per mouse formulated in PBS and delivered intravenously. The clodronate liposome and cyclophosphamide injections were repeated on days 5, 9, 11, 13. Human RBC were injected daily in a volume of 300-700 μL to keep the percentage of hRBC stable around 50-60%. If the percentage reached more than 70%, the mice were not injected with hRBC to limit morbidity. On days 9, 11 and 13 each mouse was bled from the retro-orbital plexus to sample antibody levels.

Quantification of Parasite Burden

Luciferase activity was measured in the mice using the IVIS Lumina II animal imager (Perkin Elmer). The abdomen of mice was shaved to enhance detection. Mice were injected intraperitoneally with 100 μL of luciferase substrate RediJect D-Luciferin (Perkin Elmer) to quantitate specific enzymatic activity. Animals were anesthetized and imaged within 5 min of substrate injection. Signal was acquired for 5 min using a field of view of 10 cm and medium binning factor. Living Image 3.0 software was used to measure total flux (photons/second) of a region of interest, which was placed around each mouse.

This study was carried out in accordance with the recommendations of the NIH Office of Laboratory Animal Welfare standards (OLAW welfare assurance #A3640-01). The protocol was approved by the Center for Infectious Disease Research Institutional Animal Care and Use Committee (IACUC) under protocol SK-16.

PfCyRPA/PfP113/BSG SPR Blocking Assays

Data were collected on a Biacore X100 (GE Healthcare). All data used were reference subtracted from a non-immobilized flow cell (Fc 2-1). Binding values were measured manually in the Biacore X100 control software.

PfRH5-Basigin Binding

Experiments were performed at 25° C. in SPR running buffer (PBS+0.05% Polysorbate-20, GE Healthcare). Approximately 670 RU of basigin was amine-coupled to a CM5 chip (GE Healthcare) on flow cell 2 (Fc 2) using standard NHS/EDC chemistry. PfRH5FL-mAb complexes were made by mixing PfRH5FL and mAb to a final concentration of 0.5 μM PfRH5FL and 1 μM mAb in SPR running buffer. Complexes were injected over Fc 1 and Fc 2 at a flow rate of 10 μL/min for 30 s and the surface was regenerated with 10 mM glycine pH 1.5 for at a flow rate of 10 μL/min for 60 s. Between experiments, one injection of 0.5 μM PfRH5FL was made to assess basigin degradation caused by regeneration.

PfRH5-PfCyRPA Binding

Experiments were performed at 25° C. in SPR running buffer (PBS+0.05% Polysorbate-20, GE Healthcare) using a sensor chip protein A (GE Healthcare). mAb was injected at a concentration of 20 nM at a flow rate of 5 μL/min for 35 s over Fc 2 on a protein A coated chip (GE Healthcare). Next, PfRH5FL was injected over Fc 1 and Fc 2 at a concentration of 50 nM at a flow rate of 10 μL/min for 120 s before injecting PfCyRPA at a concentration of 1 μM for 120 s, also at a flow rate of 10 μL/min. The chip surface was regenerated with 10 mM glycine pH 1.5 for at a flow rate of 10 μL/min for 60 s.

PfRH5-PfP113 Binding

Experiments were performed at 37° C. in SPR running buffer (PBS+0.05% Polysorbate-20, GE Healthcare) using a Sensor chip CAP (GE Healthcare). The whole experiment was run at a flow rate of 5 μL/min. Approximately 1500 RU of CAP reagent (GE Healthcare) was captured on Fc 1 and Fc 2. On Fc 1, approximately 500 RU of a biotinylated control CD4d3+4-tagged protein was immobilized. On Fc 2, each experiment consisted of capturing 1500 RU of CAP reagent in an 80 s injection followed by approximately 1800 RU of PfP113Nt in an 80 s injection at a concentration of 20 μg/mL. After this, PfRH5FL-mAb complex (both at 1 μM) was flowed over Fc 1 and Fc 2. Flow cell 2 was regenerated between experiments in a 110 s injection of 6 M guanidine+250 mM NaOH, as per the manufacturer's instructions.

Bio-Layer Interferometry (BLI)

All BLI was carried out on an OctetRED384 (Pall ForteBio) using streptavidin-coated biosensors (Pall ForteBio) to immobilize PfRH5FL enzymatically monobiotinylated on a C-terminal AviTag™. Assays were carried out in 96-well format in black plates (Greiner). For assaying mAb binding to PfRH5FL variants (FIG. 1C), the experiment followed a four-step sequential assay: Baseline (PBS, 30 s); Protein immobilization (neat supernatant, 180 s); Wash (PBS, 60 s); and mAb binding (150 nM mAb, 120 s). Graphed data show the fold-change in binding of each mAb to the 3D7 PfRH5FL reference protein relative to the binding of each mAb to each mutant protein after correction for PfRH5FL immobilization level on each biosensor. The fold-change values which were inferior to 1 were plotted as their inverse to avoid skewing in their data representation compared to fold-change values greater than 1. For epitope binning studies (FIG. 4A) the experiment followed a six-step sequential assay: Baseline (PBS, 30 s); Protein immobilization (neat supernatant, 120 s); Wash (PBS, 60 s); mAb1 binding (300 nM mAb1, 120 s); Wash (PBS, 60 s); mAb2 binding (150 nM mAb2, 120 s). "Relative binding" was calculated giving the ratio (Signal$_{mAb2}$ with mAb1 bound)/ (Signal$_{mAb2}$ with no mAb1) where "Signal$_{mAb2}$" was normalized for the amount of PfRH5FL bound to the biosensor such that "Signal$_{mAb2}$"=the raw signal in "mAb2 binding" divided by the raw signal in the "Protein immobilization" phase. To establish the epitope bins, binding profiles between each mAb pair was correlated using a person product-moment correlation coefficient. mAb pairs whose binding profile correlation was >0.7 were grouped into the same epitope bin.

ELISA

Qualitative mAb binding ELISAs such as those used in FIG. 3A were carried out by coating PfRH5FL, PfRH5ΔNL or PfRH5Nt on Maxisorp flat-bottom 96-well ELISA plates (Nunc) at 2 μg/mL in 50 μL at 4° C. overnight. To examine linear epitopes, PfRH5FL was heat-treated by incubation at 90° C. for 10 min. Plates were then washed twice with PBS-Tween 20 and blocked with 200 μL of Blocker™ Casein (Thermo Fischer Scientific) for 1 h. Next, wells were incubated with 1000 ng/mL of mAb for approximately 45 min at 20° C. then washed 4 times with PBS-Tween 20 before the addition of 504 of goat anti-human gamma-chain alkaline phosphatase-conjugated secondary antibody (goat anti-mouse IgG alkaline phosphatase-conjugated secondary antibody for QA1) (both Sigma-Aldrich) for 45 min at 20° C. Wells were then washed 6 times with PBS-Tween 20 and developed with 100 μL of PNPP substrate at 1 mg/mL (Sigma-Aldrich) and read at 405 nm.

Peptide ELISAs were carried out with a set of sixty-two custom-synthesized biotinylated 20-mer peptides of PfRH5 overlapping by 12 amino acids (Mimotopes). The list of peptide sequences was described previously by Payne et al., 2017 and can be found in supplementary table 4. Briefly, the peptides were designed to be oriented and tethered by their N-terminal biotinylated linker peptide (biotin-SGSG) with the exception the first peptide which contained the biotinylated linker at its C-terminus to preserve potential binding activity to the most N-terminal residues. These peptides were coated to the bottom wells of a streptavidin-coated 96-well plate in 50 μL. The next day wells were blocked with 200 μL of Blocker™ Casein (Thermo Fisher) and washed five times with PBS-Tween 20. Bound mAbs were detected using an anti-human gamma-chain-specific alkaline phosphatase-conjugated secondary antibody (Sigma-Aldrich) or the mouse equivalent for QA1 in 504 for 30 min at a dilution of 1:1000 in PBS and washed six times with PBS-Tween 20 before being developed with 100 μL of PNPP alkaline phosphatase substrate for 20 min and read at 405 nm. To determine total PfRH5FL-specific IgG as in FIGS. 3C, 3D and 3F, standardized methodology was used as described previously (Sheehy et al., 2011; Payne et al., 2017). Responses measured in AU are reported in μg/mL following generation of a conversion factor by calibration-free concentration analysis (CFCA). For the calculation of the conversion factor, see Williams et al., 2012.

Animal Vaccination Immunization Regimes

In FIGS. 3C, D two groups of six outbred New Zealand White rabbits were immunized three times three weeks apart and terminally exsanguinated two weeks following the final vaccination. Vaccines were formulated as equimolar doses (29 μg of PfRH5FL or 20 μg of PfRH5ΔNL per dose) in 50% v/v AddaVax™ adjuvant (InvivoGen), a squalene-based oil-in-water nano-emulsion, and administered by intramuscular (i.m.) route by GenScript (Piscataway, NJ, USA). In FIGS. 6E and 6I, anti-PfAMA1 and anti-PfMSP1 antisera were generated in rabbits as previously reported (Douglas et al., 2011). For PfCyRPA, rabbit immunizations to generate the IgG used in FIG. 6E were carried out by Cambridge Research Biochemicals, UK, in compliance with the UK Animals (Scientific Procedures) 1986 Act (ASPA). New Zealand white female rabbits (n=2) were immunized i.m. on day 0 with 100 μg of PfCyRPA protein formulated in AddaVax™ adjuvant (InvivoGen) followed by two i.m. booster immunizations on days 28 and 56. Serum was collected pre-immunization (day 0) and 1 week after the final immunization on day 63. To generate the PfCyRPA-reactive IgG used in FIG. 6I, a single Sprague Dawley rat was immunized three times on day 0, day 28, day 56 and terminally exsanguinated two weeks following the final vaccination. Vaccines were formulated as 50 μg doses in complete Freund's adjuvant for the initial vaccination and incomplete Freund's adjuvant for the following two, and administered i.m by GenScript (Piscataway, NJ, USA). GenScript holds a valid and current Animal Welfare Assurance in compliance with the Public Health Service (PHS) Policy on humane Care and Use of Laboratory Animals as granted by the Office of Laboratory Animal Welfare (OLAW).

Affinity Determination by SPR

Data were collected on a Biacore X100 (GE Healthcare). Experiments were performed at 25° C. in Dulbecco's PBS+ 0.05% Polysorbate-20 (GE Healthcare). A sensor chip protein A (GE Healthcare) was used to capture 50-100 RU of purified mAb diluted in SPR running buffer at a flow rate of 5 μL/min. Next, an appropriate range (typically 20 nM-0.625 nM) of six 2-fold dilutions with one replicate of PfRH5FL was injected for 90 s at 60 μL/min and dissociation was measured for 1600 s (7200 s when necessary). The PfRH5FL analyte was >95% pure as assessed by SDS-PAGE. Specific binding of the PfRH5FL protein to mAb was obtained by reference-subtracting the response of a blank surface from that of the mAb-coated surface. The sensor surface was regenerated with a 60 s pulse of 10 mM glycine-HCl pH 1.5 (GE Healthcare). Sensorgrams were fitted to a global Langmuir 1:1 interaction model, allowing determination of the kinetic association and dissociation rate constants using Biacore X100 evaluation software.

AVEXIS Blocking Assay

All AVEXIS assays were conducted at the Wellcome Trust Sanger Institute, Cambridge, UK. Biotinylated monomeric bait protein was captured on streptavidin-coated flat-bottomed 96-well microtiter plates in 50 μL volumes for 1 h at 20° C. Plates were then washed 3 times with PBS and incubated with 50 μL of human PfRH5-specific mAb for 1 h at 20° C. The plates were washed 3 more times in PBS before the addition of 50 μL of pentameric β-lactamase-tagged prey proteins for a further 1 h at 20° C. All wells were subsequently washed twice with PBS-Tween 20 and then twice with PBS before the addition of 150 μL/well of the β-lactamase substrate nitrocefin. Absorbance readings were made at 485 nm. The protein constructs were all full-length ectodomains with threonine to alanine mutations to remove N-linked glycosylation sequons (except for basigin) as previously reported (Crosnier et al., 2011; Galaway et al., 2017): PfRH5 amino acids F25-Q526; PfCyRPA amino acids D29-E362; PfP113 amino acids Y23-K942; and basigin isoform 2 amino acids M1-A23 followed by G140-L322. All bait and prey proteins were expressed as fusion proteins N-terminal of a CD4d3+4 tag, a biotin acceptor peptide and a His6 tag. Prey proteins were expressed with a C-terminal with a collagen oligomeric matrix protein (COMP) peptide to promote pentamerization and a β-lactamase enzyme for quantification purposes.

Assay of GIA

All mAb GIA assays in FIGS. 2A, B, C and 3B were performed at the GIA Reference Center, NIAID, NIH. Test mAbs were buffer exchanged against RPMI 1640 (KD Medical) and concentrated to 6 mg/mL. The one-cycle GIA was performed at indicated concentrations of mAbs in duplicate wells and a biochemical measurement using a *P. falciparum* lactate dehydrogenase assay was used to quantify parasitemia which has been described previously (Malkin et al., 2005). GIA assays performed with rabbit polyclonal antibody and mAb combinations in FIGS. 3C, D and 6 were performed at the Jenner Institute, Oxford using identical protocols and procedures to those at the NIAID but in triplicate wells.

Dot Blot

Briefly, 1.5 µL of anti-PfRH5 mAb, a human anti-Zaire Ebolavirus GP IgG1 mAb, recombinant PfRH5FL (all at 1 mg/mL) and PBS were spotted onto 0.2 µm nitrocellulose membrane and air-dried for 10 min. Afterwards, the membrane was blocked in 3% BSA+3% skimmed milk in PBS for 1 h and washed in PBS. It was then immersed in *P. falciparum* 3D7 culture supernatant for 1 h and washed again in PBS. Bound PfRH5FL was detected by incubating the membrane in PfRH5FL-immunized rabbit serum diluted 2000-fold in PBS followed by an alkaline phosphatase-conjugated anti-rabbit IgG mAb (clone RG-96, Sigma-Aldrich) also diluted 1:2000, separated by two wash steps in PBS. After a final series of five PBS washes, the dot blot was developed with Sigmafast BCIP/NBT alkaline phosphatase substrate at 1 mg/mL (Sigma-Aldrich).

Hydrogen-Deuterium Exchange Mass Spectrometry (HDX-MS)

HDX-MS was performed using a Waters HDX platform composed of a liquid handling robotic setup (LEAP technologies) for sample preparation and a nano-Acquity UPLC coupled to a Synapt G2-Si (Waters) mass spectrometer. Samples were prepared by 11-fold dilutions from 7 µM of apo PfRH5FL or PfRH5FL-mAb complex in deuterated or non-deuterated 20 mM HEPES, 150 mM NaCl pH 7.4 buffer. The pH of the sample was brought down to 2.3 by adding 50% vol/vol 150 mM HCl. Non-deuterated and deuterated samples were loaded by the robot. The apo PfRH5FL protein or PfRH5FL-mAb complex was digested in-line using a pepsin-immobilized column at 20° C. The peptides generated from pepsin digestion were trapped on a micro peptide trap for 2 min for the removal of salts at a flow rate of 200 µL/min and then separated using a C18 column with a linear gradient of 5-80% acetonitrile ($CH_3CN$) and water both supplemented with 0.1% formic acid for 12 min at flow rate of 40 µL/min. The liquid chromatography temperature was set at 0° C. to reduce back-exchange. Sequence coverage and deuterium uptake were analysed by using ProteinLynx Global Server (Waters) and DynamX (Waters) programmes, respectively. Peptide mapping was obtained by using nondeuterated samples in triplicates and only unique peptides present in all three data files were selected for deuterium uptake data analysis. Leucine enkephalin at a continuous flow rate of 5 µL/min was sprayed as a lock mass for mass correction. Apo PfRH5FL protein digests provided a list of 2056 peptides, after applying several selection filters and manual inspection only 127 peptides were selected for analysis. These peptides provided >93% sequence coverage with many overlapping peptides. The samples were labelled for 20 s, 10 min and 2 h. All HDX-MS experiments were performed in duplicate.

Statistical Analyses

Data were analysed using GraphPad Prism version 6.07 for Windows (GraphPad Software Inc.). All tests used were described in the figure legends. In FIGS. 2B and 3C, a four-parameter sigmoidal dose-response curve was fitted to the relationship between Log 10 (antibody concentration) and percentage GIA for each dataset and used to interpolate $EC_{50}$ values. In FIG. 4D, the nonparametric Spearman's rank correlation coefficient (ρ) was used to assess a correlation between the variables $K_{on}/K_{off}/K_D$ and GIA $EC_{30}$. A two-tailed value of $P<0.05$ was considered significant.

Example 1—Vaccine-Induced Human mAbs to PfRH5

Anti-PfRH5 mAbs were isolated from single-cell sorted plasmablasts of immunized volunteers enrolled in a first-in-human Phase Ia clinical trial of a PfRH5-based vaccine delivered using recombinant chimpanzee adenovirus and poxvirus viral-vectors (see Table 2).

TABLE 2

| | Vaccination details of the three volunteers from which anti-PfRH5FL mAbs were isolated. | | | |
|---|---|---|---|---|
| VAC057 Volunteer # | Trial Group | Time-point | ChAd63 PfRH5FL Prime Dose (vp) | MVA PfRH5FL Boost Dose (pfu) |
| 1017 | 2C | Day 63 (7 days post-boost) | $5 \times 10^{10}$ | $2 \times 10^8$ |
| 1019 | 2B | Day 63 (7 days post-boost) | $5 \times 10^{10}$ | $1 \times 10^8$ |
| 2207 | 2C | Day 63 (7 days post-boost) | $5 \times 10^{10}$ | $2 \times 10^8$ |

Variable region (VR)-coding genes were isolated by RT-PCR and PCR and cloned into a human IgG1 scaffold. Cognate heavy-chain and light-chain plasmids were co-transfected in HEK293 cells and PfRH5-specificity was confirmed by supernatant reactivity to full-length PfRH5 protein comprising amino acids E26-Q526 (PfRH5FL) by ELISA. Seventeen genetically distinct mAbs were isolated (FIG. 1A). Alignment with the most similar germline VR genes in IgBLAST revealed little non-germline sequence, suggesting that PfRH5 is readily recognized with high affinity by germline B cell receptors in humans. The monovalent binding affinity of each mAb was assessed by surface plasmon resonance (SPR), with anti-PfRH5 mouse or chimeric (c) mAbs c2AC7, c4BA7, c9AD4 and QA1 included because of their extensive previous characterisation (Douglas et al., 2014, Nature communications, 2, p. 601; Wright et al., 2014, Nature, 515(7527), p. 427) (FIG. 1B and

TABLE 3

These affinities were generally in the
low nanomolar to high picomolar range.

| mAb | $K_{on}$ (M$^{-1}$s$^{-1}$) | $K_{off}$ (s$^{-1}$) | $K_D$ (M) |
| --- | --- | --- | --- |
| R5.001 | 1.02E+06 | 1.65E-03 | 1.62E-09 |
| R5.002 | 3.86E+05 | 4.91E-03 | 1.27E-08 |
| R5.003 | 1.70E+06 | 1.86E-03 | 1.09E-09 |
| R5.004 | 1.71E+06 | 1.09E-03 | 6.36E-10 |
| R5.006 | 6.77E+05 | 2.34E-04 | 3.46E-10 |
| R5.007 | 3.78E+05 | 3.26E-04 | 8.63E-10 |
| R5.008 | 7.22E+05 | 6.39E-04 | 8.86E-10 |
| R5.009 | 5.12E+05 | 2.72E-04 | 5.31E-10 |
| R5.010 | 7.83E+05 | 3.63E-04 | 4.63E-10 |
| R5.011 | 1.61E+06 | 1.67E-05 | 1.03E-11 |
| R5.013 | 7.73E+05 | 6.02E-05 | 7.79E-11 |
| R5.014 | 3.15E+06 | <2.91E-06 | <9.21E-13 |
| R5.015 | 6.29E+05 | 4.23E-05 | 6.73E-11 |
| R5.016 | 1.14E+06 | 4.88E-04 | 4.28E-10 |
| R5.017 | 1.44E+06 | 2.91E-04 | 2.01E-10 |
| R5.018 | 4.25E+05 | 6.71E-06 | 1.58E-11 |
| R5.019 | 3.07E+06 | 4.72E-04 | 1.54E-10 |
| c2AC7 | 5.16E+06 | 1.62E-04 | 3.14E-11 |
| c4BA7 | 5.89E+05 | 2.55E-05 | 4.33E-11 |
| c9AD4 | 3.63E+06 | 5.04E-04 | 1.39E-10 |
| QA1 | 2.95E+05 | 7.27E-04 | 2.46E-09 |

Table 3: List of anti-PfRH5 mAb binding properties, related to FIG. 1. Association-rate ($K_{on}$), dissociation-rate ($K_{off}$) and affinity ($K_D$) are shown.

The effect of PfRH5 polymorphism on mAb recognition was determined by measuring binding to recombinant PfRH5FL variants, each carrying one of the five most common amino acid substitutions (FIG. 1C). In each case, except for the C203Y substitution, the generated PfRH5FL variants carried the minor allele. All global minor allele frequencies were below 0.19 (MalariaGEN v4.0). In addition, using a dot blot against *P. falciparum* 3D7 clone in vitro culture supernatant, all mAbs were shown to be able to bind parasite-expressed PfRH5 (not shown) which consists of a processed ~45 kDa form.

Example 2—the Neutralizing Capacity of Human mAbs Binding PfRH5

To characterize the ability of the human mAbs to block merozoite entry into the RBC, they were all tested for in vitro GIA against 3D7 clone *P. falciparum*. An initial screen was carried out at high concentration to broadly determine which mAbs are capable of neutralization (FIG. 2A). They were grouped into three categories: "GIA-high" (GIA≥75%), "GIA-low" (75%<GIA>25%) and "GIA-negative" (GIA≤25%). Dilution curves of GIA-high mAbs were made against the 3D7 clone parasites to determine a hierarchy of potency (FIG. 2B). The two most potent mAbs (R5.016 and R5.004) had EC$_{50}$ values comparable to the most potent anti-merozoite mouse-derived mAbs previously described (Douglas et al., 2014; Ord et al., 2014). A strong correlation was also observed between the association-rate ($K_{on}$) of the neutralizing mAbs (nAb) and GIA (data not shown), indicating that mAb-PfRH5 binding in the context of merozoite invasion is likely time-limited. The GIA assays were repeated against six heterologous strains and isolates originating from diverse geographical locations (FIG. 2C), revealing some strain-dependent differences in anti-PfRH5 mAb potency, albeit with very similar hierarchies. Indeed, GB4 was more easily neutralized by all mAbs relative to 3D7, whilst M-Camp was less easily neutralized. The reason for these in vitro differences, and their relevance to in vivo neutralization, remains to be investigated. Notably the M-Camp isolate has previously been shown to be as susceptible as 3D7 to PfRH5 vaccine-induced polyclonal human IgG from the same origin as the mAbs tested here. One notable exception was R5.017, which showed a conspicuous lack of efficacy against the FVO strain and Cp845 isolate. Sequencing the rh5 gene in these six parasites revealed that only these two carry the S197Y polymorphism (FIG. 2D), a substitution known to reduce binding of R5.017 from data in FIG. 1C. This sequencing also revealed that this selection of parasites contains all five of the most common PfRH5 polymorphisms (FIG. 2D).

Example 3—all Major Neutralizing PfRH5 Epitopes are Contained in Truncated PfRH5ΔNL Protein Previous crystallization of PfRH5 protein was aided by removal of two sections of disordered sequence resulting in a truncation lacking 188 of 526 residues (M1-Y139 and N248-M296), termed PfRH5ΔNL. Notably this truncated protein lacks the N-terminal region of PfRH5 (PfRH5Nt), including amino acids K33-K51 previously reported to be the minimal PfP113 binding region and thus a potential site for antibody-mediated neutralization.

Interestingly, all of the GIA-high mAbs and two of three GIA-low mAbs bound PfRH5ΔNL, suggesting that this construct contains the major neutralizing epitopes (FIG. 3A). Only R5.007 and c4BA7 were unable to bind this construct. Their binding site was mapped by ELISA to the internal disordered loop and not the N-terminal region, using an array of overlapping peptides; both of these mAbs bound the same linear PfRH5 peptide (amino acids Y242-D261) (data not shown), consistent with their recognition of heat-treated PfRH5FL protein (data not shown). Furthermore, no mAbs bound recombinant PfRH5Nt by ELISA (amino acids F25-K140) (data not shown).

To investigate this further, the effect of PfRH5FL or PfRH5ΔNL proteins on the GIA of total polyclonal IgG purified from sera of PfRH5FL-immunized human vaccines was assessed. The in vitro GIA could be reversed by adding 0.5 μM of recombinant PfRH5FL or PfRH5ΔNL into the IgG sample. In samples from all seven vaccinated volunteers, the GIA of their IgG was completely reversed following the addition of either PfRH5 variant protein (FIG. 3B), a finding which also repeated when using purified IgG from rabbits immunized with PfRH5FL (data not shown). Notably vaccine-induced IgG against PfRH5Nt was previously reported in the serum of these volunteers by ELISA, suggesting minimal or no contribution of these responses to overall GIA.

To confirm that PfRH5ΔNL vaccination is also capable of eliciting antibody to the most functionally relevant neutralizing epitopes present in PfRH5FL, two groups of rabbits were immunized with equimolar doses of PfRH5FL or PfRH5ΔNL. The resulting purified IgG showed comparable potency in the GIA assay across both groups, indicating that no major neutralizing epitopes are lost in PfRH5ΔNL (FIGS. 3C, D). Passive transfer of PfRH5ΔNL-immunized rabbit IgG into humanized mice, carrying human hepatocytes and erythrocytes and challenged by *P. falciparum*-infected mosquito bites, resulted in a significant reduction of blood-stage parasite burden, further serving to highlight that vaccine-induced IgG to this PfRH5 truncation is sufficient to efficaciously retard or arrest blood-stage parasitemia in vivo (FIG. 3E). Analysis of PfRH5-specific pAb concentrations in the serum of passively immunized mice (FIG. 3F) were consistent with the levels that led to control of blood-stage parasitemia, but not sterilizing immunity, in PfRH5FL-vaccinated Aotus monkeys (Douglas et al., 2015, Nature communications, 2, p. 601). The rigid α-helical core of PfRH5, lacking PfRH5Nt, is thus likely to contain all major neutralizing epitopes and is sufficient to recapitulate antibody raised to the full-length PfRH5 antigen.

Example 3—Clustering of PfRH5-Specific mAbs into Functional Groups

In an effort to better understand the relationship between mAb binding site and function, all mAbs were tested in pairs for their ability to bind simultaneously to monobiotinylated PfRH5FL by BLI (data not shown). This defined seven distinct epitope bins, with each bin containing mAbs that bind overlapping epitopes (FIG. 4A). The resulting bins strongly correlated with GIA, with the red and blue bins containing the most potent anti-PfRH5 mAbs and the purple, yellow, green and orange bins exclusively containing GIA-low or GIA-negative antibodies (FIG. 4B). The epitope bins also proved successful in clustering together those mAbs whose binding blocked in vitro interactions between PfRH5FL and the invasion complex protein PfCyRPA as well as the RBC receptor BSG (FIG. 4C). Indeed, the blue and olive bins contained all the mAbs capable of blocking BSG binding by both SPR and AVEXIS; whilst the purple, yellow and orange bins contained all the mAbs capable of blocking PfCyRPA binding in the SPR assay and the most potent blockers in the AVEXIS assay. Some incomplete blockade of the PfRH5-BSG and PfRH5-PfCyRPA interactions was seen in the AVEXIS assay for some other mAbs, with a similar result for the PfP113-PfRH5 interaction; however, these results were not replicated using SPR. Incomplete PfP113 blockade is unsurprising since no mAbs bind PfRH5 near the PfP113 binding site (data not shown). Collectively, these data highlight the vicinity of the BSG binding site, and not the PfCyRPA binding site, as the key target of growth inhibitory mAbs, and that the most potent nAbs bind to these regions with the highest association-rates (FIG. 4D).

Example 4—Identifying the Epitopes for Key Neutralizing mAbs

The binding modes of R5.016 (also referred to as mAb16) and R5.004 (also referred to as mAb4), the two most potent known human anti-PfRH5 nAbs, were next determined by X-ray crystallography. The structure of a co-crystal containing PfRH5ΔNL, one R5.016 Fab fragment and one R5.004 Fab fragment diffracted to a resolution of 4.0 Å (FIG. 5A and Table 3). High-resolution structures of unbound R5.016 and R5.004 Fab fragment crystals were also determined, with clear electron density observed for all CDR loops in the bound states, facilitating determination of the complex structure (Table 4). The R5.004 and R5.016 binding sites in solution were corroborated by hydrogen-deuterium exchange mass spectrometry (HDX-MS) using full-length PfRH5 and parental R5.016 and R5.004 mAbs (FIG. 5B). R5.004 binds PfRH5 towards the tip of the "kite-like" structure, contacting the N-terminus of helix 4 and each of the three loops that link the converging helices at this apex of PfRH5. These interactions are mediated by five of the CDR loops of the antibody, with only L2 not participating (Table 5). R5.016 binds predominantly to the N-terminus of helix 2 of PfRH5. The major contact is mediated by the H3 loop, which lies along the groove between helices 2 and 3. Additional interactions are mediated by the H1, H2 and L2 loops (Table 4). While the CDR loops of R5.004 are not altered upon binding (RMSD=0.58 Å aligning 59/68 CDR α-carbon atoms), four of the CDR loops of R5.016 (H3, L1, L2 and L3) show significant rearrangement upon binding (data not shown).

Superimposition of the R5.004 and R5.016 Fab structures on the structure of PfRH5ΔNL-BSG (PDB entry 4U0Q) reveals major overlap between the BSG binding site and R5.004 (FIG. 5C). In contrast, of the two copies of BSG in the PfRH5ΔNL:BSG

TABLE 4

Crystallographic data collection and refinement statistics of Fab fragments and complexes, related to FIGS. 5 and 7

|  | R5.004 Fab | R5.011 Fab | R5.016 Fab | PfRH5ΔNL:R5.004:R5.016 | PfRH5ΔNL:R5.011:R5.016 |
| --- | --- | --- | --- | --- | --- |
| Data collection | | | | | |
| Space group | P1 | P2$_1$2$_1$2$_1$ | P4$_1$2$_1$2 | C 1 2 1 | P2$_1$2$_1$2$_1$ |
| Cell dimensions | | | | | |
| a, b, c (Å) | 55.21, 70.18, 73.26 | 47.86, 86.38, 127.4 | 80.08, 80.08, 162.69 | 235.15, 58.78, 116.79 | 140.99, 150.99, 163.97 |
| α, β, γ (°) | 101.42, 92.97, 112.47 | 90.0, 90.0, 90.0 | 90.0, 90.0, 90.0 | 90.0, 106.41, 90.0 | 90.0, 90.0, 90.0 |
| Wavelength (Å) | 0.9999 | 0.9786 | 0.92819 | 0.9795 | 0.9763 |
| Resolution (Å) | 42.45-1.66 (1.69-1.66) | 47.86-2.28 (2.36-2.28) | 15.24-2.10 (2.14-2.10) | 46.92-4.01 (4.07-4.01) | 49.16-3.58 (3.73-3.58) |
| Total observations | 389497 (18845) | 316738 (27746) | 39702 (1666) | 42257 (1687) | 281346 (41777) |
| Total unique | 111530 (5493) | 24770 (2284) | 31807 (1564) | 13131 (522) | 30867 (4579) |
| R$_{pim}$ | 3.9 (83.9) | 7.0 (35.2) | 2.9 (55.5) | 8.1 (50.8) | 13.6 (51.4) |
| R$_{merge}$ (%) | 6.2 (131.1) | 17.1 (86.3) | 10.0 (173.1) | 12.3 (78.1) | 30.3 (114.6) |
| R$_{meas}$ (%) | 7.3 (156.3) | 18.5 (90.6) | 10.5 (182.5) | 14.8 (93.4) | 35.8 (135.0) |

TABLE 4-continued

Crystallographic data collection and refinement statistics of Fab fragments and complexes, related to FIGS. 5 and 7

|  | R5.004 Fab | R5.011 Fab | R5.016 Fab | PfRH5ΔNL:R5.004:R5.016 | PfRH5ΔNL:R5.011:R5.016 |
|---|---|---|---|---|---|
| CC$_{1/2}$ (%) | 99.7 (49.9) | 99.5 (85.3) | 99.9 (53.6) | 98.8 (64.1) | 99.1 (86.3) |
| I/s(I) | 8.6 (1.0) | 11.0 (3.5) | 16.4 (1.3) | 5.9 (1.4) | 4.7 (1.6) |
| Completeness (%) | 95.7 (94.5) | 99.3 (92.7) | 100 (100) | 99.0 (80.7) | 99.7 (98.4) |
| Multiplicity | 3.5 (3.4) | 12.8 (12.1) | 12.5 (10.7) | 3.2 (3.2) | 6.7 (6.7) |
| Refinement |  |  |  |  |  |
| Reflections | 111570 | 23457 | 31616 | 13016 | 41714 |
| R$_{work}$/R$_{free}$ | 18.3/20.4 | 18.6/22.7 | 20.4/22.3 | 32.6/37.7 | 27.4/31.0 |
| Number of residues |  |  |  |  |  |
| Protein | 872 | 431 | 413 | 1175 | 2343 |
| Water | 833 | 238 | 203 | 0 | 0 |
| Ligands | 7 | 2 | 3 | 0 | 0 |
| R.m.s deviations |  |  |  |  |  |
| Bond lengths (Å) | 0.01 | 0.01 | 0.01 | 0.01 | 0.01 |
| Band angles (°) | 1.09 | 1.23 | 1.11 | 1.19 | 1.2 |
| Ramachandran plot |  |  |  |  |  |
| Favored (%) | 97.8 | 96.7 | 97.3 | 92.9 | 93.6 |
| Allowed (%) | 2.2 | 3.3 | 2.7 | 7.1 | 6.4 |
| Outliers (%) | 0 | 0 | 0 | 0 | 0 |

TABLE 5

Proposed interactions between R5.004 and PfRH5 and between R5.016 and PfRH5, related to FIG. 5

| R5.004 |  |  | PfRH5 |  |  |  |
|---|---|---|---|---|---|---|
| FWR/CDR region | Residue (chain) | Group | Structural element | Residue (chain) | Group | Interaction type |
| CDR H1 | Asn 31 (B) | Side chain | Helix 4 | His 365 (A) | Side chain | Hydrogen |
| CDR H1 | Asn 31 (B) | Side chain | Helix 4 | Asp 361 (A) | Side chain | Hydrogen |
| CDR H2 | Ile 52 (B) | Side chain | 5/6 loop | Trp 447 (A) | Side chain | Hydrophobic |
| CDR H2 | Phe 55 (B) | Side chain | Helix 5 | Lys 443 (A) | Side chain | Hydrophobic |
| CDR H2 | Thr 57 (B) | Side chain | Helix 5 | Lys 443 (A) | Side chain | Hydrogen |
| CDR H3 | Asp 99 (B) | Side chain | Helix 4 | Arg 357 (A) | Side chain | Hydrogen |
| CDR H3 | His 101 (B) | Side chain | Helix 4 | Glu 362 (A) | Side chain | Hydrogen |
| CDR H3 | Tyr 105 (B) | Side chain | Helix 4 | Asp 361 (A) | Side chain | Hydrogen |
| CDR L1 | Ser 31 (C) | Side chain | 1/2 loop | Lys 196 (A) | Side chain | Hydrogen |
| CDR L1 | Ser 31 (C) | Main chain | 1/2 loop | Ser 197 (A) | Side chain | Hydrogen |
| CDR L3 | Trp 92 (C) | Side chain | 3/4 loop | Asn 352 (A) | Side chain | Hydrogen |
| CDR L3 | Asp 94 (C) | Side chain | 3/4 loop | Asn 347 (A) | Side chain | Hydrogen |
| CDR L3 | Asn 97 (C) | Side chain | 5/6 loop | Trp 447 (A) | Main chain | Hydrogen |
| CDR L3 | Asn 97 (C) | Side chain | 5/6 loop | Arg 448 (A) | Main chain | Hydrogen |

| R5.016 |  |  | PfRH5 |  |  |  |
|---|---|---|---|---|---|---|
| FWR/CDR region | Residue (chain) | Group | Structural element | Residue (chain) | Group | Interaction type |
| CDR H1 | Thr 28 (E) | Side chain | Helix 2 | Lys 211 (A) | Side chain | Hydrogen |
| CDR H1 | Ser 31 (E) | Side chain | Helix 2 | Asp 207 (A) | Side chain | Hydrogen |
| CDR H1 | Tyr 32 (E) | Side chain | Helix 2 | Ala 208 (A) | Main chain | Hydrogen |
| CDR H2 | Tyr 54 (E) | Side chain | Helix 2 | Ile 204 (A) | Side chain | Hydrophobic |
| Heavy chain FWR3 | Arg 98 (E) | Side chain | Helix 2 | Glu 215 (A) | Side chain | Hydrogen |
| CDR H3 | Pro 101 (E) | Side chain | Helix 2 | Ile 204 (A) | Side chain | Hydrophobic |
| CDR H3 | Gln 102 (E) | Side chain | Helix 2 | Gly 201 (A) | Main chain | Hydrogen |
| CDR H3 | Asp 105 (E) | Side chain | Helix 2 | Lys 202 (A) | Side chain | Hydrogen |
| CDR H3 | Tyr 111 (E) | Side chain | Helix 2 | Lys 202 (A) | Side chain | Hydrophobic |
| CDR H3 | Tyr 111 (E) | Main chain | Helix 3 | Tyr 335 (A) | Side chain | Hydrogen |
| CDR H3 | Tyr 113 (E) | Side chain | Helix 3 | Asp 331 (A) | Side chain | Hydrogen |
| CDR H3 | Tyr 113 (E) | Side chain | Helix 2 | Phe 209 (A) | Side chain | Hydrophobic |
| CDR H3 | Asp 117 (E) | Side chain | Helix 2 | Lys 212 (A) | Side chain | Hydrogen |
| CDR L2 | Leu 54 (D) | Main Chain | Helix 3 | Lys 327 (A) | Side chain | Hydrogen |

TABLE 5-continued

Proposed interactions between R5.004 and PfRH5 and between R5.016 and PfRH5, related to FIG. 5

| CDR L2 | Glu 55 (D) | Side chain | Helix 2 | Lys 212 (A) | Side chain | Hydrogen |
| CDR L2 | Ser 56 (D) | Side chain | Helix 2 | Lys 219 (A) | Side chain | Hydrogen | structure, one overlaps with R5.016 while one does not. This suggests that, while simultaneous binding is possible, the proximity of R5.016 to the BSG binding site is likely to lead to steric occlusion in the context of an intact IgG antibody and membrane attachment of both components. In comparison to previously studied murine mAbs, R5.016 shares much of its binding site with 9AD4, while R5.004 binds to a distinct epitope which shows some overlap with that of QA1. Indeed, 9AD4 and QA1 compete for binding with R5.016 and R5.004, respectively (FIG. 4A). These data serve to further confirm the BSG binding area and the helical face composed of helices 2 and 3 as being the two major sites of antibody-mediated neutralization on PfRH5, and identify epitopes for neutralizing antibodies that are close to human germline that are readily elicited following vaccination.

Example 5—a Class of Non-Neutralizing mAb Potentiates the Effect of Anti-PfRH5, -PfCyRPA and -PfAMA1 Antibodies Having observed one example of antagonism, functional assessment was continued in relation to alternative mAb pairs that bind non-overlapping epitopes on PfRH5 and which do not apparently compete for binding. Combinations of mAbs were tested in the GIA assay to determine whether such mAb combinations lead to improved inhibition of invasion either additively or synergistically.

Remarkably, we determined that mAb R5.011 (also referred to as mAb11) potentiated the inhibitory effect of all eight of the most potent nAbs against 3D7 clone parasites, showing a clear synergistic effect despite showing no neutralizing capacity when tested alone. This effect did not extend to GIA-low mAbs R5.001 and R5.015 or any GIA-negative mAbs (FIG. 6B and see FIG. 2A).

R5.011 shares the same green epitope bin as R5.014 and R5.010 (FIG. 4A). Notably, R5.014 was also capable of synergy, potentiating the effect of a nAb (tested here with R5.016). It is likely R5.011 and R5.014 represent a distinct type of clone that bind within the green epitope bin.

The synergistic effect of mAb R5.011 was investigated further. Interestingly, this was maintained when using a nAb Fab fragment or a R5.011 Fab fragment, ruling out mechanisms linked to IgG bivalency or the Fc (FIG. 6F). Furthermore, the dose-response curve of the nAb+R5.011 IgG combination is altered to resemble the curve shape of nAb Fab fragment alone. These data suggest a degree of self-competition of nAb IgG binding to merozoite-bound PfRH5 at higher concentrations, which appears to be relieved in the presence of mAb R5.011 (FIG. 6F). Synergistic effects were also seen upon addition of R5.011 mAb to polyclonal IgG from PfRH5-vaccinated human volunteers (FIG. 6C), as well as rabbits (data not shown), indicating that this potentiating phenomenon is far from being maximized in these naturally-elicited vaccine-induced pAb.

Dilutions of nAb in the presence of a large excess of R5.011 revealed the maximum possible synergistic effect. Under these conditions, the $EC_{80}$ of R5.016 is reduced from 500 µg/mL to ~55 µg/mL and, likewise, the $EC_{80}$ of R5.004 is reduced from 550 µg/mL to ~55 µg/mL (FIG. 6D). Furthermore, titrating R5.011 into several fixed concentrations of nAb showed that this maximal potentiating effect is achieved from ~200 µg/mL of R5.011 (FIG. 6G). The optimal ratio of nAb:R5.011 across the concentration range was approximately 4:1, with nAb-biased ratios being more effective at lower concentrations and all ratios roughly equivalent at concentrations above 100 µg/mL (FIG. 6H).

It was also investigated whether the effect of R5.011 was PfRH5-specific and the potential for synergy with antibodies targeting merozoite invasion ligands involved in chronologically distinct steps of the RBC invasion process. The addition of R5.011 mAb to polyclonal IgG from rabbits or rats immunized with PfRH4, PfRipr, PfAMA1 or PfCyRPA leads to substantially increased GIA (FIGS. 6E and 8A and B), whereas its addition to anti-PfMSP1 IgG had no effect (FIGS. 6E and 8A and B). These data suggest R5.011-like antibodies can act synergistically with other functional antibodies targeting the PfRH5 invasion complex antigens as well as downstream targets such as PfRH4 and PfAMA1 involved in tight junction formation; whereas this effect is not observed for antibodies targeting antigens that function upstream of the PfRH5-BSG interaction, such as PfMSP1 involved with initial RBC attachment events. Supporting this conclusion, the addition of R5.011 mAb to polyclonal IgG from rabbits immunized with PfRipr also leads to substantially increased GIA (FIGS. 6E and 8).

Finally, it was investigated whether the functionality of R5.016 and R5.011 can be combined into a single molecule, by production of a bispecific dual variable domain immunoglobulin (DVD-Ig™) containing both the variable domains of R5.011 and R5.016. To achieve high levels of growth inhibition, a R5.016+R5.011 mAb combination required fewer total molecules than R5.016 alone (FIG. 6I). Furthermore, these data show that approximately half the molar concentration of the 1611 DVD-Ig is required to achieve the same levels of GIA as compared to the parental R5.016+R5.011 mAb combination, hinting to a bivalent binding mode of this DVD-Ig™ molecule. It is believed that this DVD-Ig™ shows the lowest reported $EC_{80}$ for an anti-merozoite antibody-like molecule. Because high levels of merozoite neutralization are known to be required for protection (Douglas et al., 2015), the antibody $EC_{80}$ or $EC_{90}$ may prove to be a more useful measure of efficacy than the more widely used $EC_{50}$.

Overall, these data identify R5.011 as an example of a class of antimalarial mAb that displays a new functionality by potentiating the effect of all tested anti-PfRH5 nAbs and pAb, as well as pAb directed against other merozoite antigens, despite having no intrinsic neutralizing properties when tested alone. This raises the critical importance of inducing such antibodies in next-generation PfRH5-based vaccination strategies.

Example 6—the Epitope for Potentiating mAb R5.011 Lies at the N-Terminus of PfRH5ΔNL To identify the R5.011 epitope, a crystal structure of PfRH5ΔNL bound to one R5.011 Fab fragment and one R5.016 Fab fragment was determined to a resolution of 3.6 Å, with all CDR loops clearly resolved (FIG. 7A and Table 4). A high-resolution structure of the unbound R5.011 Fab fragment was also determined and used, together with structures of R5.016 Fab fragment and PfRH5ΔNL, to provide model restraints (Table 4). R5.011 binds PfRH5 primarily at the interface between the disordered N-terminus and the rigid α-helical core at residues Y155-L162, a finding also confirmed by HDX-MS (FIG. 7A lower left inset box). Residues F144-N159 of PfRH5 are variably ordered in different crystal structures but most frequently show disorder. R5.011 binds to these residues and constrains and orders their conformation as they emerge from the α-helical core of PfRH5 (FIG. 7C). All of the CDR loops except L3 make contact to PfRH5, with the predominant interaction mediated by H3 (Table 6). Indeed, this is accompanied by a major change in the conformation of the H3 CDR loop of R5.011, which packs against residues Y155-D162 upon binding (FIG. 7D).

The position of R5.016 in PfRH5ΔNL:R5.011:R5.016 is equivalent to that in PfRH5ΔNL:R5.004:R5.016. There is no structural change in the binding site of R5.016 or R5.004 when R5.011 is bound, ruling out an allosteric mechanism for potentiation. FIG. 7B shows an overlay of R5.004, R5.011 and R5.016 Fab fragments bound to PfRH5ΔNL, radiating in different directions. Thus R5.011 accesses an epitope largely devoid of secondary structure at a new site on PfRH5.

whether this mAb slows down the invasion process, thus giving longer for these many different nAbs to reach their binding sites.

Live-cell imaging revealed that the time taken for merozoites to invade RBC is significantly longer (around three-fold) in the presence of R5.011 versus a control mAb targeting Ebolavirus surface protein (FIG. 9A, 10A) and versus non-neutralizing, non-potentiating anti-PfRH5 mAb R5.009 (FIG. 10B). Concentrations of R5.016 around the EC50 did not slow the invasion of those merozoites which were able to invade, whereas high concentrations of R5.016 blocked invasion altogether (FIG. 10B). The observed delay is largely attributed to the phase of invasion preceding merozoite penetration (FIG. 9B, 10A), when invasion ligands PfRH4, PfRH5, PfCyRPA, PfRipr and PfAMA1 are thought to act. Therefore R5.011 lengthens the exposure window of critical merozoite targets to nAbs by slowing RBC entry, thus increasing their opportunity to bind and prevent invasion.

Discussion

The Examples herein determine the features of a desirable human antibody response to the most advanced blood-stage malaria vaccine candidate antigen, by relating the functions of mAbs to their binding sites on PfRH5. The existence of different classes of anti-PfRH5 mAb are revealed including highly-neutralizing mAbs and a novel class of synergistic non-neutralizing mAbs with the unexpected ability to potentiate the invasion inhibition properties of all other neutral-

TABLE 6

Proposed interactions between R5.011 and PfRH5, related to FIG. 7

| | R5.011 | | | PfRH5 | | |
|---|---|---|---|---|---|---|
| FWR/CDR region | Residue (chain) | Group | Structural element | Residue (chain) | Group | Interaction type |
| CDR H1 | Thr 30 (C/H) | Main chain | N-terminal coil | Asn 154 (A/F) | Side chain | Hydrogen |
| CDR H1 | Ser 31 (C/H) | Side chain | N-terminal coil | Ser 153 (A/F) | Main chain | Hydrogen |
| CDR H1 | Ser 31 (C/H) | Main chain | N-terminal coil | Tyr 155 (A/F) | Main chain | Hydrogen |
| CDR H1 | Tyr 32 (C/H) | Side chain | N-terminal coil | Tyr 155 (A/F) | Side chain | Hydrophobic |
| CDR H2 | Asn 52 (C/H) | Side chain | N-terminal coil | Asn 156 (A/F) | Side chain | Hydrogen |
| CDR H2 | Thr 53 (C/H) | Main chain | N-terminal coil | Asn 156 (A/F) | Side chain | Hydrogen |
| CDR H2 | Thr 53 (C/H) | Side chain | N-terminal coil | Asn 156 (A/F) | Side chain | Hydrogen |
| CDR H2 | Asn 54 (C/H) | Main chain | N-terminal coil | Asn 156 (A/F) | Side chain | Hydrogen |
| CDR H3 | Asn 102 (C/H) | Main chain | N-terminal coil | Asn 159 (A/F) | Main chain | Hydrogen |
| CDR H3 | Tyr 104 (C/H) | Main chain | Beta-strand 1 | Ile 161 (A/F) | Main chain | Hydrogen |
| CDR H3 | Ser 106 (C/H) | Main chain | Beta-strand 1 | Ile 161 (A/F) | Main chain | Hydrogen |
| CDR H3 | Ser 106 (C/H) | Side chain | Beta-strand 1 | Ile 163 (A/F) | Main chain | Hydrogen |
| CDR H3 | Ser 107 (C/H) | Side chain | Helix 3 | Lys 311 (A/F) | Side chain | Hydrogen |
| CDR H3 | Tyr 109 (C/H) | Side chain | Helix 3 | Asn 308 (A/F) | Side chain | Hydrogen |
| CDR H3 | Ser 111 (C/H) | Side chain | Helix 3 | Lys 319 (A/F) | Side chain | Hydrogen |
| CDR H3 | Tyr 114 (C/H) | Side chain | Helix 3 | Lys 319 (A/F) | Side chain | Hydrogen |
| CDR L1 | Gly 28 (B/G) | Main chain | Helix 3 | Lys 312 (A/F) | Side chain | Hydrogen |
| CDR L1 | Gly 28 (B/G) | Main chain | Helix 3 | Asn 308 (A/F) | Side chain | Hydrogen |
| CDR L1 | Ser 29 (B/G) | Side chain | Helix 3 | Asn 308 (A/F) | Side chain | Hydrogen |
| CDR L2 | Asp 49 (B/G) | Side chain | Helix 3 | Lys 316 (A/F) | Side chain | Hydrogen |
| CDR L2 | Asp 50 (B/G) | Side chain | Helix 3 | Lys 312 (A/F) | Side chain | Hydrogen |
| CDR L2 | Asp 52 (B/G) | Main chain | Helix 3 | Lys 316 (A/F) | Main chain | Hydrogen |
| Light chain FWR3 | Asn 65 (8/G) | Side chain | Helix 3 | Lys 312 (A/F) | Side chain | Hydrogen |
| Light chain FWR3 | Gly 67 (B/G) | Main chain | Helix 3 | Asp 305 (A/F) | Side chain | Hydrogen |

Example 6—mAb R5.011 Potentiates Anti-Merozoite nAbs by Increasing the Time Required for Invasion Examples 4 demonstrates the ability of R5.011 to potentiate the activity of nAbs which bind to various merozoite invasion proteins, and Example 2 demonstrates that antibody on-rate is likely a critical determinant of neutralizing efficacy. Therefore, it was next decided to investigate izing mAbs, including others that target different invasion proteins such as PfCyRPA and PfAMA1, by slowing invasion.

All of these mAb clones were elicited by PfRH5FL vaccination in humans using a modestly immunogenic viral-vectored vaccine delivery platform. Indeed, the panel of mAbs was limited in size as a result of relatively low B cell induction, a feature typical of viral-vectored vaccination. It is therefore possible that not all mAb classes have been explored and, furthermore, that more potent members of each mAb class may exist, as determined by their association-rate within that class. However, more potent mAbs may be uncommon, as $K_{on}$ values for the mAbs identified here approach the kinetic limits commonly seen in normal B cell development post-vaccination and there is no particular inbuilt in vivo mechanism to select for B cells expressing ultra-high association-rate mAbs (or indeed ultra-slow dissociation-rate mAbs) during affinity maturation. The fact that antibody association-rate, as opposed to the often-measured dissociation-rate, emerged as a key indicator of antibody potency implies highly dynamic processes are involved in invasion. This relationship has been noted before for a viral pathogen; nevertheless, this is an often-neglected parameter that appears highly relevant to malaria vaccine design. Minimal deviation from germline sequences was noted in these mAb clones, potentially related to: i) their isolation from plasmablasts 7 days post-booster vaccination rather than the memory B cell pool, or ii) their isolation after only two PfRH5 vaccinations, and/or iii) their induction by a modestly immunogenic vaccine delivery platform.

Three epitope bins contained GIA-high mAbs: red, blue and olive. The mechanism of action of those contained in the blue and olive bins is undoubtedly blockade of BSG binding, supported by in vitro SPR and AVEXIS assays as well as X-ray crystallography data for exemplar mAb R5.004. However, the crystal structure showed that, unlike R5.004, mAb R5.016 (from the more potent red bin) and BSG can simultaneously bind PfRH5 in solution. The question of why nAbs such as R5.016 are more potent than overt BSG-blocking nAbs such as R5.004 leaves room for additional biological mechanisms to be defined. Experiments in FIG. 4C were designed to answer this question, and revealed that mAbs of the red epitope bin interfere little with binding to BSG, PfCyRPA or PfP113. Without being bound by theory, for now the most likely explanation for their efficacy seems linked to their close proximity of binding on PfRH5 to the BSG binding site. With both PfRH5 and BSG constrained through attachment to their cognate membrane, R5.016 whole IgG molecules and other similar antibodies probably act by preventing PfRH5 from binding to BSG. If so, their improved potency over the BSG-blocking nAbs could be due to increased ease of epitope access on merozoite-bound PfRH5. This is supported by the data which demonstrate a three-fold lengthening of invasion time correlates with a potentiation of nAb activity.

R5.011 is not inhibitory in the time scale of a GIA experiment (one single cycle of blood-stage invasion and growth), it probably mediates its function by increasing the likelihood of nAb binding to PfRH5. This effect is not due to an R5.011-induced increase in the binding affinity for nAbs, as the crystal structures revealed that the R5.004 and R5.016 binding sites are unaltered (<0.5 Å RMSD aligned over 39 and 30 α-carbon atoms, respectively) by the presence of R5.011. Furthermore, the binding affinity and $K_{on}$ of nAbs R5.004 and R5.016 for PfRH5 are unchanged by R5.011 binding, dismissing structural allostery as a mechanism of anti-PfRH5 nAb potentiation. Thus, R5.011 accesses an epitope largely devoid of secondary structure at a new site on PfRH5. Moreover, the effect occurs for all GIA-high nAbs tested as well as R5.007, and these bind four distinct epitope regions on PfRH5. Instead R5.011 reduces the rate of RBC invasion by the merozoite, such that nAbs have longer to access to their epitopes on PfRH5 and are thus more likely to mediate their function. In agreement with this view, R5.011 enhances the effect of antibodies binding merozoite proteins thought to act at the time of PfRH5-BSG binding or afterwards, but not before, consistent with R5.011 causing a retardation in the merozoite invasion process. This is supported by the data which demonstrate that R5.011 significantly slows the invasion process, allowing more time for nAb to bind to their epitopes on various merozoite surface proteins. The ability to delay parasite invasion would represent a highly novel and attractive means of improving vaccine-induced neutralizing antibody efficacy.

One possible mechanism is suggested by the proximity of the R5.011 binding site to the predicted N-terminal cleavage site of PfRH5, the processing of which yields the ~45 kDa fragment. Indeed, if proteolytic cleavage of PfRH5 is necessary for successful merozoite invasion and if R5.011 binding reduces this cleavage rate but not below the rate necessary for successful invasion, protease occlusion would be a plausible mechanism to explain this synergistic cooperation between antibodies (again, not being bound by this theory). Cooperativity between pairs of mAbs targeting a single pathogen protein has been described before, whereby two mAbs specific for the same protein display synergistic neutralizing effects. For instance, cooperativity involving non-neutralizing mAbs to Ebolavirus glycoprotein has been described, as it has previously been with *Neisseria meningitidis* fHBP. However, to the inventors' knowledge, non-neutralizing antibodies like R5.011 that specifically potentiate multiple neutralizing antibodies against the same and other antigenic targets have not been described for other pathogens.

Whatever the mechanism (and the present invention is not bound by theory in this regard), R5.011-like mAbs may explain the high potency of anti-PfRH5 pAb. Indeed the 3D7 *P. falciparum* GIA $EC_{50}$ of anti-PfRH5-specific polyclonal IgG has previously been reported to be ~9 μg/mL across eight vaccinated volunteers, equivalent to that of the most potent of all known anti-PfRH5 mAbs (red epitope bin) and substantially lower than reported for historical vaccine candidates such as PfMSP1 and PfAMA1. The possibility of ultra-potent serum antibody clones contributing most of the GIA at low concentrations in all eight volunteers cannot be excluded, however, synergistic functional interactions between mAbs in the polyclonal IgG seems a more likely explanation. Given that two of the seventeen mAbs in this study displayed potentiating activity, the induction of such clones does not appear to be a rare event following human immunization with PfRH5. Notably, the results herein demonstrate there was still substantial room for improvement through spiking in mAb R5.011 to all the vaccine-induced human pAb samples, suggesting new avenues to maximize the potency of next-generation PfRH5-based vaccines destined for clinical development.

Overall, the data presented here support the view that vaccine-induced anti-PfRH5 pAb growth inhibition represents a synthesis between the neutralizing effect of nAb and synergy from R5.011-type antibodies. Immuno-focusing on these key epitope regions will be critical for next-generation PfRH5 vaccine design, and the ability of the GIA assay to correlate with in vivo protection in NHP, as well as identify anti-PfRH5 mAb clones with in vivo efficacy against *P. falciparum* in a humanized mouse model, further underpins this strategy.

Notably, we demonstrated there was still substantial room for improvement through spiking in mAb R5.011 to all the vaccine-induced human pAb samples, suggesting new avenues to maximize the potency of next-generation PfRH5-based vaccines destined for clinical development. Although relatively high concentrations (around 200 μg/mL) of R5.011 are needed to leverage this effect to its fullest, antigen-specific antibody titers of this magnitude can be achieved in humans. Alternatively, delivering potentiating antibody clones alongside a traditional vaccine using vectored immunoprophylaxis could be a viable alternative.

The development of synergistic and functionally important "non-neutralizing" epitopes challenges the paradigm of structural vaccinology which traditionally sees the advancement of epitopes against which overtly neutralizing antibodies are directed. It is therefore important that future immunogen design strategies for the development of PfRH5-based vaccines use the structural insights obtained here to focus the human immune response to generate both neutralizing and potentiating antibodies. These data thus provide a strategy to design effective PfRH5-based blood-stage malaria vaccines that provide functional anti-merozoite immunity at lower overall concentrations of PfRH5-specific human IgG.

SEQUENCE LISTING

```
<160> NUMBER OF SEQ ID NOS: 146

<210> SEQ ID NO 1
<211> LENGTH: 526
<212> TYPE: PRT
<213> ORGANISM: Plasmodium falciparum

<400> SEQUENCE: 1

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
            180                 185                 190

Ile Tyr His Lys Ser Ser Thr Tyr Gly Lys Cys Ile Ala Val Asp Ala
        195                 200                 205

Phe Ile Lys Lys Ile Asn Glu Thr Tyr Asp Lys Val Lys Ser Lys Cys
    210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Asp Ser Tyr Arg Tyr Asp Ile
                245                 250                 255

Ser Glu Glu Ile Asp Asp Lys Ser Glu Glu Thr Asp Asp Glu Thr Glu
            260                 265                 270

Glu Val Glu Asp Ser Ile Gln Asp Thr Asp Ser Asn His Thr Pro Ser
        275                 280                 285

Asn Lys Lys Lys Asn Asp Leu Met Asn Arg Thr Phe Lys Lys Met Met
    290                 295                 300

Asp Glu Tyr Asn Thr Lys Lys Lys Lys Leu Ile Lys Cys Ile Lys Asn
```

His Glu Asn Asp Phe Asn Lys Ile Cys Met Asp Met Lys Asn Tyr Gly
305                 310                 315                 320

Thr Asn Leu Phe Glu Gln Leu Ser Cys Tyr Asn Asn Asn Phe Cys Asn
            325                 330                 335

Thr Asn Gly Ile Arg Tyr His Tyr Asp Glu Tyr Ile His Lys Leu Ile
        340                 345                 350

Leu Ser Val Lys Ser Lys Asn Leu Asn Lys Asp Leu Ser Asp Met Thr
    355                 360                 365

Asn Ile Leu Gln Gln Ser Glu Leu Leu Leu Thr Asn Leu Asn Lys Lys
370                 375                 380

Met Gly Ser Tyr Ile Tyr Ile Asp Thr Ile Lys Phe Ile His Lys Glu
385                 390                 395                 400

Met Lys His Ile Phe Asn Arg Ile Glu Tyr His Thr Lys Ile Ile Asn
                405                 410                 415

Asp Lys Thr Lys Ile Ile Gln Asp Lys Ile Lys Leu Asn Ile Trp Arg
            420                 425                 430

Thr Phe Gln Lys Asp Glu Leu Leu Lys Arg Ile Leu Asp Met Ser Asn
        435                 440                 445

Glu Tyr Ser Leu Phe Ile Thr Ser Asp His Leu Arg Gln Met Leu Tyr
    450                 455                 460

Asn Thr Phe Tyr Ser Lys Glu Lys His Leu Asn Asn Ile Phe His His
465                 470                 475                 480

Leu Ile Tyr Val Leu Gln Met Lys Phe Asn Asp Val Pro Ile Lys Met
                485                 490                 495

Glu Tyr Phe Gln Thr Tyr Lys Lys Asn Lys Pro Leu Thr Gln
            500                 505                 510

515                 520                 525

<210> SEQ ID NO 2
<211> LENGTH: 526
<212> TYPE: PRT
<213> ORGANISM: Plasmodium falciparum

<400> SEQUENCE: 2

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
            165                 170                 175

Pro His Tyr Thr Phe Leu Asp Tyr Tyr Lys His Leu Ser Tyr Asn Ser
        180                 185                 190

Ile Tyr His Lys Ser Ser Thr Tyr Gly Lys Tyr Ile Ala Val Asp Ala
    195                 200                 205

Phe Ile Lys Lys Ile Asn Glu Thr Tyr Asp Lys Val Lys Ser Lys Cys
210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Asp Ser Tyr Arg Tyr Asp Ile
                245                 250                 255

Ser Glu Glu Ile Asp Asp Lys Ser Glu Glu Thr Asp Asp Glu Thr Glu
                260                 265                 270

Glu Val Glu Asp Ser Ile Gln Asp Thr Asp Ser Asn His Thr Pro Ser
            275                 280                 285

Asn Lys Lys Lys Asn Asp Leu Met Asn Arg Thr Phe Lys Lys Met Met
        290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Phe Cys Asn
            340                 345                 350

Thr Asn Gly Ile Arg Tyr His Tyr Asp Glu Tyr Ile His Lys Leu Ile
        355                 360                 365

Leu Ser Val Lys Ser Lys Asn Leu Asn Lys Asp Leu Ser Asp Met Thr
370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
        435                 440                 445

Thr Phe Gln Lys Asp Glu Leu Leu Lys Arg Ile Leu Asp Met Ser Asn
450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
        515                 520                 525

<210> SEQ ID NO 3
<211> LENGTH: 387
<212> TYPE: PRT
<213> ORGANISM: Plasmodium falciparum

<400> SEQUENCE: 3

Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
        35                  40                  45

Leu Ser Tyr Asn Ser Ile Tyr His Lys Ser Ser Thr Tyr Gly Lys Cys
    50                  55                  60

Ile Ala Val Asp Ala Phe Ile Lys Lys Ile Asn Glu Thr Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Asp Asp Ser
            100                 105                 110

Tyr Arg Tyr Asp Ile Ser Glu Glu Ile Asp Asp Lys Ser Glu Glu Thr
        115                 120                 125

Asp Asp Glu Thr Glu Glu Val Glu Asp Ser Ile Gln Asp Thr Asp Ser
    130                 135                 140

Asn His Thr Pro Ser Asn Lys Lys Asn Asp Leu Met Asn Arg Thr
145                 150                 155                 160

Phe Lys Lys Met Met Asp Glu Tyr Asn Thr Lys Lys Lys Leu Ile
            165                 170                 175

Lys Cys Ile Lys Asn His Glu Asn Asp Phe Asn Lys Ile Cys Met Asp
        180                 185                 190

Met Lys Asn Tyr Gly Thr Asn Leu Phe Glu Gln Leu Ser Cys Tyr Asn
    195                 200                 205

Asn Asn Phe Cys Asn Thr Asn Gly Ile Arg Tyr His Tyr Asp Glu Tyr
    210                 215                 220

Ile His Lys Leu Ile Leu Ser Val Lys Ser Lys Asn Leu Asn Lys Asp
225                 230                 235                 240

Leu Ser Asp Met Thr Asn Ile Leu Gln Gln Ser Glu Leu Leu Leu Thr
            245                 250                 255

Asn Leu Asn Lys Lys Met Gly Ser Tyr Ile Tyr Ile Asp Thr Ile Lys
            260                 265                 270

Phe Ile His Lys Glu Met Lys His Ile Phe Asn Arg Ile Glu Tyr His
        275                 280                 285

Thr Lys Ile Ile Asn Asp Lys Thr Lys Ile Ile Gln Asp Lys Ile Lys
    290                 295                 300

Leu Asn Ile Trp Arg Thr Phe Gln Lys Asp Glu Leu Leu Lys Arg Ile
305                 310                 315                 320

Leu Asp Met Ser Asn Glu Tyr Ser Leu Phe Ile Thr Ser Asp His Leu
            325                 330                 335

Arg Gln Met Leu Tyr Asn Thr Phe Tyr Ser Lys Glu Lys His Leu Asn
            340                 345                 350

Asn Ile Phe His His Leu Ile Tyr Val Leu Gln Met Lys Phe Asn Asp
        355                 360                 365

Val Pro Ile Lys Met Glu Tyr Phe Gln Thr Tyr Lys Lys Asn Lys Pro
    370                 375                 380

Leu Thr Gln
385

<210> SEQ ID NO 4
<211> LENGTH: 387
<212> TYPE: PRT
<213> ORGANISM: Plasmodium falciparum

<400> SEQUENCE: 4

```
Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
        35                  40                  45

Leu Ser Tyr Asn Ser Ile Tyr His Lys Ser Ser Thr Tyr Gly Lys Tyr
    50                  55                  60

Ile Ala Val Asp Ala Phe Ile Lys Lys Ile Asn Glu Thr Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Asp Asp Ser
            100                 105                 110

Tyr Arg Tyr Asp Ile Ser Glu Glu Ile Asp Asp Lys Ser Glu Glu Thr
        115                 120                 125

Asp Asp Glu Thr Glu Glu Val Glu Asp Ser Ile Gln Asp Thr Asp Ser
130                 135                 140

Asn His Thr Pro Ser Asn Lys Lys Asn Asp Leu Met Asn Arg Thr
145                 150                 155                 160

Phe Lys Lys Met Met Asp Glu Tyr Asn Thr Lys Lys Lys Leu Ile
                165                 170                 175

Lys Cys Ile Lys Asn His Glu Asn Asp Phe Asn Lys Ile Cys Met Asp
            180                 185                 190

Met Lys Asn Tyr Gly Thr Asn Leu Phe Glu Gln Leu Ser Cys Tyr Asn
        195                 200                 205

Asn Asn Phe Cys Asn Thr Asn Gly Ile Arg Tyr His Tyr Asp Glu Tyr
210                 215                 220

Ile His Lys Leu Ile Leu Ser Val Lys Ser Lys Asn Leu Asn Lys Asp
225                 230                 235                 240

Leu Ser Asp Met Thr Asn Ile Leu Gln Gln Ser Glu Leu Leu Leu Thr
                245                 250                 255

Asn Leu Asn Lys Lys Met Gly Ser Tyr Ile Tyr Ile Asp Thr Ile Lys
            260                 265                 270

Phe Ile His Lys Glu Met Lys His Ile Phe Asn Arg Ile Glu Tyr His
        275                 280                 285

Thr Lys Ile Ile Asn Asp Lys Thr Lys Ile Ile Gln Asp Lys Ile Lys
    290                 295                 300

Leu Asn Ile Trp Arg Thr Phe Gln Lys Asp Glu Leu Leu Lys Arg Ile
305                 310                 315                 320

Leu Asp Met Ser Asn Glu Tyr Ser Leu Phe Ile Thr Ser Asp His Leu
                325                 330                 335

Arg Gln Met Leu Tyr Asn Thr Phe Tyr Ser Lys Glu Lys His Leu Asn
            340                 345                 350

Asn Ile Phe His His Leu Ile Tyr Val Leu Gln Met Lys Phe Asn Asp
        355                 360                 365

Val Pro Ile Lys Met Glu Tyr Phe Gln Thr Tyr Lys Lys Asn Lys Pro
    370                 375                 380

Leu Thr Gln
385
```

<210> SEQ ID NO 5

<211> LENGTH: 367
<212> TYPE: PRT
<213> ORGANISM: Plasmodium falciparum

<400> SEQUENCE: 5

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
            20                  25                  30

Ser Ile Tyr His Lys Ser Ser Thr Tyr Gly Lys Cys Ile Ala Val Asp
        35                  40                  45

Ala Phe Ile Lys Lys Ile Asn Glu Thr Tyr Asp Lys Val Lys Ser Lys
    50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Asp Ser Tyr Arg Tyr Tyr Asp
                85                  90                  95

Ile Ser Glu Glu Ile Asp Lys Ser Glu Glu Thr Asp Asp Glu Thr
            100                 105                 110

Glu Glu Val Glu Asp Ser Ile Gln Asp Thr Asp Ser Asn His Thr Pro
    115                 120                 125

Ser Asn Lys Lys Lys Asn Asp Leu Met Asn Arg Thr Phe Lys Lys Met
130                 135                 140

Met Asp Glu Tyr Asn Thr Lys Lys Lys Leu Ile Lys Cys Ile Lys
145                 150                 155                 160

Asn His Glu Asn Asp Phe Asn Lys Ile Cys Met Asp Met Lys Asn Tyr
                165                 170                 175

Gly Thr Asn Leu Phe Glu Gln Leu Ser Cys Tyr Asn Asn Phe Cys
            180                 185                 190

Asn Thr Asn Gly Ile Arg Tyr His Tyr Asp Glu Tyr Ile His Lys Leu
        195                 200                 205

Ile Leu Ser Val Lys Ser Lys Asn Leu Asn Lys Asp Leu Ser Asp Met
    210                 215                 220

Thr Asn Ile Leu Gln Gln Ser Glu Leu Leu Thr Asn Leu Asn Lys
225                 230                 235                 240

Lys Met Gly Ser Tyr Ile Tyr Ile Asp Thr Ile Lys Phe Ile His Lys
                245                 250                 255

Glu Met Lys His Ile Phe Asn Arg Ile Glu Tyr His Thr Lys Ile Ile
            260                 265                 270

Asn Asp Lys Thr Lys Ile Ile Gln Asp Lys Ile Lys Leu Asn Ile Trp
        275                 280                 285

Arg Thr Phe Gln Lys Asp Glu Leu Leu Lys Arg Ile Leu Asp Met Ser
    290                 295                 300

Asn Glu Tyr Ser Leu Phe Ile Thr Ser Asp His Leu Arg Gln Met Leu
305                 310                 315                 320

Tyr Asn Thr Phe Tyr Ser Lys Glu Lys His Leu Asn Asn Ile Phe His
                325                 330                 335

His Leu Ile Tyr Val Leu Gln Met Lys Phe Asn Asp Val Pro Ile Lys
            340                 345                 350

Met Glu Tyr Phe Gln Thr Tyr Lys Lys Asn Lys Pro Leu Thr Gln
        355                 360                 365

<210> SEQ ID NO 6
<211> LENGTH: 367
<212> TYPE: PRT

<213> ORGANISM: Plasmodium falciparum

<400> SEQUENCE: 6

| | | | | | | | | | | | | | | |
|---|---|---|---|---|---|---|---|---|---|---|---|---|---|---|
| Ser | Ile | Asp | Ile | Leu | Gln | Glu | Lys | Glu | Gly | His | Leu | Asp | Phe | Val | Ile |
| 1 | | | | 5 | | | | | 10 | | | | | 15 | |
| Ile | Pro | His | Tyr | Thr | Phe | Leu | Asp | Tyr | Tyr | Lys | His | Leu | Ser | Tyr | Asn |
| | | | 20 | | | | | 25 | | | | | 30 | | |
| Ser | Ile | Tyr | His | Lys | Ser | Ser | Thr | Gly | Lys | Tyr | Ile | Ala | Val | Asp |
| | | 35 | | | | | 40 | | | | | 45 | | |
| Ala | Phe | Ile | Lys | Lys | Ile | Asn | Glu | Thr | Tyr | Asp | Lys | Val | Lys | Ser | Lys |
| | 50 | | | | | 55 | | | | | 60 | | | | |
| Cys | Asn | Asp | Ile | Lys | Asn | Asp | Leu | Ile | Ala | Thr | Ile | Lys | Lys | Leu | Glu |
| 65 | | | | | 70 | | | | | 75 | | | | | 80 |
| His | Pro | Tyr | Asp | Ile | Asn | Asn | Lys | Asn | Asp | Asp | Ser | Tyr | Arg | Tyr | Asp |
| | | | | 85 | | | | | 90 | | | | | 95 | |
| Ile | Ser | Glu | Glu | Ile | Asp | Asp | Lys | Ser | Glu | Glu | Thr | Asp | Asp | Glu | Thr |
| | | | 100 | | | | | 105 | | | | | 110 | | |
| Glu | Glu | Val | Glu | Asp | Ser | Ile | Gln | Asp | Thr | Asp | Ser | Asn | His | Thr | Pro |
| | | | 115 | | | | | 120 | | | | | 125 | | |
| Ser | Asn | Lys | Lys | Lys | Asn | Asp | Leu | Met | Asn | Arg | Thr | Phe | Lys | Lys | Met |
| | 130 | | | | | 135 | | | | | 140 | | | | |
| Met | Asp | Glu | Tyr | Asn | Thr | Lys | Lys | Lys | Leu | Ile | Lys | Cys | Ile | Lys |
| 145 | | | | | 150 | | | | | 155 | | | | | 160 |
| Asn | His | Glu | Asn | Asp | Phe | Asn | Lys | Ile | Cys | Met | Asp | Met | Lys | Asn | Tyr |
| | | | | 165 | | | | | 170 | | | | | 175 | |
| Gly | Thr | Asn | Leu | Phe | Glu | Gln | Leu | Ser | Cys | Tyr | Asn | Asn | Phe | Cys |
| | | | 180 | | | | | 185 | | | | | 190 | | |
| Asn | Thr | Asn | Gly | Ile | Arg | Tyr | His | Tyr | Asp | Glu | Tyr | Ile | His | Lys | Leu |
| | | | 195 | | | | | 200 | | | | | 205 | | |
| Ile | Leu | Ser | Val | Lys | Ser | Lys | Asn | Leu | Asn | Lys | Asp | Leu | Ser | Asp | Met |
| | | 210 | | | | | 215 | | | | | 220 | | | |
| Thr | Asn | Ile | Leu | Gln | Gln | Ser | Glu | Leu | Leu | Leu | Thr | Asn | Leu | Asn | Lys |
| 225 | | | | | 230 | | | | | 235 | | | | | 240 |
| Lys | Met | Gly | Ser | Tyr | Ile | Tyr | Ile | Asp | Thr | Ile | Lys | Phe | Ile | His | Lys |
| | | | | 245 | | | | | 250 | | | | | 255 | |
| Glu | Met | Lys | His | Ile | Phe | Asn | Arg | Ile | Glu | Tyr | His | Thr | Lys | Ile | Ile |
| | | | 260 | | | | | 265 | | | | | 270 | | |
| Asn | Asp | Lys | Thr | Lys | Ile | Ile | Gln | Asp | Lys | Ile | Lys | Leu | Asn | Ile | Trp |
| | | 275 | | | | | 280 | | | | | 285 | | | |
| Arg | Thr | Phe | Gln | Lys | Asp | Glu | Leu | Leu | Lys | Arg | Ile | Leu | Asp | Met | Ser |
| | 290 | | | | | 295 | | | | | 300 | | | | |
| Asn | Glu | Tyr | Ser | Leu | Phe | Ile | Thr | Ser | Asp | His | Leu | Arg | Gln | Met | Leu |
| 305 | | | | | 310 | | | | | 315 | | | | | 320 |
| Tyr | Asn | Thr | Phe | Tyr | Ser | Lys | Glu | Lys | His | Leu | Asn | Asn | Ile | Phe | His |
| | | | | 325 | | | | | 330 | | | | | 335 | |
| His | Leu | Ile | Tyr | Val | Leu | Gln | Met | Lys | Phe | Asn | Asp | Val | Pro | Ile | Lys |
| | | | 340 | | | | | 345 | | | | | 350 | | |
| Met | Glu | Tyr | Phe | Gln | Thr | Tyr | Lys | Lys | Asn | Lys | Pro | Leu | Thr | Gln |
| | | | 355 | | | | | 360 | | | | | 365 | | |

<210> SEQ ID NO 7
<211> LENGTH: 338
<212> TYPE: PRT
<213> ORGANISM: Artificial Sequence
<220> FEATURE:

<223> OTHER INFORMATION: PfRH5 amino acid sequence (3D7) excluding
    signal sequence, flexible N-terminal (amino acids 1 to 139) and
    flexible loop (amino acids 248 to 296) regions

<400> SEQUENCE: 7

```
Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Lys His
        35                  40                  45

Leu Ser Tyr Asn Ser Ile Tyr His Lys Ser Ser Thr Tyr Gly Lys Cys
    50                  55                  60

Ile Ala Val Asp Ala Phe Ile Lys Lys Ile Asn Glu Thr Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Arg Thr Phe
            100                 105                 110

Lys Lys Met Met Asp Glu Tyr Asn Thr Lys Lys Lys Leu Ile Lys
            115                 120                 125

Cys Ile Lys Asn His Glu Asn Asp Phe Asn Lys Ile Cys Met Asp Met
130                 135                 140

Lys Asn Tyr Gly Thr Asn Leu Phe Glu Gln Leu Ser Cys Tyr Asn Asn
145                 150                 155                 160

Asn Phe Cys Asn Thr Asn Gly Ile Arg Tyr His Tyr Asp Glu Tyr Ile
            165                 170                 175

His Lys Leu Ile Leu Ser Val Lys Ser Lys Asn Leu Asn Lys Asp Leu
        180                 185                 190

Ser Asp Met Thr Asn Ile Leu Gln Gln Ser Glu Leu Leu Leu Thr Asn
    195                 200                 205

Leu Asn Lys Lys Met Gly Ser Tyr Ile Tyr Ile Asp Thr Ile Lys Phe
210                 215                 220

Ile His Lys Glu Met Lys His Ile Phe Asn Arg Ile Glu Tyr His Thr
225                 230                 235                 240

Lys Ile Ile Asn Asp Lys Thr Lys Ile Ile Gln Asp Lys Ile Lys Leu
            245                 250                 255

Asn Ile Trp Arg Thr Phe Gln Lys Asp Glu Leu Leu Lys Arg Ile Leu
            260                 265                 270

Asp Met Ser Asn Glu Tyr Ser Leu Phe Ile Thr Ser Asp His Leu Arg
        275                 280                 285

Gln Met Leu Tyr Asn Thr Phe Tyr Ser Lys Gly Lys His Leu Asn Asn
    290                 295                 300

Ile Phe His His Leu Ile Tyr Val Leu Gln Met Lys Phe Asn Asp Val
305                 310                 315                 320

Pro Ile Lys Met Glu Tyr Phe Gln Thr Tyr Lys Lys Asn Lys Pro Leu
            325                 330                 335

Thr Gln
```

<210> SEQ ID NO 8
<211> LENGTH: 338
<212> TYPE: PRT
<213> ORGANISM: Artificial Sequence
<220> FEATURE:
<223> OTHER INFORMATION: PfRH5 amino acid sequence (7G8) excluding
    signal sequence, flexible N-terminal (amino acids 1 to 139) and flexible loop (amino acids 248 to 296) regions

<400> SEQUENCE: 8

```
Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
        35                  40                  45

Leu Ser Tyr Asn Ser Ile Tyr His Lys Ser Ser Thr Tyr Gly Lys Tyr
    50                  55                  60

Ile Ala Val Asp Ala Phe Ile Lys Lys Ile Asn Glu Thr Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Arg Thr Phe
            100                 105                 110

Lys Lys Met Met Asp Glu Tyr Asn Thr Lys Lys Lys Leu Ile Lys
            115                 120                 125

Cys Ile Lys Asn His Glu Asn Asp Phe Asn Lys Ile Cys Met Asp Met
130                 135                 140

Lys Asn Tyr Gly Thr Asn Leu Phe Glu Gln Leu Ser Cys Tyr Asn Asn
145                 150                 155                 160

Asn Phe Cys Asn Thr Asn Gly Ile Arg Tyr His Tyr Asp Glu Tyr Ile
                165                 170                 175

His Lys Leu Ile Leu Ser Val Lys Ser Lys Asn Leu Asn Lys Asp Leu
            180                 185                 190

Ser Asp Met Thr Asn Ile Leu Gln Gln Ser Glu Leu Leu Leu Thr Asn
            195                 200                 205

Leu Asn Lys Lys Met Gly Ser Tyr Ile Tyr Ile Asp Thr Ile Lys Phe
210                 215                 220

Ile His Lys Glu Met Lys His Ile Phe Asn Arg Ile Glu Tyr His Thr
225                 230                 235                 240

Lys Ile Ile Asn Asp Lys Thr Lys Ile Ile Gln Asp Lys Ile Lys Leu
                245                 250                 255

Asn Ile Trp Arg Thr Phe Gln Lys Asp Glu Leu Leu Lys Arg Ile Leu
            260                 265                 270

Asp Met Ser Asn Glu Tyr Ser Leu Phe Ile Thr Ser Asp His Leu Arg
            275                 280                 285

Gln Met Leu Tyr Asn Thr Phe Tyr Ser Lys Glu Lys His Leu Asn Asn
            290                 295                 300

Ile Phe His His Leu Ile Tyr Val Leu Gln Met Lys Phe Asn Asp Val
305                 310                 315                 320

Pro Ile Lys Met Glu Tyr Phe Gln Thr Tyr Lys Lys Asn Lys Pro Leu
                325                 330                 335

Thr Gln
```

<210> SEQ ID NO 9
<211> LENGTH: 318
<212> TYPE: PRT
<213> ORGANISM: Artificial Sequence
<220> FEATURE:
<223> OTHER INFORMATION: PfRH5 amino acid sequence (3D7) excluding
      signal sequence, flexible N-terminal (amino acids 1 to 159) and
      flexible loop (amino acids 248 to 296) regions

<400> SEQUENCE: 9

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
            20                  25                  30

Ser Ile Tyr His Lys Ser Ser Thr Tyr Gly Lys Cys Ile Ala Val Asp
        35                  40                  45

Ala Phe Ile Lys Lys Ile Asn Glu Thr Tyr Asp Lys Val Lys Ser Lys
50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Arg Thr Phe Lys Lys Met Met
                85                  90                  95

Asp Glu Tyr Asn Thr Lys Lys Lys Lys Leu Ile Lys Cys Ile Lys Asn
            100                 105                 110

His Glu Asn Asp Phe Asn Lys Ile Cys Met Asp Met Lys Asn Tyr Gly
        115                 120                 125

Thr Asn Leu Phe Glu Gln Leu Ser Cys Tyr Asn Asn Asn Phe Cys Asn
130                 135                 140

Thr Asn Gly Ile Arg Tyr His Tyr Asp Glu Tyr Ile His Lys Leu Ile
145                 150                 155                 160

Leu Ser Val Lys Ser Lys Asn Leu Asn Lys Asp Leu Ser Asp Met Thr
                165                 170                 175

Asn Ile Leu Gln Gln Ser Glu Leu Leu Leu Thr Asn Leu Asn Lys Lys
            180                 185                 190

Met Gly Ser Tyr Ile Tyr Ile Asp Thr Ile Lys Phe Ile His Lys Glu
        195                 200                 205

Met Lys His Ile Phe Asn Arg Ile Glu Tyr His Thr Lys Ile Ile Asn
210                 215                 220

Asp Lys Thr Lys Ile Ile Gln Asp Lys Ile Lys Leu Asn Ile Trp Arg
225                 230                 235                 240

Thr Phe Gln Lys Asp Glu Leu Leu Lys Arg Ile Leu Asp Met Ser Asn
                245                 250                 255

Glu Tyr Ser Leu Phe Ile Thr Ser Asp His Leu Arg Gln Met Leu Tyr
            260                 265                 270

Asn Thr Phe Tyr Ser Lys Glu Lys His Leu Asn Asn Ile Phe His His
        275                 280                 285

Leu Ile Tyr Val Leu Gln Met Lys Phe Asn Asp Val Pro Ile Lys Met
290                 295                 300

Glu Tyr Phe Gln Thr Tyr Lys Lys Asn Lys Pro Leu Thr Gln
305                 310                 315

<210> SEQ ID NO 10
<211> LENGTH: 318
<212> TYPE: PRT
<213> ORGANISM: Artificial Sequence
<220> FEATURE:
<223> OTHER INFORMATION: PfRH5 amino acid sequence (7G8) excluding
      signal sequence, flexible N-terminal (amino acids 1 to 159) and
      flexible loop (amino acids 248 to 296) regions

<400> SEQUENCE: 10

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
            20                  25                  30

-continued

```
Ser Ile Tyr His Lys Ser Ser Thr Tyr Gly Lys Tyr Ile Ala Val Asp
        35                  40                  45

Ala Phe Ile Lys Lys Ile Asn Glu Thr Tyr Asp Lys Val Lys Ser Lys
50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Arg Thr Phe Lys Lys Met Met
                85                  90                  95

Asp Glu Tyr Asn Thr Lys Lys Lys Leu Ile Lys Cys Ile Lys Asn
                    100                 105                 110

His Glu Asn Asp Phe Asn Lys Ile Cys Met Asp Met Lys Asn Tyr Gly
                115                 120                 125

Thr Asn Leu Phe Glu Gln Leu Ser Cys Tyr Asn Asn Phe Cys Asn
    130                 135                 140

Thr Asn Gly Ile Arg Tyr His Tyr Asp Glu Tyr Ile His Lys Leu Ile
145                 150                 155                 160

Leu Ser Val Lys Ser Lys Asn Leu Asn Lys Asp Leu Ser Asp Met Thr
                165                 170                 175

Asn Ile Leu Gln Gln Ser Glu Leu Leu Leu Thr Asn Leu Asn Lys Lys
                180                 185                 190

Met Gly Ser Tyr Ile Tyr Ile Asp Thr Ile Lys Phe Ile His Lys Glu
            195                 200                 205

Met Lys His Ile Phe Asn Arg Ile Glu Tyr His Thr Lys Ile Ile Asn
        210                 215                 220

Asp Lys Thr Lys Ile Ile Gln Asp Lys Ile Lys Leu Asn Ile Trp Arg
225                 230                 235                 240

Thr Phe Gln Lys Asp Glu Leu Leu Lys Arg Ile Leu Asp Met Ser Asn
                245                 250                 255

Glu Tyr Ser Leu Phe Ile Thr Ser Asp His Leu Arg Gln Met Leu Tyr
                260                 265                 270

Asn Thr Phe Tyr Ser Lys Glu Lys His Leu Asn Asn Ile Phe His His
            275                 280                 285

Leu Ile Tyr Val Leu Gln Met Lys Phe Asn Asp Val Pro Ile Lys Met
        290                 295                 300

Glu Tyr Phe Gln Thr Tyr Lys Lys Asn Lys Pro Leu Thr Gln
305                 310                 315
```

<210> SEQ ID NO 11
<211> LENGTH: 5
<212> TYPE: PRT
<213> ORGANISM: Artificial Sequence
<220> FEATURE:
<223> OTHER INFORMATION: mAb11 heavy chain CDR1

<400> SEQUENCE: 11

```
Ser Tyr Ala Met Asn
1               5
```

<210> SEQ ID NO 12
<211> LENGTH: 17
<212> TYPE: PRT
<213> ORGANISM: Artificial Sequence
<220> FEATURE:
<223> OTHER INFORMATION: mAb11 heavy chain CDR2

<400> SEQUENCE: 12

Trp Ile Asn Thr Asn Thr Gly Asn Pro Thr Tyr Ala Gln Gly Phe Thr 1 5 10 15

Gly

<210> SEQ ID NO 13
<211> LENGTH: 19
<212> TYPE: PRT
<213> ORGANISM: Artificial Sequence
<220> FEATURE:
<223> OTHER INFORMATION: mAb11 heavy chain CDR3

<400> SEQUENCE: 13

Glu Ser Pro Asn Tyr Tyr Asp Ser Ser Gly Tyr Tyr Ser Gly Tyr Tyr
1 5 10 15

Phe Asp Tyr

<210> SEQ ID NO 14
<211> LENGTH: 5
<212> TYPE: PRT
<213> ORGANISM: Artificial Sequence
<220> FEATURE:
<223> OTHER INFORMATION: mAb14 heavy chain CDR1

<400> SEQUENCE: 14

Asp Tyr Ala Met His
1 5

<210> SEQ ID NO 15
<211> LENGTH: 17
<212> TYPE: PRT
<213> ORGANISM: Artificial Sequence
<220> FEATURE:
<223> OTHER INFORMATION: mAb14 heavy chain CDR2

<400> SEQUENCE: 15

Gly Ile Ser Trp Asn Ser Ala Ser Met Asp Tyr Ala Asp Ser Val Lys
1 5 10 15

Gly

<210> SEQ ID NO 16
<211> LENGTH: 17
<212> TYPE: PRT
<213> ORGANISM: Artificial Sequence
<220> FEATURE:
<223> OTHER INFORMATION: mAb14 heavy chain CDR3

<400> SEQUENCE: 16

Asp Pro Ala Pro Pro Tyr Cys Gly Gly Asp Cys Tyr Pro Ser Phe Asp
1 5 10 15

Tyr

<210> SEQ ID NO 17
<211> LENGTH: 5
<212> TYPE: PRT
<213> ORGANISM: Artificial Sequence
<220> FEATURE:
<223> OTHER INFORMATION: mAb10 heavy chain CDR1

<400> SEQUENCE: 17

Ser Tyr Trp Met Ser
1 5

<210> SEQ ID NO 18
<211> LENGTH: 17
<212> TYPE: PRT
```
<213> ORGANISM: Artificial Sequence
<220> FEATURE:
<223> OTHER INFORMATION: mAb10 heavy chain CDR2

<400> SEQUENCE: 18

Asn Ile Lys Gln Asp Gly Ser Glu Lys Tyr Tyr Val Asp Ser Val Lys
1               5                   10                  15
Gly

<210> SEQ ID NO 19
<211> LENGTH: 14
<212> TYPE: PRT
<213> ORGANISM: Artificial Sequence
<220> FEATURE:
<223> OTHER INFORMATION: mAb10 heavy chain CDR3

<400> SEQUENCE: 19

Gly Ala Ser Gly Tyr Tyr Tyr Asn Tyr Gly Met Asp Val
1               5                   10

<210> SEQ ID NO 20
<211> LENGTH: 11
<212> TYPE: PRT
<213> ORGANISM: Artificial Sequence
<220> FEATURE:
<223> OTHER INFORMATION: mAb11 light chain CDR1

<400> SEQUENCE: 20

Gly Gly Lys Asn Ile Gly Ser Lys Ser Val His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: mAb11/mAb10 light chain CDR2

<400> SEQUENCE: 21

Asp Asp Ser Asp Arg Pro Ser
1               5

<210> SEQ ID NO 22
<211> LENGTH: 11
<212> TYPE: PRT
<213> ORGANISM: Artificial Sequence
<220> FEATURE:
<223> OTHER INFORMATION: mAb11 light chain CDR3

<400> SEQUENCE: 22

Gln Val Trp Asp Ser Ser Ser Asp His Arg Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: mAb14 light chain CDR1

<400> SEQUENCE: 23

Gly Asn Asn Ile Gly Ser Lys Ser Val His
1               5                   10

<210> SEQ ID NO 24
<211> LENGTH: 7
```

```
<212> TYPE: PRT
<213> ORGANISM: Artificial Sequence
<220> FEATURE:
<223> OTHER INFORMATION: mAb14 light chain CDR2

<400> SEQUENCE: 24

Tyr Asp Ser Asp Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: mAb14 light chain CDR3

<400> SEQUENCE: 25

Gln Val Trp Asp Ser Ser Arg Asp His Val Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: mAb10 light chain CDR1

<400> SEQUENCE: 26

Gly Gly Asn Asn Ile Gly Ile Lys Ser Val His
1               5                   10

<210> SEQ ID NO 27
<211> LENGTH: 12
<212> TYPE: PRT
<213> ORGANISM: Artificial Sequence
<220> FEATURE:
<223> OTHER INFORMATION: mAb10 light chain CDR3

<400> SEQUENCE: 27

Gln Val Trp Asp Ser Ser Ser Asp His Pro Gly Val
1               5                   10

<210> SEQ ID NO 28
<211> LENGTH: 30
<212> TYPE: PRT
<213> ORGANISM: Artificial Sequence
<220> FEATURE:
<223> OTHER INFORMATION: mAb11 heavy chain FR1

<400> SEQUENCE: 28

Glu Val Gln Leu Val Gln Ser Gly Ser Asp Leu Lys Lys Pro Gly Ala
1               5                   10                  15
Ser Val Lys Val Ser Cys Lys Ala Ser Gly Tyr Thr Phe Thr
            20                  25                  30

<210> SEQ ID NO 29
<211> LENGTH: 14
<212> TYPE: PRT
<213> ORGANISM: Artificial Sequence
<220> FEATURE:
<223> OTHER INFORMATION: mAb11 heavy chain FR2

<400> SEQUENCE: 29

Trp Val Arg Gln Ala Pro Gly Gln Gly Leu Glu Trp Val Gly
1               5                   10
```

```
<210> SEQ ID NO 30
<211> LENGTH: 32
<212> TYPE: PRT
<213> ORGANISM: Artificial Sequence
<220> FEATURE:
<223> OTHER INFORMATION: mAb11 heavy chain FR3

<400> SEQUENCE: 30

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 31
<211> LENGTH: 11
<212> TYPE: PRT
<213> ORGANISM: Artificial Sequence
<220> FEATURE:
<223> OTHER INFORMATION: mAb11/mAb14 heavy chain FR4

<400> SEQUENCE: 31

Trp Gly Gln Gly Thr Leu Val Thr Val Ser Ser
1               5                   10

<210> SEQ ID NO 32
<211> LENGTH: 30
<212> TYPE: PRT
<213> ORGANISM: Artificial Sequence
<220> FEATURE:
<223> OTHER INFORMATION: mAb14 heavy chain FR1

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 33
<211> LENGTH: 14
<212> TYPE: PRT
<213> ORGANISM: Artificial Sequence
<220> FEATURE:
<223> OTHER INFORMATION: mAb14 heavy chain FR2

<400> SEQUENCE: 33

Trp Val Arg Gln Ala Pro Gly Lys Gly Leu Glu Trp Val Ser
1               5                   10

<210> SEQ ID NO 34
<211> LENGTH: 32
<212> TYPE: PRT
<213> ORGANISM: Artificial Sequence
<220> FEATURE:
<223> OTHER INFORMATION: mAb14 heavy chain FR3

<400> SEQUENCE: 34

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

<210> SEQ ID NO 35
<211> LENGTH: 30
<212> TYPE: PRT
<213> ORGANISM: Artificial Sequence
<220> FEATURE:
```

<223> OTHER INFORMATION: mAb10 heavy chain FR1

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 36
<211> LENGTH: 14
<212> TYPE: PRT
<213> ORGANISM: Artificial Sequence
<220> FEATURE:
<223> OTHER INFORMATION: mAb10 heavy chain FR2

<400> SEQUENCE: 36

Trp Val Arg Gln Ala Pro Gly Lys Gly Leu Glu Trp Val Ala
1               5                   10

<210> SEQ ID NO 37
<211> LENGTH: 32
<212> TYPE: PRT
<213> ORGANISM: Artificial Sequence
<220> FEATURE:
<223> OTHER INFORMATION: mAb10 heavy chain FR3

<400> SEQUENCE: 37

Arg Phe Thr Ile Ser Gly Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: mAb10 heavy chain FR4

<400> SEQUENCE: 38

Trp Gly Gln Gly Thr Arg Val Thr Val Ser Ser
1               5                   10

<210> SEQ ID NO 39
<211> LENGTH: 22
<212> TYPE: PRT
<213> ORGANISM: Artificial Sequence
<220> FEATURE:
<223> OTHER INFORMATION: mAb11 light chain FR1

<400> SEQUENCE: 39

Ser Tyr Glu Leu Thr Gln Pro Pro Ser Val Ser Val Ala Pro Gly Gln
1               5                   10                  15

Thr Ala Thr Ile Thr Cys
            20

<210> SEQ ID NO 40
<211> LENGTH: 15
<212> TYPE: PRT
<213> ORGANISM: Artificial Sequence
<220> FEATURE:
<223> OTHER INFORMATION: mAb11/mAb10 light chain FR2

<400> SEQUENCE: 40

Trp Tyr Gln Gln Lys Pro Gly Gln Ala Pro Val Leu Val Val Tyr

```
<210> SEQ ID NO 41
<211> LENGTH: 32
<212> TYPE: PRT
<213> ORGANISM: Artificial Sequence
<220> FEATURE:
<223> OTHER INFORMATION: mAb11/mAb14 light chain FR3

<400> SEQUENCE: 41

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 42
<211> LENGTH: 13
<212> TYPE: PRT
<213> ORGANISM: Artificial Sequence
<220> FEATURE:
<223> OTHER INFORMATION: mAb11/mAb14/mAb10 light chain FR4

<400> SEQUENCE: 42

Phe Gly Gly Gly Thr Lys Leu Thr Val Leu Gly Gln Pro
1               5                   10

<210> SEQ ID NO 43
<211> LENGTH: 23
<212> TYPE: PRT
<213> ORGANISM: Artificial Sequence
<220> FEATURE:
<223> OTHER INFORMATION: mAb14 light chain FR1

<400> SEQUENCE: 43

Ser Tyr Glu Leu Thr Gln Pro Pro Ser Met Ser Val Ala Pro Gly Lys
1               5                   10                  15

Thr Ala Arg Ile Thr Cys Gly
            20

<210> SEQ ID NO 44
<211> LENGTH: 15
<212> TYPE: PRT
<213> ORGANISM: Artificial Sequence
<220> FEATURE:
<223> OTHER INFORMATION: mAb14 light chain FR2

<400> SEQUENCE: 44

Trp Tyr Gln Gln Lys Pro Gly Gln Ala Pro Val Leu Val Ile Tyr
1               5                   10                  15

<210> SEQ ID NO 45
<211> LENGTH: 22
<212> TYPE: PRT
<213> ORGANISM: Artificial Sequence
<220> FEATURE:
<223> OTHER INFORMATION: mAb10 light chain FR1

<400> SEQUENCE: 45

Gln Pro Val Leu Thr Gln Pro Pro Ser Val Ser Val Ala Pro Gly Gln
1               5                   10                  15

Thr Ala Arg Ile Thr Cys
            20

<210> SEQ ID NO 46
<211> LENGTH: 32
```

```
<212> TYPE: PRT
<213> ORGANISM: Artificial Sequence
<220> FEATURE:
<223> OTHER INFORMATION: mAb10 light chain FR3

<400> SEQUENCE: 46

Gly Ile Pro Glu Arg Phe Ser Gly Ser Asn Ser Ala Asn Thr Ala Thr
1               5                   10                  15

Leu Thr Ile Ser Arg Val Glu Ala Gly Asp Glu Ala Asp Tyr Phe Cys
            20                  25                  30

<210> SEQ ID NO 47
<211> LENGTH: 128
<212> TYPE: PRT
<213> ORGANISM: Artificial Sequence
<220> FEATURE:
<223> OTHER INFORMATION: mAb11 VH sequence

<400> SEQUENCE: 47

Glu Val Gln Leu Val Gln Ser Gly Ser Asp Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Val
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Ser Pro Asn Tyr Tyr Asp Ser Ser Gly Tyr Tyr Ser Gly
            100                 105                 110

Tyr Tyr Phe Asp Tyr Trp Gly Gln Gly Thr Leu Val Thr Val Ser Ser
        115                 120                 125

<210> SEQ ID NO 48
<211> LENGTH: 111
<212> TYPE: PRT
<213> ORGANISM: Artificial Sequence
<220> FEATURE:
<223> OTHER INFORMATION: mAb11 VL sequence

<400> SEQUENCE: 48

Ser Tyr Glu Leu Thr Gln Pro Pro Ser Val Ser Val Ala Pro Gly Gln
1               5                   10                  15

Thr Ala Thr Ile Thr Cys Gly Gly Lys Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Val Phe Gly Gly Gly Thr Lys Leu Thr Val Leu Gly Gln Pro
            100                 105                 110
```

-continued

```
<210> SEQ ID NO 49
<211> LENGTH: 126
<212> TYPE: PRT
<213> ORGANISM: Artificial Sequence
<220> FEATURE:
<223> OTHER INFORMATION: mAb14 VH sequence

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Ala Ser Met Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Pro Ala Pro Pro Tyr Cys Gly Asp Cys Tyr Pro Ser
            100                 105                 110

Phe Asp Tyr Trp Gly Gln Gly Thr Leu Val Thr Val Ser Ser
        115                 120                 125

<210> SEQ ID NO 50
<211> LENGTH: 111
<212> TYPE: PRT
<213> ORGANISM: Artificial Sequence
<220> FEATURE:
<223> OTHER INFORMATION: mAb14 VL sequence

<400> SEQUENCE: 50

Ser Tyr Glu Leu Thr Gln Pro Pro Ser Met Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp His
                85                  90                  95

Val Val Phe Gly Gly Gly Thr Lys Leu Thr Val Leu Gly Gln Pro
            100                 105                 110

<210> SEQ ID NO 51
<211> LENGTH: 123
<212> TYPE: PRT
<213> ORGANISM: Artificial Sequence
<220> FEATURE:
<223> OTHER INFORMATION: mAb10 VH sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Gly Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Ser Gly Tyr Tyr Tyr Asn Tyr Gly Met Asp Val
            100                 105                 110

Trp Gly Gln Gly Thr Arg Val Thr Val Ser Ser
            115                 120

<210> SEQ ID NO 52
<211> LENGTH: 112
<212> TYPE: PRT
<213> ORGANISM: Artificial Sequence
<220> FEATURE:
<223> OTHER INFORMATION: mAb10 VL sequence

<400> SEQUENCE: 52

Gln Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ile Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Ala Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp His
                85                  90                  95

Pro Gly Val Phe Gly Gly Gly Thr Lys Leu Thr Val Leu Gly Gln Pro
            100                 105                 110

<210> SEQ ID NO 53
<211> LENGTH: 26
<212> TYPE: PRT
<213> ORGANISM: Artificial Sequence
<220> FEATURE:
<223> OTHER INFORMATION: Epitope for the non-neutralising antibodies of
      the invention

<400> SEQUENCE: 53

Ser Asn Tyr Asn Ile Ala Asn Ser Ile Asp Ile Asp Glu Tyr Asn Thr
1               5                   10                  15

Lys Lys Lys Lys Leu Ile Lys Cys Ile Lys
            20                  25

<210> SEQ ID NO 54
<211> LENGTH: 5
<212> TYPE: PRT
<213> ORGANISM: Artificial Sequence
<220> FEATURE:
<223> OTHER INFORMATION: mAb16 heavy chain CDR1

<400> SEQUENCE: 54

Ser Tyr Gly Ile Ser
1               5

```
<210> SEQ ID NO 55
<211> LENGTH: 17
<212> TYPE: PRT
<213> ORGANISM: Artificial Sequence
<220> FEATURE:
<223> OTHER INFORMATION: mAb16 heavy chain CDR2

<400> SEQUENCE: 55

Trp Ile Ser Gly Tyr Asp Gly Asn Thr Asn Tyr Ala Gln Lys Leu Gln
1               5                   10                  15

Gly

<210> SEQ ID NO 56
<211> LENGTH: 20
<212> TYPE: PRT
<213> ORGANISM: Artificial Sequence
<220> FEATURE:
<223> OTHER INFORMATION: mAb16 heavy chain CDR3

<400> SEQUENCE: 56

Asp Gly Pro Gln Val Gly Asp Phe Asp Trp Gln Val Tyr Tyr Tyr Tyr
1               5                   10                  15

Gly Met Asp Val
            20

<210> SEQ ID NO 57
<211> LENGTH: 5
<212> TYPE: PRT
<213> ORGANISM: Artificial Sequence
<220> FEATURE:
<223> OTHER INFORMATION: mAb4 heavy chain CDR1

<400> SEQUENCE: 57

Asn Tyr Ala Ile Asn
1               5

<210> SEQ ID NO 58
<211> LENGTH: 17
<212> TYPE: PRT
<213> ORGANISM: Artificial Sequence
<220> FEATURE:
<223> OTHER INFORMATION: mAb4 heavy chain CDR2

<400> SEQUENCE: 58

Gly Ile Ile Pro Ile Phe Ala Thr Thr Asn Tyr Ala Gln Lys Phe Gln
1               5                   10                  15

Gly

<210> SEQ ID NO 59
<211> LENGTH: 11
<212> TYPE: PRT
<213> ORGANISM: Artificial Sequence
<220> FEATURE:
<223> OTHER INFORMATION: mAb4 heavy chain CDR3

<400> SEQUENCE: 59

Asp Lys His Ser Trp Ser Tyr Ala Phe Asp Ile
1               5                   10

<210> SEQ ID NO 60
<211> LENGTH: 11
<212> TYPE: PRT
<213> ORGANISM: Artificial Sequence
<220> FEATURE:
```

```
<223> OTHER INFORMATION: mAb16 light chain CDR1

<400> SEQUENCE: 60

Arg Ala Ser Gln Ser Ile Asn Thr Trp Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: mAb16 light chain CDR2

<400> SEQUENCE: 61

Lys Ala Ser Ser Leu Glu Ser
1               5

<210> SEQ ID NO 62
<211> LENGTH: 9
<212> TYPE: PRT
<213> ORGANISM: Artificial Sequence
<220> FEATURE:
<223> OTHER INFORMATION: mAb16 light chain CDR3

<400> SEQUENCE: 62

Gln Gln Tyr Asn Ser Tyr Leu Tyr Thr
1               5

<210> SEQ ID NO 63
<211> LENGTH: 13
<212> TYPE: PRT
<213> ORGANISM: Artificial Sequence
<220> FEATURE:
<223> OTHER INFORMATION: mAb4 light chain CDR1

<400> SEQUENCE: 63

Ser Gly Ser Ser Ser Asn Ile Gly Ser Asn Thr Val Asn
1               5                   10

<210> SEQ ID NO 64
<211> LENGTH: 7
<212> TYPE: PRT
<213> ORGANISM: Artificial Sequence
<220> FEATURE:
<223> OTHER INFORMATION: mAb4 light chain CDR2

<400> SEQUENCE: 64

Ser Asn Asn Gln Arg Pro Ser
1               5

<210> SEQ ID NO 65
<211> LENGTH: 11
<212> TYPE: PRT
<213> ORGANISM: Artificial Sequence
<220> FEATURE:
<223> OTHER INFORMATION: mAb4 light chain CDR3

<400> SEQUENCE: 65

Ala Ala Trp Asp Asp Ser Leu Asn Gly Trp Val
1               5                   10

<210> SEQ ID NO 66
<211> LENGTH: 30
<212> TYPE: PRT
<213> ORGANISM: Artificial Sequence
<220> FEATURE:
<223> OTHER INFORMATION: mAb16 heavy chain FR1
```

<400> SEQUENCE: 66

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr
            20                  25                  30

<210> SEQ ID NO 67
<211> LENGTH: 14
<212> TYPE: PRT
<213> ORGANISM: Artificial Sequence
<220> FEATURE:
<223> OTHER INFORMATION: mAb16/mAb4 heavy chain FR2

<400> SEQUENCE: 67

Trp Val Arg Gln Ala Pro Gly Gln Gly Leu Glu Trp Met Gly
1               5                   10

<210> SEQ ID NO 68
<211> LENGTH: 32
<212> TYPE: PRT
<213> ORGANISM: Artificial Sequence
<220> FEATURE:
<223> OTHER INFORMATION: mAb16 heavy chain FR3

<400> SEQUENCE: 68

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 69
<211> LENGTH: 11
<212> TYPE: PRT
<213> ORGANISM: Artificial Sequence
<220> FEATURE:
<223> OTHER INFORMATION: mAb16 heavy chain FR4

<400> SEQUENCE: 69

Trp Gly Gln Gly Thr Thr Val Thr Val Ser Ser
1               5                   10

<210> SEQ ID NO 70
<211> LENGTH: 30
<212> TYPE: PRT
<213> ORGANISM: Artificial Sequence
<220> FEATURE:
<223> OTHER INFORMATION: mAb4 heavy chain FR1

<400> SEQUENCE: 70

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: mAb4 heavy chain FR3

<400> SEQUENCE: 71

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 72
<211> LENGTH: 11
<212> TYPE: PRT
<213> ORGANISM: Artificial Sequence
<220> FEATURE:
<223> OTHER INFORMATION: mAb4 heavy chain FR4

<400> SEQUENCE: 72

Trp Gly Gln Gly Thr Met Val Thr Val Ser Ser
1               5                   10

<210> SEQ ID NO 73
<211> LENGTH: 23
<212> TYPE: PRT
<213> ORGANISM: Artificial Sequence
<220> FEATURE:
<223> OTHER INFORMATION: mAb16 light chain FR1

<400> SEQUENCE: 73

Ala Ile Arg Met Thr Gln Ser Pro Ser Thr Leu Ser Ala Ser Val Gly
1               5                   10                  15

Asp Arg Val Thr Ile Thr Cys
            20

<210> SEQ ID NO 74
<211> LENGTH: 15
<212> TYPE: PRT
<213> ORGANISM: Artificial Sequence
<220> FEATURE:
<223> OTHER INFORMATION: mAb16 light chain FR2

<400> SEQUENCE: 74

Trp Tyr Gln Gln Lys Pro Gly Lys Ala Pro Asn Leu Leu Ile Ser
1               5                   10                  15

<210> SEQ ID NO 75
<211> LENGTH: 32
<212> TYPE: PRT
<213> ORGANISM: Artificial Sequence
<220> FEATURE:
<223> OTHER INFORMATION: mAb16 light chain FR3

<400> SEQUENCE: 75

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Phe Cys
            20                  25                  30

<210> SEQ ID NO 76
<211> LENGTH: 13
<212> TYPE: PRT
<213> ORGANISM: Artificial Sequence
<220> FEATURE:
<223> OTHER INFORMATION: mAb16 light chain FR4

<400> SEQUENCE: 76

Phe Gly Gln Gly Thr Lys Val Glu Ile Arg Arg Thr Val
1               5                   10

<210> SEQ ID NO 77
<211> LENGTH: 22
<212> TYPE: PRT

```
<213> ORGANISM: Artificial Sequence
<220> FEATURE:
<223> OTHER INFORMATION: mAb4 light chain FR1

<400> SEQUENCE: 77

Gln Ser Val Leu Thr Gln Pro Pro Ser Ala Ser Gly Thr Pro Gly Leu
1               5                   10                  15

Arg Val Thr Ile Ser Cys
            20

<210> SEQ ID NO 78
<211> LENGTH: 15
<212> TYPE: PRT
<213> ORGANISM: Artificial Sequence
<220> FEATURE:
<223> OTHER INFORMATION: mAb4 light chain FR2

<400> SEQUENCE: 78

Trp Tyr Gln His Leu Pro Gly Thr Ala Pro Lys Leu Leu Ile His
1               5                   10                  15

<210> SEQ ID NO 79
<211> LENGTH: 32
<212> TYPE: PRT
<213> ORGANISM: Artificial Sequence
<220> FEATURE:
<223> OTHER INFORMATION: mAb4 light chain FR3

<400> SEQUENCE: 79

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 80
<211> LENGTH: 13
<212> TYPE: PRT
<213> ORGANISM: Artificial Sequence
<220> FEATURE:
<223> OTHER INFORMATION: mAb4 light chain FR4

<400> SEQUENCE: 80

Phe Gly Gly Gly Thr Lys Leu Thr Val Leu Gly Gln Pro
1               5                   10

<210> SEQ ID NO 81
<211> LENGTH: 129
<212> TYPE: PRT
<213> ORGANISM: Artificial Sequence
<220> FEATURE:
<223> OTHER INFORMATION: mAb16 VH sequence

<400> SEQUENCE: 81

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asp Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
                85                  90                  95

Ala Arg Asp Gly Pro Gln Val Gly Asp Phe Asp Trp Gln Val Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 82
<211> LENGTH: 110
<212> TYPE: PRT
<213> ORGANISM: Artificial Sequence
<220> FEATURE:
<223> OTHER INFORMATION: mAb16 VL sequence

<400> SEQUENCE: 82

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Asn Leu Leu Ile
        35                  40                  45

Ser Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asn Ser Tyr Leu Tyr
                85                  90                  95

Thr Phe Gly Gln Gly Thr Lys Val Glu Ile Arg Arg Thr Val
            100                 105                 110

<210> SEQ ID NO 83
<211> LENGTH: 120
<212> TYPE: PRT
<213> ORGANISM: Artificial Sequence
<220> FEATURE:
<223> OTHER INFORMATION: mAb4 VH sequence

<400> SEQUENCE: 83

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Ala Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Lys His Ser Trp Ser Tyr Ala Phe Asp Ile Trp Gly Gln
            100                 105                 110

Gly Thr Met Val Thr Val Ser Ser
            115                 120

<210> SEQ ID NO 84
<211> LENGTH: 113

```
<212> TYPE: PRT
<213> ORGANISM: Artificial Sequence
<220> FEATURE:
<223> OTHER INFORMATION: mAb4 VL sequence

<400> SEQUENCE: 84

Gln Ser Val Leu Thr Gln Pro Pro Ser Ala Ser Gly Thr Pro Gly Leu
1               5                   10                  15

Arg Val Thr Ile Ser Cys Ser Gly Ser Ser Ser Asn Ile Gly Ser Asn
            20                  25                  30

Thr Val Asn Trp Tyr Gln His Leu Pro Gly Thr Ala Pro Lys Leu Leu
        35                  40                  45

Ile His Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110

Pro

<210> SEQ ID NO 85
<211> LENGTH: 23
<212> TYPE: PRT
<213> ORGANISM: Artificial Sequence
<220> FEATURE:
<223> OTHER INFORMATION: Epitope for the neutralising antibody mAb4 of
      the invention

<400> SEQUENCE: 85

Lys Ser Asn Asn Asn Phe Cys Asn Arg Tyr His Tyr Asp Glu Tyr Ile
1               5                   10                  15

His Lys Leu Asn Ile Trp Arg
            20

<210> SEQ ID NO 86
<211> LENGTH: 28
<212> TYPE: PRT
<213> ORGANISM: Artificial Sequence
<220> FEATURE:
<223> OTHER INFORMATION: Epitope for the neutralising antibody mAb16 of
      the invention

<400> SEQUENCE: 86

Gly Lys Cys Ile Ala Val Asp Ala Phe Ile Lys Lys Ile Asn Glu Thr
1               5                   10                  15

Tyr Asp Lys Lys Ile Cys Met Asp Met Lys Asn Tyr
            20                  25

<210> SEQ ID NO 87
<211> LENGTH: 35
<212> TYPE: PRT
<213> ORGANISM: Artificial Sequence
<220> FEATURE:
<223> OTHER INFORMATION: The neutralising antibody red epitope bin
      sequence

<400> SEQUENCE: 87

Gly Lys Cys Ile Ala Val Asp Ala Phe Ile Lys Lys Ile Asn Glu Thr
1               5                   10                  15

Tyr Asp Lys Lys Ile Cys Met Asp Met Lys Asn Tyr Gly Thr Asn Leu
```

```
                        20                  25                  30
Phe Glu Gln
        35

<210> SEQ ID NO 88
<211> LENGTH: 21
<212> TYPE: PRT
<213> ORGANISM: Artificial Sequence
<220> FEATURE:
<223> OTHER INFORMATION: The neutralising antibody blue epitope bin
      sequence

<400> SEQUENCE: 88

Lys Ser Tyr Asn Asn Asn Phe Cys Asn Thr Asn Lys Leu Asn Ile Trp
1               5                   10                  15

Arg Thr Phe Gln Lys
            20

<210> SEQ ID NO 89
<211> LENGTH: 505
<212> TYPE: PRT
<213> ORGANISM: Artificial Sequence
<220> FEATURE:
<223> OTHER INFORMATION: RH5.1 amino acid sequence

<400> SEQUENCE: 89

Glu Asn Ala Ile Lys Lys Thr Lys Asn Gln Glu Asn Asn Leu Ala Leu
1               5                   10                  15

Leu Pro Ile Lys Ser Thr Glu Glu Lys Asp Asp Ile Lys Asn Gly
        20                  25                  30

Lys Asp Ile Lys Lys Glu Ile Asp Asn Asp Lys Glu Asn Ile Lys Thr
            35                  40                  45

Asn Asn Ala Lys Asp His Ser Thr Tyr Ile Lys Ser Tyr Leu Asn Thr
        50                  55                  60

Asn Val Asn Asp Gly Leu Lys Tyr Leu Phe Ile Pro Ser His Asn Ser
65                  70                  75                  80

Phe Ile Lys Lys Tyr Ser Val Phe Asn Gln Ile Asn Asp Gly Met Leu
                85                  90                  95

Leu Asn Glu Lys Asn Asp Val Lys Asn Asn Glu Asp Tyr Lys Asn Val
            100                 105                 110

Asp Tyr Lys Asn Val Asn Phe Leu Gln Tyr His Phe Lys Glu Leu Ser
        115                 120                 125

Asn Tyr Asn Ile Ala Asn Ser Ile Asp Ile Leu Gln Glu Lys Glu Gly
    130                 135                 140

His Leu Asp Phe Val Ile Ile Pro His Tyr Thr Phe Leu Asp Tyr Tyr
145                 150                 155                 160

Lys His Leu Ser Tyr Asn Ser Ile Tyr His Lys Ser Ser Thr Tyr Gly
                165                 170                 175

Lys Cys Ile Ala Val Asp Ala Phe Ile Lys Lys Ile Asn Glu Ala Tyr
            180                 185                 190

Asp Lys Val Lys Ser Lys Cys Asn Asp Ile Lys Asn Asp Leu Ile Ala
        195                 200                 205

Thr Ile Lys Lys Leu Glu His Pro Tyr Asp Ile Asn Asn Lys Asn Asp
    210                 215                 220

Asp Ser Tyr Arg Tyr Asp Ile Ser Glu Glu Ile Asp Asp Lys Ser Glu
225                 230                 235                 240

Glu Thr Asp Asp Glu Thr Glu Glu Val Glu Asp Ser Ile Gln Asp Thr
                245                 250                 255
```

```
Asp Ser Asn His Ala Pro Ser Asn Lys Lys Asn Asp Leu Met Asn
            260                 265                 270

Arg Ala Phe Lys Lys Met Met Asp Glu Tyr Asn Thr Lys Lys Lys
        275                 280                 285

Leu Ile Lys Cys Ile Lys Asn His Glu Asn Asp Phe Asn Lys Ile Cys
    290                 295                 300

Met Asp Met Lys Asn Tyr Gly Thr Asn Leu Phe Glu Gln Leu Ser Cys
305                 310                 315                 320

Tyr Asn Asn Asn Phe Cys Asn Thr Asn Gly Ile Arg Tyr His Tyr Asp
                325                 330                 335

Glu Tyr Ile His Lys Leu Ile Leu Ser Val Lys Ser Lys Asn Leu Asn
            340                 345                 350

Lys Asp Leu Ser Asp Met Thr Asn Ile Leu Gln Gln Ser Glu Leu Leu
        355                 360                 365

Leu Thr Asn Leu Asn Lys Lys Met Gly Ser Tyr Ile Tyr Ile Asp Thr
    370                 375                 380

Ile Lys Phe Ile His Lys Glu Met Lys His Ile Phe Asn Arg Ile Glu
385                 390                 395                 400

Tyr His Thr Lys Ile Ile Asn Asp Lys Thr Lys Ile Ile Gln Asp Lys
                405                 410                 415

Ile Lys Leu Asn Ile Trp Arg Thr Phe Gln Lys Asp Glu Leu Leu Lys
            420                 425                 430

Arg Ile Leu Asp Met Ser Asn Glu Tyr Ser Leu Phe Ile Thr Ser Asp
        435                 440                 445

His Leu Arg Gln Met Leu Tyr Asn Thr Phe Tyr Ser Lys Glu Lys His
    450                 455                 460

Leu Asn Asn Ile Phe His His Leu Ile Tyr Val Leu Gln Met Lys Phe
465                 470                 475                 480

Asn Asp Val Pro Ile Lys Met Glu Tyr Phe Gln Thr Tyr Lys Lys Asn
                485                 490                 495

Lys Pro Leu Thr Gln Glu Pro Glu Ala
            500                 505
```

<210> SEQ ID NO 90
<211> LENGTH: 528
<212> TYPE: PRT
<213> ORGANISM: Artificial Sequence
<220> FEATURE:
<223> OTHER INFORMATION: PfRH5 (PfRH5FL) sequence of amino acids
    E26-Q526 of the 3D7 clone P. falciparum reference sequence, with
    mutations to delete N-linked glycosylation (N38Q and N214Q) and
    with an additional C-terminal AviTag™ and Strep-II® tag in tandem

<400> SEQUENCE: 90

```
Glu Asn Ala Ile Lys Lys Thr Lys Asn Gln Glu Asn Gln Leu Thr Leu
1               5                   10                  15

Leu Pro Ile Lys Ser Thr Glu Glu Lys Asp Asp Ile Lys Asn Gly
            20                  25                  30

Lys Asp Ile Lys Lys Glu Ile Asp Asn Asp Lys Glu Asn Ile Lys Thr
        35                  40                  45

Asn Asn Ala Lys Asp His Ser Thr Tyr Ile Lys Ser Tyr Leu Asn Thr
50                  55                  60

Asn Val Asn Asp Gly Leu Lys Tyr Leu Phe Ile Pro Ser His Asn Ser
65                  70                  75                  80

Phe Ile Lys Lys Tyr Ser Val Phe Asn Gln Ile Asn Asp Gly Met Leu
                85                  90                  95
```

```
Leu Asn Glu Lys Asn Asp Val Lys Asn Asn Glu Asp Tyr Lys Asn Val
            100                 105                 110

Asp Tyr Lys Asn Val Asn Phe Leu Gln Tyr His Phe Lys Glu Leu Ser
            115                 120                 125

Asn Tyr Asn Ile Ala Asn Ser Ile Asp Ile Leu Gln Glu Lys Glu Gly
            130                 135                 140

His Leu Asp Phe Val Ile Ile Pro His Tyr Thr Phe Leu Asp Tyr Tyr
145                 150                 155                 160

Lys His Leu Ser Tyr Asn Ser Ile Tyr His Lys Ser Ser Thr Tyr Gly
                165                 170                 175

Lys Cys Ile Ala Val Asp Ala Phe Ile Lys Lys Ile Gln Glu Thr Tyr
                180                 185                 190

Asp Lys Val Lys Ser Lys Cys Asn Asp Ile Lys Asn Asp Leu Ile Ala
            195                 200                 205

Thr Ile Lys Lys Leu Glu His Pro Tyr Asp Ile Asn Asn Lys Asn Asp
            210                 215                 220

Asp Ser Tyr Arg Tyr Asp Ile Ser Glu Glu Ile Asp Asp Lys Ser Glu
225                 230                 235                 240

Glu Thr Asp Asp Glu Thr Glu Glu Val Glu Asp Ser Ile Gln Asp Thr
                245                 250                 255

Asp Ser Asn His Thr Pro Ser Asn Lys Lys Asn Asp Leu Met Asn
            260                 265                 270

Arg Thr Phe Lys Lys Met Met Asp Glu Tyr Asn Thr Lys Lys Lys Lys
                275                 280                 285

Leu Ile Lys Cys Ile Lys Asn His Glu Asn Asp Phe Asn Lys Ile Cys
            290                 295                 300

Met Asp Met Lys Asn Tyr Gly Thr Asn Leu Phe Glu Gln Leu Ser Cys
305                 310                 315                 320

Tyr Asn Asn Phe Cys Asn Thr Asn Gly Ile Arg Tyr His Tyr Asp
                325                 330                 335

Glu Tyr Ile His Lys Leu Ile Leu Ser Val Lys Ser Lys Asn Leu Asn
            340                 345                 350

Lys Asp Leu Ser Asp Met Thr Asn Ile Leu Gln Gln Ser Glu Leu Leu
            355                 360                 365

Leu Thr Asn Leu Asn Lys Lys Met Gly Ser Tyr Ile Tyr Ile Asp Thr
            370                 375                 380

Ile Lys Phe Ile His Lys Glu Met Lys His Ile Phe Asn Arg Ile Glu
385                 390                 395                 400

Tyr His Thr Lys Ile Ile Asn Asp Lys Thr Lys Ile Ile Gln Asp Lys
                405                 410                 415

Ile Lys Leu Asn Ile Trp Arg Thr Phe Gln Lys Asp Glu Leu Leu Lys
            420                 425                 430

Arg Ile Leu Asp Met Ser Asn Glu Tyr Ser Leu Phe Ile Thr Ser Asp
            435                 440                 445

His Leu Arg Gln Met Leu Tyr Asn Thr Phe Tyr Ser Lys Glu Lys His
            450                 455                 460

Leu Asn Asn Ile Phe His His Leu Ile Tyr Val Leu Gln Met Lys Phe
465                 470                 475                 480

Asn Asp Val Pro Ile Lys Met Glu Tyr Phe Gln Thr Tyr Lys Lys Asn
                485                 490                 495

Lys Pro Leu Thr Gln Gly Ser Ala Ser Gly Leu Asn Asp Ile Phe Glu
                500                 505                 510
```

```
Ala Gln Lys Ile Glu Trp His Glu Trp Ser His Pro Gln Phe Glu Lys
            515                 520                 525
```

<210> SEQ ID NO 91
<211> LENGTH: 342
<212> TYPE: PRT
<213> ORGANISM: Artificial Sequence
<220> FEATURE:
<223> OTHER INFORMATION: PfRH5deltaNL amino acid sequence based on the
      3D7 clone P. falciparum reference sequence - residues K140-K247
      and N297-Q526 with mutations to delete N-linked glycosylation
      sequons (T216A and T299A) and with the addition of a C-terminal
      C-tag

<400> SEQUENCE: 91

```
Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
            35                  40                  45

Leu Ser Tyr Asn Ser Ile Tyr His Lys Ser Ser Thr Tyr Gly Lys Cys
    50                  55                  60

Ile Ala Val Asp Ala Phe Ile Lys Lys Ile Asn Glu Ala Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Arg Ala Phe
            100                 105                 110

Lys Lys Met Met Asp Glu Tyr Asn Thr Lys Lys Lys Leu Ile Lys
            115                 120                 125

Cys Ile Lys Asn His Glu Asn Asp Phe Asn Lys Ile Cys Met Asp Met
130                 135                 140

Lys Asn Tyr Gly Thr Asn Leu Phe Glu Gln Leu Ser Cys Tyr Asn Asn
145                 150                 155                 160

Asn Phe Cys Asn Thr Asn Gly Ile Arg Tyr His Tyr Asp Glu Tyr Ile
                165                 170                 175

His Lys Leu Ile Leu Ser Val Lys Ser Lys Asn Leu Asn Lys Asp Leu
            180                 185                 190

Ser Asp Met Thr Asn Ile Leu Gln Gln Ser Glu Leu Leu Leu Thr Asn
            195                 200                 205

Leu Asn Lys Lys Met Gly Ser Tyr Ile Tyr Ile Asp Thr Ile Lys Phe
    210                 215                 220

Ile His Lys Glu Met Lys His Ile Phe Asn Arg Ile Glu Tyr His Thr
225                 230                 235                 240

Lys Ile Ile Asn Asp Lys Thr Lys Ile Ile Gln Asp Lys Ile Lys Leu
                245                 250                 255

Asn Ile Trp Arg Thr Phe Gln Lys Asp Glu Leu Leu Lys Arg Ile Leu
            260                 265                 270

Asp Met Ser Asn Glu Tyr Ser Leu Phe Ile Thr Ser Asp His Leu Arg
            275                 280                 285

Gln Met Leu Tyr Asn Thr Phe Tyr Ser Lys Glu Lys His Leu Asn Asn
        290                 295                 300

Ile Phe His His Leu Ile Tyr Val Leu Gln Met Lys Phe Asn Asp Val
305                 310                 315                 320

Pro Ile Lys Met Glu Tyr Phe Gln Thr Tyr Lys Lys Asn Lys Pro Leu
                325                 330                 335
```

Thr Gln Glu Pro Glu Ala
                340

<210> SEQ ID NO 92
<211> LENGTH: 557
<212> TYPE: PRT
<213> ORGANISM: Artificial Sequence
<220> FEATURE:
<223> OTHER INFORMATION: PfCyRPA based on the 3D7 clone P. falciparum
      sequence and comprised amino acids D29-E362 with mutations
      introduced to ablate N-linked glycosylation (S147A, T324A and
      T340A) and also included a C-terminal CD4 tag comprising rat
      domains 3 and 4

<400> SEQUENCE: 92

Asp Ser Arg His Val Phe Ile Arg Thr Glu Leu Ser Phe Ile Lys Asn
1               5                   10                  15

Asn Val Pro Cys Ile Arg Asp Met Phe Phe Ile Tyr Lys Arg Glu Leu
            20                  25                  30

Tyr Asn Ile Cys Leu Asp Asp Leu Lys Gly Glu Glu Asp Glu Thr His
        35                  40                  45

Ile Tyr Val Gln Lys Lys Val Lys Asp Ser Trp Ile Thr Leu Asn Asp
50                  55                  60

Leu Phe Lys Glu Thr Asp Leu Thr Gly Arg Pro His Ile Phe Ala Tyr
65                  70                  75                  80

Val Asp Val Glu Glu Ile Ile Leu Leu Cys Glu Asp Glu Phe
                    85                  90                  95

Ser Asn Arg Lys Lys Asp Met Thr Cys His Arg Phe Tyr Ser Asn Asp
            100                 105                 110

Gly Lys Glu Tyr Asn Asn Ala Glu Ile Thr Ile Ser Asp Tyr Ile Leu
        115                 120                 125

Lys Asp Lys Leu Leu Ser Ser Tyr Val Ser Leu Pro Leu Lys Ile Glu
130                 135                 140

Asn Arg Glu Tyr Phe Leu Ile Cys Gly Val Ser Pro Tyr Lys Phe Lys
145                 150                 155                 160

Asp Asp Asn Lys Lys Asp Asp Ile Leu Cys Met Ala Ser His Asp Lys
            165                 170                 175

Gly Glu Thr Trp Gly Thr Lys Ile Val Ile Lys Tyr Asp Asn Tyr Lys
        180                 185                 190

Leu Gly Val Gln Tyr Phe Phe Leu Arg Pro Tyr Ile Ser Lys Asn Asp
    195                 200                 205

Leu Ser Phe His Phe Tyr Val Gly Asp Asn Ile Asn Asn Val Lys Asn
210                 215                 220

Val Asn Phe Ile Glu Cys Thr His Glu Lys Asp Leu Glu Phe Val Cys
225                 230                 235                 240

Ser Asn Arg Asp Phe Leu Lys Asp Asn Lys Val Leu Gln Asp Val Ser
            245                 250                 255

Thr Leu Asn Asp Glu Tyr Ile Val Ser Tyr Gly Asn Asp Asn Asn Phe
        260                 265                 270

Ala Glu Cys Tyr Ile Phe Phe Asn Asn Glu Asn Ser Ile Leu Ile Lys
    275                 280                 285

Pro Glu Lys Tyr Gly Asn Thr Ala Ala Gly Cys Tyr Gly Gly Thr Phe
290                 295                 300

Val Lys Ile Asp Glu Asn Arg Ala Leu Phe Ile Tyr Ser Ser Ser Gln
305                 310                 315                 320

Gly Ile Tyr Asn Ile His Thr Ile Tyr Tyr Ala Asn Tyr Glu Gly Ala 325                 330                 335
Pro Ser Thr Ser Ile Thr Ala Tyr Lys Ser Glu Gly Glu Ser Ala Glu
                340                 345                 350

Phe Ser Phe Pro Leu Asn Leu Gly Glu Glu Ser Leu Gln Gly Glu Leu
            355                 360                 365

Arg Trp Lys Ala Glu Lys Ala Pro Ser Ser Gln Ser Trp Ile Thr Phe
        370                 375                 380

Ser Leu Lys Asn Gln Lys Val Ser Val Gln Lys Ser Thr Ser Asn Pro
385                 390                 395                 400

Lys Phe Gln Leu Ser Glu Thr Leu Pro Leu Thr Leu Gln Ile Pro Gln
                405                 410                 415

Val Ser Leu Gln Phe Ala Gly Ser Gly Asn Leu Thr Leu Thr Leu Asp
            420                 425                 430

Arg Gly Ile Leu Tyr Gln Glu Val Asn Leu Val Val Met Lys Val Thr
        435                 440                 445

Gln Pro Asp Ser Asn Thr Leu Thr Cys Glu Val Met Gly Pro Thr Ser
450                 455                 460

Pro Lys Met Arg Leu Ile Leu Lys Gln Glu Asn Gln Glu Ala Arg Val
465                 470                 475                 480

Ser Arg Gln Glu Lys Val Ile Gln Val Gln Ala Pro Glu Ala Gly Val
                485                 490                 495

Trp Gln Cys Leu Leu Ser Glu Gly Glu Glu Val Lys Met Asp Ser Lys
            500                 505                 510

Ile Gln Val Leu Ser Lys Gly Leu Asn Ser Gly Ser Leu His His Ile
        515                 520                 525

Leu Asp Ala Gln Lys Met Leu Trp Asn His Arg Asp Arg Asn Leu Pro
530                 535                 540

Pro Leu Ala Pro Leu Gly Pro His His His His His
545                 550                 555

<210> SEQ ID NO 93
<211> LENGTH: 343
<212> TYPE: PRT
<213> ORGANISM: Artificial Sequence
<220> FEATURE:
<223> OTHER INFORMATION: PfCyRPA based on the 3D7 clone P. falciparum
      sequence and comprised amino acids D29-E362 with mutations
      introduced to ablate N-linked glycosylation (S147A, T324A and
      T340A) and also included a C-terminal 4-amino acid C-tag

<400> SEQUENCE: 93

Asp Ser Arg His Val Phe Ile Arg Thr Glu Leu Ser Phe Ile Lys Asn
1               5                   10                  15

Asn Val Pro Cys Ile Arg Asp Met Phe Phe Ile Tyr Lys Arg Glu Leu
            20                  25                  30

Tyr Asn Ile Cys Leu Asp Asp Leu Lys Gly Glu Glu Asp Glu Thr His
        35                  40                  45

Ile Tyr Val Gln Lys Lys Val Lys Asp Ser Trp Ile Thr Leu Asn Asp
    50                  55                  60

Leu Phe Lys Glu Thr Asp Leu Thr Gly Arg Pro His Ile Phe Ala Tyr
65              70                  75                  80

Val Asp Val Glu Glu Ile Ile Leu Leu Cys Glu Asp Glu Glu Phe
                85                  90                  95

Ser Asn Arg Lys Lys Asp Met Thr Cys His Arg Phe Tyr Ser Asn Asp
            100                 105                 110

Gly Lys Glu Tyr Asn Asn Ala Glu Ile Thr Ile Ser Asp Tyr Ile Leu

```
            115                 120                 125
Lys Asp Lys Leu Leu Ser Ser Tyr Val Ser Leu Pro Leu Lys Ile Glu
    130                 135                 140

Asn Arg Glu Tyr Phe Leu Ile Cys Gly Val Ser Pro Tyr Lys Phe Lys
145                 150                 155                 160

Asp Asp Asn Lys Lys Asp Asp Ile Leu Cys Met Ala Ser His Asp Lys
                165                 170                 175

Gly Glu Thr Trp Gly Thr Lys Ile Val Ile Lys Tyr Asp Asn Tyr Lys
            180                 185                 190

Leu Gly Val Gln Tyr Phe Phe Leu Arg Pro Tyr Ile Ser Lys Asn Asp
        195                 200                 205

Leu Ser Phe His Phe Tyr Val Gly Asp Asn Ile Asn Asn Val Lys Asn
    210                 215                 220

Val Asn Phe Ile Glu Cys Thr His Glu Lys Asp Leu Glu Phe Val Cys
225                 230                 235                 240

Ser Asn Arg Asp Phe Leu Lys Asp Asn Lys Val Leu Gln Asp Val Ser
                245                 250                 255

Thr Leu Asn Asp Glu Tyr Ile Val Ser Tyr Gly Asn Asp Asn Asn Phe
            260                 265                 270

Ala Glu Cys Tyr Ile Phe Phe Asn Asn Glu Asn Ser Ile Leu Ile Lys
        275                 280                 285

Pro Glu Lys Tyr Gly Asn Thr Ala Ala Gly Cys Tyr Gly Gly Thr Phe
    290                 295                 300

Val Lys Ile Asp Glu Asn Arg Ala Leu Phe Ile Tyr Ser Ser Ser Gln
305                 310                 315                 320

Gly Ile Tyr Asn Ile His Thr Ile Tyr Tyr Ala Asn Tyr Glu Gly Gly
                325                 330                 335

Gly Gly Ser Glu Pro Glu Ala
            340

<210> SEQ ID NO 94
<211> LENGTH: 420
<212> TYPE: PRT
<213> ORGANISM: Artificial Sequence
<220> FEATURE:
<223> OTHER INFORMATION: PfP113Nt, encoding amino acids Y23-K219 of
      PfP113 (3D7) was expressed encoding C-terminal tags comprising
      CD4d3+4, a biotin acceptor peptide and a His6 tag in tandem

<400> SEQUENCE: 94

Tyr Val His Asn Asp Val Ile Lys Phe Gly Glu Glu Asn Ser Leu Lys
1               5                   10                  15

Cys Ser Gln Gly Asn Leu Tyr Val Leu His Cys Glu Val Gln Cys Leu
            20                  25                  30

Asn Gly Asn Asn Glu Ile Ile His Lys Arg Cys Asn Asp Asp Ile Glu
        35                  40                  45

Lys Lys Cys Asn Gly Asn Asn Lys Cys Ile Tyr Phe Phe Glu Tyr Glu
    50                  55                  60

Leu Arg Lys Lys Thr Gln Ser Phe Arg Asn Lys Asn Ser Ile Glu Ile
65                  70                  75                  80

Ser Glu Cys Val Glu Ser Glu Gln Asn Glu Val Lys Thr Ser Thr Thr
                85                  90                  95

Cys Leu Leu Ser Asn Ser Phe Ile Leu Asp Glu Ala Phe Ile Gln Tyr
            100                 105                 110

Phe Phe Phe Ile Lys Asn Lys Asn Glu Glu Pro Val Ile Cys Lys Asp
        115                 120                 125
```

```
Gly Asn Ile Asn Ile Lys Ser Ala Leu Leu His Ser Pro Phe Cys Glu
            130                 135                 140

Ile Lys Leu Lys Asp Ile Ser Glu Tyr Ile Arg Lys Cys Asp Asn
145                 150                 155                 160

Asn Lys Glu Cys Leu Ile Asp Pro Leu Asp Val Gln Lys Asn Leu Leu
                165                 170                 175

Asn Glu Glu Asp Pro Cys Tyr Ile Asn Asn Ala Tyr Val Ser Val Asn
            180                 185                 190

Val Val Cys Asn Lys Gly Ala Pro Ser Thr Ser Ile Thr Ala Tyr Lys
            195                 200                 205

Ser Glu Gly Glu Ser Ala Glu Phe Ser Phe Pro Leu Asn Leu Gly Glu
            210                 215                 220

Glu Ser Leu Gln Gly Glu Leu Arg Trp Lys Ala Glu Lys Ala Pro Ser
225                 230                 235                 240

Ser Gln Ser Trp Ile Thr Phe Ser Leu Lys Asn Gln Lys Val Ser Val
                245                 250                 255

Gln Lys Ser Thr Ser Asn Pro Lys Phe Gln Leu Ser Glu Thr Leu Pro
            260                 265                 270

Leu Thr Leu Gln Ile Pro Gln Val Ser Leu Gln Phe Ala Gly Ser Gly
            275                 280                 285

Asn Leu Thr Leu Thr Leu Asp Arg Gly Ile Leu Tyr Gln Glu Val Asn
            290                 295                 300

Leu Val Val Met Lys Val Thr Gln Pro Asp Ser Asn Thr Leu Thr Cys
305                 310                 315                 320

Glu Val Met Gly Pro Thr Ser Pro Lys Met Arg Leu Ile Leu Lys Gln
                325                 330                 335

Glu Asn Gln Glu Ala Arg Val Ser Arg Gln Glu Lys Val Ile Gln Val
            340                 345                 350

Gln Ala Pro Glu Ala Gly Val Trp Gln Cys Leu Leu Ser Glu Gly Glu
            355                 360                 365

Glu Val Lys Met Asp Ser Lys Ile Gln Val Leu Ser Lys Gly Leu Asn
370                 375                 380

Ser Gly Ser Leu His His Ile Leu Asp Ala Gln Lys Met Leu Trp Asn
385                 390                 395                 400

His Arg Asp Arg Asn Leu Pro Pro Leu Ala Pro Leu Gly Pro His His
                405                 410                 415

His His His His
        420

<210> SEQ ID NO 95
<211> LENGTH: 339
<212> TYPE: PRT
<213> ORGANISM: Artificial Sequence
<220> FEATURE:
<223> OTHER INFORMATION: PfRH5Nt encoding amino acids F25-K140 of PfRH5
      (3D7) was expressed encoding C-terminal tags comprising CD4d3+4, a
      biotin acceptor peptide and a His6 tag in tandem

<400> SEQUENCE: 95

Phe Glu Asn Ala Ile Lys Lys Thr Lys Asn Gln Glu Asn Asn Leu Ala
1               5                   10                  15

Leu Leu Pro Ile Lys Ser Thr Glu Glu Lys Asp Asp Ile Lys Asn
            20                  25                  30

Gly Lys Asp Ile Lys Lys Glu Ile Asp Asn Asp Lys Glu Asn Ile Lys
            35                  40                  45
```

```
Thr Asn Asn Ala Lys Asp His Ser Thr Tyr Ile Lys Ser Tyr Leu Asn
     50                  55                  60

Thr Asn Val Asn Asp Gly Leu Lys Tyr Leu Phe Ile Pro Ser His Asn
 65                  70                  75                  80

Ser Phe Ile Lys Lys Tyr Ser Val Phe Asn Gln Ile Asn Asp Gly Met
             85                  90                  95

Leu Leu Asn Glu Lys Asn Asp Val Lys Asn Asn Glu Asp Tyr Lys Asn
            100                 105                 110

Val Asp Tyr Lys Gly Ala Pro Ser Thr Ser Ile Thr Ala Tyr Lys Ser
                115                 120                 125

Glu Gly Glu Ser Ala Glu Phe Ser Phe Pro Leu Asn Leu Gly Glu Glu
        130                 135                 140

Ser Leu Gln Gly Glu Leu Arg Trp Lys Ala Glu Lys Ala Pro Ser Ser
145                 150                 155                 160

Gln Ser Trp Ile Thr Phe Ser Leu Lys Asn Gln Lys Val Ser Val Gln
                165                 170                 175

Lys Ser Thr Ser Asn Pro Lys Phe Gln Leu Ser Glu Thr Leu Pro Leu
            180                 185                 190

Thr Leu Gln Ile Pro Gln Val Ser Leu Gln Phe Ala Gly Ser Gly Asn
        195                 200                 205

Leu Thr Leu Thr Leu Asp Arg Gly Ile Leu Tyr Gln Glu Val Asn Leu
    210                 215                 220

Val Val Met Lys Val Thr Gln Pro Asp Ser Asn Thr Leu Thr Cys Glu
225                 230                 235                 240

Val Met Gly Pro Thr Ser Pro Lys Met Arg Leu Ile Leu Lys Gln Glu
                245                 250                 255

Asn Gln Glu Ala Arg Val Ser Arg Gln Glu Lys Val Ile Gln Val Gln
            260                 265                 270

Ala Pro Glu Ala Gly Val Trp Gln Cys Leu Leu Ser Glu Gly Glu Glu
        275                 280                 285

Val Lys Met Asp Ser Lys Ile Gln Val Leu Ser Lys Gly Leu Asn Ser
    290                 295                 300

Gly Ser Leu His His Ile Leu Asp Ala Gln Lys Met Leu Trp Asn His
305                 310                 315                 320

Arg Asp Arg Asn Leu Pro Pro Leu Ala Pro Leu Gly Pro His His His
                325                 330                 335

His His His

<210> SEQ ID NO 96
<211> LENGTH: 24
<212> TYPE: DNA
<213> ORGANISM: Artificial Sequence
<220> FEATURE:
<223> OTHER INFORMATION: Primer number 1

<400> SEQUENCE: 96
acaggtgccc actcccaggt gcag                                          24

<210> SEQ ID NO 97
<211> LENGTH: 23
<212> TYPE: DNA
<213> ORGANISM: Artificial Sequence
<220> FEATURE:
<223> OTHER INFORMATION: Primer number 2

<400> SEQUENCE: 97
aaggtgtcca gtgtgargtg cag                                           23
```

```
<210> SEQ ID NO 98
<211> LENGTH: 27
<212> TYPE: DNA
<213> ORGANISM: Artificial Sequence
<220> FEATURE:
<223> OTHER INFORMATION: Primer number 3

<400> SEQUENCE: 98
cccagatggg tcctgtccca ggtgcag                                          27

<210> SEQ ID NO 99
<211> LENGTH: 24
<212> TYPE: DNA
<213> ORGANISM: Artificial Sequence
<220> FEATURE:
<223> OTHER INFORMATION: Primer number 4

<400> SEQUENCE: 99
caaggagtct gttccgaggt gcag                                             24

<210> SEQ ID NO 100
<211> LENGTH: 23
<212> TYPE: DNA
<213> ORGANISM: Artificial Sequence
<220> FEATURE:
<223> OTHER INFORMATION: Primer number 5

<400> SEQUENCE: 100
ggaaggtgtg cacgccgctg gtc                                              23

<210> SEQ ID NO 101
<211> LENGTH: 25
<212> TYPE: DNA
<213> ORGANISM: Artificial Sequence
<220> FEATURE:
<223> OTHER INFORMATION: Primer number 6

<400> SEQUENCE: 101
atgaggstcc cygctcagct gctgg                                            25

<210> SEQ ID NO 102
<211> LENGTH: 28
<212> TYPE: DNA
<213> ORGANISM: Artificial Sequence
<220> FEATURE:
<223> OTHER INFORMATION: Primer number 7

<400> SEQUENCE: 102
ctcttcctcc tgctactctg gctcccag                                         28

<210> SEQ ID NO 103
<211> LENGTH: 25
<212> TYPE: DNA
<213> ORGANISM: Artificial Sequence
<220> FEATURE:
<223> OTHER INFORMATION: Primer number 8

<400> SEQUENCE: 103
atttctctgt tgctctggat ctctg                                            25

<210> SEQ ID NO 104
<211> LENGTH: 24
<212> TYPE: DNA
<213> ORGANISM: Artificial Sequence
<220> FEATURE:
```

```
<223> OTHER INFORMATION: Primer number 9

<400> SEQUENCE: 104
gtttctcgta gtctgctttg ctca                                        24

<210> SEQ ID NO 105
<211> LENGTH: 23
<212> TYPE: DNA
<213> ORGANISM: Artificial Sequence
<220> FEATURE:
<223> OTHER INFORMATION: Primer number 10

<400> SEQUENCE: 105
ggtcctgggc ccagtctgtg ctg                                         23

<210> SEQ ID NO 106
<211> LENGTH: 23
<212> TYPE: DNA
<213> ORGANISM: Artificial Sequence
<220> FEATURE:
<223> OTHER INFORMATION: Primer number 11

<400> SEQUENCE: 106
ggtcctgggc ccagtctgcc ctg                                         23

<210> SEQ ID NO 107
<211> LENGTH: 23
<212> TYPE: DNA
<213> ORGANISM: Artificial Sequence
<220> FEATURE:
<223> OTHER INFORMATION: Primer number 12

<400> SEQUENCE: 107
gctctgtgac ctcctatgag ctg                                         23

<210> SEQ ID NO 108
<211> LENGTH: 23
<212> TYPE: DNA
<213> ORGANISM: Artificial Sequence
<220> FEATURE:
<223> OTHER INFORMATION: Primer number 13

<400> SEQUENCE: 108
ggtctctctc scagcytgtg ctg                                         23

<210> SEQ ID NO 109
<211> LENGTH: 23
<212> TYPE: DNA
<213> ORGANISM: Artificial Sequence
<220> FEATURE:
<223> OTHER INFORMATION: Primer number 14

<400> SEQUENCE: 109
gttcttgggc caattttatg ctg                                         23

<210> SEQ ID NO 110
<211> LENGTH: 23
<212> TYPE: DNA
<213> ORGANISM: Artificial Sequence
<220> FEATURE:
<223> OTHER INFORMATION: Primer number 15

<400> SEQUENCE: 110
ggtccaattc ycaggctgtg gtg                                         23
```

```
<210> SEQ ID NO 111
<211> LENGTH: 23
<212> TYPE: DNA
<213> ORGANISM: Artificial Sequence
<220> FEATURE:
<223> OTHER INFORMATION: Primer number 16

<400> SEQUENCE: 111
gagtggattc tcagactgtg gtg                                    23

<210> SEQ ID NO 112
<211> LENGTH: 24
<212> TYPE: DNA
<213> ORGANISM: Artificial Sequence
<220> FEATURE:
<223> OTHER INFORMATION: Primer number 17

<400> SEQUENCE: 112
caccagtgtg gccttgttgg cttg                                   24

<210> SEQ ID NO 113
<211> LENGTH: 54
<212> TYPE: DNA
<213> ORGANISM: Artificial Sequence
<220> FEATURE:
<223> OTHER INFORMATION: Primer number 18

<400> SEQUENCE: 113 cttttctag tagcaactgc aaccggtgta cattccgagg tgcagctggt gcag    54

<210> SEQ ID NO 114
<211> LENGTH: 54
<212> TYPE: DNA
<213> ORGANISM: Artificial Sequence
<220> FEATURE:
<223> OTHER INFORMATION: Primer number 19

<400> SEQUENCE: 114 cttttctag tagcaactgc aaccggtgta cattctgagg tgcagctggt ggag    54

<210> SEQ ID NO 115
<211> LENGTH: 54
<212> TYPE: DNA
<213> ORGANISM: Artificial Sequence
<220> FEATURE:
<223> OTHER INFORMATION: Primer number 20

<400> SEQUENCE: 115 cttttctag tagcaactgc aaccggtgta cattcccagg tgcagctgca ggag    54

<210> SEQ ID NO 116
<211> LENGTH: 54
<212> TYPE: DNA
<213> ORGANISM: Artificial Sequence
<220> FEATURE:
<223> OTHER INFORMATION: Primer number 21

<400> SEQUENCE: 116 cttttctag tagcaactgc aaccggtgta cattctgagg tgcagctgtt ggag    54

<210> SEQ ID NO 117
<211> LENGTH: 56
<212> TYPE: DNA
<213> ORGANISM: Artificial Sequence
<220> FEATURE:
<223> OTHER INFORMATION: Primer number 22
```

```
<400> SEQUENCE: 117 cttttttctag tagcaactgc aaccggtgta cattcccagg tgcagctaca gcagtg        56

<210> SEQ ID NO 118
<211> LENGTH: 54
<212> TYPE: DNA
<213> ORGANISM: Artificial Sequence
<220> FEATURE:
<223> OTHER INFORMATION: Primer number 23

<400> SEQUENCE: 118 cttttttctag tagcaactgc aaccggtgta cattcccagg ttcagctggt gcag          54

<210> SEQ ID NO 119
<211> LENGTH: 54
<212> TYPE: DNA
<213> ORGANISM: Artificial Sequence
<220> FEATURE:
<223> OTHER INFORMATION: Primer number 24

<400> SEQUENCE: 119 cttttttctag tagcaactgc aaccggtgta cattcccagg tccagctggt acag          54

<210> SEQ ID NO 120
<211> LENGTH: 54
<212> TYPE: DNA
<213> ORGANISM: Artificial Sequence
<220> FEATURE:
<223> OTHER INFORMATION: Primer number 25

<400> SEQUENCE: 120 cttttttctag tagcaactgc aaccggtgta cattctgaag tgcagctggt ggag          54

<210> SEQ ID NO 121
<211> LENGTH: 54
<212> TYPE: DNA
<213> ORGANISM: Artificial Sequence
<220> FEATURE:
<223> OTHER INFORMATION: Primer number 26

<400> SEQUENCE: 121 cttttttctag tagcaactgc aaccggtgta cattcccagg tacagctgca gcag          54

<210> SEQ ID NO 122
<211> LENGTH: 54
<212> TYPE: DNA
<213> ORGANISM: Artificial Sequence
<220> FEATURE:
<223> OTHER INFORMATION: Primer number 27

<400> SEQUENCE: 122 cttttttctag tagcaactgc aaccggtgta cattcccagc tgcagctgca ggag          54

<210> SEQ ID NO 123
<211> LENGTH: 54
<212> TYPE: DNA
<213> ORGANISM: Artificial Sequence
<220> FEATURE:
<223> OTHER INFORMATION: Primer number 28

<400> SEQUENCE: 123 cttttttctag tagcaactgc aaccggtgta cattctcagg tgcagctggt ggag          54

<210> SEQ ID NO 124
<211> LENGTH: 38
```

```
<212> TYPE: DNA
<213> ORGANISM: Artificial Sequence
<220> FEATURE:
<223> OTHER INFORMATION: Primer number 29

<400> SEQUENCE: 124
gatgggccct tggtcgacgc tgaggagacg gtgaccag                              38

<210> SEQ ID NO 125
<211> LENGTH: 40
<212> TYPE: DNA
<213> ORGANISM: Artificial Sequence
<220> FEATURE:
<223> OTHER INFORMATION: Primer number 30

<400> SEQUENCE: 125
gatgggccct tggtcgacgc tgaagagacg gtgaccattg                            40

<210> SEQ ID NO 126
<211> LENGTH: 39
<212> TYPE: DNA
<213> ORGANISM: Artificial Sequence
<220> FEATURE:
<223> OTHER INFORMATION: Primer number 31

<400> SEQUENCE: 126
gatgggccct tggtcgacgc tgaggagacg gtgaccgtg                             39

<210> SEQ ID NO 127
<211> LENGTH: 56
<212> TYPE: DNA
<213> ORGANISM: Artificial Sequence
<220> FEATURE:
<223> OTHER INFORMATION: Primer number 32

<400> SEQUENCE: 127 cttttctag tagcaactgc aaccggtgta cattctgaca tccagatgac ccagtc          56

<210> SEQ ID NO 128
<211> LENGTH: 57
<212> TYPE: DNA
<213> ORGANISM: Artificial Sequence
<220> FEATURE:
<223> OTHER INFORMATION: Primer number 33

<400> SEQUENCE: 128 cttttctag tagcaactgc aaccggtgta cattcagaca tccagttgac ccagtct         57

<210> SEQ ID NO 129
<211> LENGTH: 56
<212> TYPE: DNA
<213> ORGANISM: Artificial Sequence
<220> FEATURE:
<223> OTHER INFORMATION: Primer number 34

<400> SEQUENCE: 129 cttttctag tagcaactgc aaccggtgta cattgtgcca tccggatgac ccagtc          56

<210> SEQ ID NO 130
<211> LENGTH: 56
<212> TYPE: DNA
<213> ORGANISM: Artificial Sequence
<220> FEATURE:
<223> OTHER INFORMATION: Primer number 35

<400> SEQUENCE: 130
``` cttttctag tagcaactgc aaccggtgta catggggata ttgtgatgac ccagac         56

<210> SEQ ID NO 131
<211> LENGTH: 56
<212> TYPE: DNA
<213> ORGANISM: Artificial Sequence
<220> FEATURE:
<223> OTHER INFORMATION: Primer number 36

<400> SEQUENCE: 131 cttttctag tagcaactgc aaccggtgta catggggata ttgtgatgac tcagtc         56

<210> SEQ ID NO 132
<211> LENGTH: 56
<212> TYPE: DNA
<213> ORGANISM: Artificial Sequence
<220> FEATURE:
<223> OTHER INFORMATION: Primer number 37

<400> SEQUENCE: 132 cttttctag tagcaactgc aaccggtgta cattcagaaa ttgtgttgac acagtc         56

<210> SEQ ID NO 133
<211> LENGTH: 56
<212> TYPE: DNA
<213> ORGANISM: Artificial Sequence
<220> FEATURE:
<223> OTHER INFORMATION: Primer number 38

<400> SEQUENCE: 133 cttttctag tagcaactgc aaccggtgta cattcagaaa tagtgatgac gcagtc         56

<210> SEQ ID NO 134
<211> LENGTH: 57
<212> TYPE: DNA
<213> ORGANISM: Artificial Sequence
<220> FEATURE:
<223> OTHER INFORMATION: Primer number 39

<400> SEQUENCE: 134 cttttctag tagcaactgc aaccggtgta cattcagaaa ttgtgttgac gcagtct        57

<210> SEQ ID NO 135
<211> LENGTH: 56
<212> TYPE: DNA
<213> ORGANISM: Artificial Sequence
<220> FEATURE:
<223> OTHER INFORMATION: Primer number 40

<400> SEQUENCE: 135 cttttctag tagcaactgc aaccggtgta cattcggaca tcgtgatgac ccagtc         56

<210> SEQ ID NO 136
<211> LENGTH: 38
<212> TYPE: DNA
<213> ORGANISM: Artificial Sequence
<220> FEATURE:
<223> OTHER INFORMATION: Primer number 41

<400> SEQUENCE: 136
atggtgcagc caccgtacgt ttgatytcca ccttggtc                           38

<210> SEQ ID NO 137
<211> LENGTH: 38
<212> TYPE: DNA
<213> ORGANISM: Artificial Sequence

```
<220> FEATURE:
<223> OTHER INFORMATION: Primer number 42

<400> SEQUENCE: 137
atggtgcagc caccgtacgt ttgatatcca ctttggtc                              38

<210> SEQ ID NO 138
<211> LENGTH: 38
<212> TYPE: DNA
<213> ORGANISM: Artificial Sequence
<220> FEATURE:
<223> OTHER INFORMATION: Primer number 43

<400> SEQUENCE: 138
atggtgcagc caccgtacgt ttaatctcca gtcgtgtc                              38

<210> SEQ ID NO 139
<211> LENGTH: 38
<212> TYPE: DNA
<213> ORGANISM: Artificial Sequence
<220> FEATURE:
<223> OTHER INFORMATION: Primer number 44

<400> SEQUENCE: 139
atggtgcagc caccgtacgt ctgatttcca ccttggtc                              38

<210> SEQ ID NO 140
<211> LENGTH: 54
<212> TYPE: DNA
<213> ORGANISM: Artificial Sequence
<220> FEATURE:
<223> OTHER INFORMATION: Primer number 45

<400> SEQUENCE: 140 cttttctag tagcaactgc aaccggttcc tgggcccagt ctgtgctgac kcag             54

<210> SEQ ID NO 141
<211> LENGTH: 54
<212> TYPE: DNA
<213> ORGANISM: Artificial Sequence
<220> FEATURE:
<223> OTHER INFORMATION: Primer number 46

<400> SEQUENCE: 141 cttttctag tagcaactgc aaccggttcc tgggcccagt ctgccctgac tcag             54

<210> SEQ ID NO 142
<211> LENGTH: 54
<212> TYPE: DNA
<213> ORGANISM: Artificial Sequence
<220> FEATURE:
<223> OTHER INFORMATION: Primer number 47

<400> SEQUENCE: 142 cttttctag tagcaactgc aaccggttct gtgacctcct atgagctgac wcag             54

<210> SEQ ID NO 143
<211> LENGTH: 53
<212> TYPE: DNA
<213> ORGANISM: Artificial Sequence
<220> FEATURE:
<223> OTHER INFORMATION: Primer number 48

<400> SEQUENCE: 143 cttttctag tagcaactgc aaccggttct ctctcscagc ytgtgctgac tca              53
```

```
<210> SEQ ID NO 144
<211> LENGTH: 54
<212> TYPE: DNA
<213> ORGANISM: Artificial Sequence
<220> FEATURE:
<223> OTHER INFORMATION: Primer number 49

<400> SEQUENCE: 144 cttttctag tagcaactgc aaccggttct tgggccaatt ttatgctgac tcag          54

<210> SEQ ID NO 145
<211> LENGTH: 54
<212> TYPE: DNA
<213> ORGANISM: Artificial Sequence
<220> FEATURE:
<223> OTHER INFORMATION: Primer number 50

<400> SEQUENCE: 145 cttttctag tagcaactgc aaccggttcc aattcycagr ctgtggtgac ycag           54

<210> SEQ ID NO 146
<211> LENGTH: 37
<212> TYPE: DNA
<213> ORGANISM: Artificial Sequence
<220> FEATURE:
<223> OTHER INFORMATION: Primer number 51

<400> SEQUENCE: 146
ggcttgaagc tcctcactcg agggygggaa cagagtg                             37
```

The invention claimed is:

1. A non-neutralizing antibody, or binding fragment thereof, comprising:
   (a) a heavy chain comprising a CDR1 sequence of SEQ ID NO: 11; a CDR2 sequence of SEQ ID NO: 12 and a CDR3 sequence of SEQ ID NO: 13, and a light chain comprising a CDR1 sequence of SEQ ID NO: 20; a CDR2 sequence of SEQ ID NO: 21 and a CDR3 sequence of SEQ ID NO: 22; or
   (b) a heavy chain comprising a CDR1 sequence of SEQ ID NO: 14; a CDR2 sequence of SEQ ID NO: 15 and a CDR3 sequence of SEQ ID NO: 16, and a light chain comprising a CDR1 sequence of SEQ ID NO: 23; a CDR2 sequence of SEQ ID NO: 24 and a CDR3 sequence of SEQ ID NO: 25; or
   (c) a heavy chain comprising a CDR1 sequence of SEQ ID NO: 17; a CDR2 sequence of SEQ ID NO: 18 and a CDR3 sequence of SEQ ID NO: 19, and a light chain comprising a CDR1 sequence of SEQ ID NO: 26; a CDR2 sequence of SEQ ID NO: 21 and a CDR3 sequence of SEQ ID NO: 27.

2. The non-neutralizing antibody, or binding fragment thereof of claim 1, comprising:
   (a) a heavy chain variable region sequence having at least 90% identity to SEQ ID NO: 47 and a light chain variable region sequence having at least 90% identity to SEQ ID NO: 48;
   (b) a heavy chain variable region sequence having at least 90% identity to SEQ ID NO: 49 and a light chain variable region sequence having at least 90% identity to SEQ ID NO: 50; or
   (c) a heavy chain variable region sequence having at least 90% identity to SEQ ID NO: 51 and a light chain variable region sequence having at least 90% identity to SEQ ID NO: 52.

3. The non-neutralizing antibody, or binding fragment thereof of claim 1, wherein:
   (d) the heavy chain variable region comprises a sequence having at least 95% identity to SEQ ID NO: 47 and the light chain variable region comprises a sequence having at least 95% identity to SEQ ID NO: 48;
   (e) the heavy chain variable region comprises a sequence having at least 95% identity to SEQ ID NO: 49 and the light chain variable region comprises a sequence having at least 95% identity to SEQ ID NO: 50; or
   (f) the heavy chain variable region comprises a sequence having at least 95% identity to SEQ ID NO: 51 and the light chain variable region comprises a sequence having at least 95% identity to SEQ ID NO: 52.

4. The non-neutralizing antibody, or binding fragment thereof of claim 1, which is:
   (a) a monoclonal or polyclonal antibody; or
   (b) a Fab, F(ab')2, Fv, scFv, Fd or dAb.

5. A bispecific dual variable domain molecule comprising a non-neutralizing antibody, or binding fragment thereof, of claim 1 and a neutralizing antibody, or binding fragment thereof, of claim 2.

6. A composition comprising:
   (a) one or more non-neutralizing antibody, or binding fragment thereof as defined in claim 1; and
   (b) one or more neutralizing antibody, or binding fragment thereof, that specifically binds a *Plasmodium* merozoite antigen,
      wherein the *Plasmodium* merozoite antigen is PfRH5 and the one or more neutralizing antibody, or binding fragment thereof, specifically binds an epitope within SEQ ID NO: 3 (RH5ΔN) or SEQ ID NO: 7 (RH5ΔNL), and the one or more neutralizing antibody, or binding fragment thereof, specifically binds an epitope corresponding to residues Gly201 to Lys219 and Lys327 to Gln342 of PfRH5 (SEQ ID NO: 1).

7. The composition of claim 6, wherein the one or more neutralizing antibody, or binding fragment thereof; comprises:
- (a) a heavy chain with a CDR1 sequence of SEQ ID NO: 54; a CDR2 sequence of SEQ ID NO: 55 and a CDR3 sequence of SEQ ID NO: 56, and a light chain with a CDR1 sequence of SEQ ID NO: 60; a CDR2 sequence of SEQ ID NO: 61 and a CDR3 sequence of SEQ ID NO: 62;
- (b) a heavy chain with a CDR1 sequence of SEQ ID NO: 57; a CDR2 sequence of SEQ ID NO: 58 and a CDR3 sequence of SEQ ID NO: 59, and a light chain with a CDR1 sequence of SEQ ID NO: 63; a CDR2 sequence of SEQ ID NO: 64 and a CDR3 sequence of SEQ ID NO: 65;

wherein optionally the one or more neutralizing antibody, or binding fragment thereof; comprises:
- (i) a heavy chain variable region sequence of SEQ ID NO: 81 and a light chain variable region sequence of SEQ ID NO: 82;
- (ii) a heavy chain variable region sequence of SEQ ID NO: 83 and a light chain variable region sequence of SEQ ID NO: 84.

8. The composition of claim 6, wherein each of the one or more non-neutralizing antibodies and the one or more neutralizing antibodies, or binding fragment thereof, is independently selected from:
- (a) a monoclonal or polyclonal antibody; or
- (b) a Fab, F(ab')2, Fv, scFv, Fd or dAb.

* * * * *